(12) United States Patent
Trimbur et al.

(10) Patent No.: US 8,889,402 B2
(45) Date of Patent: Nov. 18, 2014

(54) CHLORELLA SPECIES CONTAINING EXOGENOUS GENES

(75) Inventors: Donald E. Trimbur, Palo Alto, CA (US); Chung-Soon Im, Palo Alto, CA (US); Harrison F. Dillon, San Mateo, CA (US); Anthony G. Day, San Francisco, CA (US); Scott Franklin, La Jolla, CA (US); Anna Coragliotti, San Francisco, CA (US)

(73) Assignee: Solazyme, Inc., South San Francisco, CA (US)

( * ) Notice: Subject to any disclaimer, the term of this patent is extended or adjusted under 35 U.S.C. 154(b) by 369 days.

(21) Appl. No.: 13/273,179

(22) Filed: Oct. 13, 2011

(65) Prior Publication Data
US 2012/0028319 A1 Feb. 2, 2012

Related U.S. Application Data

(63) Continuation of application No. 12/772,173, filed on Apr. 30, 2010, now Pat. No. 8,512,999, which is a continuation of application No. 12/131,783, filed on Jun. 2, 2008.

(60) Provisional application No. 60/941,581, filed on Jun. 1, 2007, provisional application No. 60/959,174, filed on Jul. 10, 2007, provisional application No. 60/968,291, filed on Aug. 27, 2007, provisional application No. 61/024,069, filed on Jan. 28, 2008.

(51) Int. Cl.
| | |
|---|---|
| C12P 7/64 | (2006.01) |
| C12N 1/12 | (2006.01) |
| C11C 3/00 | (2006.01) |
| C10L 1/02 | (2006.01) |
| C12N 1/32 | (2006.01) |
| C12N 9/04 | (2006.01) |
| C12N 9/02 | (2006.01) |
| C12N 9/12 | (2006.01) |
| C12N 9/16 | (2006.01) |
| C12N 9/20 | (2006.01) |
| C12N 9/26 | (2006.01) |
| C12N 9/88 | (2006.01) |
| C12P 5/02 | (2006.01) |

(52) U.S. Cl.
CPC . *C11C 3/00* (2013.01); *C10L 1/026* (2013.01); *C12N 1/32* (2013.01); *C12N 9/0006* (2013.01); *C12N 9/0008* (2013.01); *C12N 9/1205* (2013.01); *C12N 9/16* (2013.01); *C12N 9/20* (2013.01); *C12N 9/2408* (2013.01); *C12N 9/88* (2013.01); *C12P 5/02* (2013.01); *C12P 7/6409* (2013.01); *C12P 7/6463* (2013.01); *C12P 7/649* (2013.01); *Y02E 50/13* (2013.01); *Y02T 50/678* (2013.01); *C12P 7/6436* (2013.01)
USPC ...................... 435/257.2; 435/134; 435/257.1

(58) Field of Classification Search
CPC ........... C12P 7/6463; C12P 7/20; C12N 9/16; C12N 15/79
USPC .................................... 435/134, 257.1, 257.2
See application file for complete search history.

(56) References Cited

U.S. PATENT DOCUMENTS

| | | |
|---|---|---|
| 2,235,056 A | 3/1941 | Walmesley |
| 3,320,693 A | 5/1967 | Shirota et al. |
| 3,957,578 A | 5/1976 | Narita et al. |
| 4,341,038 A | 7/1982 | Bloch et al. |
| 4,390,561 A | 6/1983 | Blair et al. |
| 4,519,845 A | 5/1985 | Ou |
| 4,673,490 A | 6/1987 | Subramanian et al. |
| 4,755,467 A | 7/1988 | Scopes et al. |
| 4,992,605 A | 2/1991 | Craig et al. |
| 5,001,059 A | 3/1991 | Skatrud et al. |
| 5,091,116 A | 2/1992 | Krishnamurthy et al. |
| 5,130,242 A | 7/1992 | Barclay |
| 5,212,087 A | 5/1993 | Fournier et al. |
| 5,252,198 A | 10/1993 | Harrison et al. |
| 5,270,175 A | 12/1993 | Moll et al. |
| 5,270,177 A | 12/1993 | Ramos Lazcano et al. |
| 5,304,481 A | 4/1994 | Davies et al. |
| 5,338,673 A | 8/1994 | Thepenier et al. |
| 5,354,878 A | 10/1994 | Connemann et al. |
| 5,391,724 A | 2/1995 | Kindl et al. |
| 5,395,455 A | 3/1995 | Scott et al. |
| 5,436,394 A | 7/1995 | Willmitzer et al. |

(Continued)

FOREIGN PATENT DOCUMENTS

| | | |
|---|---|---|
| CN | 1940021 A | 4/2007 |
| CN | 101037639 A | 9/2007 |

(Continued)

OTHER PUBLICATIONS

Aguirre et al., 2013, Critical Review in Biotechnology, vol. 33, No. 3, p. 293-308.*

(Continued)

*Primary Examiner* — Shin Lin Chen
(74) *Attorney, Agent, or Firm* — Alston & Bird LLP

(57) ABSTRACT

The invention provides methods of cultivating oil-bearing microbes using xylose alone or in combination with other depolymerized cellulosic material. Also provided are microorganisms comprising an exogenous gene encoding a polysaccharide degrading enzyme, such as a cellulase, a hemicellulase, a pectinase, or a driselase. Some methods of microbial fermentation are provided that comprise the use of xylose and depolymerized cellulosic materials for the production of oil-bearing microorgansims.

4 Claims, 29 Drawing Sheets

(56) References Cited

U.S. PATENT DOCUMENTS

| | | |
|---|---|---|
| 5,455,167 A | 10/1995 | Voelker et al. |
| 5,492,938 A | 2/1996 | Kyle et al. |
| 5,518,918 A | 5/1996 | Barclay et al. |
| 5,547,699 A | 8/1996 | Iizuka et al. |
| 5,595,965 A | 1/1997 | Wiggins |
| 5,597,400 A | 1/1997 | Nonomura et al. |
| 5,693,507 A | 12/1997 | Daniell et al. |
| 5,711,983 A | 1/1998 | Kyle et al. |
| 5,792,631 A | 8/1998 | Running |
| 5,888,947 A | 3/1999 | Lambert et al. |
| 5,900,370 A | 5/1999 | Running |
| 6,255,505 B1 | 7/2001 | Bijl et al. |
| 6,338,866 B1 | 1/2002 | Criggall et al. |
| 6,372,460 B1 | 4/2002 | Gladue et al. |
| 6,441,208 B2 | 8/2002 | Bijl et al. |
| 6,589,923 B2 | 7/2003 | Lenuck et al. |
| 6,680,426 B2 | 1/2004 | Daniell et al. |
| 6,762,345 B1 | 7/2004 | Cahoon et al. |
| 7,053,267 B2 | 5/2006 | Knauf et al. |
| 7,063,957 B2 | 6/2006 | Chen |
| 7,081,567 B2 | 7/2006 | Xue et al. |
| 7,135,620 B2 | 11/2006 | Daniell et al. |
| 7,268,276 B2 | 9/2007 | Ruezinsky et al. |
| 7,309,602 B2 | 12/2007 | David |
| 7,468,267 B2 | 12/2008 | Monod et al. |
| 7,588,931 B2 | 9/2009 | Damude et al. |
| 7,622,570 B2 | 11/2009 | Oswald et al. |
| 7,851,199 B2 | 12/2010 | Bailey et al. |
| 7,879,591 B2 | 2/2011 | Damude et al. |
| 7,883,882 B2 | 2/2011 | Franklin et al. |
| 7,935,515 B2 | 5/2011 | Franklin et al. |
| 7,939,710 B1 | 5/2011 | Apt et al. |
| 8,029,579 B2 | 10/2011 | Knuth et al. |
| 8,187,860 B2 | 5/2012 | Franklin et al. |
| 8,278,261 B2 | 10/2012 | Day et al. |
| 8,435,767 B2 | 5/2013 | Franklin et al. |
| 8,450,083 B2 | 5/2013 | Day et al. |
| 8,497,116 B2 | 7/2013 | Trimbur et al. |
| 2002/0012979 A1 | 1/2002 | Berry |
| 2002/0059661 A1 | 5/2002 | Dehesh |
| 2002/0144455 A1 | 10/2002 | Bertrand et al. |
| 2002/0178467 A1 | 11/2002 | Dehesh |
| 2003/0054524 A1 | 3/2003 | Spener et al. |
| 2003/0082595 A1 | 5/2003 | Jiang et al. |
| 2003/0097686 A1 | 5/2003 | Knauf et al. |
| 2003/0145350 A1 | 7/2003 | Spener et al. |
| 2003/0211594 A1 | 11/2003 | Rosebrook |
| 2004/0053235 A1 | 3/2004 | Smirnoff et al. |
| 2004/0230085 A1 | 11/2004 | Jakkula et al. |
| 2004/0235123 A1 | 11/2004 | Liao et al. |
| 2005/0005333 A1 | 1/2005 | Ruezinsky et al. |
| 2005/0084941 A1 | 4/2005 | Abe et al. |
| 2005/0102716 A1 | 5/2005 | Venkatramesh et al. |
| 2005/0112735 A1 | 5/2005 | Zappi et al. |
| 2005/0262588 A1 | 11/2005 | Dehesh et al. |
| 2005/0266537 A1 | 12/2005 | Chen |
| 2006/0048240 A1 | 3/2006 | Alexandrov et al. |
| 2006/0075522 A1 | 4/2006 | Cleveland et al. |
| 2006/0094089 A1 | 5/2006 | Barclay |
| 2006/0107346 A1 | 5/2006 | Schneeberger et al. |
| 2006/0130182 A1 | 6/2006 | Heim et al. |
| 2006/0153826 A1 | 7/2006 | Arnould et al. |
| 2006/0156436 A1 | 7/2006 | Nakamura et al. |
| 2006/0162006 A9 | 7/2006 | Sherman et al. |
| 2006/0199984 A1 | 9/2006 | Kuechler et al. |
| 2006/0225341 A1 | 10/2006 | Rohr et al. |
| 2007/0004016 A1 | 1/2007 | Picataggio et al. |
| 2007/0009988 A1 | 1/2007 | Monod et al. |
| 2007/0048848 A1 | 3/2007 | Sears |
| 2007/0099280 A1 | 5/2007 | Barclay |
| 2007/0118916 A1 | 5/2007 | Puzio et al. |
| 2007/0166266 A1 | 7/2007 | Dillon et al. |
| 2007/0167396 A1 | 7/2007 | Dillon et al. |
| 2007/0254354 A1 | 11/2007 | Millis et al. |
| 2007/0261138 A1 | 11/2007 | Graham et al. |
| 2007/0275438 A1 | 11/2007 | David et al. |
| 2007/0286908 A1 | 12/2007 | Clampitt |
| 2008/0014620 A1 | 1/2008 | Op Den Camp et al. |
| 2008/0038804 A1 | 2/2008 | Du et al. |
| 2008/0160593 A1 | 7/2008 | Oyler |
| 2008/0206379 A1 | 8/2008 | Fabritius et al. |
| 2008/0229451 A1 | 9/2008 | Cao et al. |
| 2008/0256666 A1 | 10/2008 | Zhu et al. |
| 2009/0004715 A1 | 1/2009 | Trimbur et al. |
| 2009/0011480 A1 | 1/2009 | Trimbur et al. |
| 2009/0018300 A1 | 1/2009 | Bloom et al. |
| 2009/0035842 A1 | 2/2009 | Trimbur et al. |
| 2009/0047721 A1 | 2/2009 | Trimbur et al. |
| 2009/0061493 A1 | 3/2009 | Trimbur et al. |
| 2009/0064567 A1 | 3/2009 | Lippmeier et al. |
| 2009/0142322 A1 | 6/2009 | Ye |
| 2009/0145392 A1 | 6/2009 | Clark et al. |
| 2009/0148918 A1 | 6/2009 | Trimbur et al. |
| 2009/0176272 A1 | 7/2009 | Champagne et al. |
| 2009/0197312 A1 | 8/2009 | Pastinen et al. |
| 2009/0211150 A1 | 8/2009 | Wu et al. |
| 2009/0234146 A1 | 9/2009 | Cooney et al. |
| 2009/0274736 A1 | 11/2009 | Dillon et al. |
| 2009/0298159 A1 | 12/2009 | Wu et al. |
| 2009/0305942 A1 | 12/2009 | Day et al. |
| 2009/0317878 A1 | 12/2009 | Champagne et al. |
| 2010/0021912 A1 | 1/2010 | Farese et al. |
| 2010/0035320 A1 | 2/2010 | Blanchard et al. |
| 2010/0058651 A1 | 3/2010 | Knuth et al. |
| 2010/0093031 A1 | 4/2010 | Kobayashi et al. |
| 2010/0105955 A1 | 4/2010 | Alibhai et al. |
| 2010/0151112 A1 | 6/2010 | Franklin et al. |
| 2010/0151538 A1 | 6/2010 | Franklin et al. |
| 2010/0151567 A1 | 6/2010 | Franklin et al. |
| 2010/0154293 A1 | 6/2010 | Hom et al. |
| 2010/0170144 A1 | 7/2010 | Day et al. |
| 2010/0239712 A1 | 9/2010 | Brooks et al. |
| 2010/0297292 A1 | 11/2010 | Brooks et al. |
| 2010/0297295 A1 | 11/2010 | Brooks et al. |
| 2010/0297296 A1 | 11/2010 | Brooks et al. |
| 2010/0297323 A1 | 11/2010 | Brooks et al. |
| 2010/0297325 A1 | 11/2010 | Brooks et al. |
| 2010/0297331 A1 | 11/2010 | Brooks et al. |
| 2010/0303957 A1 | 12/2010 | Brooks et al. |
| 2010/0303961 A1 | 12/2010 | Brooks et al. |
| 2010/0303989 A1 | 12/2010 | Brooks et al. |
| 2010/0303990 A1 | 12/2010 | Brooks et al. |
| 2010/0323413 A1 | 12/2010 | Trimbur et al. |
| 2010/0323414 A1 | 12/2010 | Trimbur et al. |
| 2011/0014665 A1 | 1/2011 | Trimbur et al. |
| 2011/0015417 A1 | 1/2011 | Trimbur et al. |
| 2011/0047863 A1 | 3/2011 | Trimbur et al. |
| 2011/0165634 A1 | 7/2011 | Franklin et al. |
| 2011/0190522 A1 | 8/2011 | Trimbur et al. |
| 2011/0203168 A1 | 8/2011 | Franklin et al. |
| 2012/0009636 A1 | 1/2012 | Berry et al. |
| 2012/0034662 A1 | 2/2012 | Hu et al. |
| 2012/0128851 A1 | 5/2012 | Brooks et al. |
| 2012/0164701 A1 | 6/2012 | Trimbur et al. |
| 2012/0277453 A1 | 11/2012 | Franklin et al. |
| 2012/0288930 A1 | 11/2012 | Trimbur et al. |
| 2013/0089916 A1 | 4/2013 | Franklin et al. |
| 2013/0122180 A1 | 5/2013 | Brooks et al. |
| 2013/0165677 A1 | 6/2013 | Franklin et al. |
| 2013/0273621 A1 | 10/2013 | Franklin et al. |
| 2013/0295268 A1 | 11/2013 | Day et al. |
| 2013/0296591 A1 | 11/2013 | Day et al. |
| 2013/0330790 A1 | 12/2013 | Trimbur et al. |

FOREIGN PATENT DOCUMENTS

| | | |
|---|---|---|
| CN | 101130513 A | 2/2008 |
| DE | 2756977 A1 | 6/1978 |
| EP | 1178118 A1 | 2/2002 |
| EP | 1681337 A1 | 7/2006 |
| EP | 1741767 A1 | 1/2007 |
| FR | 2924126 A1 | 5/2009 |
| JP | 60006799 A | 1/1985 |
| JP | 06-253872 A | 9/1994 |

(56) References Cited

FOREIGN PATENT DOCUMENTS

| | | |
|---|---|---|
| JP | 07-075557 | 3/1995 |
| WO | WO 92/11373 A1 | 7/1992 |
| WO | WO 94/10288 A2 | 5/1994 |
| WO | WO 95/13390 A2 | 5/1995 |
| WO | WO 99/64618 A1 | 11/1999 |
| WO | WO 00/61740 A1 | 10/2000 |
| WO | WO 02/08403 A2 | 1/2002 |
| WO | WO 2004/101753 A2 | 11/2004 |
| WO | WO 2005/035693 A2 | 4/2005 |
| WO | WO 2007/027669 A1 | 3/2007 |
| WO | WO 2007/038566 A2 | 4/2007 |
| WO | WO 2007/117511 A2 | 10/2007 |
| WO | WO 2007/134294 A2 | 11/2007 |
| WO | WO 2008/002643 A2 | 1/2008 |
| WO | WO 2008/011811 A1 | 1/2008 |
| WO | WO 2008/083352 A1 | 7/2008 |
| WO | WO 2008/130372 A2 | 10/2008 |
| WO | WO 2008/134836 A2 | 11/2008 |
| WO | WO 2008/151149 A2 | 12/2008 |
| WO | WO 2009/126843 A2 | 10/2009 |
| WO | WO 2010/019813 A2 | 2/2010 |
| WO | WO 2010/045368 A2 | 4/2010 |
| WO | WO 2010/063031 A2 | 6/2010 |
| WO | WO 2010/063032 A2 | 6/2010 |
| WO | WO 2010/120923 A1 | 10/2010 |

OTHER PUBLICATIONS

Bhunia et al., 2010, "Algal biodiesel production: challenges and opportunities", Bioenergy and Biofuel from Biowastes and Biomass, p. 313-345, Editor(s): Khanal, Samir K. Publisher: American Society of Civil Engineers, Reston, VA.*
U.S. Appl. No. 60/941,581, Jun. 1, 2007, Trimbur et al.
U.S. Appl. No. 60/959,174, Jul. 10, 2007, Trimbur et al.
U.S. Appl. No. 60/968,291, Aug. 27, 2007, Trimbur et al.
U.S. Appl. No. 61/024,069, Jan. 28, 2008, Trimbur et al.
U.S. Appl. No. 61/118,590, Jan. 28, 2008, Franklin et al.
U.S. Appl. No. 61/118,994, Dec. 1, 2008, Franklin et al.
U.S. Appl. No. 61/174,357, Apr. 30, 2009, Franklin et al.
U.S. Appl. No. 61/219,525, Jun. 23, 2009, Franklin et al.
A Look Back at the U.S. Department of Energy's Aquatic Species Program: Biodiesel from Algae, NREL/TP-580-24190, John Sheehan, Terri Dunahay, John Benemann and Paul Roessler, (1998).
Abbadi et al., "Knockout of the regulatory site of 3-ketoacyl-ACP synthase III enhances short-and medium-chain acyl-ACP synthesis," *The Plant Journal*, 24(1):1-9, (2000).
Alvarez et al., "Triacylglycerols in prokaryotic microorganisms," *Appl Microbiol Biotechnol*, 60:367-376, (2002).
Angerbauer et al., "Conversion of sewage sludge into lipids by Lipomyces starkeyi for biodiesel production," *Bioresource Technology*, 99:3051-3056, (2008).
Bonaventure et al., "Disruption of the FATB Gene in Arabidopsis Dethonstrates an Essential Role of Saturated Fatty Acids in Plant Growth," *The Plant Cell* 15:1020-1033, (2003).
Borza et al., "Multiple Metabolic Roles for the Nonphotosynthetic Plastid of the Green Alga Prototheca Wickerhamii," *EUKARYOTIC CELL*, 4(2):253-261, (2005).
Bouchard et al., "Characterization of Depolymerized Cellulosic Residues," *Wood Sci. Technol.*, 23:343-355, (1989).
Broun et al., "A bifunctional oleate 12-hydroxylase: desaturase from Lesquerella fendleri," *The Plant Journal*, 13(2):201-210, (1998).
Canakci et al., "Biodiesel production from oils and fats with high free fatty acids," *Transactions of the ASAE*, 44(6):1429-1436, (2001).
Cartens et al,. "Eicosapentaenoic Acid (20:5n-3) from the Marine Microalga Phaeodactylum tricornutum," *Journal of the American Oil Chemists' Society*, 73(8):1025-1031, (1996).
Chasan, "Engineering Fatty Acids—The Long and Short of It," *Plant Cell*, 7:235-237, (1995).
Chen et al., "High cell density culture of microalgae in heterotrophic growth," *Trends In Biotechnology*, 14:421-426, (1996).
Chen et al., "Highly Effective Expression of Rabbit Neutrophil Peptide-1 Gene in Chlorella Ellipsoidea Cells," *Current Genetics*, 39:365-370, (2001).
Chisti et al., "Biodiesel from microalgae," *Biotechnology Advances*, 25:294-306, (2007).
Chow et al., "Electrotranformation of Chlorella Vulgaris," *Plant Cell Reports*, 18:778-780, (1999).
Cobley et al., Construction of Shuttle Plasmids Which Can Be Efficiently Mobilized From *Escherichia coli* Into The Chromatically Adapting Cyanobacterium, *Plasmid*, 30:90-105, (1993).
Courchesne et al., "Enhancement of Lipid Production Using Biochemical, Genetic and Transcription Factor Engineering Approaches," *J Biotechnol. Epub*, 141(1-2):31-41, (2009).
Covello et al., "Functional Expression of the Extraplastidial Arabidopsis thaliana Oleate Desaturase Gene (FAD2) in Saccharomyces cerevisiae'," *Plant Physiol.*, 111:223-226, (1996).
Dai et al., "Biodiesel generation from oleaginous yeast Rhodotorula glutinis with xylose assimilating capacity," *African Journal of Biotechnology*, 6(18):2130-2134, (2007).
Dawson et al., "Stable Transformation of Chlorella: Rescure of Nitrate Reductase-Deficient Mutants with the Nitrate Reductase Gene," *Current Microbiology*, 35:356-362, (1997).
Dehesh et al., "Production of high levels of 8:0 and 10:0 fatty acids in transgenic canola by overexpression of the Ch FatB2, a thioesterase cDNA from Cuphea hookeriana," *The Plant Journal*, 9(2):167-172, (1996).
Deng et al., "Ionic Liquid as a Green Catalystic Reaction Medium for Esterifications," *J. Mol. Catalysis A: Chemical*, 165:33-36, (2001).
Dunahay et al., "Manipulation of Microalgal Lipid Production Using Genetic Engineering," *Applied Biochemistry and Biotechnology*, 57/58:223-231, (1996).
Eccleston et al., "Medium-chain Fatty Acid Biosynthesis and Utilization in Brassica Mapus Plants Expressing Lauroyl-Acyl Carrier Protein Thioesterase," *Planta* 198:46-53, (1996).
El-Fadaly et al., "Single Cell Oil Production by an Oleaginous Yeast Strain in a Low Cost Cultivation Medium," *Research Journal of Microbiology*, 4(8):301-313, (2009).
El-Sheekh, MM., Stable Transformation of the Intact Cells of Chlorella Kessleri With High Velocity Microprojectiles, *Biologia Plantarium* 42(2): 209-216, (1999).
European Search Report and European Search Opinion for application EP08769988 mailed Jul. 1, 2011.
European Search Report and European Search Opinion for application EP11158642 mailed Jul. 1, 2011.
Evans et al., "A comparison of the oleaginous yeast, Candida curvata, grown on different carbon sources in continuous and batch culture," *Lipids*, 18(09):623-629, (1983).
Facciotti et al., "Improved stearate phenotype in transgenic canola expressing a modified acyl-acyl carrier protein thioesterase," *Nat Biotechnol.*, 17(6):593-597, (1999).
Falciatore et al., "Transformation of Nonselectable Reporter Genes in Marine Diatoms," *Marine Biotechnology*, 1:239-251, (1999).
Fukuda et al., "Biodiesel Fuel Production by transesterification of Oils," *J. Biosci. Bioeng.*, 92(5):405-416, (2001).
GenBank: "Codon usage Database file for Chlorella vulgaris," Jun. 2007. [Retrieved from the Internet Aug. 26, 2010: <URL: http://www.kazusa.or.jp/codon/cgi-bin/showcodon.cgi?species=3077 >].
GenBank: Accession No. L42851.1, "Prototheca wickerhamii large subunit ribosomal RNA (rrnL) gene, partial sequence; chloroplast gene for chloroplast product," Nov. 21, 2001.
Gill et al., "Lipid Accumulation in an Oleaginous Yeast (Candida 107) Growing on Glucose in Single-Stage Continuous Culture," *Applied and Environmental Microbiology*, 33(02):231-239, (1977).
Grinna et al., "Size Distribution and General Structual Features of N-Linked Oligosaccharides from the Methylotrophic Yeast, *Pichia pastoris*," *Yeast*, 5:107-115, (1989).
Guo-Zhong et al., "The Actin Gene Promoter-driven Bar as a Dominant Selectable Marker for Nuclear Transformation of *Dunaliella Salina*," Acta Genetica Sinica, 32(4): 424-433, (2005).
Gusakov et al., "Design of Highly Efficenet Cellulase Mixtures for Enzymatic Hydrolysis of Cellulose," *Biotechnol. and Bioengineering*, 97(5)1028-1038, (2007).

(56) References Cited

OTHER PUBLICATIONS

Hall et al., "Lipid Accumulation in an Oleaginous Yeast (Candida 107) Growing on Glucose Under Various Conditions in a One- and Two-Stage Continuous Culture," *Applied and Environmental Microbiology*, 33(3):577-584, (2009).

Hallman et al., "Reporter Genes and Highly Regulated Promoters as Tools for Transformation Experiments in *Volvox Carteri*," *Proc Natl Acad Sci U S A.*, 91(24):11562-11566, (1994).

Hawkins et al., "Expression of Human Growth Hormone by the Eukaryotic Alga, *Chlorella*," Current Microbiology, 38:335-341, (1999).

Heifetz, "Genetic Engineering of the Chloroplast," *Biochimie*, 82:655-666, (2000).

Heise et al., "Factors Controlling Medium-Chain Fatty Acid Synthesis In Plastids From Cuphea Embryos," *Prog. Lipid Res.*, 33(1/2):87-95, (1994).

Heredia et al., "Simultaneous utilization of glucose and xylose by Candida curvata D in continuous culture," *Biotechnology Letters*, 10(01):25-30, (1988).

Hossain et al., "The effect of the sugar source on citric acid production by *Aspergillus niger*," *Appl Microbiol Biotechnol*, 19:393-397, (1984).

Hsieh et al., "A PII-like Protein in Arabidopsis: Putative Role in Nitrogen Sensing," *Proc Natl Acad Sci USA*, 95(23):13965-13970, (1998).

Hu et al., "Microalgal Triacylglycerols as Feedstocks for Biofuel Production: Perspectives and Advances," *The Plant Journal* 54:621-639, (2008).

Huang et al., "Expression of Mercuric Reductase From *Bacillus Megaterium* MB1 in Eukaryotic Microalga Chlorella sp. DT: An Approach for Mercury Phytoremediation," *Appl. Microbiol. Biotechnol.*, 72:197-205, (2006).

Huber et al., "Production of Liquid Alkanes by Aqueous-Phase Processing of Biomass-Derived Carbohydrates," *Science*, 308:1446-1450, (2005).

Huber et al., "Synthesis of Transportation Fuels from Biomass: Chemistry, Catalysts, and Engineering," *Chem. Rev.*, 106: 4044-4098, (2006).

Jarvis et al. " Transient Expression of Firefly Luciferase in Protoplasts of the Green Alga Chlorella Ellipsoidea," *Current Genet.*, 19: 317-322, (1991).

Jaworski et al., "Industrial oils from transgenic plants," *Current Opinion in Plant Biology*, 6:178-184, (2003).

Jeoh et al., " Cellulase Digestibility of Pretreated Biomass Is Limited by Cellulose Acessibility," *Biotechnol Bioeng.*, 98(1)112-122, (2007).

Jha et al., "Cloning and functional expression of an acyl-ACP thioesterase FatB type from *Diploknema (Madhuca) butyracea* seeds in *Escherichia coli*," *Plant Physiology and Biochemistry*, 44:645-655, (2006).

Kalscheuer et al., " Establishment of a Gene Transfer System for *Rhodococcus Opacus* PD630 Based on Electroporation and its Application for Recombinant Biosynthesis of Poly(3-hyroxyalkanoic acids)," *Applied Microbiology and Biotechnology*, 52(4):508-515, (1999).

Kang et al., "The regulation activity of Chlorella virus gene 5' upstream sequence in *Escherichia coli* and eucaryotic alage," *Institute of Microbiology, Chinese Academy of Sciences, Beijing*, 16(4):443-6, (2000). Abstract only.

Katayama et al., "Alpha-Linolenate and Photosynethetic Activity in *Chlorella Protothecoides*," Plant Physiol., 42:308-313, (1967).

Kim et al. "Stable Integraion and Functional Expression of Flounder Growth Hormone Gene in Tranformed Microalga, Chlorella Ellipsoidea," (*Mar. Biotechnol.* 4:63-73 (2002).

Koksharova, "Genetic Tools for Cyanobacteria," *Appl Microbiol Biotechnol*, 58(2):123-37, (2002).

Kong et al., "Microbial production of lipids by cofermentation of glucose and xylose with Lipomyces starkeyi 2#," *Chinese Journal of Bioprocess Engineering*, 05(02):36, (2007). Abstract.

Lawford et al., "Performance Testing of Zymomonas Mobilis Metabolically Engeineered for Confermation of Glucose, Xylose, and Arabinose," *Appl Biochem Biotechnol.*, 98-100:429-48, (2002).

Li et al., "Large-scale biodiesel production from microalga Chlorella protothecoides through heterotrophic cultivation in bioreactors," *Biotechnology and Bioengineering*, 98(04):764-771, (2007).

Li et al., "Articles: Biocatalysts and Bioreactor Design, Biofuels From Microalgae," *Biotechnol. Prog.*, 24:815-820, (2008).

Li et al., "Enzymatic transesterification of yeast oil for biodiesel fuel production," *The Chinese Journal of Process Engineering*, 07(01):137-140 (2007), and machine translation.

Li et al., "High-density cultivation of oleaginous yeast *Rhodosporidium toruloides* Y4 in fed-batch culture," *Enzyme and Microbial Technology*, 41:312-317, (2007).

Li et al., "Screening of oleaginous yeasts for broad-spectrum carbohydrates assimilating capacity," *China Biotechnology*, 25(12):39-44 (2005), and machine translation.

Liu et al., "Biodiesel production by direct methanolysis of oleaginous microbial biomass," *Journal of Chemical Technology and Biotechnology*, 82:775-780, (2007).

Lumbreras et al., "Efficient Foreign Gene Expression in *Chlamydonnonas Reinhardtii* Mediated by an Endogenous Intron," *Plant Journal*, 14(4):441-447, (1998).

Maruyama et al., "Introduction of Foreign DNA Into Chlorella Saccharophila by Electroporation," *Biotechnology Techniques*, 8:821-826, (2004).

Matsuka et al., *Plant and Cell Physiol.*, 7:149-162 (1966).

Mayer et al., "A Structural Model of the Plant Acyl-Acyl Carrier Protein Thioesterase FatB Comprises Two Helix/4-Stranded Sheet Domains, the N-terminal Domain Containing Residues That Affect Specificity and the C-terminal Domain Containing Catalytic Residues," *The Journal of Biological Chemistry*, 280(5):3621-3627, (2005).

Meesters et al., "High-cell-density cultivation of the lipid accumulating yeast *Cryptococcus curvatus* using glycerol as a carbon source," *Applied Microbiology and Biotechnology*, 45:575-579 (1996).

Miao et al., "Biodiesel Production From Heterotrophic Microalgal Oil," *Biosource Technology*, 97(06):841-846, (2006).

Miao et al., "High Yield Bio-Oil Production from Fast Pyrolysis by Metabolic Controlling of Chlorella Protothecoides," *J. Biotech.*, 110:85-93, (2004).

Muller et al., "Nitrogen and hormonal responsiveness of the 22 kDa alpha-zein and b-32 genes in maize endosperm is displayed in the absence of the transcriptional regulator Opaque-2," *Plant J.*, 12(2):281-291, Abstract, (1997).

Murakami et al., "Lipid Composition of Commercial Bakers' Yeasts Having Different Freeze-tolerance in Frozen Dough," *Biosci. Biotechnol. Biochem.*, 60(11)1874-1876, (1996).

Nes et al., "Sterol phylogenesis and algal evolution," *Proc Natl Acad Sci U S A*, 87(19):7565-7569, (1990).

Onai et al., "Natural Tranformation of the Termophillic Cyanbacterium Thermosynechococcus Elongatus BP-1: A Simple and Efficicent Method for Gene Transfer," *Mol Genet Genomics*, 271(1):50-9, (2004).

Papanikolaou et al., *J. Chem. Technol. Biotechnol.*, 79: 1189-1196 (2004).

Park et al., "Isolation and Characterization of Chlorella Virus From Fresh Water in Korea and Application in Chlorella Transformation System," *Plant Pathol. J.*, 21(1):13-20, (2005).

PCT International Preliminary Report on Patentability (Chapter I) of Dec. 7, 2009 for application PCT/US08/65563.

PCT International Preliminary Report on Patentability (Chapter I) of May 31, 2011 for application PCT/US09/066142.

PCT International Preliminary Report on Patentability (Chapter I) of Oct. 12, 2010 for application PCT/US2009/040123.

PCT Search Report for application PCT/US2009/040123 mailed Oct. 5, 2009.

PCT Search Report for application PCT/US2011/0032582 mailed Aug. 9, 2011.

PCT Search Report of Aug. 20, 2010 for application PCT/US2009/066142.

(56) References Cited

OTHER PUBLICATIONS

PCT Search Report of Nov. 5, 2010 for application PCT/US2009/066141.
PCT Search Report of Nov. 6, 2008 for application PCT/US08/65563.
PCT Written Opinion of the International Search Authority of Aug. 20, 2010 for application PCT/US2009/066142.
PCT Written Opinion of the International Searching Authority for application PCT/US2011/0032582 mailed Aug. 9, 2011.
PCT Written Opinion of the International Searching Authority of Nov. 6, 2008 for application PCT/US08/65563.
PCT Written Opinion of the International Searching Authority of Nov. 5, 2010 for application PCT/US2009/066141.
Radakovits et al., "Genetic Engineering of Algae for Enhanced Biofuel Production," *Eukaryotic Cell*, 9(04): 486-501, (2010).
Rastogi et al., "Footprinting of the spinach nitrite reductase gene promoter reveals the preservation of nitrate regulatory elements between fungi and higher plants," Plant Mol Biol., 34(3):465-476, Abstract (1997).
Rehm et al., "Heterologous expression of the acyl-acyl carrier protein thioesterase gene from the plant *Umbellularia califomica* mediates polyhydroxyalkanoate biosynthesis in recombinant *Escherichia coli*," *Appl Microbiol Biotechnol*, 55:205-209, (2001).
Rosenberg et al., "A Green Light for Engineered Algae: Redirecting Metabolism to Fuel a Biotechnology Revolution," *Current Opinion in Biotechnology. Tissue, Cell and Pathyway Engineering*, E-Pub 19:430-436, (2008).
Roy et al., "Production of Intracellular Fat by the Yeast Lipomyces starkeyi," *Indian Journal of Experimental Biology*, 16(4):511-512, (1978).
Running et al., "Extracellular production of L-ascorbic acid by Chlorella protothecoides, Prototheca species, and mutants of P. moriformis during aerobic culturing at low pH," Journal of Industrial Microbiology & Biotechnology, 29:93-98, (2002).
Running et al., "The Pathway of L-ascorbic acid biosynthesis in the colourless microalga Prototheca moriformis," *Journal of Experimental Botany*, 54(389):1841-1849, (2003).
Salou et al., "Growth and Energetics of Leuconostoc oenos during Cometabolism of Glucose with Citrate or Fructose," *Applied and Environmental Microbiology*, 60(5):1459-1466, (1994).
Schütt et al., "The role of acyl carrier protein isoforms from *Cuphea lanceolata* seeds in the de-novo biosynthesis of medium-chain fatty acids," Publication, *Planta*, 205:263-268, (1998).
Schütti et al., "β-Ketoacyl-acyl carrier protein synthase IV: a key enzyme for regulation of medium-chain fatty acid synthesis in *Cuphea lanceolata* seeds," *Planta*, 215:847-854, (2002).
Son et al., "Induction and Cultures of Mountain Genseng Adventitious Roots and AFLP Analysis for Identifying Mountain Ginseng," *Biotechnol. Bioprocess Eng.*, 4:119-123, (1999).
Suh et al., "What limits production of unusual monoenoic fatty acids in transgenic plants?," *Planta*, 215:584-595, (2002).
Takashima et al., "Furthur Noted on the Growth and Chlorophyll Formation of Chlorella Protothecoides," *Plant & Cell Physiol.*, 5:321-332, (1964).
Tan et al., "Saponified Palm Kernel Oil and Its Major Free Fatty-Acids as Carbon Substrated for the Production of Polyhydroxyalkanoated in *Pseudomonas-Putida* Pga1," *Applied Microbiology and Biotechnology*, 47(3)207-211, (1997).
Tan et al., "Establishment of a Micro-Particle Bombardment Transformation System for *Dunaliella Salina*," *J Microbiol*.;43(4):361-365, (2005).
Thavarungkul et al., "Batch injection analysis for the determination of sucrose in sugar cane juice using immobilized invertase and thermometric detection," *Biosensors & Bioelectronics*, 14:19-25, (1999).
Thiry et al., "Optimizing scale-up fermentation processes," *Trends in Biotechnology*, 20:103-105, (2002).
Trimble et al., "Structure of Oligosaccharides on *Saccharomyces* SUC2 Invertase Secreted by the Methylotrophic Yeast Pichia Pastoris," *J. Biol. Chem.*, 266(34):22807-22817, (1991).

U.S. Appl. No. 12/131,766, Non-Final Office Action mailed Aug. 1, 2011.
U.S. Appl. No. 12/131,766, Non-Final Office Action mailed Dec. 10, 2009.
U.S. Appl. No. 12/131,766, Non-Final Office Action mailed Nov. 23, 2010.
U.S. Appl. No. 12/131,766, Requirement for Restriction/Election mailed Aug. 17, 2010.
U.S. Appl. No. 12/131,766, Requirement for Restriction/Election mailed Aug. 5, 2009.
U.S. Appl. No. 12/131,773, Final Office Action mailed Mar. 21, 2011.
U.S. Appl. No. 12/131,773, Non-Final Office Action mailed Jun. 25, 2010.
U.S. Appl. No. 12/131,773, Non-Final Office Action mailed Dec. 15, 2009.
U.S. Appl. No. 12/131,773, Requirement for Restriction/Election mailed Aug. 6, 2009.
U.S. Appl. No. 12/131,783, Non-Final Office Action mailed Jun. 6, 2011.
U.S. Appl. No. 12/131,783, Requirement for Restriction/Election mailed Apr. 19, 2011.
U.S. Appl. No. 12/131,793, Final Office Action mailed Mar. 30, 2010.
U.S. Appl. No. 12/131,793, Non-Final Office Action mailed Sep. 16, 2009.
U.S. Appl. No. 12/131,793, Requirement for Restriction/Election mailed Aug. 6, 2009.
U.S. Appl. No. 12/131,804, Final Office Action mailed Feb. 2, 2011.
U.S. Appl. No. 12/131,804, Non-Final Office Action mailed Mar. 3, 2010.
U.S. Appl. No. 12/131,804, Requirement for Restriction/Election mailed Nov. 18, 2009.
U.S. Appl. No. 12/131,804, Requirement for Restriction/Election mailed Sep. 17, 2009.
U.S. Appl. No. 12/194,389, Final Office Action mailed Jan. 5, 2011.
U.S. Appl. No. 12/194,389, Non-Final Office Action mailed Feb. 4, 2010.
U.S. Appl. No. 12/194,389, Requirement for Restriction/Election mailed Oct. 5, 2010.
U.S. Appl. No. 12/194,389, Requirement for Restriction/Election mailed Nov. 2, 2009.
U.S. Appl. No. 12/499,033, Non-Final Office Action mailed Feb. 18, 2011.
U.S. Appl. No. 12/499,033, Requirement for Restriction/Election mailed Oct. 15, 2010.
U.S. Appl. No. 12/628,144, Final Office Action mailed Nov. 16, 2010.
U.S. Appl. No. 12/628,144, Non-Final Office Action mailed Jul. 8, 2010.
U.S. Appl. No. 12/628,144, Non-Final Office Action mailed Jun. 7, 2011.
U.S. Appl. No. 12/628,147, Examiner Interview Summary Record mailed Mar. 3, 2011.
U.S. Appl. No. 12/628,147, Final Office Action mailed Oct. 1, 2010.
U.S. Appl. No. 12/628,147, Non-Final Office Action mailed May 25, 2010.
U.S. Appl. No. 12/628,149, Non-Final Office Action mailed Jun. 25, 2010.
U.S. Appl. No. 12/628,149, Non-Final Office Action mailed Sep. 16, 2010.
U.S. Appl. No. 12/628,149, Notice of Allowance mailed Dec. 15, 2010.
U.S. Appl. No. 12/628,150, Non-Final Office Action mailed Apr. 29, 2010.
U.S. Appl. No. 12/628,150, Non-Final Office Action mailed Oct. 13, 2010.
U.S. Appl. No. 12/628,150, Notice of Allowance mailed Mar. 21, 2011.
U.S. Appl. No. 12/772,163, Requirement for Restriction/Election mailed Jun. 24, 2011.
U.S. Appl. No. 12/772,164, Requirement for Restriction/Election mailed Jul. 20, 2011.
U.S. Appl. No. 12/772,170, Non-Final Office Action mailed Sep. 13, 2011.

(56) References Cited

OTHER PUBLICATIONS

U.S. Appl. No. 12/772,170, Requirement for Restriction/Election mailed Jul. 13, 2011.
U.S. Appl. No. 12/772,174, Requirement for Restriction/Election mailed Aug. 10, 2011.
U.S. Appl. No. 13/073,757, Non-Final Office Action mailed Aug. 15, 2011.
Uniprot Accession No. P41758. Phosphoglycerate kinase, chloroplastic. Nov. 25, 2008. [Retrieved from the Internet Aug. 12, 2010: <http://www.uniprot.org/uniprot/P41758.txt?version=46>].
Uniprot Accession No. P41758. Phosphoglycerate kinase, chloroplastic. Jul. 22, 2008. [Retrieved from the Internet Aug. 25, 2010: <http://http://www.uniprot.org/uniprot/P41758.txt?version=44 >]; amino acids 1-60.
Van De Loo et al., "An oleate 12-hydroxylase from *Ricinus communis* L. is a fatty acyl desaturase homolog," *Proc. Natl. Acad. Sci. USA*, 92:6743-6747, (1995).
Van Gerpen, "Commercial Biodiesel Production," Oilseed and Biodiesel Workshop, Billings, Montana, Jan. 9, 2008, downloaded from http://www.deq.state.mt.us/Energy/bioenergy/Biodiesel_Production_Educ_Presentations/10Montana_Production_Jan_2008_JVP.pdf on Mar. 10, 2010.
Van Gerpen, *Fuel Processing Technology*, 86:1097-1107 (2005).
Voelker et al., "Alteration of the Specificity and Regulation of Fatty Acid Synthesis of *Escherichia coli* by Expression of a Plant Medium Chain Acyl-Acyl Carrier Protein Thioesterase," *Journal of Bacteriology*, 176(23):7320-7327, (1994).
Voelker et al., "Broad-Range and Binary-Range Acyl-Acyl-Carrier-Protein Thioesterases Suggest an Alternative Mechanism for Medium-Chain Production in Seeds," *Plant Physiol.*, 114:669-677, (1997).
Voetz et al., "Three Different cDNAs Encoding Acyl Carrier Proteins from *Cuphea lanceolate'*," *Plant Physiol.*, 106:785-786, (1994).
Wang et al., "Quantitative estimate of the effect of cellulase components during degradation of cotton fibers," *Carbohydrate Research*, 339:819-824, (2004).
Westphal, et al., "Vipp1 Deletion Mutant of Synechocystis: A Connection Between Bacterial Phage Shock and Thylakoid Biogenesis," *Proc Natl Acad Sci U S A.*, 98(7):4243-4248, (2007).
Wiberg et al., "The distribution of caprylate, caprate and laurate in lipids from developing and mature seeds of transgenic *Brassica napus L.*," *Planta*, 212:33-40, (2000).
Wirth et al., "Transforamtion of Various Species of Gram-Negitive Bacteria Belonging to 11 Difference Genera by Electroporation," *Mol Gen Genet.*; 216(1):175-177, (1989).
Wolk et al., "Construction of Shuttle Vectors Capable of Conjugative Transfer From *Escherichia coli* to Nitrogen-Fixing Filamentous Cyanobacteria," *Proc Natl Acad Sci U S A.*, 81(5):1561-1565, (1984).
Wyman et al., "Comparative Sugar Recovery Data From Laboratory Scale Application of Leading Pretreatment Technologies to Corn Stover," *Bioresour Technol.*, 96(18):2026-2032, (2005).
Xu et al., "High quality biodiesel production from a microalga Chlorella protothecoides by heterotrophic growth in fermenters," *Journal of Biotechnology*, 126:499-507, (2006).
Zhao et al., "Toward cheaper microbial oil for biodiesel oil," *China Biotechnology*, 25(02):8-11 (2005).
"Enzymatic Assay of Invertase (EC 3.2.1.26)," Sigma-Aldrich Co. LLC., (1999). [Retrieved from the Internet Aug. 21, 2012: <http://www.sigmaaldrich.com/etc/medialib/docs/Sigma/General_Information/invertase_temp_25.Par.0001.File.tmp/invertase_temp_25.pdf.
Aggelis et al., "Enhancement of single cell oil production by Yarrowia lipolytica growing in the presence of Teucrium polium L. aqueous extract," Biotechnology Letters, 21:747-749, (1999).
Alberto et al., "Crystal structure of inactivated Thermotoga maritima invertase in complex with the trisaccharide substrate raffinose," Biochem. J., 395:457-462,, (2006).
Altschul et al., "Basic local alignment search tool," J Mol Biol, 215(3):403-410, (1990).

Appel et al., "A multicopy vector system for genetic studies in Mucor circinelloides and other zygomycetes," Molecular Genetics and Genomics, 271(5):595-602, (2004).
Apt et al., "Stable nuclear transformation of the diatom Phaeodactylum tricornutum," Mol Gen Genet, 252(5):572-579, (1996).
Barnes et al., "Contribution of 5'- and 3'-untranslated regions of plastid mRNAs to the expression of *Chlamydomonas reinhardtii* chloroplast genes," Mol Genet Genomics, 274(6):625-636, (2005).
Bergh et al., "Expression of the *Saccharomyces cerevisiae* glycoprotein invertase in mouse fibroblasts: Glycosylation, secretion, and enzymatic activity," Proc. Natl. Acad. Sci. USA, 84:3570-3574, (1987).
Bigogno et al., "Biosynthesis of arachidonic acid in the oleaginous microalga *Parietochloris incisa* (Cholorphyceae): Radiolabeling studies," Lipids 37(2):209-216 (2002); Abstract Only.
Blowers et al., "Studies on *Chlamydomonas* chloroplast transformation: foreign DNA can be stably maintained in the chromosome," Plant Cell, 1(1):123-132, (1989).
Bordes et al., "A new recombinant protein expression system for high-throughput screening in the yeast *Yarrowia lipolytica*," Journal of Microbiological Methods, 70(3):493-502, (2007).
Boutry et al., "Targeting of bacterial chloramphenicol acetyltransferase to mitochondria in transgenic plants," Nature, 328(6128):340-2, (1987).
Boynton et al., "Chloroplast Transformation in *Chlamydomonas* with High Velocity Microprojectiles," Science, 240(4858):1534-1538, (1988).
Broun et al., "Accumulation of Ricinoleic, Lesquerolic, and Densipolic Acids in Seeds of Transgenic *Arabidopsis* Plants That Express a Fatty Acyl Hydroxylase cDNA from Castor Bean," Plant Physiol., 113:933-942, (1997).
Broun et al., "Catalytic Plasticity of Fatty Acid Modification Enzymes Underlying Chemical Diversity of Plant Lipids," Science, 282:1315-1317, (1998). [Retrieved from the Internet Feb. 27, 2007: <URL: http://www.sciencemag.org>].
Brown et al., "The amino-acid and sugar composition of 16 species of micralgae used in mariculture," J. Exp. Mar. Biol. Ecol. 145:79-99 abstract (1991).
Burgal et al., "Metabolic engineering of hydroxy fatty acid production in plants: RcDGAT2 drives dramatic increases in ricinoleate levels in seed oil," Plant Biotechnol J., 6(8):819-831, (2008).
Cahoon et al., "A Determinant of Substrate Specificity Predicted from the Acyl-Acyl Carrier Protein Desaturase of Developing Cat's Claw Seed," Plant Physiol., 117:593-598, (1998).
Campbell et al., "Codon Usage in Higher Plants, Green Algae, and Cyanobacteria," Plant Physiol., (92):1-11, (1990).
Canam, "An Investigation of the Physiological Roles and Enzymatic Properties of Invertases in Tobacco and Hybrid Poplar," Thomas Benjamin Canam, 165 pages, (2008).
Carlson et al., "The Secreted Form of Invertase in *Saccharomyces cerevisiae* is Synthesized from mRNA Encoding a Signal Sequence," Molecular and Cellular Biology,3(3):439-447, (1983).
Chen et al., "Recognition of prokaryotic transcription terminators by spinach chloroplast RNA polymerase," Nucleic Acids Research, 16(17):8411-8431, (1988).
Chen et al., "Heterotrophic Growth of *Chlamydomonas reinhardtii* on Acetate in Chemostat Culture," Process Biochemistry, 31(6):601-604, (1996).
Cheng et al., "Sugars modulate an unusual mode of control of the cell-wall invertase gene (Incw1) through its 3' untranslated region in a cell suspension culture of maize," Proc. Natl. Acad. Sci. USA, 96:10512-10517, (1999).
Chica et al., "Semi-rational approaches to engineering enzyme activity: combining the benefits of directed evolution and rational design ," Current Opinion in Biotechnology, 16:378-384, (2005).
Cho et al., "Molecular cloning and expression analysis of the cell-wall invertase gene family in rice (*Oryza sativa* L.)," Plant Cell Rep , 24:225-236 , (2005).
Ciferri, "Thiamine-deficiency of *Prototheca*, a Yeast-like Achloric Alga," Nature, 178:1475-1476, (1956).
Cobley et al., "CpeR is an activator required for expression of the phycoerythrin operon (cpeBA) in the cyanobacterium Fremyella

(56) References Cited

OTHER PUBLICATIONS diplosiphon and is encoded in the phycoerythrin linker-polypeptide operon (cpeCDESTR)," Molecular Microbiology, 44(6):1517-1531, (2002).

Comai et al., "Chloroplast Transport of a Ribulose Biphosphate Carboxylase Small Subunit-5-Enolpyruvyl 3-Phosphoshikimate Synthase Chimeric Protein Requires Part of the Mature Small Subunit in Addition to the Transit Peptide," Journal of Biological Chemistry, 263(29):15104-15109 (1988).

Davies et al.,"Expression of the Arylsulfatase Gene from the Beta 2-Tubulin Promoter in *Chlamydomonas reinhardtii*," Nucleic Acids Research, 20(12):2959-2965, (1992).

De Coninck et al., "Arabidopsis AtcwINV3 and 6 are not invertases but are fructan exohydrolases (FEHs) with different substrate specificities," Plant, Cell and Environment, 28,:432-443, (2005).

Debuchy et al., "The argininosuccinate lyase gene of *Chlamydomonas reinhardtii*: an important tool for nuclear transformation and for correlating the genetic and molecular maps of the ARG7 locus," EMBO J., 8(10):2803-2809, (1989).

Dehesh et al., "KAS IV: a 3-ketoacyl-ACP synthase from Cuphea sp. is a medium chain specific condensing enzyme," The Plant Journal, 15:383-390, (1998).

Deshnium et al., "Transformation of *Synechococcus* with a gene for choline oxidase enhances tolerance to salt stress," Plant Mol Biol, 29(5):897-907, (1995).

Devos et al., "Practical Limits of Function Prediction," Proteins: Structure, Function, and Genetics, 41:98-107, (2000).

Dimou et al., "Genes coding for a putative cell-wall invertase and two putative monosaccharide/H+ transporters are expressed in roots of etiolated Glycine max seedlings," Plant Science, 169:798-804, (2005).

Dormann et al., "Cloning and Expression in *Escherichia coli* of a Novel Thioesterase from *Arabidopsis thaliana* Specific for Long-Chain Acyl-Acyl Carrier Proteins," Archives of Biochemistry and Biophysics, 316(1):612-618, (1995).

Dunahay et al., "Genetic Engineering of Microalgae for Fuel Production," Applied Biochemistry and Biotechnology, 34/35:331-339 (1992).

Ehneβ et al., "Co-ordinated induction of mRNAs for extracellular invertase and a glucose transporter in Chenopodium rubrum by cytokinins,"The Plant Journal, 11(3):539-548, (1997).

Fall et al., "Bioconversion of Xylan to Triglycerides by Oil-Rich Yeasts," Applied and Environmental Microbiology, 47(5):1130-1134, (1984).

Forester et al., "Critic acid production from sucrose using a recombinant strain of the yeast *Yarrowia lipolyticae*," Appl Microbiol Biotechnol, 75:1409-1417, (2007).

Foyer et al., "Sucrose and Invertase, an Uneasy Alliance," Iger Innovations, pp. 18-21, (1997).

Franklin et al., "Prospects for molecular farming in the green alga *Chlamydomonas reinhardtii*," Current Opinion in Plant Biology, 7:159-165, (2004).

Franzen et al., "Chloroplast transit peptides from the green alga *Chlamydomonas reinhardtii* share features with both mitochondrial and higher plant chloroplast presequences," FEBS Letters, 260(2):165-168, (1990).

Frenz et al., "Hydrocarbon recovery by extraction with a biocompatible solvent from free and immobilized cultures of *Botryococcus braunii*," Enzyme Microb Technol, 11(11):717-724, (1989).

Frohns et al., "Potassium ion channels of Chlorella viruses cause rapid depolarization of host cells during infection," J Virol, 80(5):2437-2444, (2006).

Fromm et al., "Expression of Genes Transferred into Monocot and Dicot Plant Cells by Electroporation," Proc Natl Acad Sci, 82:5824-5828, (1985).

Funes et al., "The typically mitochondrial DNA-encoded ATP6 subunit of the F1F0-ATPase is encoded by a nuclear gene in *Chlamydomonas reinhardtii*," J Biol Chem, 277(8):6051-6058, (2002).

Gallagher et al., "Isolation and characterization of a cDNA clone from *Lolium temulentum* L. encoding for a sucrose hydrolytic enzyme which shows alkaline/neutral invertase activity'," Journal of Experimental Bota, 49(322.):789-795, (1998).

Gasc'on et al., "Comparative Study of the Properties of the Purified Internal and External Invertases from Yeast," The Journal of Biological Chemistry, 243(7):1573-1577, (1968).

Godt et al., "Regulation and Tissue-Specific Distribution of mRNAs for Three Extracellular Invertase Isoenzymes of Tomato Suggests an Important Function in Establishing and Maintaining Sink Metabolism'," Plant Physiol, 115:273-282, (1997).

Goetz et al., "The different pH optima and substrate specificities of extracellular and vacuolar invertases from plants are determined by a single amino-acid substitution," The Plant Journal, 20(6):707-711, (1999).

Graves et al., "Hyaluronan synthesis in virus PBCV-1-infected chlorella-like green algae," Virology, 257(1):15-23, (1999).

Gruber et al., "*Escherichia coli*-Anacystis nidulans plasmid shuttle vectors containing the PL promoter from bacteriophage lambda," Current Microbiology, 22(1):15-19, (1991).

Guschina et al., "Lipids and lipid metabolism in eukaryotic algae," Progress in Lipis Research, 45:160-186, (2006).

Hajirezaeil et al., "Impact of elevated cytosolic and apoplastic invertase activity on carbon metabolism during potato tuber development," Journal of Experimental Botany, GMP Special Issue, 51:439-445, (2000).

Hall et al., "Expression of a foreign gene in *Chlamydomonas reinhardtii*," Gene, 124(1):75-81, (1993).

Hall et al., "Lipid Accumulation in an Oleaginous Yeast (Candida 107) Growing on Glucose Under Variou Conditions in a One- and Two-Stage Continuous Culture," Applied and Environmental Microbiology, 33(3):577-584, (1977).

Hanley-Bowdoin et al., "Chloroplast promoters," Trends in Biochemical Sciences, 12:67-70, (1987).

Hawkins, et al., "Expression of Human Growth Hormone by the Eukaryotic Alga, *Chlorella*," Current Microbiology, 38:335-341, (1999).

Henderson et al., "Lipid Composition and Biosynthesis in the Marine Dinoflagellate Crypthecodznzum Cohnii" Phytochem. 27(6)1679-1683 (1988).

Henikoff et al., "Amino Acid Substitution Matrices from Protein Blocks," Proc Natl Acad of Sci, 89(22):10915-10919, (1992).

Hillen et al., "Hydrocracking of the Oils of *Botryococcus braunii* to Transport Fuels," Biotechnology and Bioengineering, 24(1):193-205, (1982).

Hiramatsu et al., "Expression of a chitinase gene and lysis of the host cell wall during *Chlorella* virus CVK2 infection," Virology, 260(2):308-315, (1999).

Hitz et al.,"Cloning of a Higher-Plant Plastid Omega-6 Fatty Acid Desaturase cDNA and Its Expression in a Cyanobacterium," Plant Physiology, 105(2):635-641, (1994).

Inoue et al., "Analysis of oil derived from liquefaction of *Botryococcus Braunii*," Biomass and Bioenergy, 6(4):269-274, (1994).

Iturriaga et al. "Heterologous transformation of Mucor circinelloides with the *Phycomyces blakesleeanus* leu1 gene," Current Genetics, 21(3):215-223, (1992).

Jakobiak et al., "The Bacterial Paromomycin Resistance Gene, aphH, as a Dominant Selectable Marker in *Volvox carteri*," Protist, 55: 381-393, (2004).

Ji et al., "The rice genome encodes two vacuolar invertases with fructan exohydrolase activity but lacks the related fructan biosynthesis genes of the *Pooideae*," New Phytologist, 173:50-62, (2007).

Jiang et al., "The actin gene promoter-driven bar as a dominant selectable marker for nuclear transformation of *Dunaliella salina*,"Yi Chuan Xue Bao, 32(4):424-433, (2005).

Kamiya, "Effects of Blue Light and Ammonia on Nitrogen Metabolism in a colorless Mutant of *Chlorella*," Plant Cell Physiol., 30(4):513-521, (1989).

Kang et al., "Genetic diversity in *chlorella* viruses flanking kcv, a gene that encodes a potassium ion channel protein," Virology, 326(1):150-159, (2004).

(56) References Cited

OTHER PUBLICATIONS

Karlin et al., "Applications and statistics for multiple high-scoring segments in molecular sequences," Proc Natl Acad Sci, 90(12):5873-5877, (1993).
Kawasaki et al., "Characterization of Immediate Early Genes Expressed in Chlorovirus Infections," Nucleic Acids Symp Ser, 44:161-162, (2000).
Kawasaki et al., "Immediate Early Genes Expressed in Chlorovirus Infections," Virology, 318(1):214-223, (2004).
Kenyon, "Fatty Acid Composition of Unicellular Strains of Blue-Green Algae," J. Bacteriology 109(2):827-834 (1972).
Kern et al., "Stability, quaternary structure, and folding of internal, external, and core-glycosylated invertase from yeast," Protein Sci., 1:120-131, (1992).
Kessler et al., "Physiological and Biochemical Contributions to the Taxonomy of the Genus Prototheca III. Utilization of Organic Carbon and Nitrogen Compounds," Arch Microbiol, 132:103-106, (1982).
Kimchi-Sarfaty et al., " A 'Silent' Polymorphism in the MDR1 Gene Changes Substrate Specificity," Science, 315:525-528, (2007). [Retrieved from the Internet Nov. 1, 2007: <URL: http://www.sciencemag.org>].
Kindle, "High-Frequency Nuclear Transformation of *Chlamydomonas reinhardtii*," Proc Natl Acad Sci, 87(3)1228-1232, (1990).
Kisselev, "Polypeptide Release Factors in Prokaryotes and Eukaryotes: Same Function, Different Structure," Structure, 10:8-9, (2002).
Klein et al., "High-velocity microprojectiles for delivering nucleic acids into living cells," Nature, 327:70-73, (1987).
Knauf, "The application of genetic engineering to oilseed crops," Trends in Biotechnology, 5(2):40-47, (1987).
Kohler et al., "The green fluorescent protein as a marker to visualize plant mitochondria in vivo," Plant J, 11(3):613-621, (1997).
Krebbers et al., "The maize chloroplast genes for the beta and epsilon subunits of the photosynthetic coupling factor CF1 are fused," Nucleic Acids Res, 10(16): 4985-5002, (1982).
Krinsky et al., "The Appearance of Neoxanthin during the Regreening of Dark-grown *Euglena*," Plant Physiol. 39(3):441-445 (1964).
Kuo et al., "Diversity of Oleic Acid, Ricinoleic Acid and Linoleic Acid Conversions Among *Pseudomonas aeruginosa* Strains," Current Microbiology, 49:261-266, (2004).
Lalonde et al., "The Dual Function of Sugar Carriers: Transport and Sugar Sensing," The Plant Cell 11:707-726, (1999).
Lammens et al., "Arabidopsis thaliana cell wall invertase in complex with ligands," HASYLAB, Annual Report 2006, Part II, Scientific User Contributions Part II, Protein Crystallography at EMBL Beamlines, pp. 61-62, (2006). [Retrieved from the Internet August.
Lapidot et al., "Stable Choroplast Transformation of the Unicellular Red Alga Porphyridium Species," Plant Physiol, 129:7-12, (2002).
Lara et al., "Extracellular Intertase is an Essential Component of Cytokinin-Mediated Delay of Senescence," The Plant Cell, 16:1276-1287, (2004).
Le Roy et al., "Unraveling the Difference between Invertases and Fructan Exohydrolases: A Single Amino Acid (Asp-239) Substitution Transforms Arabidopsis Cell Wall Invertasel into a Fructan 1-Exohydrolase," Plant Physiology, 145:616-625, (2007).
Leon-Banares et al., "Transgenic microalgae as green cell-factories," TRENDS in Biotechnology, 22(1):45-52, (2004).
Levitan et al., "Dual targeting of the protein disulfide isomerase RB60 to the chloroplast and the endoplasmic reticulum," Proc Natl Acad Sci, 102(17):6225-6230, (2005).
Li et al., "DNA variation at the invertase locus invGE/GF is associated with tuber quality traits in populations of potato breeding clones," Genetics, 40 pages, (2005). Published on Mar. 31, 2005 as 10.1534/genetics.104.040006.
Lindley, "The impact of food processing antioxidants in vegetable oils, fruits, and vegetables," Trends in Food Science & Technology. 9:336-340, (1998).

Liras et al., "Biosynthesis and Secretion of Yeast Invertase Effect of Cycloheximide and 2-Deoxy-D-glucose," Eur. J. Biochem., 23:160-165, (1971).
Lubitz, "The Protein Quality, Digestibility, and Composition of Algae, *Chlorella* 71105," J. Food Sci. 28(2):229-232 (1963).
Manuell et al., "Robust expression of a bioactive mammalian protein in Chlamydomonas chloroplast," Plant Biotech J, 5(3):402-412, (2007).
Mayer et al., "Identification of amino acid residues involved in substrate specificity of plant acyl-ACP thioesterases using a bioinformatics-guided approach," BMC Plant Biology, 7(1):1-11, (2007).
Mayfield et al., "Expression and Assembly of a Fully Active Antibody in Algae," Proc Natl Acad Sci, 100(2):438-442, (2003).
Mayfield et al., "Stable nuclear transformation of *Chlamydomonas reinhardtii* by using a *C. reinhardtii* gene as the selectable marker," Pro. Natl. Acad. Sci. USA, Cell Biology, 87:2087-2091, (1990).
Mekhedov et al., "Toward a Functional Catalog of the Plant Genome. A Survey of Genes for Lipid Biosynthesis," Plant Physiology, 122:389-401, (2000).
Mendes et al., "Supercritical Carbon Dioxide of Compounds with Pharmaceutical Importance from Microalgae," Inorganica Chimica Acta, 356:328-334, (2003).
Metzger et al., "*Botryococcus braunii*: A Rich Source for Hydrocarbons and Related Ether Lipids," Applied Microbiology and Biotechnology, 66(5):486-496, (2005).
Minowa et al., "Oil Production from Algal Cells of *Dunaliella tertiolecta* by Direct Thermochemical Liquefaction," Fuel, 74(12)1735-1738, (1995).
Mitra et al., "A Chlorella Virus Gene Promoter Functions as a Strong Promoter Both in Plants and Bacteria," Biochemical and Biophysical Research Communications, 204(1):189-194, (1994).
Mitra et al., "The *Chlorella* Virus Adenine Methyltransferase Gene Promoter is a Strong Promoter in Plants," Plant Molecular Biology, 26(1):85-93, (1994).
Mitsljhashi et al., "Differential Expression of Acid Invertase Genes during Seed Germination in *Arabidopsis thaliana*," Biosci. Biotechnol. Biochem, 68(3):602-608, (2004).
Mullet et al., "Multiple transcripts for higher plantrbcL andatpB genes and localization of the transcription initiation site of therbcL gene," Plant Molecular Biology, 4(1):39-54, (1985).
Murakami et al., "Lipids and Fatty Acid Custipvsi lions of *Chlorella*," Nihon Yuka gakkai-shi, 46(4):423-427, (1997).
Nackley et al., "Human Catechol-O-Methyltransferase Haplotypes Modulate Protein Expression by Altering mRNA Secondary Structure," Science, 314:1930-1933, (2006).[Retrieved from the Internet Nov. 1 , 2007: <URL: http://www.sciencemag.org>].
Needleman et al., "A general method applicable to the search for similarities in the amino acid sequence of two proteins," Journal of Molecular Biology, 48(3):443-453, (1970).
Neigeborn et al., "Genes Affecting the Regulation of Suc2 Gene Expression by Glucose Repression in *Saccharomyces Cerevisiae*," Genetics, 108:845-858, (1984).
Neigeborn et al., "Mutations Causing Constitutive Invertase Synthesis in Yeast: Genetic Interactions with snf Mutations," Genetics, 115:247-253, (1987).
Nguyen-Quoc et al., "A role for 'futile cycles' involving invertase and sucrose synthase in sucrose metabolism of tomato fruit," Journal of Experimental Botany, 52(358):881-889, (2001).
O'Mullan et al., "Purification and some properties of extracellular invertase B from Zymomonas rrtobiris," Appl Microbiol Biotechnol, 38:341-346, (1992).
Otles et al., "Fatty Acid Composition of *Chlorella* and Spirulina Microalgae Species," Journal of AOAC International, 84(6):1708-1714, (2001).
Pagny et al., "Fusion with HDEL Protects Cell Wall Invertase from Early Degradation when N-glycosylation is Inhibited," Plant Cell Physiol., 44(2):173-182 , (2003).
Papanikolaou et al., "Lipid production by *Yarrowia lipolytica* growing on industrial glycerol in a single-stage continuous culture," Bioresource Technology, 82:43-49, (2002).
PCT International Preliminary Report on Patentability (Chapter I) of Aug. 13, 2012 for application PCT/US11/38463.

(56) References Cited

OTHER PUBLICATIONS

PCT International Preliminary Report on Patentability for application PCT/US2011/059224 mailed May 16, 2013.
PCT International Search Report and Written Opinion of the International Searching Authority for application PCT/US2013/037261 mailed Aug. 23, 2013.
PCT International Search Report for application PCT/US2011/038463 mailed Jan. 18, 2012.
PCT International Search Report for application PCT/US2011/059224 mailed Jun. 27, 2012.
PCT International Search Report for application PCT/US2012/023696 mailed May 23, 2012.
PCT International Search Report for application PCT/US2012/036690 mailed Aug. 30, 2012.
PCT Written Opinion of the International Searching Authority for application PCT/US2011/038463 mailed Jan. 18, 2012.
PCT Written Opinion of the International Searching Authority for application PCT/US2012/023696 mailed May 23, 2012.
PCT Written Opinion of the International Searching Authority for application PCT/US2012/036690 mailed Aug. 30, 2012.
Pearson et al., "Improved tools for biological sequence comparison," Proc Natl Acad Sci, 85(8):2444-2448, (1988).
Perlman et al., "Mutations affecting the signal sequence alter synthesis and secretion of yeast invertase," Proc. Natl. Acad. Sci. USA, 83:5033-5037, (1986).
Petkov et al., "Which are fatty acids of the green alga *Chlorella*?," Biochemical Systematics and Ecology, 35:281-285, (2007).
Pons et al., "Three Acidic Residues Are at the Active Site of a β-Propeller Architecture in Glycoside Hydrolase Families 32, 43, 62, and 68," PROTEINS: Structure, Function, and Bioinformatics , 54:424-432, (2004).
Powell et al., "Algae Feeding in Humans," J. Nutrition, 75:7-12, (1961).
Proels et al., "Novel mode of hormone induction of tandem tomato invertase genes in floral tissue," Plant Molecular Bioingy , 52:191-201, (2003).
Proschold et al., "Portrait of a Species: *Chlamydomonas reinhardtii*," Genetics, 170(4):1601-1610, (2005).
Qingyu et al., "Fine Cell Structure and Biochemical Compositions of Chlorella Protothecoides after Transferring from Autotrophic to Heterotrophic Metabolism," Journal of Nanjing University, Natural Sciences Edition, 29(4):622-630, (1993). Abstract.
Randolph-Anderson et al., "Further characterization of the respiratory deficient dum-1 mutation of *Chlamydomonas reinhardtii* and its use as a recipient for mitochondrial transformation," Mol Gen Genet, 236(2-3):235-244, (1993).
Ratledge, "Regulation of lipid accumulation in oleaginous microorganisms," Biochem Soc Trans., 30(Pt 6):1047-1050, (2002).
Reddy et al., "Characterization of the Glycosylation Sites in Yeast External inver," The Journal of Biological Chemistry, 263(15):6978-6955, (1988).
Riesmeier et al., "Potato Sucrose Transporter Expression in Minor Veins Indicates a Role in Phloem Loading," The Plant Cell, 5:1591-1598, (1993).
Ritsema et al., "Engineering fructan metabolism in plants," J. Plant Physiol., 160:811-820, (2003).
Roig et al., "*Candida albicans* UBI3 and 11814 promoter regions confer differential regulation of invertase production to *Saccharomyces cerevisiae* cells in response to stress," Int Microbiol, 5:33-36, (2002).
Roitsch et al., "Expression of yeast invertase in oocytes from *Xenopus laevis*," Eur. J. Biochem, 181:733-739, (1989).
Roitsch et al., "Extracellular invertase: key metabolic enzyme and PR protein," Journal of Experimental Botany, Regulation of Carbon Metabolism Special Issue, 54(382):513-524, (2003).
Roitsch et al., "Function and regulation of plant invertases: sweet sensations," TRENDS in Plant Science , .9(12):606-613 , (2004).
Roitsch et al., "Induction of Apoplastic Invertase of *Chenopodium rubrum* by ID-Glucose and a Glucose Analog and Tissue-Specific Expression Suggest a Role in Sink-Source Regulation," Plant Physiol.,108:285-294, (1995).
Saha et al., "Transformation in *Aspergillus ochraceus*," Current Microbiology, 30(2):83-86, (1995).
Sakuradani, "Studies of Metabolic Engineering of Useful Lipid-producing Microorganisms,"NISR Research Grant, (2004).
Sanford, "The biolistic process," Trends in Biotechnology, 6(12):299-302, (1988).
Sansawa et al., "Production of Intracellular Phytochemicals in *Chlorella* under Heterotrophic Conditions," Journal of Bioscience and Bioengineering, 98(6):437-444, (2004).
Sauna et al., "Silent Polymorphisms Speak: How They Affect Pharmacogenomics and the Treatment of Cancer," Cancer Res, 67(20):9609-9612 , (2007).
Sawayama et al., "Possibility of renewable energy production and $CO_2$ mitigation by thermochemical liquefaction of microalgae," Biomass and Bioenergy, 17(1):33-39, (1999).
Schreier et al., "The use of nuclear-encoded sequences to direct the light-regulated synthesis and transport of a foreign protein into plant chloroplasts," EMBO J, 4(1):25-32, (1985).
Schultz et al., "A common core of secondary structure of the internal transcribed spacer 2 (ITS2) throughout the Eukaryota," RNA, 11(4):361-364, (2005).
Seffernick et al., "Melamine Deaminase and Atrazine Chlorohydrolase: 98 Percent Identical but Functionally Different," Journal of Bacteriology, 183(8):2405-2410, (2001).
Sen et al., "Developments in Directed Evolution for Improving Enzyme Functions," Appl Biochem Biotechnol, 143:212-223, (2007).
Sergeeva et al., "Vacuolar invertase regulates elongationof *Arabidopsis thaliana* roots as revealed by QTL and mutant analysis," PNAS, 103(8):2994-2999, (2006).
Shao et al., "Cloning and expression of metallothionein mutant α-KKS-α in Anabaena sp. PCC 7120," Marine Pollution Bulletin, 45(1012):163-167, (2002).
Sherson et al., "Roles of cell-wall invertases and monosaccharide transporters in the growth and development of *Arabidopsis*," Journal of Experimental Botany, 54(382):525-531, (2003).
Simpson et al., "Requirements for mini-exon inclusion in potato invertase mRNAs provides evidence for exon-scanning interactions in plants," RNA, 6:422-433, (2000).
Sinha et al., "Metabolizable and Non-Metabolizable Sugars Activate Different Signal Transduction Pathways in Tomato," Plant Physiology, 128:1480-1489, (2002).
Sitthiwong et al., "Changes in Carbohydrate Content and the Activities of Acid Invertase, Sucrose Synthase and Sucrose Phosphate Synthase in Vegetable Soybean During Fruit Development," Asian Journal of Plant Sciences, 4(6):684-690, (2005).
Smith et al., "Comparison of Biosequences," Adv Appl Math, 2(4):482-489, (1981).
Smith et al., "Production of hydroxy fatty acids in the seeds of *Arabidopsis thaliana*," Biochemical Society Transactions, 28(6):947-950, (2000).
Sonnewald et al., "Transgenic tobacco plants expressing yeast-derived invertase in either the cytosol, vacuole or apoplast: a powerful tool for studying sucrose metabolism and sink/source interactions," The Plant Journal , 1(1):95-106, (1991).
Sorger et al., "Triacylglycerol biosynthesis in yeast," AppL Microbiol Biotechnol, 61:289-299, (2003).
Spolaore et al., "Commercial Applications of Microalgae," J. Biosci. Bioeng. 101(2):87-96 (2006).
Stemmer et al., "Single-Step Assembly of a Gene and Entire Plasmid from Large Numbers of Oligodeoxyribonucleotides," Gene, 164:49-53, (1995).
Suda, et al., "Evidence for a novel *Chlorella* virus-encoded alginate lyase," FEMS Microbiology Letters, 180(1):45-53, (1999).
Sun et al., "Characterization of two chitinase genes and one chitosanase gene encoded by *Chlorella* virus PBCV-1," Virology, 263(2):376-387, (1999).

(56) References Cited

OTHER PUBLICATIONS

Tang et al., "Insertion mutagenesis of *Chlamydomonas reinhardtii* by electroporation and heterologous DNA," Biochem Mol Biol Int, 36(5):1025-1035, (1995).
Trimble et al., "Structure of oligosaccharides on *Saccharomyces* SUC2 Invertase Secreted by the Methylotrophic Yeast Pichia pastoris," The Journal of Biological Chemistry, 266(34):22807-22817, (1991).
Tymowska-Lalanne et al., "Expression of the *Arabidopsis thaliana* invertase gene family," Planta, 207: 259-265, (1998).
U.S. Appl. No. 12/131,766, Advisory Action mailed Oct. 13, 2011.
U.S. Appl. No. 12/131,773, Final Office Action mailed Oct. 15, 2013.
U.S. Appl. No. 12/131,773, Non-Final Office Action mailed Jun. 5, 2013.
U.S. Appl. No. 12/131,783, Final Office Action mailed Jan. 12, 2012.
U.S. Appl. No. 12/131,783, Non-Final Office Action mailed Jul. 18, 2013.
U.S. Appl. No. 12/131,793, Non-Final Office Action mailed Apr. 3, 2013.
U.S. Appl. No. 12/131,793, Non-Final Office Action mailed Jun. 21, 2012.
U.S. Appl. No. 12/131,793, Non-Final Office Action mailed Nov. 13, 2012.
U.S. Appl. No. 12/131,793, Notice of Allowance mailed Apr. 3, 2013.
U.S. Appl. No. 12/131,804, Non-Final Office Action mailed Oct. 26, 2012.
U.S. Appl. No. 12/131,804, Non-Final Office Action mailed Jun. 7, 2012.
U.S. Appl. No. 12/628,140, Final Office Action mailed Mar. 15, 2013.
U.S. Appl. No. 12/628,140, Final Office Action mailed Sep. 12, 2013.
U.S. Appl. No. 12/628,140, Non-Final Office Action mailed Oct. 30, 2012.
U.S. Appl. No. 12/628,144, Final Office Action mailed Dec. 5, 2011.
U.S. Appl. No. 12/628,147, Final Office Action mailed Jul. 12, 2012.
U.S. Appl. No. 12/628,147, Non-Final Office Action mailed Oct. 25, 2011.
U.S. Appl. No. 12/772,163, Non-Final Office Action mailed May 25, 2012.
U.S. Appl. No. 12/772,163, Non-Final Office Action mailed Dec. 12, 2012.
U.S. Appl. No. 12/772,163, Notice of Allowance mailed May 28, 2013.
U.S. Appl. No. 12/772,164, Final Office Action mailed May 24, 2012.
U.S. Appl. No. 12/772,164, Non-Final Office Action mailed Oct. 12, 2011.
U.S. Appl. No. 12/772,170, Final Office Action mailed Feb. 21, 2012.
U.S. Appl. No. 12/772,173, Final Office Action mailed May 7, 2012.
U.S. Appl. No. 12/772,173, Non-Final Office Action mailed Dec. 16, 2011.
U.S. Appl. No. 12/772,173, Notice of Allowance mailed Mar. 29, 2013.
U.S. Appl. No. 12/772,173, Requirement for Restriction/Election mailed Oct. 26, 2011.
U.S. Appl. No. 12/772,174, Non-Final Office Action mailed Nov. 29, 2011.
U.S. Appl. No. 12/960,388, Notice of Allowance mailed May 28, 2013.
U.S. Appl. No. 12/960,388, Requirement for Restriction/Election mailed Apr. 1, 2013.
U.S. Appl. No. 12/981,409, Non-Final Office Action mailed Jan. 6, 2012.
U.S. Appl. No. 12/981,409, Notice of Allowance mailed May 29, 2012.
U.S. Appl. No. 12/981,409, Requirement for Restriction/Election mailed Apr. 19, 2012.
U.S. Appl. No. 12/981,409, Requirement for Restriction/Election mailed Oct. 28, 2011.
U.S. Appl. No. 13/029,061, Requirement for Restriction/Election mailed Nov. 29, 2011.
U.S. Appl. No. 13/045,500, Non-Final Office Action mailed Mar. 9, 2012.
U.S. Appl. No. 13/045,500, Final Office Action mailed Sep. 26, 2012.
U.S. Appl. No. 13/073,757, Non-Final Office Action mailed Dec. 29, 2011.
U.S. Appl. No. 13/073,757, Notice of Allowance mailed Apr. 17, 2012.
U.S. Appl. No. 13/087,311, Non-Final Office Action mailed Apr. 23, 2013.
U.S. Appl. No. 13/118,365, Final Office Action mailed Jul. 22, 2013.
U.S. Appl. No. 13/118,365, Non-Final Office Action mailed Feb. 11, 2013.
U.S. Appl. No. 13/118,365, Requirement for Restriction/Election mailed Oct. 11, 2012.
U.S. Appl. No. 13/406,417, Non-Final Office Action mailed Nov. 5, 2012.
U.S. Appl. No. 13/406,417, Requirement for Restriction/Election mailed Apr. 30, 2012.
U.S. Appl. No. 13/464,948, Non-Final Office Action mailed Oct. 9, 2013.
U.S. Appl. No. 13/464,948, Requirement for Restriction/Election mailed Aug. 21, 2013.
U.S. Appl. No. 13/479,200, Non-Final Office Action mailed Apr. 10, 2013.
U.S. Appl. No. 13/479,200, Non-Final Office Action mailed Sep. 9, 2013.
U.S. Appl. No. 13/479,200, Requirement for Restriction/Election mailed Jan. 15, 2013.
U.S. Appl. No. 13/527,480, Non-Final Office Action mailed Jun. 26, 2013.
U.S. Appl. No. 13/527,480, Requirement for Restriction/Election mailed May 3, 2013.
U.S. Appl. No. 13/543,666, Non-Final Office Action mailed Sep. 5, 2013.
U.S. Appl. No. 13/543,666, Requirement for Restriction/Election mailed Jan. 3, 2013.
U.S. Appl. No. 13/547,457, Non-Final Office Action mailed Jul. 8, 2013.
U.S. Appl. No. 13/558,252, Notice of Allowance mailed Oct. 23, 2013.
U.S. Appl. No. 13/550,412, Non-Final Office Action mailed Oct. 29, 2012.
U.S. Appl. No. 13/550,412, Notice of Allowance mailed Feb. 21, 2013.
U.S. Appl. No. 13/558,252, Final Office Action mailed Jul. 9, 2013.
U.S. Appl. No. 13/558,252, Non-Final Office Action mailed Jan. 18, 2013.
U.S. Appl. No. 13/601,928, Non-Final Office Action mailed Jan. 31, 2013.
U.S. Appl. No. 13/601,928, Notice of Allowance mailed Feb. 26, 2013.
U.S. Appl. No. 13/621,722, Requirement for Restriction/Election mailed Jan. 31, 2013.
U.S. Appl. No. 13/621,722, Final Office Action mailed Oct. 25, 2013.
U.S. Appl. No. 13/621,722, Non-Final Office Action mailed May 9, 2013.
U.S. Appl. No. 13/628,039, Non-Final Office Action mailed Jun. 4, 2013.
U.S. Appl. No. 13/628,039, Requirement for Restriction/Election mailed Mar. 7, 2013.
U.S. Appl. No. 13/650,018, Requirement for Restriction/Election mailed Aug. 22, 2013.
U.S. Appl. No. 13/650,024, Non-Final Office Action mailed Jul. 2, 2013.
U.S. Appl. No. 13/889,214, Non-Final Office Action mailed Sep. 18, 2013.
U.S. Appl. No. 13/889,221, Non-Final Office Action mailed Sep. 6, 2013.
U.S. Appl. No. 12/628,147, Notice of Allowance and Examiner Initiated Interview Summary mailed Aug. 7, 2012.
U.S. Appl. No. 12/772,173, Notice of Allowance mailed Jul. 10, 2013.

(56) References Cited

OTHER PUBLICATIONS

Urano, et al., "Effect of Osmotic Stabilizers on Protoplast Generation of *Chlorella* ellipsoidea Yellow/White Color Mutants," Journal of Bioscience and Bioengineering, 90(5):567-569, (2000).
Van Etten et al., "Giant viruses infecting algae," Annu Rev Microbiol, 53:447-494, (1999).
Vazquez-Bermudez et al., "Carbon Supply and 2-Oxoglutarate Effects on Expression of Nitrate Reductase and Nitrogen-Regulated Genes in *Synechococcus* sp. strain PCC 7942,"FEMS Microbiology Letters, 221(2):155-159, (2003).
Vazquez-Bermudez et al., "Uptake of 2-Oxoglutarate in *Synechococcus* Strains Transformed with the *Escherichia coli* kgtP Gene," Journal of Bacteriology, 182(1):211-215, (2000).
Voegele et al., "Cloning and Characterization of a Novel Invertase from the Obligate Biotroph Uromyces fabae and Analysis of Expression Patterns of Host and Pathogen Invertases in the Course of Infection," Molecular Plant Microbe Interactions, 19:625-634, (2006).
Walker et al., "Characterization of the *Dunaliella tertiolecta* RbcS Genes and Their Promoter ctivity in *Chlamydomonas reinhardtii*," Plant Cell Rep, 23(10-11):727-735, (2005).
Weber et al., "Invertases and life beyond sucrose cleavage," Trends in Plant Science, 5(2):47-48, (2000).
Whisstock et al., "Prediction of protein function from protein sequence and structure," Quarterly Reviews of Biophysics, 36(3):307-340, (2003).
Whittle et al., "Engineering Δ9-16:0-Acyl Carrier Protein (ACP) Desaturase Specificity Based on Combinatorial Saturation Mutagenesis and Logical Redesign of the Castor Δ9-18:0-ACP Desaturase," The Journal of Biological Chemistry, 276(24):21500-21505, (2001).
Wishart et al., "A Single Mutation Converts a Novel Phosphotyrosine Binding Domain into a Dual-specificity Phosphatase," The Journal of Biological Chemistry, 270(45):26782-26785, (1995).
Witkowski et al., "Conversion of a β-Ketoacyl Synthase to a Malonyl Decarboxylase by Replacement of the Active-Site Cysteine with Glutamine," Biochemistry, 38:11643-11650, (1999).
Wong et al., "*Arabidopsis thaliana* small subunit leader and transit peptide enhance the expression of *Bacillus thuringiensis* proteins in transgenic plants," Plant Mol Biol, 20(1):81-93, (1992).
Wu et al., "A Comparative Study of Gases Generated from Simulant Thermal Degradation of Autotrophic and Heterotrophic *Chlorella*," Progress in Natural Science, 2(4):311-318, (1992).
Wu et al., "Comparative study on Liposoluble Compounds in Autotrophic and Heterotrophic *Chlorella* Protothecoides," Acta Botanica Sinica, 35(11):849-858, (1992).
Wu et al., "New Discoveries in Study on Hydrocarbons From Thermal Degradation of Heterotrophically Yellowing Algae," Science In China, 37(3):326-35, (1994).
Xiong et al., "High-density fermentation of microalga *Chlorella* protothecoides in bioreactor for microbio-diesel production," Appl. Microbiol. Biotechnol., 78:29-36, (2008).
Yamada et al., "Alternative expression of a chitosanase gene produces two different proteins in cells infected with *Chlorella* virus CVK2," Virology, 230(2):361-368, (1997).
Yamada et al., "*Chlorella* viruses," Adv Virus Res, 66:293-336, (2006).
Yanase et al., "Expression of the Extracellular Levansucrase and Invertase Genes from *Zymomonas mobilis* in *Escherichia coli* Cells," Biosci, Biotechnol. Biochem., 62(9):1802-1805, (1998).
Yuan et al., "Modification of the substrate specificity of an acyl-acyl carrier protein thioesterase by protein engineering," Proc. NatL Acad. Sci. USA, Biochemistry, 92:10639-10643, (1995).
Zárate et al., "Characterization of the heterologous invertase produced by *Schizosaccharomyces pombe* from the SUC2 gene of *Saccharomyces cerevisiae*," Journal of Applied Bacteriology, 80:45-52, (1996).
Zarowska et al., "Production of Citric Acid on Sugar Beet Molasses by Single and Mixed Cultures of *Yarrowia Lipolytica*," Electronic Journal of Polish Agricultural Universities, 4(2):1-7, (2001). [Retrieved from the Internet Oct. 3, 2011: <URL: http://www.ejpau.media.pl/volume4/issue2/biotechnology/art-01.html>].
Zhang et al., "Matic enzyme: the controlling activity for lipid production? Overexpression of malic enzyme in Mucor circinelloides leads to a 2.5-fold increase in lipid accumulation," Microbiology, 153(7):2013-2025, (2007).
Zhang et al., "Cloning and Characterization of an Invertase Gene From the Garden Pea (*Pisum sativum* L)," Jiesheng Zhang, M.S. Plant Biology Thesis, 82 pages, (2003).
Zhang et al., Geneseq Database, Accession No. AED66345, CN1618976, May 25, 2005.
Zhao et al., "Medium optimization for lipid production through co-fermentation of glucose and xylose by the oleaginous yeast Lipomyces starkeyi," Eur. J. Lipid Sci. Technol., 110:405-412, (2008).
Zurawski et al., "Nucleotide sequence of the gene for the Mr 32,000 thylakoid membrane protein from *Spinacia oleracea* and Nicotiana debneyi predicts a totally conserved primary translation product of Mr 38,950," Proc Natl Acad Sci, 79(24):7699-7703, (1982).
Andersen, "Biology and Systematics of Heterokont and Haptophyte Algae," American Journal of Botany, 91(10):1508-1522, (2004).
Bigogno et al., "Lipid and fatty acid composition of the green oleaginous alga *Parietochloris incisa*, the richest plant source of arachidonic acid," Pytochemistry, 60:497-503, (2002).
Chattopadhyay et al., "Effect of single amino acid mutations in the conserved GDNQ motif of L protein of Rinderpest virus on RNA synthesis in vitro and in vivo," Virus Research, 99:139-145, (2004).
Lu, "Biosynthesis and Gene Engineering of Plant Fatty Acids," Chinese Bulletin of Botany, 17(6):481-491, (2000). Abstract only.
Pratoomyot et al., "Fatty acids composition of 10 microalgal species," Songklanakarin J. Sci. Technol., 27(6):1179-1187, (2005).
Roessler et al., "Genetic Engineering Approaches for Enhanced Production of Biodiesel Fuel from Microalgae," Enzymatic Conversion of Biomass for Fuels Production, Chapter 13, American Chemical Society, doi: 10.1021/bk-1994-0566.ch013, pp. 255-270, (1994).
Roscoe et al., "Mutations in the fatty acid elongation 1 gene are associated with a loss of beta-ketoacyl-CoA synthase activity in low erucic acid rapeseed," FEBS Letters, 492:107-111, (2001).
Shi et al., "High-Yield Production of Lutein by the Green Microalga *Chlorella* protothecoides in Heterotrophic Fed-Batch Culture," Biotechnol. Prog., 18(4):723-727 (2002).
Skolnick et al., "From genes to protein structure and function: novel applications of computational approaches in the genomic era," TIBTECH, 18: 34-39, (2000).
Smallwood et al., "Different Substitutions at Conserved Amino Acids in Domains II and III in the Sendai L RNA Polymerase Protein Inactivate Viral RNA Synthesis," Virology, 304:135-145, (2002).
Tasaki et al., "Digestibility of Yellow *Chlorella* in Suckling Goat Kids,"The Japanese Journal of Zootechnical Science, 48(11):661-663, (1977).
Tomasinsig et al., "The Cathelicidins—Structure, Function and Evolution," Current Protein and Peptide Science, 6: 23-34, (2005).
U.S. Appl. No. 12/131,773, Advisory Action mailed Jan. 27, 2014.
U.S. Appl. No. 12/131,773, Notice of Allowance and Examiner Initiated Interview Summary mailed Apr. 1, 2014.
U.S. Appl. No. 12/131,783, Final Office Action mailed Dec. 13, 2013.
U.S. Appl. No. 12/131,783, Notice of Allowance and Examiner Initiated Interview Summary mailed Mar. 24, 2014.
U.S. Appl. No. 12/194,389, Notice of Allowance mailed Jan. 15, 2014.
U.S. Appl. No. 12/772,170, Non-Final Office Action mailed Dec. 17, 2013.
U.S. Appl. No. 13/087,311, Final Office Action mailed Dec. 16, 2013.
U.S. Appl. No. 13/288,815, Requirement for Restriction/Election mailed Jan. 30, 2014.
U.S. Appl. No. 13/464,948, Final Office Action mailed Feb. 13, 2014.
U.S. Appl. No. 13/479,194, Non-Final Office Action mailed Mar. 26, 2014.
U.S. Appl. No. 13/479,200, Notice of Allowance mailed Nov. 25, 2013.
U.S. Appl. No. 13/527,480, Final Office Action mailed Jan. 16, 2014.
U.S. Appl. No. 13/543,666, Notice of Allowance mailed Feb. 10, 2014.

(56) References Cited

OTHER PUBLICATIONS

U.S. Appl. No. 13/547,457, Non-Final Office Action mailed Mar. 20, 2014.
U.S. Appl. No. 13/601,937, Final Office Action mailed Nov. 22, 2013.
U.S. Appl. No. 13/621,722, Notice of Allowance and Examiner Initiated Interview Summary mailed Jan. 10, 2014.
U.S. Appl. No. 13/628,039, Notice of Allowance and Examiner-Initiated Interview Summary mailed Feb. 20, 2014.
U.S. Appl. No. 13/650,018, Non-Final Office Action mailed Dec. 23, 2013.
U.S. Appl. No. 13/650,024, Notice of Allowance mailed Oct. 17, 2013.
U.S. Appl. No. 13/852,116, Non-Final Office Action mailed Mar. 26, 2014.
U.S. Appl. No. 13/865,974, Requirement for Restriction/Election mailed Jan. 29, 2014.
U.S. Appl. No. 13/941,346, Non-Final Office Action mailed Jan. 21, 2014.
U.S. Appl. No. 13/941,353, Requirement for Restriction/Election mailed Jan. 16, 2014.
U.S. Appl. No. 13/941,357, Requirement for Restriction/Election mailed Jan. 7, 2014.

* cited by examiner

Figure 14
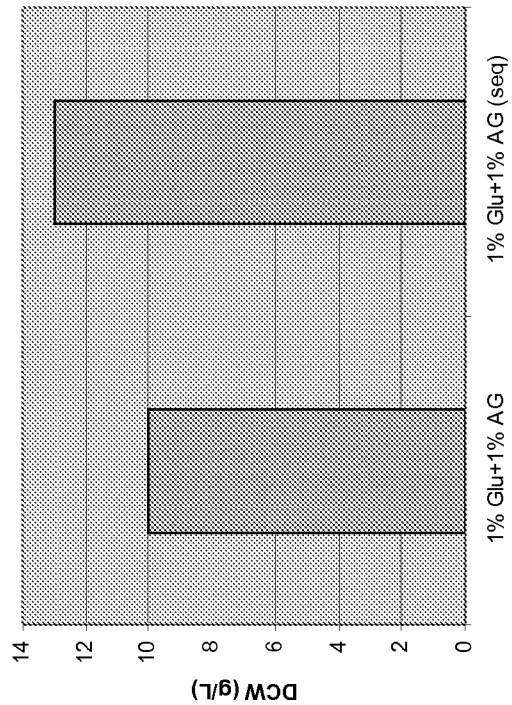
(b) Navicula pelliculosa
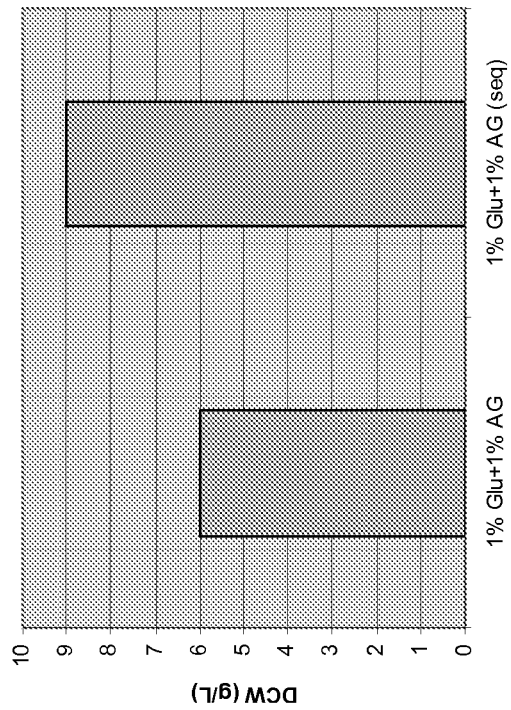
(a) Scenedesmus armatus

Figure 17

*Chlorella protothecoides* codon usage table

| | | | | | | | |
|---|---|---|---|---|---|---|---|
| Phe | UUU | 39 (0.82) | Ser | UCU | 50 (1.04) | | |
| | UUC | 56 (1.18) | | UCC | 60 (1.25) | | |
| Leu | UUA | 10 (0.20) | | UCA | 46 (0.96) | | |
| | UUG | 46 (0.91) | | UCG | 43 (0.89) | | |
| Tyr | UAU | 15 (0.59) | Cys | UGU | 46 (0.77) | | |
| | UAC | 36 (1.41) | | UGC | 73 (1.23) | | |
| ter | UAA | 9 (0.00) | ter | UGA | 43 (0.00) | | |
| ter | UAG | 15 (0.00) | Trp | UGG | 69 (1.00) | | |
| Leu | CUU | 49 (0.97) | Pro | CCU | 80 (0.98) | | |
| | CUC | 73 (1.45) | | CCC | 88 (1.08) | | |
| | CUA | 22 (0.44) | | CCA | 93 (1.14) | | |
| | CUG | 103 (2.04) | | CCG | 65 (0.80) | | |
| His | CAU | 50 (0.88) | Arg | CGU | 39 (0.76) | | |
| | CAC | 63 (1.12) | | CGC | 63 (1.23) | | |
| Gln | CAA | 59 (0.84) | | CGA | 46 (0.90) | | |
| | CAG | 82 (1.16) | | CGG | 47 (0.92) | | |
| Ile | AUU | 24 (0.69) | Thr | ACU | 32 (0.67) | | |
| | AUC | 61 (1.76) | | ACC | 76 (1.60) | | |
| | AUA | 19 (0.55) | | ACA | 41 (0.86) | | |
| Met | AUG | 42 (1.00) | | ACG | 41 (0.86) | | |
| Asn | AAU | 26 (0.75) | Ser | AGU | 23 (0.48) | | |
| | AAC | 43 (1.25) | | AGC | 67 (1.39) | | |
| Lys | AAA | 32 (0.54) | Arg | AGA | 51 (1.00) | | |
| | AAG | 86 (1.46) | | AGG | 61 (1.19) | | |
| Val | GUU | 36 (0.75) | Ala | GCU | 57 (0.79) | | |
| | GUC | 54 (1.13) | | GCC | 97 (1.34) | | |
| | GUA | 30 (0.63) | | GCA | 89 (1.23) | | |
| | GUG | 71 (1.49) | | GCG | 47 (0.65) | | |
| Asp | GAU | 60 (0.95) | Gly | GGU | 35 (0.60) | | |
| | GAC | 66 (1.05) | | GGC | 78 (1.33) | | |
| Glu | GAA | 41 (0.68) | | GGA | 54 (0.92) | | |
| | GAG | 80 (1.32) | | GGG | 67 (1.15) | | |

Figure 18

A. Dunaliella salina most preferred codons

TTC (Phe)
TAC (Tyr)
TGC (Cys)
TAA (Stop)
TGG (Trp)
CCC (Pro)
CAC (His)
CGC (Arg)
CTG (Leu)
CAG (Gln)
ATC (Ile)
ACC (Thr)
AAC (Asn)
AGC (Ser)
ATG (Met)
AAG (Lys)
GCC (Ala)
GAC (Asp)
GGC (Gly)
GTG (Val)
GAG (Glu)

B. Chlorella pyrenoidosa most preferred codons

TTC (Phe)
TAC (Tyr)
TGC (Cys)
TGA (Stop)
TGG (Trp)
CCC (Pro)
CAC (His)
CGC (Arg)
CTG (Leu)
CAG (Gln)
ATC (Ile)
ACC (Thr)
GAC (Asp)
TCC (Ser)
ATG (Met)
AAG (Lys)
GCC (Ala)
AAC (Asn)
GGC (Gly)
GTG (Val)
GAG (Glu)

Figure 21
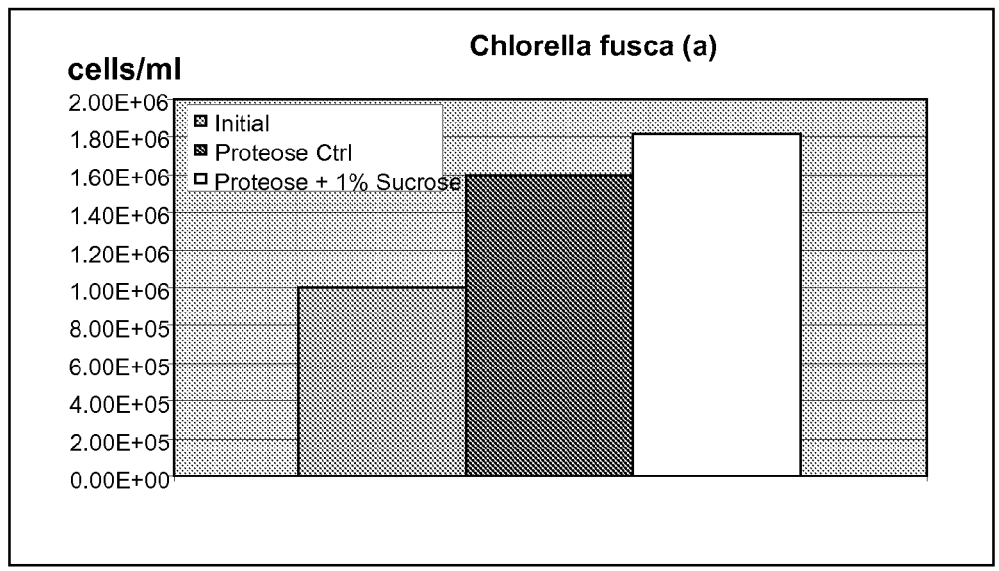
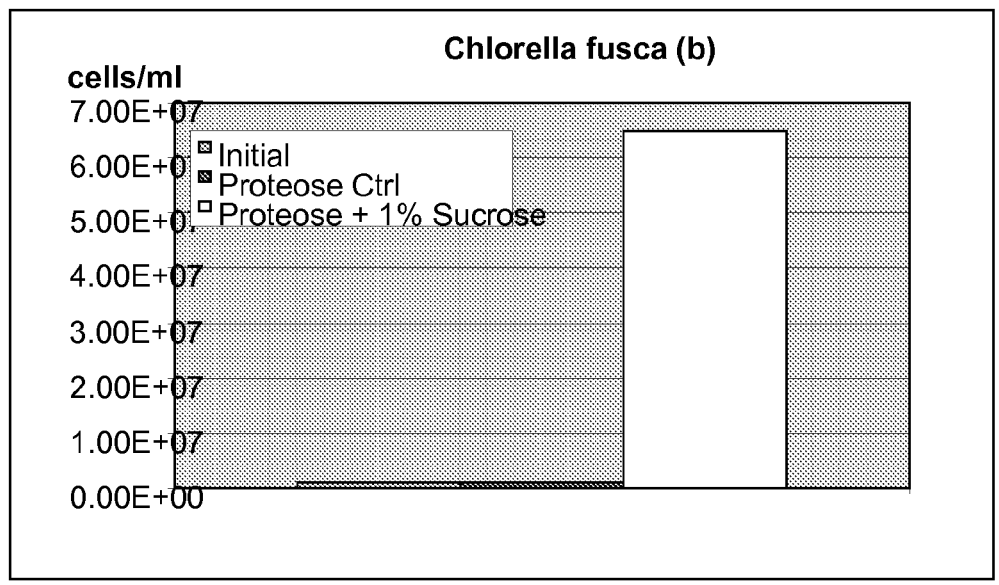

Figure 22
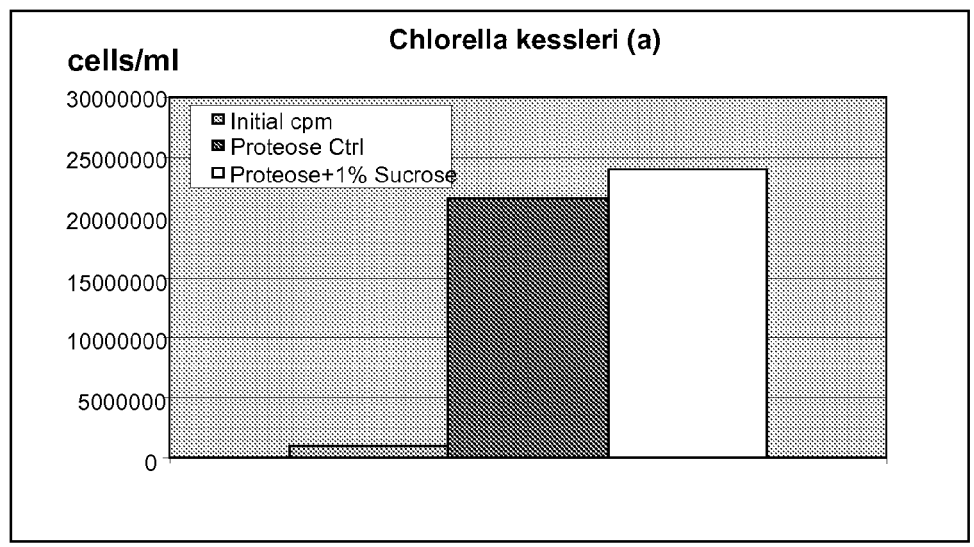
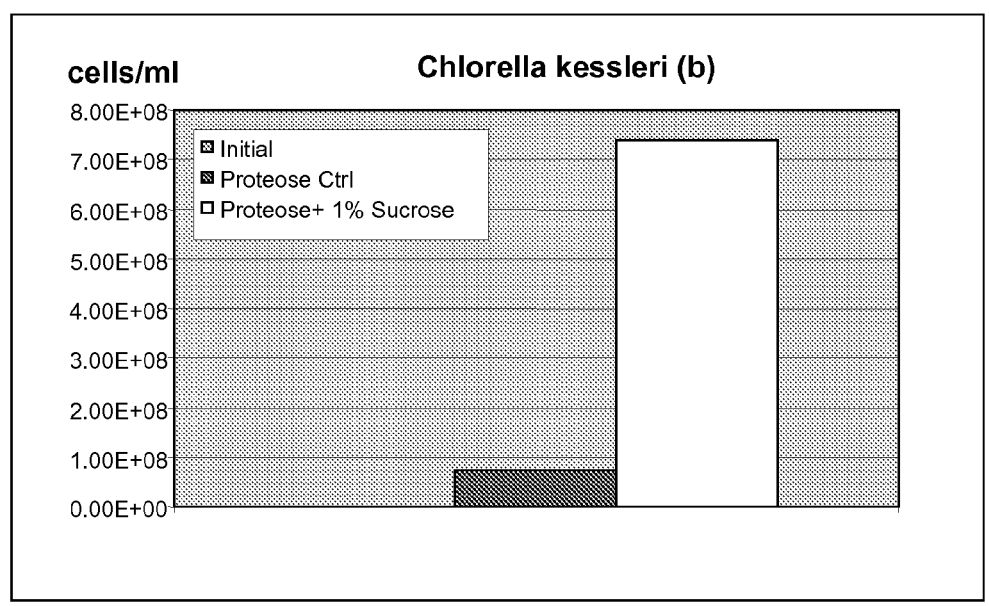

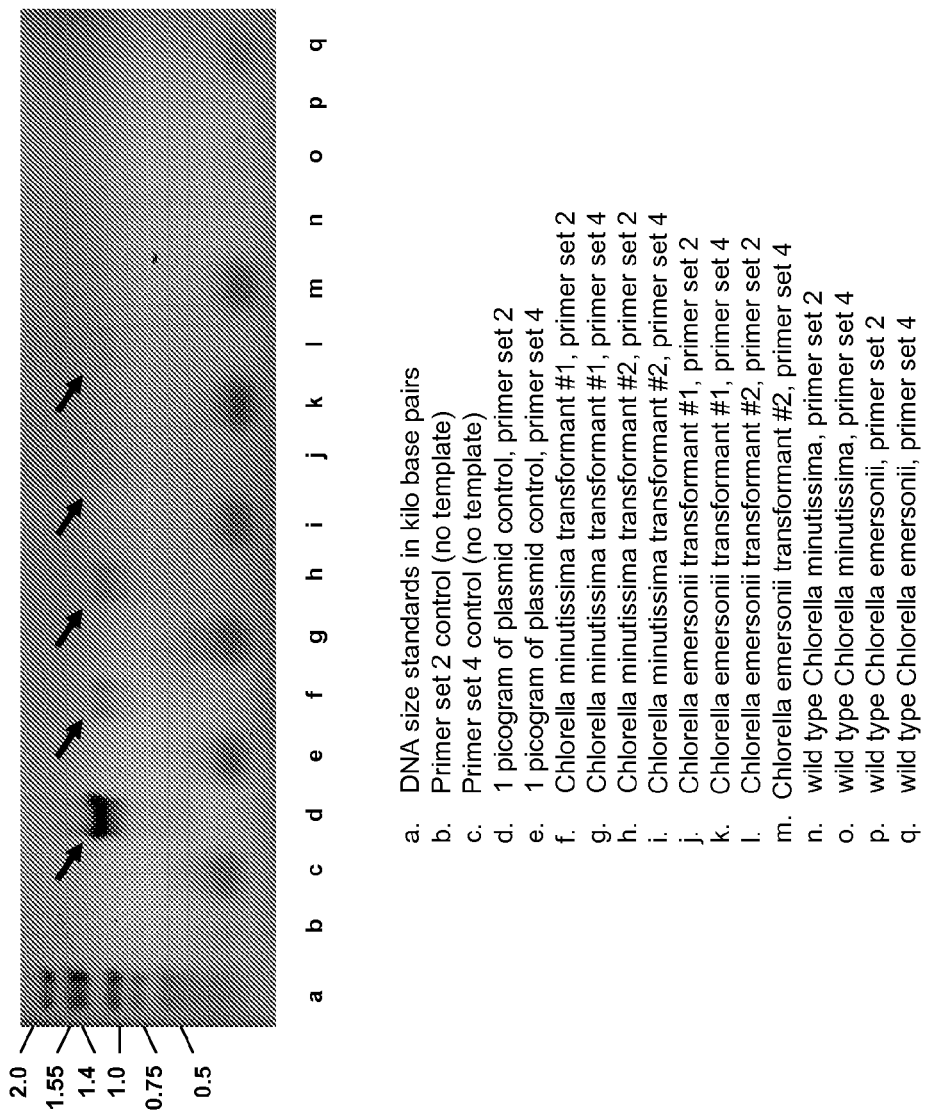

Figure 28 a. DNA size standards in kilo base pairs
b. Primer set 2 control (no template)
c. Primer set 4 control (no template)
d. 1 picogram of plasmid control, primer set 2
e. 1 picogram of plasmid control, primer set 4
f. Chlorella minutissima transformant #1, primer set 2
g. Chlorella minutissima transformant #1, primer set 4
h. Chlorella minutissima transformant #2, primer set 2
i. Chlorella minutissima transformant #2, primer set 4
j. Chlorella emersonii transformant #1, primer set 2
k. Chlorella emersonii transformant #1, primer set 4
l. Chlorella emersonii transformant #2, primer set 2
m. Chlorella emersonii transformant #2, primer set 4
n. wild type Chlorella minutissima, primer set 2
o. wild type Chlorella minutissima, primer set 4
p. wild type Chlorella emersonii, primer set 2
q. wild type Chlorella emersonii, primer set 4

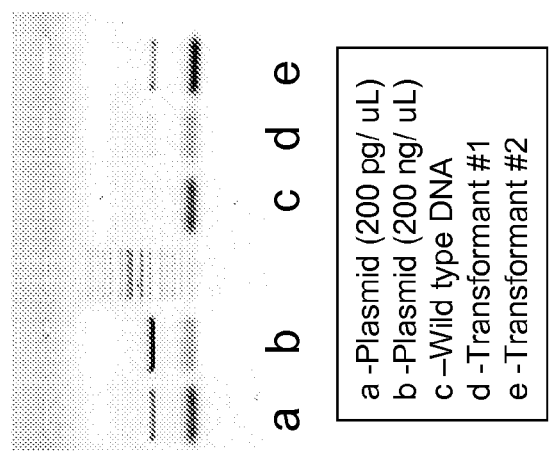

Figure 27 a - Plasmid (200 pg/ uL)
b - Plasmid (200 ng/ uL)
c - Wild type DNA
d - Transformant #1
e - Transformant #2

CHLORELLA SPECIES CONTAINING EXOGENOUS GENES

CROSS-REFERENCE TO RELATED APPLICATIONS

This application is a continuation of U.S. application Ser. No. 12/772,173, filed Apr. 30, 2010, which is a continuation of U.S. application Ser. No. 12/131,783, filed Jun. 2, 2008, which claims the benefit under 35 U.S.C. 119(e) of U.S. Provisional Application No. 60/941,581, filed Jun. 1, 2007, U.S. Provisional Application No. 60/959,174, filed Jul. 10, 2007, U.S. Provisional Application No. 60/968,291, filed Aug. 27, 2007, and U.S. Provisional Application No. 61/024,069, filed Jan. 28, 2008, the disclosures of which are incorporated herein by reference in their entirety for all purposes.

REFERENCE TO A SEQUENCE LISTING

This application includes a sequence listing, as filed in U.S. application Ser. No. 12/131,783, in a text file entitled SEQLIS026172002460US.txt, created on Aug. 13, 2008, and containing 27934 bytes. The material contained in the text file is hereby incorporated by reference.

FIELD OF THE INVENTION

This disclosure relates to the production of oils, fuels, and oleochemicals made from microorganisms. In particular, the disclosure relates to oil-bearing microorganisms, including microalgae, yeast and fungi, and to methods of cultivating such microorganisms for the production of useful compounds, including lipids, fatty acid esters, fatty acids, aldehydes, alcohols, and alkanes, for use in industry or as an energy or food source. The microorganisms of the invention can be selected or genetically engineered for use in the methods or other aspects of the invention described herein.

BACKGROUND OF THE INVENTION

Fossil fuel is a general term for buried combustible geologic deposits of organic materials, formed from decayed plants and animals that have been converted to crude oil, coal, natural gas, or heavy oils by exposure to heat and pressure in the earth's crust over hundreds of millions of years.

In common dialogue, fossil fuel, also known as mineral fuel, is used synonymously with other hydrocarbon-containing natural resources such as coal, oil and natural gas. The utilization of fossil fuels has enabled large-scale industrial development and largely supplanted water driven mills, as well as the combustion of wood or peat for heat. Fossil fuels are a finite, non-renewable resource.

When generating electricity, energy from the combustion of fossil fuels is often used to power a turbine. Older generations often used steam generated by the burning of the fuel to turn the turbine, but in newer power plants, the gases produced by burning of the fuel turn a gas turbine directly. With global modernization in the 20th and 21st centuries, the thirst for energy from fossil fuels, especially gasoline derived from oil, is one of the causes of major regional and global conflicts.

The burning of fossil fuels by humans is the largest source of emissions of carbon dioxide, which is one of the greenhouse gases that allows radiative forcing and contributes to global warming. In the United States, more than 90% of greenhouse gas emissions come from the combustion of fossil fuels. In addition, other air pollutants, such as nitrogen oxides, sulfur dioxide, volatile organic compounds (VOCs), and heavy metals are produced.

Human activity raises levels of greenhouse gases primarily by releasing carbon dioxide from fossil fuel combustion, but other gases, e.g., methane, are not negligible. The concentrations of several greenhouse gases have increased over time due to human activities, such as burning of fossil fuels and deforestation leading to higher carbon dioxide concentrations. According to the global warming hypothesis, greenhouse gases from industry and agriculture have played a major role in the recently observed global warming.

Increased demand for energy by the global economy has also placed increasing pressure on the cost of hydrocarbons. Aside from energy, many industries, including plastics and chemical manufacturers, rely heavily on the availability of hydrocarbons as a feedstock for their manufacturing processes. Cost-effective alternatives to current sources of supply could help mitigate the upward pressure on energy and these raw material costs.

SUMMARY OF THE INVENTION

In one aspect, the present invention is directed to a microbe, which in various embodiments can comprise a microalgae cell, an oleaginous yeast, or a fungus containing an exogenous gene that encodes a protein selected from the group consisting of a lipase, sucrose transporter, sucrose invertase, fructokinase, polysaccharide-degrading enzyme, a fatty acyl-ACP thioesterase, a fatty acyl-CoA/aldehyde reductase, a fatty acyl-CoA reductase, a fatty aldehyde reductase, a fatty aldehyde decarbonylase, and an acyl carrier protein (ACP). The microbe (e.g., microalgae cell) can, for example, be selected from Table 1. In particular embodiments, the cell is a species of the genus *Chlorella*, such as, e.g., *Chlorella fusca*, *Chlorella protothecoides*, *Chlorella pyrenoidosa*, *Chlorella kessleri*, *Chlorella vulgaris*, *Chlorella saccharophila*, *Chlorella sorokiniana* or *Chlorella ellipsoidea*. In other embodiments, the microbe is an oleaginous yeast selected from the group consisting of *Cryptococcus curvatus*, *Cryptococcus terricolus*, *Candida* sp., *Lipomyces starkeyi*, *Lipomyces lipofer*, *Endomycopsis vernalis*, *Rhodotorula glutinis*, *Rhodotorula gracilis*, and *Yarrowia lipolytica*. In still other embodiments, the microbe is a fungus selected from the group consisting of a species of the genus *Mortierella*, *Mortierrla vinacea*, *Mortierella alpine*, *Pythium debaryanum*, *Mucor circinelloides*, *Aspergillus ochraceus*, *Aspergillus terreus*, *Pennicillium iilacinum*, a species of the genus *Hensenulo*, a species of the genus *Chaetomium*, a species of the genus *Cladosporium*, a species of the genus *Malbranchea*, a species of the genus *Rhizopus*, and a species of the genus *Pythium*. In other embodiments, the invention includes expression of hydrocarbon modification enzymes in bacterial hosts such as *E. Coli* and *Bacilla* method of producing renewable diesel. In one embodiment, the method comprises (a) culturing a population of microorganisms in the presence of a fixed carbon source, wherein (i) the microorganisms accumulate at least 10% of their dry cell weight as lipid, and (ii) the fixed carbon source is selected from the group consisting of glycerol, depolymerized cellulosic material, sucrose, molasses, glucose, arabinose, galactose, xylose, fructose, arabinose, mannose, acetate, and any combination of the foregoing, (b) isolating lipid components from the cultured microorganisms, and (c) subjecting the isolated lipid components to one or more chemical reactions to generate straight chain alkanes, whereby renewable diesel is produced.

In another aspect, the present invention is directed to a composition of liquid hydrocarbons made according to the method described directly above, wherein the composition conforms to the specifications of ASTM D975.

In another aspect, the present invention is directed to a method of producing jet fuel. In one embodiment, the method comprises (a) culturing a population of microorganisms in the presence of a fixed carbon source, wherein (i) the microorganisms accumulate at least 10% of their dry cell weight as lipid, and (ii) the fixed carbon source is selected from the group consisting of glycerol, depolymerized cellulosic material, sucrose, glucose, arabinose, galactose, xylose, fructose, arabinose, mannose, acetate, and any combination of the foregoing, (b) isolating lipid components from the cultured microorganisms, (c) subjecting the isolated lipid components to one or more chemical reactions to generate straight chain alkanes, (d) cracking the straight chain alkanes, whereby jet fuel is produced.

In another aspect, the present invention is directed to a composition of liquid hydrocarbons produced according to the method described directly above, wherein the composition conforms to the specifications of ASTM D1655.

In another aspect, the present invention is directed to a microalgae or yeast cell that has been genetically engineered and/or selected to express a lipid pathway enzyme at an altered level compared to a wild-type cell of the same species. In some cases, the cell produces more lipid compared to the wild-type cell when both cells are grown under the same conditions. In some cases, the cell has been genetically engineered and/or selected to express a lipid pathway enzyme at a higher level than the wild-type cell. In some cases, the lipid pathway enzyme is selected from the group consisting of pyruvate dehydrogenase, acetyl-CoA carboxylase, acyl carrier protein, and glycerol-3 phosphate acyltransferase. In some cases, the cell has been genetically engineered and/or selected to express a lipid pathway enzyme at a lower level than the wild-type cell. In at least one embodiment in which the cell expresses the lipid pathway enzyme at a lower level, the lipid pathway enzyme comprises citrate synthase.

In some embodiments, the microalgae or yeast cell described above has been genetically engineered and/or selected to express a global regulator of fatty acid synthesis at an altered level compared to the wild-type cell, whereby the expression levels of a plurality of fatty acid synthetic genes are altered compared to the wild-type cell. In some cases, the lipid pathway enzyme comprises an enzyme that modifies a fatty acid. In some cases, the lipid pathway enzyme is selected from a stearoyl-ACP desaturase and a glycerolipid desaturase.

In another aspect, the present invention is directed to an oil-producing microbe containing one or more exogenous genes, wherein the exogenous genes encode protein(s) selected from the group consisting of a fatty acyl-ACP thioesterase, a fatty acyl-CoA reductase, a fatty aldehyde reductase, a fatty acyl-CoA/aldehyde reductase, a fatty aldehyde decarbonylase, and an acyl carrier protein. In some cases, the microbe is *Chlorella protothecoides, Chlorella minutissima, Chlorella emersonii, Chlorella sorokiniana, Chlorella ellipsoidea*, or *Chlorella* sp. In other cases, the microbe is another species as described herein. In one embodiment, the exogenous gene is in operable linkage with a promoter, which is inducible or repressible in response to a stimulus. In some cases, the stimulus is selected from the group consisting of an exogenously provided small molecule, heat, cold, and light. In some cases, the exogenous gene is expressed in a cellular compartment. In some embodiments, the cellular compartment is selected from the group consisting of a chloroplast and a mitochondrion.

In one embodiment, the exogenous gene encodes a fatty acid acyl-ACP thioesterase. In some cases, the thioesterase encoded by the exogenous gene catalyzes the cleavage of an 8 to 18-carbon fatty acid from an acyl carrier protein (ACP). In some cases, the thioesterase encoded by the exogenous gene catalyzes the cleavage of a 10 to 14-carbon fatty acid from an ACP. In one embodiment, the thioesterase encoded by the exogenous gene catalyzes the cleavage of a 12-carbon fatty acid from an ACP.

In one embodiment, the exogenous gene encodes a fatty acyl-CoA/aldehyde reductase. In some cases, the reductase encoded by the exogenous gene catalyzes the reduction of a 20 to 30-carbon fatty acyl-CoA to a corresponding primary alcohol. In some cases, the reductase encoded by the exogenous gene catalyzes the reduction of an 8 to 18-carbon fatty acyl-CoA to a corresponding primary alcohol. In some cases, the reductase encoded by the exogenous gene catalyzes the reduction of a 10 to 14-carbon fatty acyl-CoA to a corresponding primary alcohol. In one embodiment, the reductase encoded by the exogenous gene catalyzes the reduction of a 12-carbon fatty acyl-CoA to dodecanol.

In one embodiment, the exogenous gene encodes a fatty acyl-CoA reductase. In some cases, the reductase encoded by the exogenous gene catalyzes the reduction of an 8 to 18-carbon fatty acyl-CoA to a corresponding aldehyde. In one embodiment, the reductase encoded by the exogenous gene catalyzes the reduction of a 12-carbon fatty acyl-CoA to dodecanal.

In at least one embodiment, the microbe of the invention further contains one or more exogenous sucrose utilization genes.

In another aspect, the present invention is directed to a microbe containing two exogenous genes, wherein a first exogenous gene encodes a fatty acyl-ACP thioesterase and a second exogenous gene encodes a protein selected from the group consisting of a fatty acyl-CoA reductase, a fatty acyl-CoA/aldehyde reductase, and an acyl carrier protein. In some cases, the microbe is *Chlorella minutissima, Chlorella emersonii, Chlorella sorokiniana, Chlorella ellipsoidea, Chlorella* sp., or *Chlorella protothecoides*. In other cases, the microbe is another species as described herein. In some cases, the two exogenous genes are each in operable linkage with a promoter, which is inducible in response to a stimulus. In some cases, each promoter is inducible in response to an identical stimulus.

In one embodiment, the thioesterase encoded by the first exogenous gene catalyzes the cleavage of an 8 to 18-carbon fatty acid from an ACP. In some embodiments, the second exogenous gene encodes a fatty acyl-CoA/aldehyde reductase which catalyzes the reduction of an 8 to 18-carbon fatty acyl-CoA to a corresponding primary alcohol. In some cases, the thioesterase encoded by the first exogenous gene catalyzes the cleavage of a 10 to 14-carbon fatty acid from an ACP, and the reductase encoded by the second exogenous gene catalyzes the reduction of a 10 to 14-carbon fatty acyl-CoA to the corresponding primary alcohol, wherein the thioesterase and the reductase act on the same carbon chain length. In one embodiment, the thioesterase encoded by the first exogenous gene catalyzes the cleavage of a 12-carbon fatty acid from an ACP, and the reductase encoded by the second exogenous gene catalyzes the reduction of a 12-carbon fatty acyl-CoA to dodecanol. In some embodiments, the second exogenous gene encodes a fatty acyl-CoA reductase which catalyzes the reduction of an 8 to 18-carbon fatty acyl-CoA to a corresponding aldehyde.

In some embodiments, the second exogenous gene encodes a fatty acyl-CoA reductase, and the microbe further contains a third exogenous gene encoding a fatty aldehyde decarbonylase. In some cases, the thioesterase encoded by the first exogenous gene catalyzes the cleavage of an 8 to 18-carbon fatty acid from an ACP, the reductase encoded by the second exogenous gene catalyzes the reduction of an 8 to 18-carbon fatty acyl-CoA to a corresponding fatty aldehyde, and the decarbonylase encoded by the third exogenous gene catalyzes the conversion of an 8 to 18-carbon fatty aldehyde to a corresponding alkane, wherein the thioesterase, the reductase, and the decarbonylase act on the same carbon chain length.

In some embodiments, the second exogenous gene encodes an acyl carrier protein that is naturally co-expressed with the fatty acyl-ACP thioesterase.

In some embodiments, the second exogenous gene encodes an acyl carrier protein, and the microbe further contains a third exogenous gene encoding a protein selected from the group consisting of a fatty acyl-CoA reductase and a fatty acyl-CoA/aldehyde reductase. In some cases, the third exogenous gene encodes a fatty acyl-CoA reductase, and the microbe further contains a fourth exogenous gene encoding a fatty aldehyde decarbonylase.

In another aspect, the present invention is directed to a method of producing a molecule in a microbe population. In one embodiment, the method comprises culturing a population of microbes in a culture medium, wherein the microbes contain (i) a first exogenous gene encoding a fatty acyl-ACP thioesterase, and (ii) a second exogenous gene encoding a fatty acyl-CoA/aldehyde reductase, and the microbes synthesize a fatty acid linked to an acyl carrier protein (ACP), the fatty acyl-ACP thioesterase catalyzes the cleavage of the fatty acid from the ACP to yield, through further processing, a fatty acyl-CoA, and the fatty acyl-CoA/aldehyde reductase catalyzes the reduction of the acyl-CoA to an alcohol.

In one embodiment of the method of producing a molecule in a microbe population, the microbe is *Chlorella minutissima, Chlorella emersonii, Chlorella sorokiniana, Chlorella ellipsoidea, Chlorella* sp. or *Chlorella protothecoides*. In other cases, the microbe is another species of microorganism as described herein. In some cases, the culture medium contains glycerol. In one embodiment, the glycerol is a byproduct of a transesterification process. In some cases, the culture medium contains glycerol and at least one other fixed carbon source. In one embodiment, the at least one other fixed carbon source is sucrose. In some cases, all of the glycerol and all of the at least one other fixed carbon source are provided to the microbes at the beginning of fermentation. In some cases, the glycerol and the at least one other fixed carbon source are fed to the microbes at a predetermined rate over the course of fermentation. In some culture methods of the invention, glycerol is provided to the microbes in the absence of the at least one other fixed carbon source for a first period of time, the at least one other fixed carbon source is provided at the end of the first period of time, and the microbes are cultured for a second period of time in the presence of the at least one other fixed carbon source.

In some embodiments, the exogenous genes are in operable linkage with a promoter that is inducible in response to a first stimulus. In some cases, the method further comprises providing the first stimulus, and incubating the population of microbes for a first period of time in the presence of the first stimulus to produce an alcohol. In some cases, the method further comprises extracting the alcohol from aqueous biomass comprising the culture medium and the microbes.

In some embodiments, the thioesterase encoded by the first exogenous gene catalyzes the cleavage of an 8 to 18-carbon fatty acid from the ACP, and the reductase encoded by the second exogenous gene catalyzes the reduction of an 8 to 18-carbon fatty acyl-CoA to a corresponding primary alcohol, wherein the thioesterase and the reductase act on the same carbon chain length. In some cases, the thioesterase encoded by the first exogenous gene catalyzes the cleavage of an 10 to 14-carbon fatty acid from the ACP, and the reductase encoded by the second exogenous gene catalyzes the reduction of an 10 to 14-carbon fatty acyl-CoA to a corresponding primary alcohol, wherein the thioesterase and the reductase act on the same carbon chain length. In one embodiment, the thioesterase encoded by the first exogenous gene catalyzes the cleavage of a 12-carbon fatty acid from the ACP, and the reductase encoded by the second exogenous gene catalyzes the reduction of a 12-carbon fatty acyl-CoA to dodecanol. In some cases, the microbes further contain a third exogenous gene encoding an acyl carrier protein. In some embodiments, the third exogenous gene encodes an acyl carrier protein that is naturally co-expressed with the fatty acyl-ACP thioesterase.

In another aspect, the present invention is directed to a method of producing a lipid molecule in a microbe population. In one embodiment, the method comprises culturing a population of microbes in a culture medium, wherein the microbes contain (i) a first exogenous gene encoding a fatty acyl-ACP thioesterase, and (ii) a second exogenous gene encoding a fatty acyl-CoA reductase, and wherein the microbes synthesize a fatty acid linked to an acyl carrier protein (ACP), the fatty acyl-ACP thioesterase catalyzes the cleavage of the fatty acid from the ACP to yield, through further processing, a fatty acyl-CoA, and the fatty acyl-CoA reductase catalyzes the reduction of the acyl-CoA to an aldehyde. In some cases, the microbe is *Chlorella minutissima, Chlorella emersonii, Chlorella sorokiniana, Chlorella ellipsoidea, Chlorella* sp., or *Chlorella protothecoides*. In other cases, the microbe is another species of microorganism as described herein.

In some embodiments, the exogenous genes are in operable linkage with a promoter that is inducible in response to a first stimulus, and the method further comprises providing the first stimulus, and incubating the population of microbes for a first period of time in the presence of the first stimulus to produce an aldehyde. In one embodiment, the method further comprises extracting the aldehyde from aqueous biomass comprising the culture medium and the population of microbes.

In some embodiments, the thioesterase encoded by the first exogenous gene catalyzes the cleavage of an 8 to 18-carbon fatty acid from the ACP, and the reductase encoded by the second exogenous gene catalyzes the reduction of an 8 to 18-carbon fatty acyl-CoA to a corresponding aldehyde, wherein the thioesterase and the reductase act on the same carbon chain length. In some cases, the microbes further contain a third exogenous gene encoding a fatty aldehyde decarbonylase that catalyzes the conversion of the aldehyde to an alkane.

In some cases, the exogenous genes are in operable linkage with a promoter that is inducible in response to a first stimulus, and the method further comprises providing the first stimulus, and incubating the population of microbes for a first period of time in the presence of the first stimulus to produce an alkane. In some cases, the method further comprises extracting the alkane from aqueous biomass comprising culture medium and the microbe population.

In some cases, the thioesterase encoded by the first exogenous gene catalyzes the cleavage of an 8 to 18-carbon fatty acid from the ACP, the reductase encoded by the second exogenous gene catalyzes the reduction of an 8 to 18-carbon fatty acyl-CoA to a corresponding aldehyde, and the decarbonylase encoded by the third exogenous gene catalyzes the conversion of an 8 to 18-carbon aldehyde to a corresponding alkane, wherein the thioesterase, the reductase, and the decarbonylase act on the same carbon chain length. In some embodiments, the microbes further contain a third exogenous gene encoding an acyl carrier protein. In some cases, the third exogenous gene encodes an acyl carrier protein that is naturally co-expressed with the fatty acyl-ACP thioesterase. In some cases, the microbes further contain a fourth exogenous gene encoding a fatty aldehyde decarbonylase that catalyzes the conversion of the aldehyde to an alkane.

In some methods, the culture medium contains glycerol. In one embodiment, the glycerol is a byproduct of a transesterification process. In some cases, the culture medium contains glycerol and at least one other fixed carbon source. In one embodiment, the at least one other fixed carbon source is sucrose. In some cases, all of the glycerol and all of the at least one other fixed carbon source are provided to the microbes at the beginning of fermentation. In some cases, the glycerol and the at least one other fixed carbon source are fed to the microbes at a predetermined rate over the course of fermentation. In one embodiment, glycerol is provided to the microbes in the absence of the at least one other fixed carbon source for a first period of time, the at least one other fixed carbon source is provided at the end of the first period of time, and the microbes are cultured for a second period of time in the presence of the at least one other fixed carbon source.

In another aspect, the present invention is directed to a method of producing a fatty acid molecule having a specified carbon chain length in a microbe population. In one embodiment, the method comprises culturing a population of lipid-producing microbes in a culture medium, wherein the microbes contain an exogenous gene encoding a fatty acyl-ACP thioesterase having an activity specific to a carbon chain length, and wherein the microbes synthesize a fatty acid linked to an acyl carrier protein (ACP) and the thioesterase catalyzes the cleavage of the fatty acid from the ACP when the fatty acid has been synthesized to the specific carbon chain length. In some cases, the microbe is *Chlorella minutissima, Chlorella emersonii, Chlorella sorokiniana, Chlorella ellipsoidea, Chlorella* sp., or *Chlorella protothecoides*. In other cases, the microbe is another species of microorganism as described herein.

In some embodiments, the exogenous gene is in operable linkage with a promoter that is inducible in response to a first stimulus, and the method further comprises providing the first stimulus, and incubating the population of microbes for a period of time in the presence of the first stimulus. In some cases, the method further comprises extracting the fatty acid from aqueous biomass comprising culture medium and the microbe population.

In some cases, the microbes further contain a second exogenous gene encoding an acyl carrier protein. In some embodiments, the second exogenous gene encodes an acyl carrier protein that is naturally co-expressed with the fatty acyl-ACP thioesterase. In one embodiment, the acyl-ACP thioesterase catalyzes the cleavage of an 8 to 18-carbon fatty acid from the ACP.

In some cases, the culture medium contains glycerol. In one embodiment, the glycerol is a byproduct of a transesterification process. In some embodiments, the culture medium contains glycerol and at least one other fixed carbon source. In one embodiment, the at least one other carbon source is sucrose. In some cases, all of the glycerol and all of the at least one other fixed carbon source are provided to the microbes at the beginning of fermentation. In some cases, the glycerol and the at least one other fixed carbon source are fed to the microbes at a predetermined rate over the course of fermentation. In one embodiment, glycerol is provided to the microbes in the absence of the at least one other fixed carbon source for a first period of time, the at least one other fixed carbon source is provided at the end of the first period of time, and the microbes are cultured for a second period of time in the presence of the at least one other fixed carbon source.

In another aspect, the present invention is directed to a microalgae cell containing an exogenous gene, wherein the exogenous gene encodes a protein selected from the group consisting of a lipase, a sucrose transporter, a sucrose invertase, a fructokinase, or a polysaccharide-degrading enzyme. In some cases, the cell is *Chlorella minutissima, Chlorella emersonii, Chlorella sorokiniana, Chlorella ellipsoidea, Chlorella* sp., or *Chlorella protothecoides*. In other cases, the cell is another species of microalgae as described herein.

In some cases, the exogenous gene is in operable linkage with a promoter. In some cases, the promoter is inducible or repressible in response to a stimulus. In various embodiments, the stimulus is selected from the group consisting of an exogenously provided small molecule, heat, cold, and light. In some cases, the exogenous gene is expressed in a cellular compartment. In some embodiments, the cellular compartment is selected from the group consisting of a chloroplast and a mitochondrion.

In some cases, the gene encodes a lipase that has at least 70% amino acid identity with a lipase selected from Table 9. In one embodiment, the lipase is novozym-435. In one embodiment, the polysaccharide-degrading enzyme is endogenous to a *Chlorella* virus.

In another aspect, the present invention is directed to a microalgae cell containing two exogenous genes, wherein a first exogenous gene encodes a lipase and a second exogenous gene encodes a polysaccharide-degrading enzyme. In some cases, the exogenous genes are each in operable linkage with a promoter. In some cases, the exogenous genes are each in operable linkage with promoters that are inducible in response to a stimulus. In some cases, the exogenous genes are each in operable linkage with promoters that are inducible in response to the same stimulus. In some cases, the exogenous genes are each in operable linkage with a promoter that is inducible in response to at least one stimulus that does not induce the other promoter.

In another aspect, the present invention is directed to a method of manufacturing a lipid molecule in a microbe. In one embodiment, the method comprises (a) culturing the microbe for a first period of time sufficient to increase the cell density, wherein the microbe contains (i) an exogenous gene encoding a lipase, and/or (ii) an exogenous gene encoding a polysaccharide-degrading enzyme, wherein the exogenous gene(s) are in operable linkage with a promoter that is inducible in response to a stimulus, (b) providing the stimulus, and (c) incubating the microbe for a second period of time in the presence of the stimulus.

In another aspect, the present invention is directed to a method of manufacturing a lipid molecule in a microbe. In one embodiment, the method comprises (a) culturing a lipid-producing microbe for a first period of time sufficient to increase the cell density, (b) providing a virus capable of infecting and lysing the microbe when in direct contact with the microbe, and (c) incubating the microbe for a second period of time to produce lysed aqueous biomass. In one embodiment, the method further comprises extracting lipid molecules from the lysed aqueous biomass.

In another aspect, the present invention is directed to a microalgae cell containing an exogenous gene, wherein the exogenous gene encodes a cofactor for a lipid pathway enzyme or encodes a protein that participates in the synthesis of the cofactor.

In another aspect, the present invention is directed to a method of culturing a lipid-producing microbe. In one embodiment, the method comprises culturing the microbe in the presence of a sufficient amount of one or more cofactor(s) for a lipid pathway enzyme to increase microbial lipid yield over microbial lipid yield in the absence of said one or more cofactors. In some cases, the one or more cofactors is a vitamin required by one or more lipid pathway enzymes. In one embodiment, the one or more cofactors is biotin. In some cases, the one or more cofactors is/are provided by including in the culture a microbe that has been genetically engineered to produce the one or more cofactors.

In another aspect, the present invention is directed to a method of fermenting a microorganism, which comprises providing a mixture comprising glucose and xylose as an energy source to the microorganism. In one embodiment, the mixture further comprises lignin. In one embodiment, the mixture further comprises at least one species of furfural. In some cases, the mixture is depolymerized cellulosic material. In some cases, the mixture further comprises as least one sucrose utilization enzyme. In one embodiment, the mixture comprises a sucrose invertase.

In some cases, the microorganism is selected from the group consisting of *Bracteococcus minor, Chlorella ellipsoidea, Chlorella kessleri, Chlorella luteoviridis, Bracteococcus medionucleatus, Chlorella minutissima, Chlorella ovalis, Chlorella protothecoides, Chlorella saccharophila, Chlorella sorokiniana, Chlorella sp., Chlorella vulgaris, Parachlorella kessleri, Prototheca moriformis*, and *Pseudochlorella aquatica*. In other cases, the microorganism is another species of microorganism as described herein. In some cases, the microorganism has been genetically engineered to express an exogenous gene encoding at least one lipid modification enzyme, hydrocarbon modification enzyme, or sucrose utilization enzyme.

In another aspect, the present invention is directed to a method of culturing a microalgae, which comprises culturing the microalgae in a culture medium including a feedstock comprising at least one carbon substrate selected from the group consisting of a cellulosic material, a 5-carbon sugar, a 6-carbon sugar, and acetate. In some cases, the carbon substrate is glucose and the microalgae is of a genus selected from the group consisting of *Chlorella, Parachlorella, Pseudochlorella, Bracteococcus, Prototheca* and *Scenedesmus*. In some cases, the carbon substrate is xylose and the microalgae is of a genus selected from the group consisting of *Chlorella, Pseudochlorella*, and *Prototheca*. In some cases, the carbon substrate is sucrose and the microalgae is of a genus selected from the group consisting of *Chlorella*, and *Bracteococcus*. In some cases, the carbon substrate is fructose and the microalgae is of a genus selected from the group consisting of *Chlorella, Parachlorella, Prototheca*, and *Scenedesmus*. In some cases, the carbon substrate is arabinose and the microalgae is *Chlorella* sp. In some cases, the carbon substrate is mannose and the microalgae is of a genus selected from the group consisting of *Chlorella, Parachlorella, Bracteococcus, Prototheca*, and *Scenedesmus*. In some cases, the carbon substrate is galactose and the microalgae is of a genus selected from the group consisting of *Bracteococcus, Parachlorella, Chlorella, Pseudochlorella, Bracteococcus*, and *Prototheca*. In some cases, the carbon substrate is acetate and the microalgae is of a genus selected from the group consisting of *Chlorella, Parachlorella*, and *Prototheca*.

In one embodiment, the culture medium further includes at least one sucrose utilization enzyme. In some cases, the microalgae has been genetically engineered to express an exogenous gene encoding at least one lipid modification enzyme, hydrocarbon modification enzyme, or sucrose utilization enzyme. In some cases, the culture medium includes a sucrose invertase.

In another aspect, the present invention is directed to a method of culturing microalgae comprising placing a plurality of microalgae cells in the presence of depolymerized cellulosic material. In some cases, the microalgae are cultured in the presence of an additional fixed carbon source selected from the group consisting of glycerol, sucrose, glucose, arabinose, galactose, xylose, fructose, arabinose, mannose, acetate, and any combination of the foregoing. In one embodiment, the microalgae are cultured in the presence of at least one sucrose utilization enzyme.

In some cases, the microalgae is selected from a species of the genus *Bracteococcus*, a species of the genus *Chlorella*, a species of the genus *Parachlorella*, a species of the genus *Prototheca*, or a species of the genus *Pseudochlorella*. In some cases, the microalgae is selected from *Bracteococcus minor, Chlorella ellipsoidea, Chlorella kessleri, Chlorella luteoviridis, Bracteococcus medionucleatus, Chlorella minutissima, Chlorella ovalis, Chlorella protothecoides, Chlorella saccharophila, Chlorella sorokiniana, Chlorella sp., Chlorella vulgaris, Parachlorella kessleri, Prototheca moriformis*, and *Pseudochlorella aquatica*. In other cases, the microalgae is another species of microalgae as described herein.

In some embodiments, the microalgae has been genetically engineered to express an exogenous gene encoding at least one lipid modification enzyme, hydrocarbon modification enzyme, or sucrose utilization enzyme. In one embodiment, the at least one sucrose utilization enzyme is a sucrose invertase. In some cases, the at least one lipid modification enzyme is selected from a stearoyl-ACP desaturase, a glycerolipid desaturase, a pyruvate dehydrogenase, an acetyl-CoA carboxylase, and a glycerol-3 phosphate acyltransferase. In some cases, the at least one hydrocarbon modification enzyme is selected from a fatty acyl-ACP thioesterase, a fatty acyl-CoA reductase, a fatty aldehyde reductase, a fatty acyl-CoA/aldehyde reductase, a fatty aldehyde decarbonylase, and an acyl carrier protein.

In another aspect, the present invention is directed to a method of culturing a lipid-producing microbe, the method comprising culturing the microbe in the presence of acetic acid and the absence of a fixed nitrogen source. In some cases, the microbe is cultured in the presence of a sufficient amount of acetic acid to increase microbial lipid yield over microbial lipid yield in the absence of acetic acid, wherein culture conditions are otherwise the same between the two cultures.

In another aspect, the present invention is directed to a microbial culture containing a population of microorganisms and a culture medium comprising glucose, xylose, and a molecule selected from the group consisting of lignin and a species of furfural. In some cases, the microorganisms are selected from *Bracteococcus minor, Chlorella ellipsoidea, Chlorella kessleri, Chlorella luteoviridis, Bracteococcus medionucleatus, Chlorella minutissima, Chlorella ovalis, Chlorella protothecoides, Chlorella saccharophila, Chlorella sorokiniana, Chlorella sp., Chlorella vulgaris, Parachlorella kessleri, Prototheca moriformis*, and *Pseudochlorella aquatica*. In other cases, the microorganisms are another species of microorganism as described herein.

In another aspect, the present invention is directed to a method of cultivating microalgae. In one embodiment, the method comprises (a) providing a microalgae cell capable of performing heterotrophic growth, (b) placing the microalgae cell in growth media, wherein the growth media comprises depolymerized cellulosic material, and (c) incubating the microalgae for a period of time sufficient to allow the cell to grow.

In another aspect, the present invention is directed to a method of biodiesel manufacturing. In one embodiment, the method comprises (a) culturing a lipid-producing microorganism in a first microbial culture, (b) recovering lipid from the biomass produced by the first microbial culture, (c) subjecting the lipid to transesterification to produce fatty acid ester(s) and glycerol, and (d) adding the glycerol to a second microbial culture. In some cases, the first and second microbial cultures are cultures of the same species of microorganism. In some cases, the second microbial culture comprises microorganisms selected from the group consisting of *Parachlorella kessleri, Chlorella protothecoides, Bracteococcus medionucleatus, Prototheca moriformis, Chlorella minutissima, Chlorella* sp., and *Chlorella sorokiniana*. In other cases, the second microbial culture comprises another species of microorganism as described herein.

In another aspect, the present invention is directed to a method of fermentation comprising culturing a microorganism in the presence of glycerol and at least one other fixed carbon source. In some cases, the glycerol and the at least one other fixed carbon source are provided to the microorganism simultaneously at a predetermined ratio. In some cases, all of the glycerol and the at least one other fixed carbon source are provided to the microorganism at the beginning of the fermentation. In some cases, all of the glycerol and the at least one other fixed carbon source are fed to the microorganism at a predetermined rate over the course of the fermentation. In one embodiment of the method, glycerol is provided to the microorganism in the absence of the at least one other fixed carbon source for a first period of time, the at least one other fixed carbon source is provided at the end of the first period of time, and the microorganism is cultured for a second period of time in the presence of the at least one other fixed carbon source. In one embodiment, the at least one other fixed carbon source is fed to the microorganism at a predetermined rate during the second period of time. In some cases, all of the at least one other fixed carbon source is provided to the microorganism at the end of the first period of time. In one embodiment of the method, the at least one other fixed carbon source is provided to the microorganism in the absence of glycerol for a first period of time, glycerol is provided at the end of the first period of time, and the microorganism is cultured for a second period of time in the presence of glycerol. In one embodiment, the glycerol is a byproduct of a transesterification process. In one embodiment, the glycerol is acidulated. In another embodiment, the glycerol is non-acidulated. In some cases, the at least one other fixed carbon source is glucose. In some cases, the at least one other fixed carbon source is depolymerized cellulosic material. In one embodiment, the at least one other fixed carbon source is sucrose.

In another aspect, the present invention is directed to a fermentor comprising a population of microorganisms, glycerol, and at least one sugar selected from the group consisting of xylose, glucose, and sucrose. In one embodiment, the glycerol is a byproduct of a lipid transesterification process. In some cases, the microorganisms are selected from the group consisting of *Parachlorella kessleri, Chlorella protothecoides, Bracteococcus medionucleatus, Prototheca moriformis, Chlorella minutissima, Chlorella* sp., and *Chlorella sorokiniana*. In other cases, the microorganisms are another species as described herein.

In another aspect, the present invention is directed to a method of fermenting a microorganism. In one embodiment, the method comprises providing byproduct glycerol from a transesterification process as a sole source of fixed carbon energy. In one embodiment, no light energy is provided to the microorganism. In another embodiment, light energy is provided to the microorganism. In some cases, the microorganism is selected from *Parachlorella kessleri, Chlorella protothecoides, Bracteococcus medionucleatus, Prototheca moriformis, Chlorella minutissima, Chlorella* sp., and *Chlorella sorokiniana*. In other cases, the microorganism is another species as described herein.

In another aspect, the present invention is directed to a microorganism containing an exogenous sucrose utilization gene. In one embodiment, the gene encodes a sucrose transporter. In one embodiment, the gene encodes a sucrose invertase. In one embodiment, the gene encodes a fructokinase. In some cases, the microorganism is a species selected from the group consisting of *Chlorella minutissima, Chlorella emersonii, Chlorella sorokiniana, Chlorella ellipsoidea, Chlorella* sp., or *Chlorella protothecoides*. In other cases, the microorganism is another species as described herein.

In another aspect, the present invention is directed to a cell of the species *Chlorella protothecoides, Chlorella emersonii*, or *Chlorella minutissima* wherein the cell contains an exogenous gene. In some cases, the exogenous gene encodes a protein selected from the group consisting of a sucrose transporter, a sucrose invertase, a lipid modification enzyme, a hydrocarbon modification enzyme and a fructokinase. In some embodiments, the protein is a sucrose invertase secreted into the extracellular space. In some embodiments, the protein is a sucrose invertase targeted to the cytoplasm.

In another aspect, the present invention is directed to a microbial culture containing a population of microorganisms, and a culture medium comprising (i) sucrose and (ii) a sucrose invertase enzyme.

In another aspect, the present invention is directed to a microbial culture containing a population of microorganisms, and a culture medium comprising (i) molasses and (ii) a sucrose invertase enzyme.

In another aspect, the present invention is directed to a microbial culture containing a population of microorganisms, and a culture medium comprising (i) sucrose, (ii) lignin, and (iii) a sucrose invertase enzyme.

In the various microbial cultures described above, the microorganisms contain at least one exogenous sucrose utilization gene. In some embodiments, the sucrose utilization gene encodes a sucrose transporter, a sucrose invertase, a hexokinase, a glucokinase, or a fructokinase. In one embodiment, the sucrose invertase enzyme is a secretable sucrose invertase enzyme encoded by an exogenous sucrose invertase gene expressed by the population of microorganisms. In some cases, the microorganisms contain at least one exogenous gene encoding a lipid pathway enzyme or a hydrocarbon modification enzyme.

In another aspect, the present invention is directed to a nucleic acid comprising a cDNA encoding a sucrose utilization gene, and a cDNA encoding a protein conferring resistance to the antibiotic hygromycin or the antibiotic G418.

In embodiments of the various methods, compositions, cells, microorganisms, microbes, microbial cultures, fermentors, and the like, described above, the microorganism or microbe can be a microalgae, an oleaginous yeast, a fungus, or a bacterium, unless otherwise specified. In some cases, the microorganism is selected from the group consisting of the microalgae listed in Table 1. In some cases, the microorganism is a species of the genus *Chlorella*. In some cases, the microorganism is selected from the group consisting of *Chlorella anitrata, Chlorella antarctica, Chlorella aureoviridis, Chlorella candida, Chlorella capsulata, Chlorella desiccata, Chlorella ellipsoidea, Chlorella emersonii, Chlorella fusca, Chlorella fusca* var. *vacuolata, Chlorella glucotropha, Chlorella infusionum, Chlorella infusionum* var. *Actophila, Chlorella infusionum* var. *Auxenophila, Chlorella kessleri, Chlorella luteoviridis, Chlorella luteoviridis* var. *aureoviridis, Chlorella luteoviridis* var. *Lutescens, Chlorella miniata, Chlorella minutissima, Chlorella mutabilis, Chlorella nocturna, Chlorella parva, Chlorella photophila, Chlorella pringsheimii, Chlorella protothecoides, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris, Chlorella vulgaris f. tertia, Chlorella vulgaris* var. *airidis, Chlorella vulgaris* var. *vulgaris, Chlorella vulgaris* var. *vulgaris f. tertia, Chlorella vulgaris* var. *vulgaris f. viridis, Chlorella xanthella*, and *Chlorella zofingiensis*. In some cases, the microorganism is an oleaginous yeast selected from the group consisting of *Cryptococcus curvatus, Cryptococcus terricolus, Candida* sp., *Lipomyces starkeyi, Lipomyces lipofer, Endomycopsis vernalis, Rhodotorula glutinis, Rhodotorula gracilis*, and *Yarrowia lipolytica*. In some cases, the microorganism is a fungus selected from the group consisting of a species of the genus *Mortierella, Mortierrla vinacea, Mortierella alpine, Pythium debaryanum, Mucor circinelloides, Aspergillus ochraceus, Aspergillus terreus, Pennicillium iilacinum*, a species of the genus *Hensenulo*, a species of the genus *Chaetomium*, a species of the genus *Cladosporium*, a species of the genus *Malbranchea*, a species of the genus *Rhizopus*, and a species of the genus *Pythium*.

In the various embodiments described above, the microorganism can contain at least one exogenous sucrose utilization gene. In some cases, the sucrose utilization gene encodes a sucrose transporter, a sucrose invertase, a hexokinase, a glucokinase, or a fructokinase.

In the various embodiments described above, the microorganism can contain at least one exogenous gene encoding a lipid pathway enzyme. In some cases, the lipid pathway enzyme is selected from the group consisting of a stearoyl-ACP desaturase, a glycerolipid desaturase, a pyruvate dehydrogenase, an acetyl-CoA carboxylase, an acyl carrier protein, and a glycerol-3 phosphate acyltransferase.

In the various embodiments described above, the microorganism can contain at least one exogenous gene encoding a hydrocarbon modification enzyme. In some cases, the hydrocarbon modification enzyme is selected from the group consisting of a fatty acyl-ACP thioesterase, a fatty acyl-CoA/aldehyde reductase, a fatty acyl-CoA reductase, a fatty aldehyde reductase, a fatty aldehyde decarbonylase, and/or an acyl carrier protein.

Any two or more of the various embodiments described above can be combined together to produce additional embodiments encompassed within the scope of the present invention.

BRIEF DESCRIPTION OF THE DRAWINGS

FIG. 11(*b*) shows lipid as a percent of dry cell weight of *Navicula pelliculosa* when cultured in the presence of various types of glycerol and in the presence of combinations of glycerol and glucose.

FIG. 12(*b*) shows dry cell weight per liter of *Scenedesmus armatus* when cultured in the presence of various types of glycerol and in the presence of a combination of biodiesel byproduct glycerol and glucose.

FIG. 14 shows dry cell weight per liter of *Scenedesmus armatus* and *Navicula pelliculosa* when cultured in the presence of acidulated and non-acidulated biodiesel byproduct glycerol with additional glucose, wherein glycerol is added sequentially or in combination with glucose.

FIG. 17 shows codon usage of *Chlorella protothecoides*.

FIG. 18 shows codon usage of *D. salina* and *Chlorella pyrenoidosa*.

FIG. 21 shows growth of *Chlorella fusca* on 1% sucrose.

FIG. 22 shows growth of *Chlorella kessleri* on 1% sucrose.

FIG. 27 shows genotyping of *Chlorella protothecoides* cells transformed with a gene encoding a secreted sucrose invertase from *S. cerevisiae*.

FIG. 28 shows genotyping of *Chlorella minutissima* and *Chlorella emersonii* cells transformed with a gene encoding a secreted sucrose invertase from *S. cerevisiae*.

DETAILED DESCRIPTION OF THE INVENTION

I. Definitions

Figure 1:
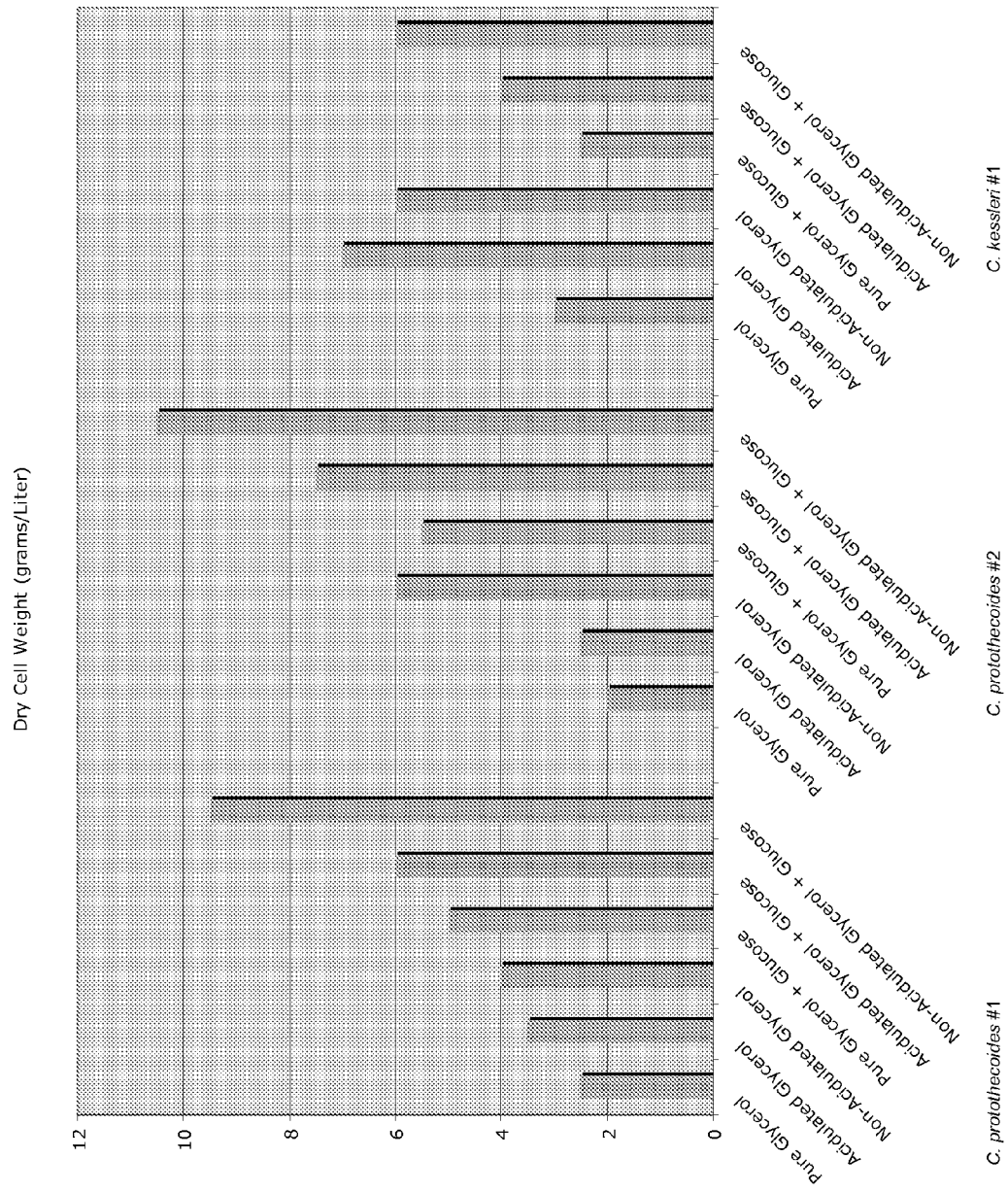
FIG. 1 shows dry cell weight per liter of multiple species and strains of *Chlorella* when cultured in the presence of various types of glycerol with and without additional glucose.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used with reference to a nucleic acid, "active in microalgae" refers to a nucleic acid that is functional in microalgae. For example, a promoter that has been used to drive an antibiotic resistance gene to impart antibiotic resistance to a transgenic microalgae is active in microalgae. Examples of promoters active in microalgae are promoters endogenous to certain algae species and promoters found in plant viruses.

An "acyl carrier protein" or "ACP" is a protein which binds a growing acyl chain during fatty acid synthesis as a thiol ester at the distal thiol of the 4'-phosphopantetheine moiety and comprises a component of the fatty acid synthase complex. The phrase "naturally co-expressed" with reference to an acyl carrier protein in conjunction with a fatty acyl-ACP thioesterase means that the ACP and the thioesterase are co-expressed naturally in a tissue or organism from which they are derived, e.g., because the genes encoding the two enzymes are under the control of a common regulatory sequence or because they are expressed in response to the same stimulus.

An "acyl-CoA molecule" or "acyl-CoA" is a molecule comprising an acyl moiety covalently attached to coenzyme A through a thiol ester linkage at the distal thiol of the 4'-phosphopantetheine moiety of coenzyme A.

"Axenic" means a culture of an organism that is free from contamination by other living organisms.

"Biodiesel" is a biologically produced fatty acid alkyl ester suitable for use as a fuel in a diesel engine.

The term "biomass" refers to material produced by growth and/or propagation of cells. Biomass may contain cells and/or intracellular contents as well as extracellular material. Extracellular material includes, but is not limited to, compounds secreted by a cell.

"Bioreactor" means an enclosure or partial enclosure in which cells are cultured, optionally in suspension.

As used herein, a "catalyst" refers to an agent, such as a molecule or macromolecular complex, capable of facilitating or promoting a chemical reaction of a reactant to a product without becoming a part of the product. A catalyst thus increases the rate of a reaction, after which, the catalyst may act on another reactant to form the product. A catalyst generally lowers the overall activation energy required for the reaction such that it proceeds more quickly or at a lower temperature. Thus a reaction equilibrium may be more quickly attained. Examples of catalysts include enzymes, which are biological catalysts, heat, which is a non-biological catalyst, and metal catalysts used in fossil oil refining processes.

"Cellulosic material" means the products of digestion of cellulose, including glucose and xylose, and optionally additional compounds such as disaccharides, oligosaccharides, lignin, furfurals and other compounds. Nonlimiting examples of sources of cellulosic material include sugar caner bagasses, sugar beet pulp, corn stover, wood chips, sawdust and switchgrass.

The term "co-culture", and variants thereof such as "co-cultivate", refer to the presence of two or more types of cells in the same bioreactor. The two or more types of cells may both be microorganisms, such as microalgae, or may be a microalgal cell cultured with a different cell type. The culture conditions may be those that foster growth and/or propagation of the two or more cell types or those that facilitate growth and/or proliferation of one, or a subset, of the two or more cells while maintaining cellular growth for the remainder.

The term "cofactor" is used herein to refer to any molecule, other than the substrate, that is required for an enzyme to carry out its enzymatic activity.

As used herein, "complementary DNA" ("cDNA") is a DNA representation of mRNA, usually obtained by reverse transcription of messenger RNA (mRNA) or amplification (e.g., via polymerase chain reaction ("PCR")).

The term "cultivated", and variants thereof, refer to the intentional fostering of growth (increases in cell size, cellular contents, and/or cellular activity) and/or propagation (increases in cell numbers via mitosis) of one or more cells by use of intended culture conditions. The combination of both growth and propagation may be termed proliferation. The one or more cells may be those of a microorganism, such as microalgae. Examples of intended conditions include the use of a defined medium (with known characteristics such as pH, ionic strength, and carbon source), specified temperature, oxygen tension, carbon dioxide levels, and growth in a bioreactor. The term does not refer to the growth or propagation of microorganisms in nature or otherwise without direct human intervention, such as natural growth of an organism that ultimately becomes fossilized to produce geological crude oil.

As used herein, the term "cytolysis" refers to the lysis of cells in a hypotonic environment. Cytolysis is caused by excessive osmosis, or movement of water, towards the inside of a cell (hyperhydration). The cell cannot withstand the osmotic pressure of the water inside, and so it explodes.

As used herein, the terms "expression vector" or "expression construct" refer to a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

"Exogenous gene" refers to a nucleic acid transformed into a cell. A transformed cell may be referred to as a recombinant cell, into which additional exogenous gene(s) may be introduced. The exogenous gene may be from a different species (and so heterologous), or from the same species (and so homologous) relative to the cell being transformed. In the case of a homologous gene, it occupies a different location in the genome of the cell relative to the endogenous copy of the gene. The exogenous gene may be present in more than one copy in the cell. The exogenous gene may be maintained in a cell as an insertion into the genome or as an episomal molecule.

"Exogenously provided" describes a molecule provided to the culture media of a cell culture.

As used herein, a "fatty acyl-ACP thioesterase" is an enzyme that catalyzes the cleavage of a fatty acid from an acyl carrier protein (ACP) during lipid synthesis.

As used herein, a "fatty acyl-CoA/aldehyde reductase" is an enzyme that catalyzes the reduction of an acyl-CoA molecule to a primary alcohol.

As used herein, a "fatty acyl-CoA reductase" is an enzyme that catalyzes the reduction of an acyl-CoA molecule to an aldehyde.

As used herein, a "fatty aldehyde decarbonylase" is an enzyme that catalyzes the conversion of a fatty aldehyde to an alkane.

As used herein, a "fatty aldehyde reductase" is an enzyme that catalyzes the reduction of an aldehyde to a primary alcohol.

"Fixed carbon source" means molecule(s) containing carbon, preferably organic, that are present at ambient temperature and pressure in solid or liquid form.

"Fungus," as used herein, means heterotrophic organisms characterized by a chitinous cell wall from the kingdom of fungi.

"Homogenate" means biomass that has been physically disrupted.

As used herein, "hydrocarbon" refers to: (a) a molecule containing only hydrogen and carbon atoms wherein the carbon atoms are covalently linked to form a linear, branched, cyclic, or partially cyclic backbone to which the hydrogen atoms are attached; or (b) a molecule that only primarily contains hydrogen and carbon atoms and that can be converted to contain only hydrogen and carbon atoms by one to four chemical reactions. Nonlimiting examples of the latter include hydrocarbons containing an oxygen atom between one carbon and one hydrogen atom to form an alcohol molecule, as well as aldehydes containing a single oxygen atom. Methods for the reduction of alcohols to hydrocarbons containing only carbon and hydrogen atoms are well known. Another example of a hydrocarbon is an ester, in which an organic group replaces a hydrogen atom (or more than one) in an oxygen acid. The molecular structure of hydrocarbon compounds varies from the simplest, in the form of methane ($CH_4$), which is a constituent of natural gas, to the very heavy and very complex, such as some molecules such as asphaltenes found in crude oil, petroleum, and bitumens. Hydrocarbons may be in gaseous, liquid, or solid form, or any combination of these forms, and may have one or more double or triple bonds between adjacent carbon atoms in the backbone. Accordingly, the term includes linear, branched, cyclic, or partially cyclic alkanes, alkenes, lipids, and paraffin. Examples include propane, butane, pentane, hexane, octane, triolein, and squalene.

"Hydrocarbon modification enzyme" refers to an enzyme that alters the covalent structure of a hydrocarbon. Examples of hydrocarbon modification enzymes include a lipase, a fatty acyl-ACP thioesterase, a fatty acyl-CoA/aldehyde reductase, a fatty acyl-CoA reductase, a fatty aldehyde reductase, and a fatty aldehyde decarbonylase. Compounds produced by the enzymatic activity of hydrocarbon modification enzymes, including fatty acids, alcohols, aldehydes, alkanes, or other compounds derived therefrom are referred to herein interchangeably as hydrocarbons or lipids.

The term "hydrogen:carbon ratio" refers to the ratio of hydrogen atoms to carbon atoms in a molecule on an atom-to-atom basis. The ratio may be used to refer to the number of carbon and hydrogen atoms in a hydrocarbon molecule. For example, the hydrocarbon with the highest ratio is methane $CH_4$ (4:1).

"Hydrophobic fraction" refers to the portion, or fraction, of a material that is more soluble in a hydrophobic phase in comparison to an aqueous phase. A hydrophobic fraction is substantially insoluble in water and usually non-polar.

As used herein, the phrase "increase lipid yield" refers to an increase in the productivity of a microbial culture by, for example, increasing dry weight of cells per liter of culture, increasing the percentage of cells that constitute lipid, or increasing the overall amount of lipid per liter of culture volume per unit time.

An "inducible promoter" is one that mediates transcription of an operably linked gene in response to a particular stimulus.

As used herein, the phrase "in operable linkage" refers to a functional linkage between two sequences, such a control sequence (typically a promoter) and the linked sequence. A promoter is in operable linkage with an exogenous gene if it can mediate transcription of the gene.

The term "in situ" means "in place" or "in its original position". For example, a culture may contain a first microalgae secreting a catalyst and a second microorganism secreting a substrate, wherein the first and second cell types produce the components necessary for a particular chemical reaction to occur in situ in the co-culture without requiring further separation or processing of the materials.

A "limiting concentration of a nutrient" is a concentration in a culture that limits the propagation of a cultured organism. A "non-limiting concentration of a nutrient" is a concentration that supports maximal propagation during a given culture period. Thus, the number of cells produced during a given culture period is lower in the presence of a limiting concentration of a nutrient than when the nutrient is non-limiting. A nutrient is said to be "in excess" in a culture, when the nutrient is present at a concentration greater than that which supports maximal propagation.

As used herein, a "lipase" is a water-soluble enzyme that catalyzes the hydrolysis of ester bonds in water-insoluble, lipid substrates. Lipases catalyze the hydrolysis of lipids into glycerols and fatty acids.

As used herein, a "lipid pathway enzyme" is any enzyme that plays a role in lipid metabolism, i.e., either lipid synthesis, modification, or degradation. This term encompasses proteins that chemically modify lipids, as well as carrier proteins.

"Lipids" are a class of hydrocarbon that are soluble in nonpolar solvents (such as ether and chloroform) and are relatively or completely insoluble in water. Lipid molecules have these properties because they consist largely of long hydrocarbon tails which are hydrophobic in nature. Examples of lipids include fatty acids (saturated and unsaturated); glycerides or glycerolipids (such as monoglycerides, diglycerides, triglycerides or neutral fats, and phosphoglycerides or glycerophospholipids); nonglycerides (sphingolipids, sterol lipids including cholesterol and steroid hormones, prenol lipids including terpenoids, fatty alcohols, waxes, and polyketides); and complex lipid derivatives (sugar-linked lipids, or glycolipids, and protein-linked lipids). "Fats" are a subgroup of lipids called "triacylglycerides."

As used herein, the term "lysate" refers to a solution containing the contents of lysed cells.

As used herein, the term "lysis" refers to the breakage of the plasma membrane and optionally the cell wall of a biological organism sufficient to release at least some intracellular content, often by mechanical, viral or osmotic mechanisms that compromise its integrity.

As used herein, the term "lysing" refers to disrupting the cellular membrane and optionally the cell wall of a biological organism or cell sufficient to release at least some intracellular content.

"Microalgae" means a eukarytotic microbial organism that contains a chloroplast, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae can refer to unicellular organisms that separate from sister cells shortly after cell division, such as *Chlamydomonas*, and can also refer to microbes such as, for example, *Volvox*, which is a simple multicellular photosynthetic microbe of two distinct cell types. "Microalgae" can also refer to cells such as *Chlorella* and *Dunaliella*. "Microalgae" also includes other microbial photosynthetic organisms that exhibit cell-cell adhesion, such as *Agmenellum, Anabaena*, and *Pyrobotrys*. "Microalgae" also includes obligate heterotrophic microorganisms that have lost the ability to perform photosynthesis, such as certain dinoflagellate algae species.

The terms "microorganism" and "microbe" are used interchangeably herein to refer to microscopic unicellular organisms.

"Oleaginous yeast," as used herein, means yeast that can naturally accumulate more than 10% of its dry cell weight as lipid or can do so as a result of genetic engineering. Oleaginous yeast includes organisms such as *Yarrowia lipolytica*, as well as engineered strains of yeast such as *Saccharomyces cerevisiae* that have been engineered to accumulate more than 10% of their dry cell weight as lipid.

As used herein, the term "osmotic shock" refers to the rupture of cells in a solution following a sudden reduction in osmotic pressure. Osmotic shock is sometimes induced to release cellular components of such cells into a solution.

"Photobioreactor" refers to a container, at least part of which is at least partially transparent or partially open, thereby allowing light to pass through, in which one or more microalgae cells are cultured. Photobioreactors may be closed, as in the instance of a polyethylene bag or Erlenmeyer flask, or may be open to the environment, as in the instance of an outdoor pond.

As used herein, a "polysaccharide-degrading enzyme" refers to any enzyme capable of catalyzing the hydrolysis, or depolymerization, of any polysaccharide. For example, cellulases catalyze the hydrolysis of cellulose.

"Polysaccharides" (also called "glycans") are carbohydrates made up of monosaccharides joined together by glycosidic linkages. Cellulose is an example of a polysaccharide that makes up certain plant cell walls. Cellulose can be depolymerized by enzymes to yield monosaccharides such as xylose and glucose, as well as larger disaccharides and oligosaccharides.

"Port", in the context of a bioreactor, refers to an opening in the bioreactor that allows influx or efflux of materials such as gases, liquids, and cells. Ports are usually connected to tubing leading from the photobioreactor.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

As used herein, the term "recombinant" when used with reference, e.g., to a cell, or nucleic acid, protein, or vector, indicates that the cell, nucleic acid, protein or vector, has been modified by the introduction of an exogenous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

As used herein, the term "renewable diesel" refers to alkanes (such as C:10:0, C12:0, C:14:0, C16:0 and C18:0) produced through hydrogenation and deoxygenation of lipids.

As used herein, the term "sonication" refers to a process of disrupting biological materials, such as a cell, by use of sound wave energy.

"Species of furfural" refers to 2-Furancarboxaldehyde or a derivative thereof which retains the same basic structural characteristics.

As used herein, "stover" refers to the dried stalks and leaves of a crop remaining after a grain has been harvested.

A "sucrose utilization gene" is a gene that, when expressed, aids the ability of a cell to utilize sucrose as an energy source. Proteins encoded by a sucrose utilization gene are referred to herein as "sucrose utilization enzymes" and include sucrose transporters, sucrose invertases, and hexokinases such as glucokinases and fructokinases.

"Wastewater" is watery waste which typically contains washing water, laundry waste, faeces, urine and other liquid or semi-liquid wastes. It includes some forms of municipal waste as well as secondarily treated sewage.

For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (at the web address www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=-4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, *Proc. Natl. Acad Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

II. General

The invention is premised in part on the insight that certain microorganisms can be used to produce oils, fuels, and other hydrocarbon or lipid compositions economically and in large quantities for use in the transportation fuel, petrochemical industry, and/or food and cosmetic industries, among other applications. Suitable microorganisms include microalgae, oleaginous yeast, and fungi. A preferred genus of microalgae for use in the invention is the lipid-producing microalgae *Chlorella*. Transesterification of lipids yields long-chain fatty acid esters useful as biodiesel. Other enzymatic and chemical processes can be tailored to yield fatty acids, aldehydes, alcohols, alkanes, and alkenes. The present application describes methods for genetic modification of multiple species and strains of microorganisms, including *Chlorella* and similar microbes to provide organisms having characteristics that facilitate the production of lipid suitable for conversion into oils, fuels, and oleochemicals. In some applications, renewable diesel, jet fuel, or other hydrocarbon compounds are produced. The present application also describes methods of cultivating microalgae for increased productivity and increased lipid yield, and/or for more cost-effective production of the compositions described herein.

In particular embodiments, the present application describes genetically engineering strains of microalgae with one or more exogenous genes. For example, microalgae that produce high levels of triacylglycerides (TAGs) suitable for biodiesel can be engineered to express a lipase, which can facilitate transesterification of microalgal TAGs. The lipase can optionally be expressed using an inducible promoter, so that the cells can first be grown to a desirable density in a fermentor and then harvested, followed by induction of the promoter to express the lipase, optionally in the presence of sufficient alcohol to drive conversion of TAGs to fatty acid esters.

Some microalgal lipid is sequestered in cell membranes and other non-aqueous parts of the cell. Therefore, to increase the yield of the transesterification reaction, it can be beneficial to lyse the cells to increase the accessibility of the lipase to the lipid. Cell disruption can be performed, for example, mechanically, through addition of pressurized steam, or by employing a virus that lyses the microalgae cells, expressing a gene to produce a lytic protein in the cell, or treating the culture with an agent that lyses microalgae cells. Steam treatment of microalgae for cell disruption is described, for example, in U.S. Pat. No. 6,750,048.

Also disclosed herein is the genetic engineering of microalgae that produce high levels of TAGs to express a gene that lyses microalgae cells, such as for example, a gene from a lytic virus. This gene can be expressed using an inducible promoter, so that the cells can first be grown to a desirable density in a fermentor and then harvested, followed by induction of the promoter to express the gene to lyse the cells. A gene encoding a polysaccharide-degrading enzyme, for example, can be expressed to lyse the cells.

Optionally, the lipase can be expressed in an intracellular compartment, where it remains separate from the majority of the microalgal lipid until transesterification. Generally, it is preferable to carry out transesterification after water has been substantially removed from the preparation and/or an excess of alcohol has been added. Lipases can use water, as well as alcohol, as a substrate in transesterification. With water, the lipid is conjugated to a hydroxyl moiety to produce a polar fatty acid, rather than an ester. With an alcohol, such as methanol, the lipid is conjugated to a methyl group, producing a non-polar fatty acid ester, which is typically preferable for a transportation fuel. To limit exposure of the lipase to microalgal lipid until conditions are suitable for transesterification to produce fatty acid esters, the lipase can be expressed, for example, in the chloroplast, mitochondria, or other cellular organelle. This compartmentalized expression results in sequestration of the lipase from the majority of the cellular lipid until after the cells have been disrupted.

In other particular embodiments, the present application describes genetically engineering strains of microalgae, oleaginous yeast, bacteria, or fungi with one or more exogenous genes to produce various hydrocarbon compounds. For example, microalgae that would naturally, or through genetic modification, produce high levels of lipids can be engineered (or further engineered) to express an exogenous fatty acyl-ACP thioesterase, which can facilitate the cleavage of fatty acids from the acyl carrier protein (ACP) during lipid synthesis. These fatty acids can be recovered or, through further enzymatic processing within the cell, yield other hydrocarbon compounds. Optionally, the fatty acyl-ACP thioesterase can be expressed from a gene operably linked to an inducible promoter, and/or can be expressed in an intracellular compartment.

The fatty acyl-ACP thioesterase can be chosen based on its specificity for a growing (during fatty acid synthesis) fatty acid having a particular carbon chain length. For example, the fatty acyl-ACP thioesterase can have a specificity for a carbon chain length ranging from 8 to 34 carbon atoms, preferably from 8 to 18 carbon atoms, and more preferably from 10 to 14 carbon atoms. A specificity for a fatty acid with 12 carbon atoms is most preferred.

Further, the invention provides genetically engineered strains of microalgae to express two or more exogenous genes, such as, for example, a lipase and a lytic gene, e.g., one encoding a polysaccharide-degrading enzyme. One or both genes can be expressed using an inducible promoter, which allows the relative timing of expression of these genes to be controlled to enhance the lipid yield and conversion to fatty acid esters. The invention also provides vectors and methods for engineering lipid-producing microbes to metabolize sucrose, which is an advantageous trait because it allows the engineered cells to convert sugar cane or other feedstocks into lipids appropriate for production of oils, fuels, oleochemicals and the like.

In other embodiments, the invention provides genetically engineered strains of microbes (e.g., microalgae, oleaginous yeast, bacteria, or fungi) that express two or more exogenous genes, such as, for example, a fatty acyl-ACP thioesterase and a fatty acyl-CoA/aldehyde reductase, the combined action of which yields an alcohol product. The invention further provides other combinations of exogenous genes, including without limitation, a fatty acyl-ACP thioesterase and a naturally co-expressed acyl carrier protein to generate length-specific fatty acids, or a fatty acyl-ACP thioesterase and a fatty acyl-CoA reductase to generate aldehydes. The invention also provides for the combination of a fatty acyl-ACP thioesterase, a fatty acyl-CoA reductase, and a fatty aldehyde decarbonylase to generate alkanes or alkenes. One or more of the exogenous genes can be expressed using an inducible promoter.

The invention provides further modifications of microalgae, for example to provide microalgae with desired growth characteristics and/or to enhance the amount and/or quality of lipids produced. For example, microalgae can be engineered to increase carbon flux into the lipid pathway and/or modify the lipid pathway to beneficially alter the proportions or properties of lipid produced by the cells.

This application discloses genetically engineering strains of microalgae to express two or more exogenous genes, one encoding a transporter of a fixed carbon source (such as sucrose) and a second encoding a sucrose invertase enzyme. The resulting fermentable organisms produce hydrocarbons at lower manufacturing cost than what has been obtainable by previously known methods of biological hydrocarbon production. The insertion of the two exogenous genes described above can be combined with the disruption of polysaccharide biosynthesis through directed and/or random mutagenesis, which steers ever greater carbon flux into hydrocarbon production. Individually and in combination, trophic conversion, engineering to alter hydrocarbon production and treatment with exogenous enzymes alter the hydrocarbon composition produced by a microorganism. The alteration can be a change in the amount of hydrocarbons produced, the amount of one or more hydrocarbon species produced relative to other hydrocarbons, and/or the types of hydrocarbon species produced in the microorganism. For example, microalgae can be engineered to produce a higher amount and/or percentage of TAGs.

III. Oil- or Lipid-Producing Microorganisms

Any species of organism that produces suitable lipid or hydrocarbon can be used, although microorganisms that naturally produce high levels of suitable lipid or hydrocarbon are preferred. Production of hydrocarbons by microorganisms is reviewed by Metzger et al. Appl Microbiol Biotechnol (2005) 66: 486-496 and A Look Back at the U.S. Department of Energy's Aquatic Species Program: Biodiesel from Algae, NREL/TP-580-24190, John Sheehan, Terri Dunahay, John Benemann and Paul Roessler (1998).

Considerations affecting the selection of microorganisms for use in the invention include, in addition to production of suitable lipids or hydrocarbons for production of oils, fuels, and oleochemicals: (1) high lipid content as a percentage of cell weight; (2) ease of growth; (3) ease of genetic engineering; and (4) ease of biomass processing. In particular embodiments, the wild-type or genetically engineered microorganism yields cells that are at least 40%, at least 45%, at least 50%, at least 55%, at least 60%, at least 65%, or at least 70% or more lipid. Preferred organisms grow heterotrophically (on sugars in the absence of light) or can be engineered to do so using, for example, methods disclosed herein. The ease of transformation and availability of selectable markers and promoters, constitutive and/or inducible, that are functional in the microorganism affect the ease of genetic engineering. Processing considerations can include, for example, the availability of effective means for lysing the cells.

A. Algae

In one embodiment of the present invention, the microorganism is a microalgae. Nonlimiting examples of microalgae that can be used in accordance with the present invention can be found in Table 1.

TABLE 1

Examples of microalgae.

*Achnanthes orientalis, Agmenellum, Amphiprora hyaline, Amphora coffeiformis, Amphora coffeiformis linea, Amphora coffeiformis punctata, Amphora coffeiformis taylori, Amphora coffeiformis tenuis, Amphora delicatissima, Amphora delicatissima capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri subsalsum, Chaetoceros* sp., *Chlorella anitrata, Chlorella Antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora* (strain SAG 37.88), *Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides* (including any of UTEX strains 1806, 411, 264, 256, 255, 250, 249, 31, 29, 25), *Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* f. *tertia, Chlorella vulgaris* var. *autotrophica, Chlorella vulgaris* var. *viridis, Chlorella vulgaris* var. *vulgaris, Chlorella vulgaris* var. *vulgaris* f. *tertia, Chlorella vulgaris* var. *vulgaris* f. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena, Franceia* sp., *Fragilaria crotonensis, Fragilaria* sp., *Gleocapsa* sp., *Gloeothamnion* sp., *Hymenomonas* sp., *Isochrysis* aff. *galbana, Isochrysis galbana, Lepocinclis, Micractinium, Micractinium* (UTEX LB 2614), *Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrina, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phagus, Phormidium, Platymonas* sp., *Pleurochrysis carterae, Pleurochrysis dentate, Pleurochrysis* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Tetraedron, Tetraselmis* sp., *Tetraselmis suecica, Thalassiosira weissflogii,* and *Viridiella fridericiana*

1. *Chlorella*

In a preferred embodiment of the present invention, the microorganism is of the genus *Chlorella*, preferably, *Chlorella protothecoides, Chlorella ellipsoidea, Chlorella minutissima,* or *Chlorella emersonii*.

*Chlorella* is a genus of single-celled green algae, belonging to the phylum Chlorophyta. It is spherical in shape, about 2 to 10 µm in diameter, and is without flagella. Some species of *Chlorella* are naturally heterotrophic.

*Chlorella*, particularly *Chlorella protothecoides*, is a preferred microorganism for use in the invention because of its high composition of lipid, particularly long-chain lipid suitable for biodiesel. In addition, this microalgae grows heterotrophically and can be genetically engineered as demonstrated in the Examples herein.

In a preferred embodiment of the present invention, the microorganism used for expression of a transgene is of the genus *Chlorella*, preferably, *Chlorella protothecoides, Chlorella minutissima,* or *Chlorella emersonii*. Examples of expression of transgenes in, e.g., *Chlorella*, can be found in the literature (see for example *Current Microbiology* Vol. 35 (1997), pp. 356-362; Sheng Wu Gong Cheng Xue Bao. 2000 July; 16(4):443-6; *Current Microbiology* Vol. 38 (1999), pp. 335-341; *Appl Microbiol Biotechnol* (2006) 72: 197-205; *Marine Biotechnology* 4, 63-73, 2002; *Current Genetics* 39:5, 365-370 (2001); *Plant Cell Reports* 18:9, 778-780, (1999); *Biologia Plantarium* 42(2): 209-216, (1999); *Plant Pathol.* J 21(1): 13-20, (2005)). Also see Examples herein. Other lipid-producing microalgae can be engineered as well, including prokaryotic Microalgae (see Kalscheuer st al., Applied Microbiology and Biotechnology, Volume 52, Number 4/October, 1999).

2. Identification of *Chlorella* Species

Species of *Chlorella* for use in the invention can be identified by amplification of certain target regions of the genome. For example, identification of a specific *Chlorella* species or strain can be achieved through amplification and sequencing of nuclear and/or chloroplast DNA using primers and methodology using any region of the genome, for example using the methods described in Wu et al., *Bot. Bull. Acad. Sin.* (2001) 42:115-121 Identification of *Chlorella* spp. isolates using ribosomal DNA sequences. Well established methods of phylogenetic analysis, such as amplification and sequencing of ribosomal internal transcribed spacer (ITS1 and ITS2 rDNA), 18S rRNA, and other conserved genomic regions can be used by those skilled in the art to identify species of not only *Chlorella*, but other hydrocarbon and lipid producing organisms capable of using the methods disclosed herein. For examples of methods of identification and classification of algae also see for example *Genetics,* 2005 August; 170(4): 1601-10 and *RNA,* 2005 April; 11(4):361-4.

B. Oleaginous Yeast

In one embodiment of the present invention, the microorganism is an oleaginous yeast. Nonlimiting examples of oleaginous yeast that can be used in accordance with the present invention can be found in Table 2.

TABLE 2

Examples of oleaginous yeast.

*Cryptococcus curvatus, Cryptococcus terricolus, Candida* sp., *Lipomyces starkeyi, Lipomyces lipofer, Endomycopsis vernalis, Rhodotorula glutinis, Rhodotorula gracilis,* and *Yarrowia lipolytica*

C. Other Fungi

In one embodiment of the present invention, the microorganism is a fungus. Nonlimiting examples of fungi that can be used in accordance with the present invention can be found in Table 3.

TABLE 3

Examples of fungi.

*Mortierella, Mortierrla vinacea, Mortierella alpine, Pythium debaryanum, Mucor circinelloides, Aspergillus ochraceus, Aspergillus terreus, Pennicillium iilacinum, Hensenulo, Chaetomium, Cladosporium, Malbranchea, Rhizopus,* and *Pythium*

D. Bacteria

In one embodiment of the present invention, the microorganism is a bacterium.

Examples of expression of exogenous genes in bacteria, such as *E. coli*, are well known; see for example *Molecular Cloning: A Laboratory Manual,* Sambrook et al. (3d edition, 2001, Cold Spring Harbor Press).

IV. Methods of Culturing Microorganisms

Microrganisms are cultured both for purposes of conducting genetic manipulations and for subsequent production of hydrocarbons (e.g., lipids, fatty acids, aldehydes, alcohols, and alkanes). The former type of culture is conducted on a small scale and initially, at least, under conditions in which the starting microorganism can grow. For example, if the starting microorganism is a photoautotroph the initial culture is conducted in the presence of light. The culture conditions can be changed if the microorganism is evolved or engineered to grow independently of light. Culture for purposes of hydrocarbon production is usually conducted on a large scale. Preferably a fixed carbon source is present. The culture can also be exposed to light some or all of the time.

Microalgae can be cultured in liquid media. The culture can be contained within a bioreactor. Optionally, the bioreactor does not allow light to enter. Alternatively, microalgae can also be cultured in photobioreactors that contain a fixed carbon source and allow light to strike the cells. Exposure of microalgae cells to light, even in the presence of a fixed carbon source that the cells transport and utilize (i.e., mixotrophic growth), nonetheless accelerates growth compared to culturing cells in the dark. Culture condition parameters can be manipulated to optimize total hydrocarbon production, the combination of hydrocarbon species produced, and/or production of a hydrocarbon species. In some instances it is preferable to culture cells in the dark, such as, for example, when using extremely large (40,000 liter and higher) fermentors that do not allow light to strike the culture.

Microalgal culture media typically contains components such as a fixed nitrogen source, trace elements, optionally a buffer for pH maintenance, and phosphate. Other components can include a fixed carbon source such as acetate or glucose, and salts such as sodium chloride, particularly for seawater microalgae. Examples of trace elements include zinc, boron, cobalt, copper, manganese, and molybdenum in, for example, the respective forms of $ZnCl_2$, $H_3BO_3$, $CoCl_2.6H_2O$, $CuCl_2.2H_2O$, $MnCl_2.4H_2O$ and $(NH_4)_6Mo_7O_{24}.4H_2O$.

For organisms able to grow on a fixed carbon source, the fixed carbon source can be, for example, glucose, fructose, sucrose, galactose, xylose, mannose, rhamnose, N-acetylglucosamine, glycerol, floridoside, and/or glucuronic acid. The one or more carbon source(s) can be supplied at a concentration of at least about 50 µM, at least about 100 µM, at least about 500 µM, at least about 5 mM, at least about 50 mM, and at least about 500 mM, of one or more exogenously provided fixed carbon source(s). Some microalgae species can grow by utilizing a fixed carbon source such as glucose or acetate in the absence of light. Such growth is known as heterotrophic growth. For *Chlorella protothecoides*, for example, heterotrophic growth results in high production of biomass and accumulation of high lipid content in cells.

Some microorganisms naturally grow on or can be engineered to grow on a fixed carbon source that is a heterogeneous source of compounds such as municipal waste, secondarily treated sewage, wastewater, and other sources of fixed carbon and other nutrients such as sulfates, phosphates, and nitrates. The sewage component serves as a nutrient source in the production of hydrocarbons, and the culture provides an inexpensive source of hydrocarbons.

Other culture parameters can also be manipulated, such as the pH of the culture media, the identity and concentration of trace elements and other media constituents.

A. Photosynthetic Growth

Microalgae can be grown in the presence of light. The number of photons striking a culture of microalgae cells can be manipulated, as well as other parameters such as the wavelength spectrum and ratio of dark:light hours per day. Microalgae can also be cultured in natural light, as well as simultaneous and/or alternating combinations of natural light and artificial light. For example, microalgae of the genus *Chlorella* can be cultured under natural light during daylight hours and under artificial light during night hours.

The gas content of a photobioreactor to grow microorganisms like microalgae can be manipulated. Part of the volume of a photobioreactor can contain gas rather than liquid. Gas inlets can be used to pump gases into the photobioreactor. Any gas can be pumped into a photobioreactor, including air, air/$CO_2$ mixtures, noble gases such as argon and others. The rate of entry of gas into a photobioreactor can also be manipulated. Increasing gas flow into a photobioreactor increases the turbidity of a culture of microalgae. Placement of ports conveying gases into a photobioreactor can also affect the turbidity of a culture at a given gas flow rate. Air/$CO_2$ mixtures can be modulated to generate optimal amounts of $CO_2$ for maximal growth by a particular organism. Microalgae grow significantly faster in the light under, for example, 3% $CO_2$/97% air than in 100% air. 3% $CO_2$/97% air is approximately 100-fold more $CO_2$ than found in air. For example, air:$CO_2$ mixtures of about 99.75% air:0.25% $CO_2$, about 99.5% air:0.5% $CO_2$, about 99.0% air:1.00% $CO_2$, about 98.0% air:2.0% $CO_2$, about 97.0% air:3.0% $CO_2$, about 96.0% air:4.0% $CO_2$, and about 95.00% air:5.0% $CO_2$ can be infused into a bioreactor or photobioreactor.

Microalgae cultures can also be subjected to mixing using devices such as spinning blades and impellers, rocking of a culture, stir bars, infusion of pressurized gas, and other instruments.

Photobioreactors can have ports allowing entry of gases, solids, semisolids and liquids into the chamber containing the microalgae. Ports are usually attached to tubing or other means of conveying substances. Gas ports, for example, convey gases into the culture. Pumping gases into a photobioreactor can serve to both feed cells $CO_2$ and other gases and to aerate the culture and therefore generate turbidity. The amount of turbidity of a culture varies as the number and position of gas ports is altered. For example, gas ports can be placed along the bottom of a cylindrical polyethylene bag. Microalgae grow faster when $CO_2$ is added to air and bubbled into a photobioreactor. For example, a 5% $CO_2$:95% air mixture is infused into a photobioreactor containing *Botryococcus* cells (see for example J Agric Food Chem. 2006 Jun. 28; 54(13):4593-9; J Biosci Bioeng. 1999; 87(6):811-5; and J Nat Prod. 2003 June; 66(6):772-8).

Photobioreactors can be exposed to one or more light sources to provide microalgae with light as an energy source via light directed to a surface of the photobioreactor. Preferably the light source provides an intensity that is sufficient for the cells to grow, but not so intense as to cause oxidative damage or cause a photoinhibitive response. In some instances a light source has a wavelength range that mimics or approximately mimics the range of the sun. In other instances a different wavelength range is used. Photobioreactors can be placed outdoors or in a greenhouse or other facility that allows sunlight to strike the surface. Preferred photon intensities for species of the genus *Botryococcus* are between 25 and 500 $\mu E\ m^{-2}\ s^{-1}$ (see for example Photosynth Res. 2005 June; 84(1-3):21-7).

Photobioreactors preferably have one or more ports that allow media entry. It is not necessary that only one substance enter or leave a port. For example, a port can be used to flow culture media into the photobioreactor and then later can be used for sampling, gas entry, gas exit, or other purposes. In some instances a photobioreactor is filled with culture media at the beginning of a culture and no more growth media is infused after the culture is inoculated. In other words, the microalgal biomass is cultured in an aqueous medium for a period of time during which the microalgae reproduce and increase in number; however quantities of aqueous culture medium are not flowed through the photobioreactor throughout the time period. Thus in some embodiments, aqueous culture medium is not flowed through the photobioreactor after inoculation.

In other instances culture media can be flowed though the photobioreactor throughout the time period during which the microalgae reproduce and increase in number. In some embodiments media is infused into the photobioreactor after inoculation but before the cells reach a desired density. In other words, a turbulent flow regime of gas entry and media entry is not maintained for reproduction of microalgae until a desired increase in number of said microalgae has been achieved.

Photobioreactors preferably have one or more ports that allow gas entry. Gas can serve to both provide nutrients such as $CO_2$ as well as to provide turbulence in the culture media. Turbulence can be achieved by placing a gas entry port below the level of the aqueous culture media so that gas entering the photobioreactor bubbles to the surface of the culture. One or more gas exit ports allow gas to escape, thereby preventing pressure buildup in the photobioreactor. Preferably a gas exit port leads to a "one-way" valve that prevents contaminating microorganisms from entering the photobioreactor. In some instances cells are cultured in a photobioreactor for a period of time during which the microalgae reproduce and increase in number, however a turbulent flow regime with turbulent eddies predominantly throughout the culture media caused by gas entry is not maintained for all of the period of time. In other instances a turbulent flow regime with turbulent eddies predominantly throughout the culture media caused by gas entry can be maintained for all of the period of time during which the microalgae reproduce and increase in number. In some instances a predetermined range of ratios between the scale of the photobioreactor and the scale of eddies is not maintained for the period of time during which the microalgae reproduce and increase in number. In other instances such a range can be maintained.

Photobioreactors preferably have at least one port that can be used for sampling the culture. Preferably a sampling port can be used repeatedly without altering compromising the axenic nature of the culture. A sampling port can be configured with a valve or other device that allows the flow of sample to be stopped and started. Alternatively a sampling port can allow continuous sampling. Photobioreactors preferably have at least one port that allows inoculation of a culture. Such a port can also be used for other purposes such as media or gas entry.

B. Heterotrophic Growth

As an alternative to photosynthetic growth of microorganisms, as described above, some microorganisms can be cultured under heterotrophic growth conditions in which a fixed carbon source provides energy for growth and lipid accumulation.

In one heterotrophic culture method in accordance with the invention, the cost of biodiesel production, crude, partially purified, or purified glycerol produced as a byproduct of lipid transesterification can be employed as a feedstock for fermenting, for example, lipid-producing microbial cultures. Thus, the invention encompasses culturing a microbe (e.g., a microalgae) in a first microbial culture; recovering microbial lipid from the culture; subjecting the microbial lipid to transesterification to produce fatty acid ester(s) and glycerol, as described above; and adding the glycerol to a second microbial culture as a feedstock. The first and second microbial cultures can, but need not, be cultures of the same microbe. If desired, a continuous system can be devised whereby glycerol produced from the lipid recovered from a culture can be fed back into the same culture.

The invention provides significantly improved culture parameters incorporating the use of glycerol for fermentation of multiple genera of both eukaryotic and prokaryotic microbes, including microbes of the genera *Chlorella, Navicula, Scenedesmus*, and *Spirulina*. As the Examples demonstrate, microbes of extremely divergent evolutionary lineages, including *Chlorella, Navicula, Scenedesmus*, and *Spirulina* as well as cultures of multiple distinct *Chlorella* species and strains grow very well on not only purified reagent-grade glycerol, but also on acidulated and non-acidulated glycerol byproduct from biodiesel transesterification. In some instances microalgae, such as *Chlorella* strains, undergo cell division faster in the presence of glycerol than in the presence of glucose. In these instances, two-stage growth processes in which cells are first fed glycerol to rapidly increase cell density, and are then fed glucose to accumulate lipids can improve the efficiency with which lipids are produced. The use of the glycerol byproduct of the transesterification process provides significant economic advantages when put back into the production process. Other feeding methods are provided as well, such as mixtures of glycerol and glucose. Feeding such mixtures also captures the same economic benefits. In addition, the invention provides methods of feeding alternative sugars to microalgae such as sucrose in various combinations with glycerol. These benefits provided by the invention have been demonstrated herein on microbes from extremely divergent evolutionary lineages, including both prokaryotes and eukaryotes, demonstrating the utility of the invention for microbial fermentation.

Standard methods for the growth and propagation of *Chlorella protothecoides* are known (see for example Miao and Wu, *J. Biotechnology*, 2004, 11:85-93 and Miao and Wu, *Biosource Technology* (2006) 97:841-846). The invention also provides novel growth conditions for *Chlorella*. For example, multiple species of *Chlorella* and multiple strains within a species can be grown in the presence of glycerol, including glycerol byproduct from biodiesel transesterification.

For hydrocarbon production, cells, including recombinant cells of the invention described herein, are preferably cultured or fermented in large quantities. The culturing may be in large liquid volumes, such as in suspension cultures as an example. Other examples include starting with a small culture of cells which expand into a large biomass in combination with cell growth and propagation as well as hydrocarbon production. Bioreactors or steel fermentors can be used to accommodate large culture volumes. A fermentor similar those used in the production of beer and/or wine is suitable, as are extremely large fermentors used in the production of ethanol.

Appropriate nutrient sources for culture in a fermentor are provided. These include raw materials such as one or more of the following: a fixed carbon source such as glucose, corn starch, depolymerized cellulosic material, sucrose, sugar cane, sugar beet, lactose, milk whey, or molasses; a fat source, such as fats or vegetable oils; a nitrogen source, such as protein, soybean meal, cornsteep liquor, ammonia (pure or in salt form), nitrate or nitrate salt, or molecular nitrogen; and a phosphorus source, such as phosphate salts. Additionally, a fermentor allows for the control of culture conditions such as temperature, pH, oxygen tension, and carbon dioxide levels. Optionally, gaseous components, like oxygen or nitrogen, can be bubbled through a liquid culture. Other Starch (glucose) sources such as wheat, potato, rice, and sorghum. Other carbon sources include process streams such as technical grade glycerol, black liquor, organic acids such as acetate, and molasses. Carbon sources can also be provided as a mixture, such as a mixture of sucrose and depolymerized sugar beet pulp.

A fermentor can be used to allow cells to undergo the various phases of their growth cycle. As an example, an inoculum of hydrocarbon-producing cells can be introduced into a medium followed by a lag period (lag phase) before the cells begin growth. Following the lag period, the growth rate increases steadily and enters the log, or exponential, phase. The exponential phase is in turn followed by a slowing of growth due to decreases in nutrients and/or increases in toxic substances. After this slowing, growth stops, and the cells enter a stationary phase or steady state, depending on the particular environment provided to the cells.

Hydrocarbon production by cells disclosed herein can occur during the log phase or thereafter, including the stationary phase wherein nutrients are supplied, or still available, to allow the continuation of hydrocarbon production in the absence of cell division.

Preferably, microorganisms grown using conditions described herein and known in the art comprise at least about 20% by weight of lipid, preferably at least about 40% by weight, more preferably at least about 50% by weight, and most preferably at least about 60% by weight.

A surprising discovery is that multiple species, and multiple strains within a species of *Chlorella* perform better in the presence of glycerol byproduct from transesterification than in an equivalent amount of reagent grade glycerol. Glycerol byproduct from transesterification usually contains residual methanol and other contaminants in addition to glycerol. For example, FIGS. 1-6 demonstrate that strains of *Chlorella protothecoides* and *Chlorella kessleri* exhibit better productivity on acidulated and non-acidulated glycerol byproduct from lipid transesterification reactions than when grown on pure reagent grade glycerol. Other microbes, such as *Scenedesmus* and *Navicula* microalgae can also perform better in the presence of glycerol byproduct from transesterification than in an equivalent amount of reagent grade glycerol.

Figure 2:
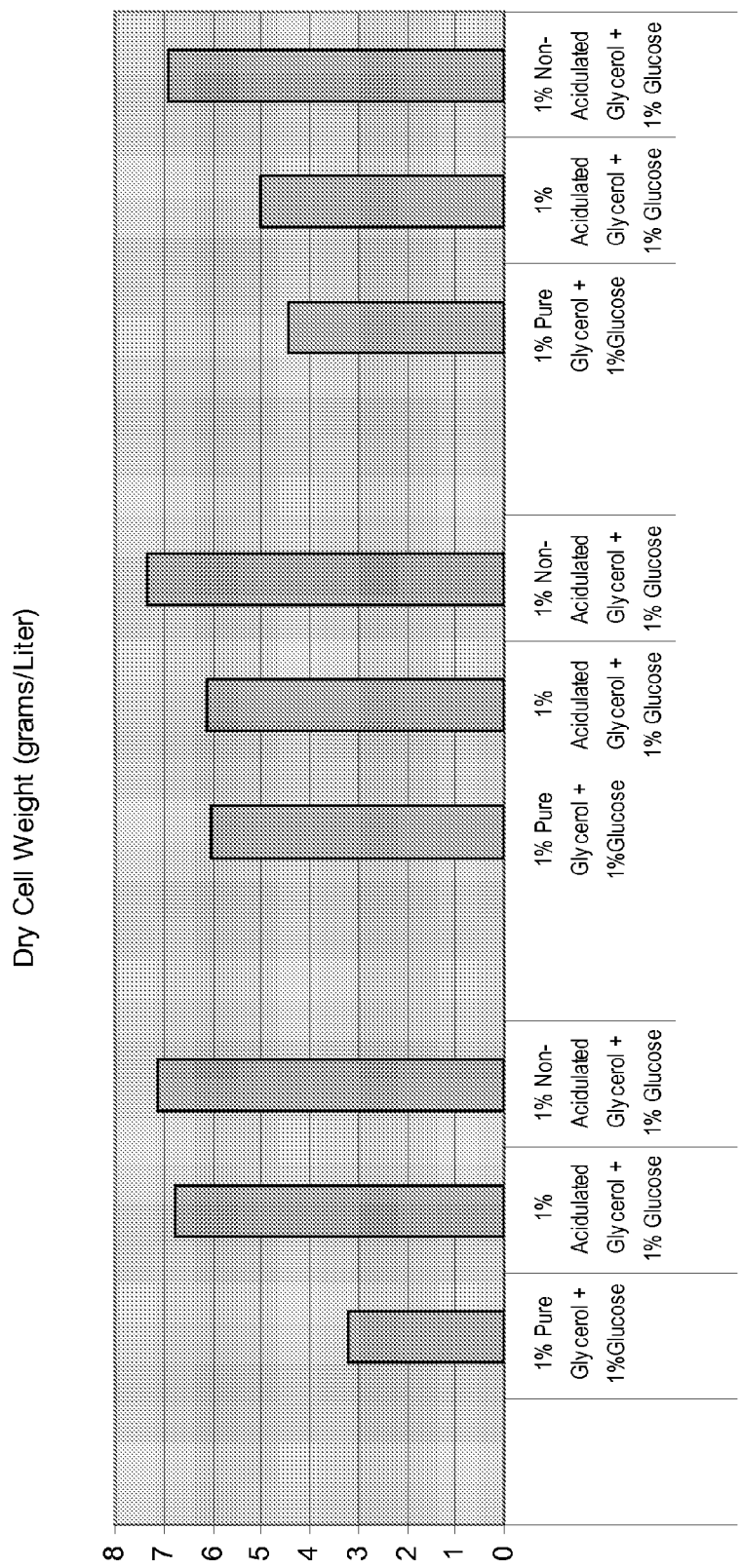
FIG. 2 shows dry cell weight per liter of multiple species and strains of *Chlorella* when cultured in the presence of various types of glycerol with additional glucose.
Figure 12:
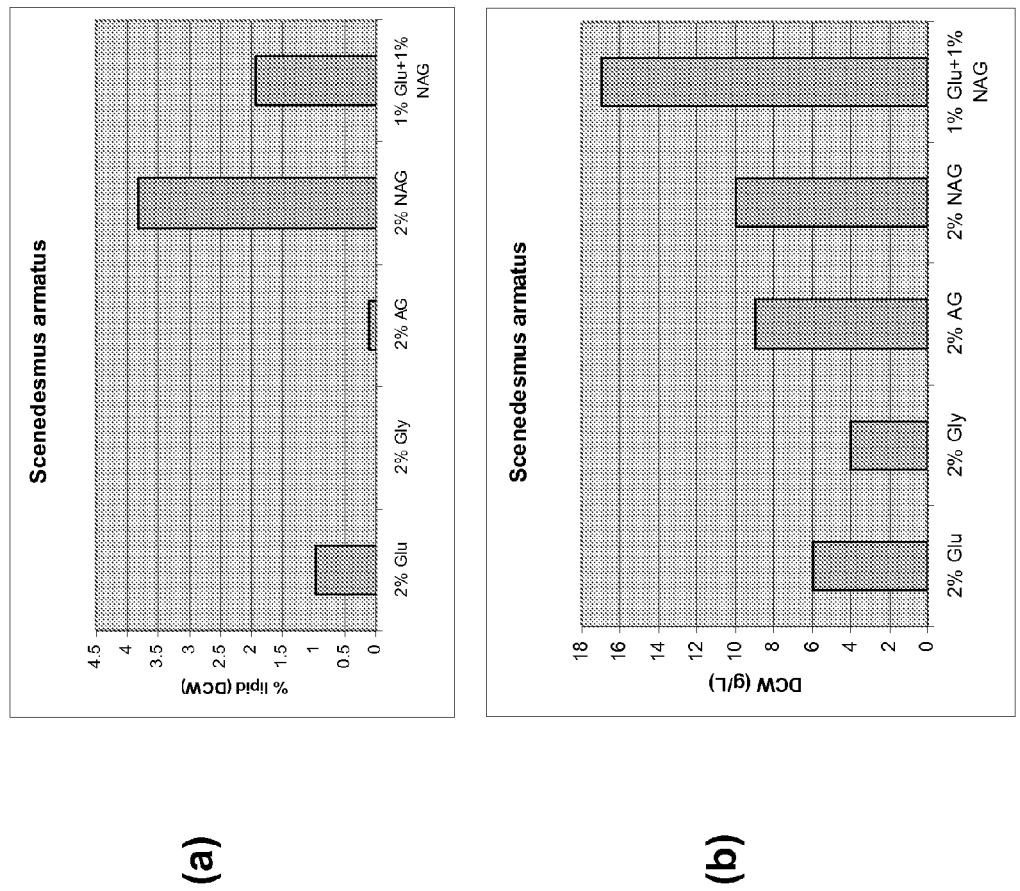
FIG. 12(*a*) shows lipid as a percent of dry cell weight of *Scenedesmus armatus* when cultured in the presence of various types of glycerol and in the presence of a combination of glycerol and glucose.
Figure 13:
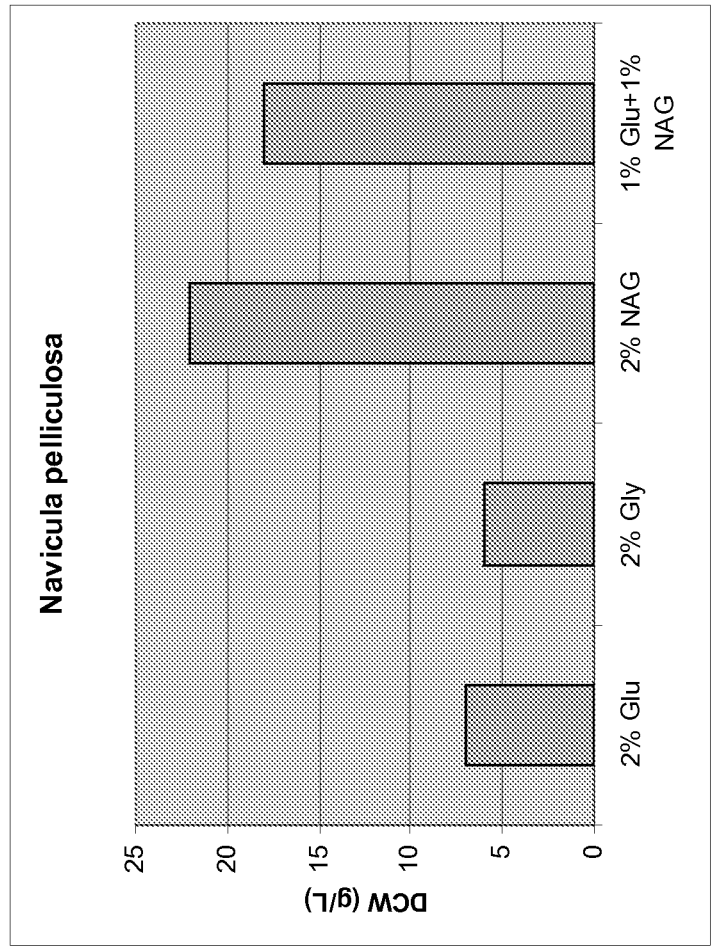
FIG. 13 shows dry cell weight per liter of *Navicula pelliculosa* when cultured in the presence of various types of glycerol and in the presence of a combination of non-acidulated biodiesel byproduct glycerol and glucose.

Dry Cell Weight per Liter: FIG. 1 demonstrates that dry cell weight was higher on biodiesel glycerol byproduct than on pure glycerol, and this trend held true when the cells were grown in glycerol by itself or in combination with glucose. FIG. 2 shows the same trends with additional strains of *Chlorella*. FIG. 12(*b*) demonstrates that dry cell weight per liter of *Scenedesmus armatus* is higher on acidulated and non-acidulated biodiesel byproducts glycerol than on pure reagent grade glycerol. FIG. 13 demonstrates that dry cell weight per liter of *Navicula pelliculosa* is higher on non-acidulated biodiesel byproduct glycerol than on pure reagent grade glycerol.

Figure 3:
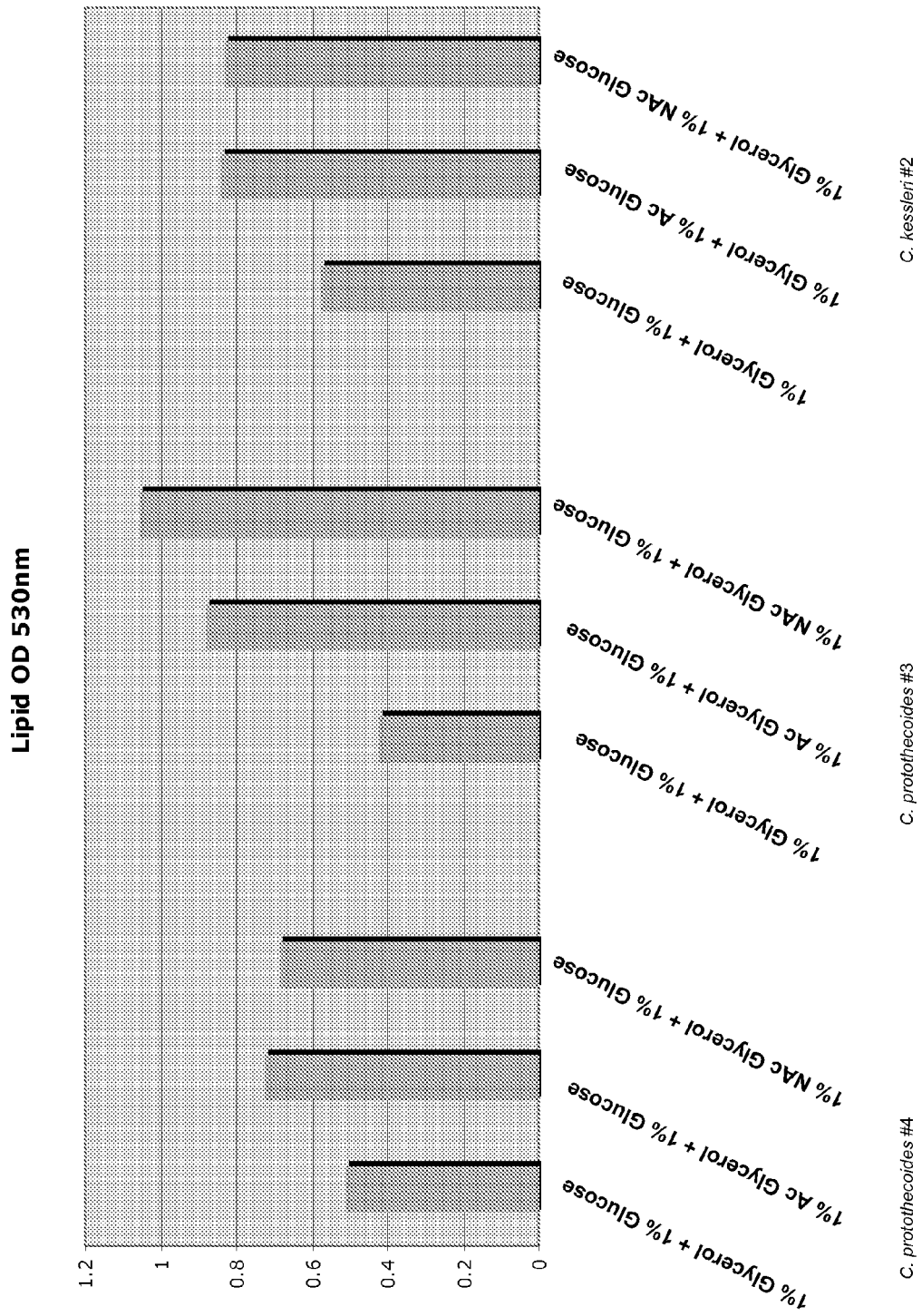
FIG. 3 shows relative lipid concentration of cultures of multiple species and strains of *Chlorella* when cultured in the presence of various types of glycerol with additional glucose.
Figure 4:
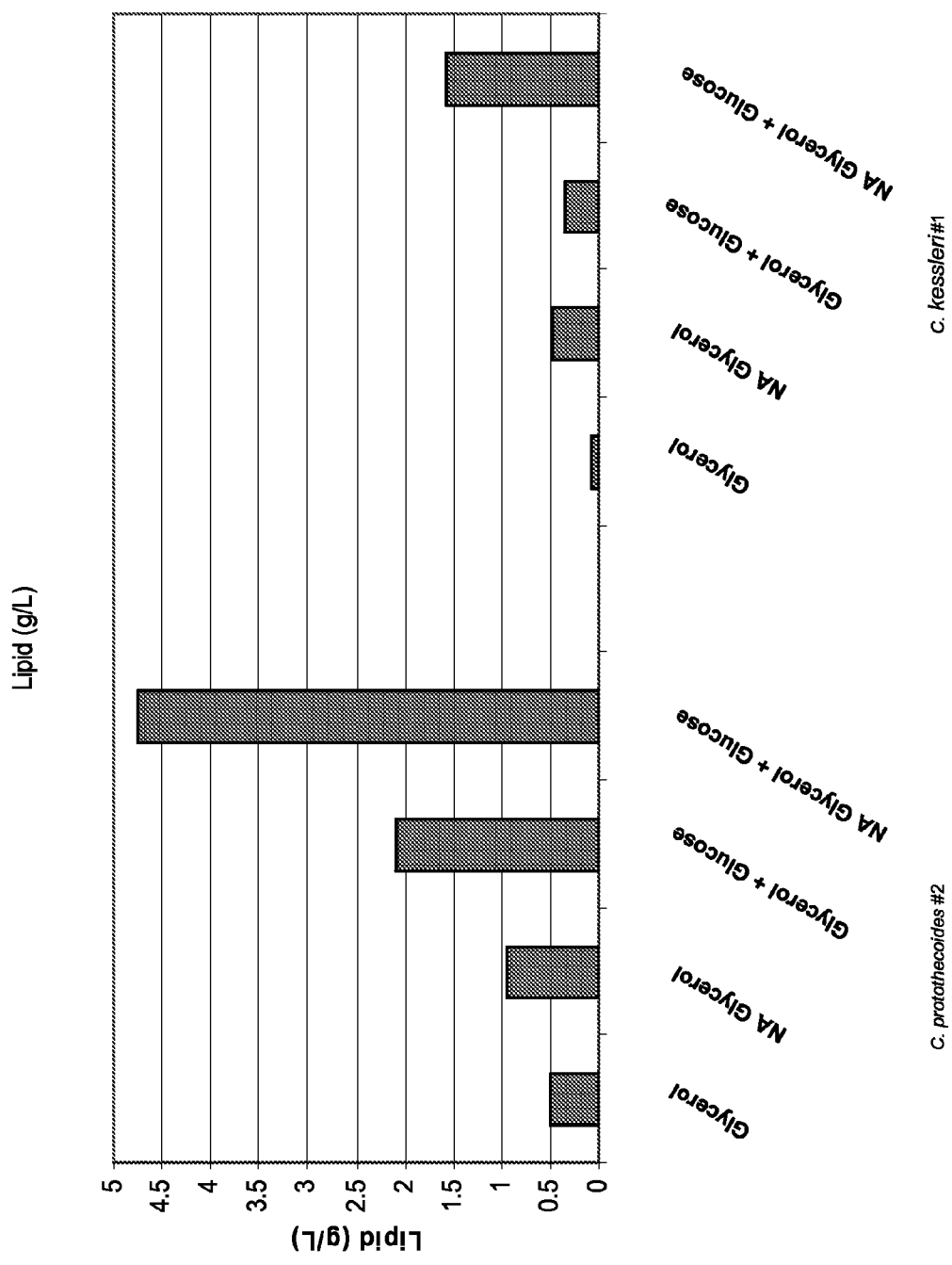
FIG. 4 shows lipid concentration of cultures of multiple species and strains of *Chlorella* when cultured in the presence of various types of glycerol with and without additional glucose.

Lipid Content per liter: FIGS. 3 and 4 demonstrates that with multiple species of *Chlorella* and multiple strains within a species of *Chlorella*, lipid levels per liter are higher when the cells are cultured in the presence of biodiesel glycerol byproduct than when cultured in the presence of equivalent concentrations of pure reagent grade glycerol.

Figure 5:
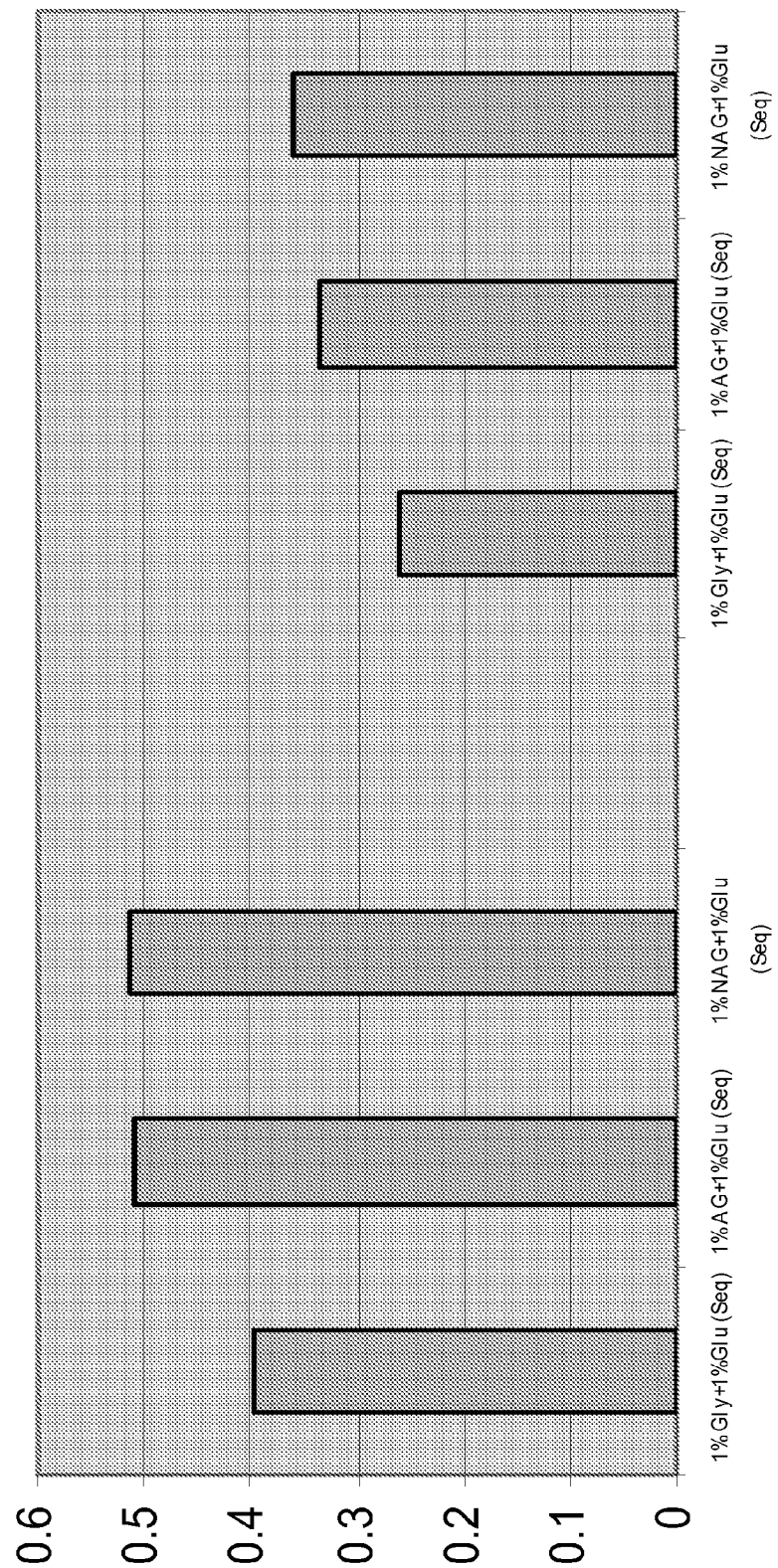
FIG. 5 shows lipid as a percent of dry cell weight of two species and strains of *Chlorella* when cultured in the presence of various types of glycerol with additional glucose, wherein glycerol is added sequentially after glucose.
Figure 6:
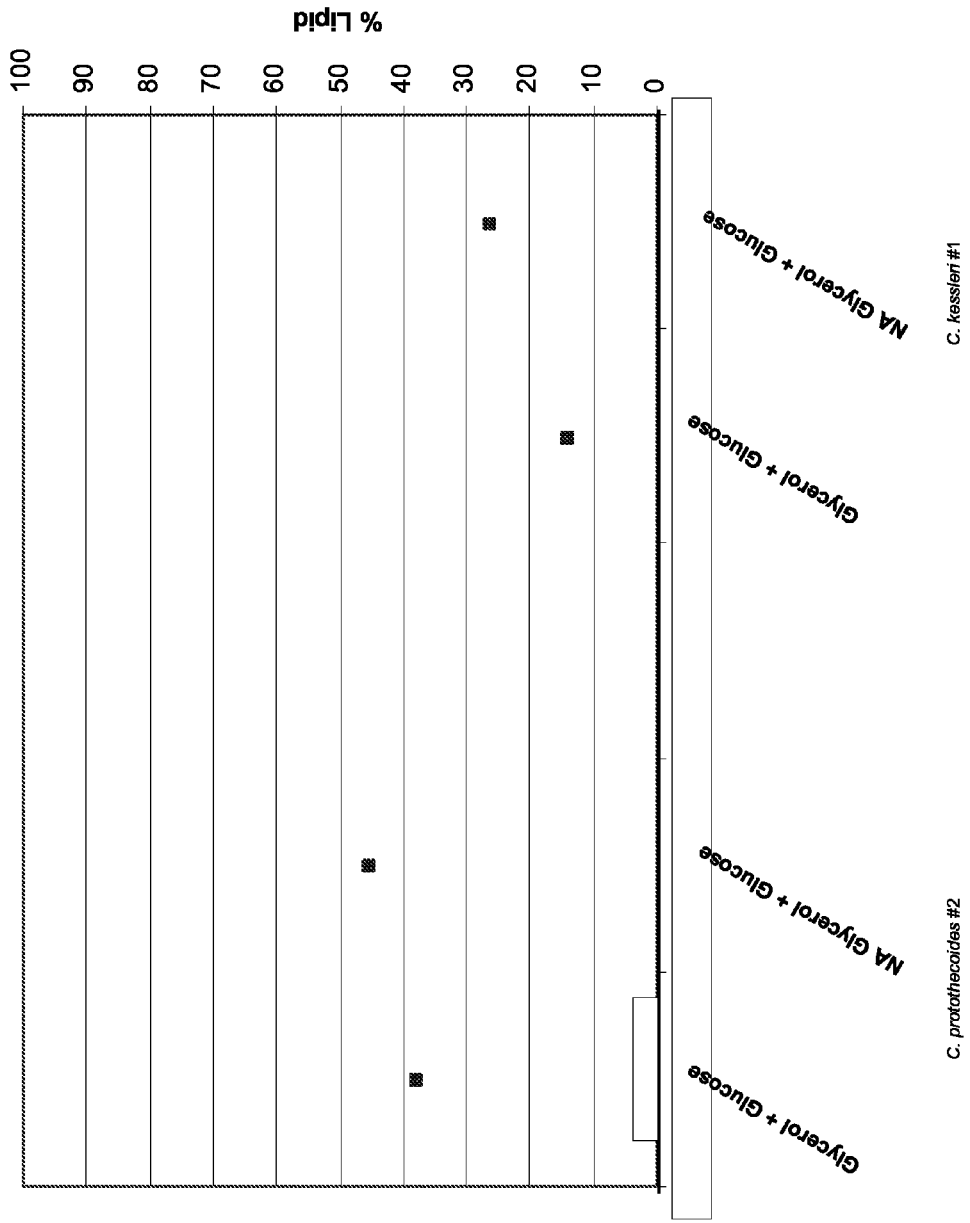
FIG. 6 shows lipid as a percent of dry cell weight of two species and strains of *Chlorella* when cultured in the presence of various types of glycerol with additional glucose.
Figure 11:
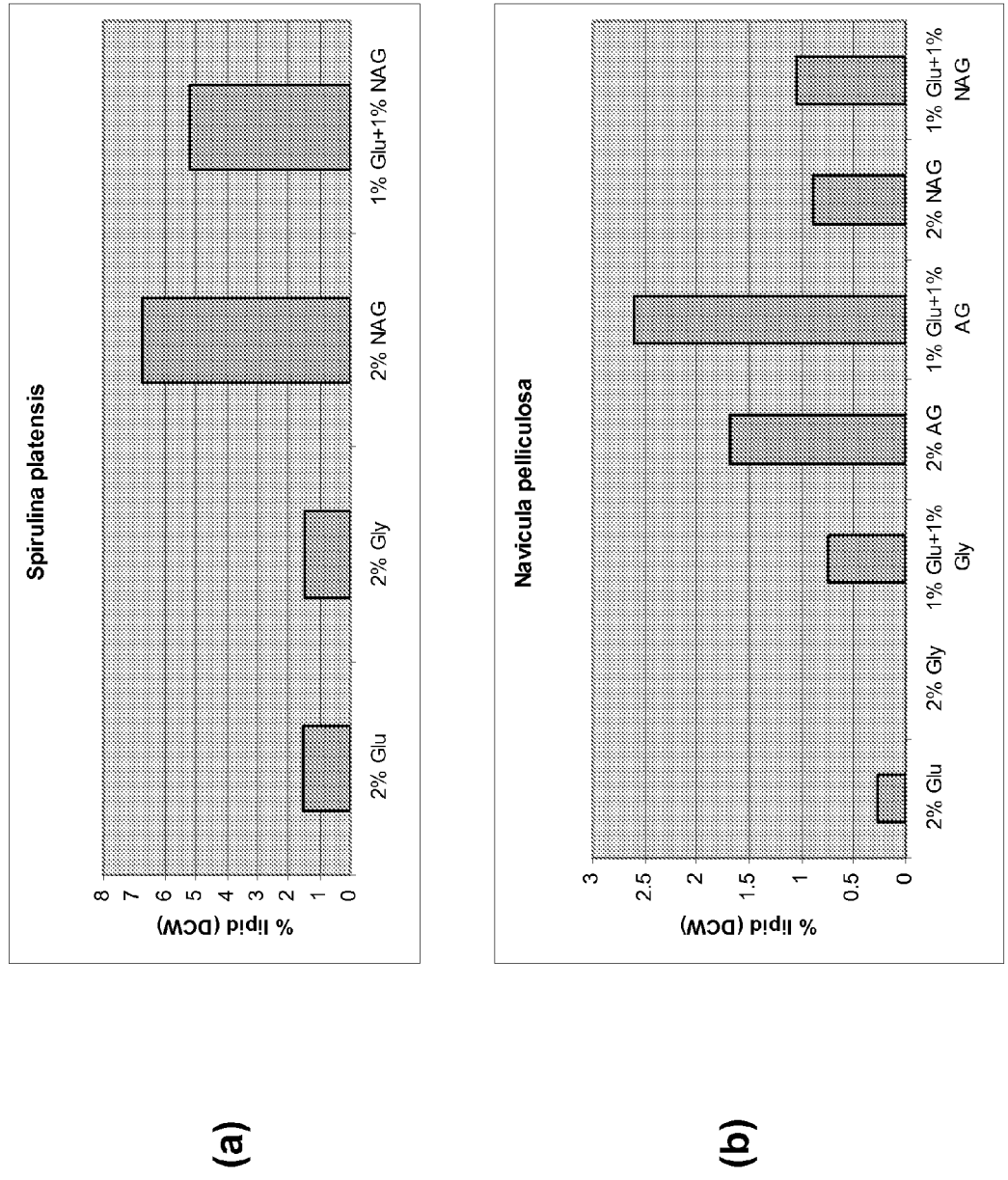
FIG. 11(*a*) shows lipid as a percent of dry cell weight of *Spirulina platensis* when cultured in the presence of glucose, reagent grade glycerol, non-acidulated biodiesel byproduct glycerol, and a combination of glycerol and glucose.

Lipid as a Percentage of Cell Weight: FIGS. 5 and 6 demonstrate that multiple species of *Chlorella* and multiple strains within a species of *Chlorella* accumulate a higher percentage of dry cell weight as lipid when cultured in the presence of biodiesel glycerol byproduct than when cultured in the presence of equivalent concentrations of pure reagent grade glycerol. FIG. 11 demonstrates that both *Spirulina platensis* and *Navicula pelliculosa* can accumulate a higher percentage of dry cell weight as lipid when cultured in the presence of biodiesel glycerol byproduct than when cultured in the presence of equivalent concentrations of pure reagent grade glycerol. FIG. 12(*a*) demonstrates that *Scenedesmus armatus* can accumulate a higher percentage of dry cell weight as lipid when cultured in the presence of biodiesel glycerol byproduct than when cultured in the presence of equivalent concentrations of pure reagent grade glycerol.

Another surprising result is that multiple species of microbes, including microalgae such as *Chlorella* and multiple strains within a species of *Chlorella*, and other microalgae such as *Scenedesmus, Navicula,* and *Spirulina* exhibit better characteristics as biodiesel producers in the presence of mixtures of glycerol and glucose than in the presence of only glucose.

Figure 7:
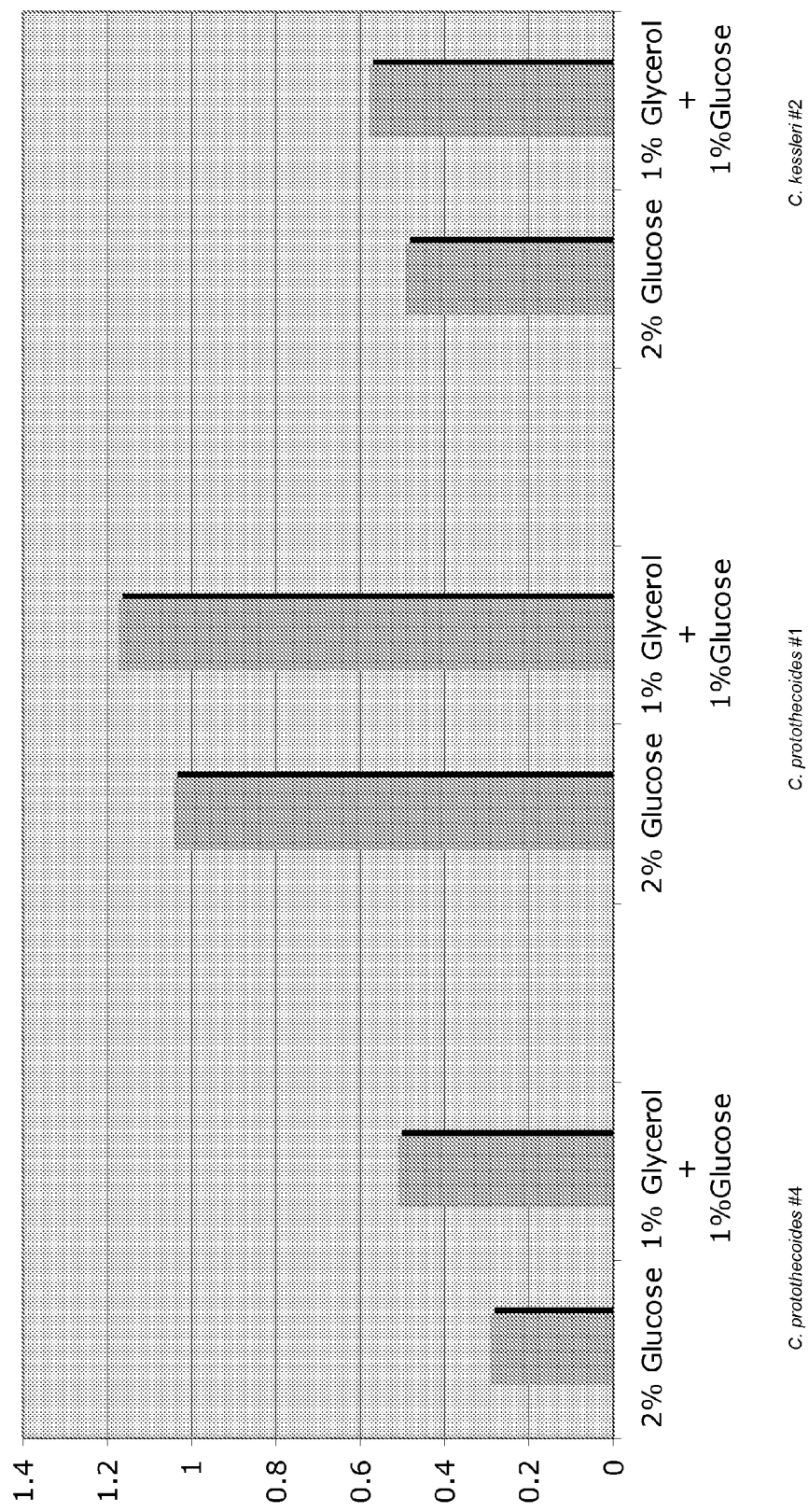
FIG. 7 shows relative lipid concentration of cultures of multiple species and strains of *Chlorella* when cultured in the presence of 2% glucose and 1% glucose+1% reagent grade glycerol.

Lipid Content per liter: FIG. 7 demonstrates that *Chlorella* can accumulate higher levels of lipid per liter of culture in the presence of 1% glycerol/1% glucose than in the presence of 2% glucose.

Dry Cell Weight per Liter: FIG. 12(b) demonstrates that dry cell weight per liter of *Scenedesmus armatus* is higher when cultured in the presence of 1% biodiesel byproduct glycerol/1% glucose than in the presence of 2% glucose. FIG. 13 demonstrates that dry cell weight per liter of *Navicula pelliculosa* is higher when cultured in the presence of 1% biodiesel byproduct glycerol/1% glucose than in the presence of 2% glucose.

Figure 8:
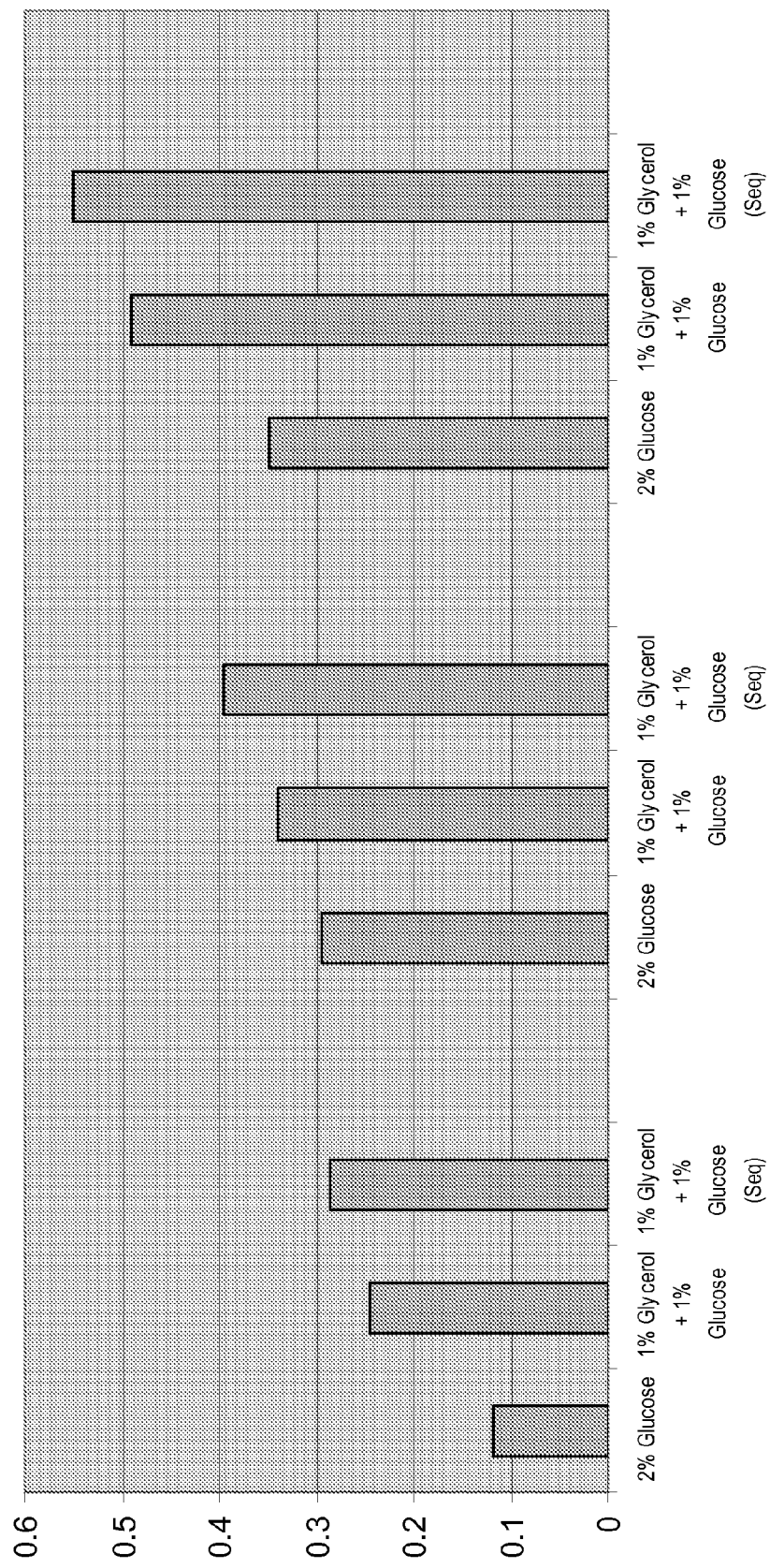
FIG. 8 shows lipid as a percent of dry cell weight of multiple species and strains of *Chlorella* when cultured in the presence of glucose with and without reagent grade glycerol, wherein glycerol is added sequentially or in combination with glucose.

Lipid as a Percentage of Cell Weight: FIG. 8 demonstrates that *Chlorella* can accumulate a higher percentage of dry cell weight as lipid when cultured in the presence of an equal concentration (weight percent) mixture of glycerol and glucose than when cultured in the presence of only glucose. FIG. 11(a) demonstrates that *Spirulina platensis* can accumulate a higher percentage of dry cell weight as lipid when cultured in the presence of an equal concentration (weight percent) mixture of biodiesel byproduct glycerol and glucose than when cultured in the presence of only glucose. FIG. 11(b) demonstrates that *Navicula pelliculosa* can accumulate a higher percentage of dry cell weight as lipid when cultured in the presence of an equal concentration (weight percent) mixture of reagent grade glycerol and glucose, as well as biodiesel byproduct glycerol and glucose, than when cultured in the presence of only glucose. FIG. 12(b) demonstrates that *Scenedesmus armatus* can accumulate a higher percentage of dry cell weight as lipid when cultured in the presence of an equal concentration (weight percent) mixture of biodiesel byproduct glycerol and glucose than when cultured in the presence of only glucose.

An additional and unexpected discovery is that adding glycerol and glucose to microbes, including microalgae such as *Chlorella, Scenedesmus*, and *Navicula* sequentially rather than as a single batch mixture of glycerol and glucose can generate additional yield gains. This attribute of multiple species of *Chlorella* and multiple strains within a species of *Chlorella* was tested in the presence of both biodiesel glycerol byproduct and reagent grade glycerol.

Lipid as a Percentage of Cell Weight: FIG. 8 demonstrates that *Chlorella* can accumulate a higher percentage of dry cell weight as lipid when glycerol is added to a culture for a first period of time, followed by addition of glucose and continued culturing for a second period of time, than when the same quantities of glycerol and glucose are added together at the beginning of the experiment.

Figure 9:
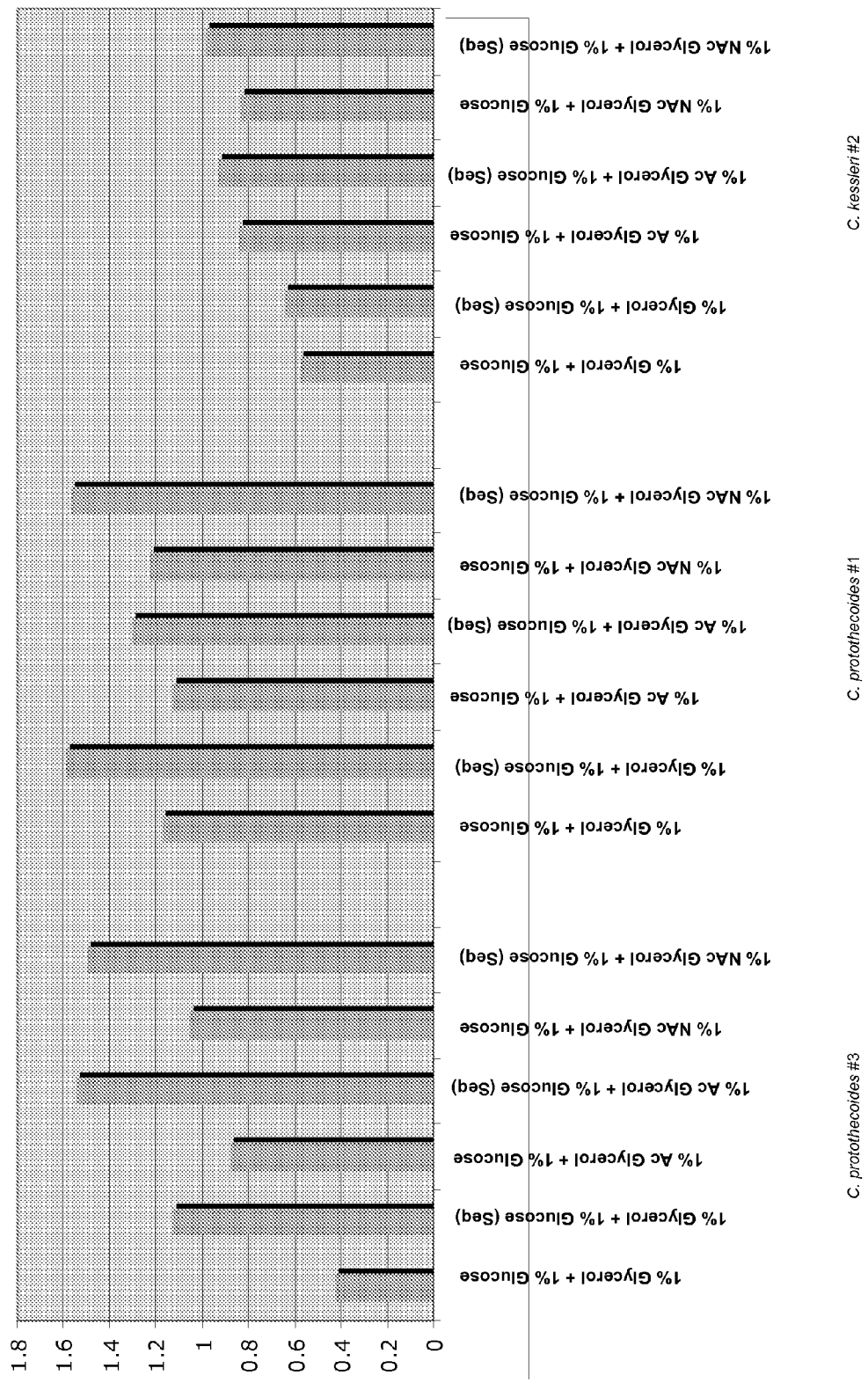
FIG. 9 shows relative lipid concentration of cultures of multiple species and strains of *Chlorella* when cultured in the presence of various types of glycerol with additional glucose, wherein glycerol is added sequentially or in combination with glucose.

Lipid Content per liter: FIG. 9 shows *Chlorella* exhibiting higher levels of lipid per liter of culture in when glycerol and glucose are added sequentially than when the same quantities of glycerol and glucose are added together at the beginning of the experiment. This trend was observed when acidulated biodiesel byproduct glycerol, non-acidulated biodiesel byproduct glycerol, or reagent grade glycerol was used.

Figure 10:
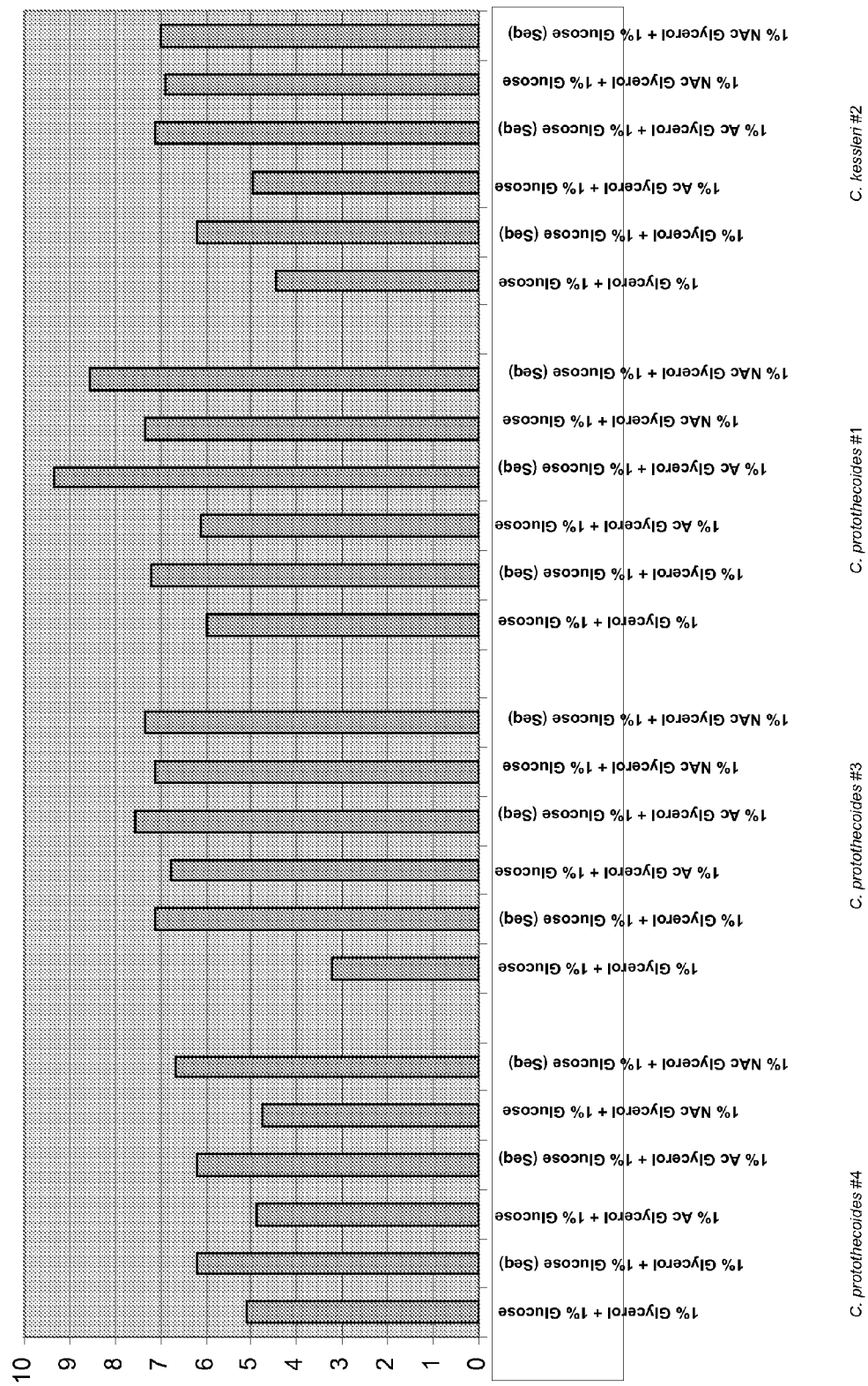
FIG. 10 shows dry cell weight per liter of multiple species and strains of *Chlorella* when cultured in the presence of various types of glycerol with additional glucose, wherein glycerol is added sequentially or in combination with glucose.

Dry Cell Weight per Liter: FIG. 10 demonstrates four different strains of *Chlorella* of two different species accumulating higher dry cell weight per liter of culture when glycerol and glucose are added sequentially than when the same quantities of glycerol and glucose are added together at the beginning of the experiment. This trend was observed when acidulated biodiesel byproduct glycerol, non-acidulated biodiesel byproduct glycerol, or reagent grade glycerol was used. FIGS. 14(a) and (b) demonstrates that both *Scenedesmus armatus* and *Navicula pelliculosa* can exhibit increases in dry cell weight per liter when biodiesel byproduct glycerol only is added to a culture for a first period of time, followed later by addition of glucose, compared to adding identical amounts of glycerol and glucose at the beginning of the fermentation.

Three different markers of productivity (dry cell weight per liter, grams per liter of lipid, and percentage of dry cell weight as lipid) in microbial lipid production are improved by the use of biodiesel byproduct and temporal separation of carbon sources. The invention therefore provides novel methods of generating higher quantities of lipid per unit time in multiple species of microbes from highly divergent areas of the evolutionary tree, including both prokaryotes and eukaryotes. The methods of manufacturing lipids and hydrocarbons disclosed herein using glycerol are not limited to microalgae, but can be used with any microbe capable of utilizing glycerol as an energy source.

In an alternate heterotrophic growth method in accordance with the present invention, microorganisms can be cultured using depolymerized cellulosic biomass as a feedstock. Cellulosic biomass (e.g., stover, such as corn stover) is inexpensive and readily available; however, attempts to use this material as a feedstock for yeast have failed. In particular, such feedstock have been found to be inhibitory to yeast growth, and yeast cannot use the 5-carbon sugars produced from cellulosic materials (e.g., xylose from hemi-cellulose). By contrast, microalgae can grow on processed cellulosic material. Accordingly, the invention provides a method of culturing a microalgae in the presence of a cellulosic material and/or a 5-carbon sugar. Cellulosic materials generally include:

| Component | Percent Dry Weight |
| --- | --- |
| Cellulose | 40-60% |
| Hemicellulose | 20-40% |
| Lignin | 10-30% |

Suitable cellulosic materials include residues from herbaceous and woody energy crops, as well as agricultural crops, i.e., the plant parts, primarily stalks and leaves, not removed from the fields with the primary food or fiber product. Examples include agricultural wastes such as sugarcane bagasse, rice hulls, corn fiber (including stalks, leaves, husks, and cobs), wheat straw, rice straw, sugar beet pulp, citrus pulp, citrus peels; forestry wastes such as hardwood and softwood thinnings, and hardwood and softwood residues from timber operations; wood wastes such as saw mill wastes (wood chips, sawdust) and pulp mill waste; urban wastes such as paper fractions of municipal solid waste, urban wood waste and urban green waste such as municipal grass clippings; and wood construction waste. Additional cellulosics include dedicated cellulosic crops such as switchgrass, hybrid poplar wood, and miscanthus, fiber cane, and fiber sorghum. Five-carbon sugars that are produced from such materials include xylose.

Figure 15:
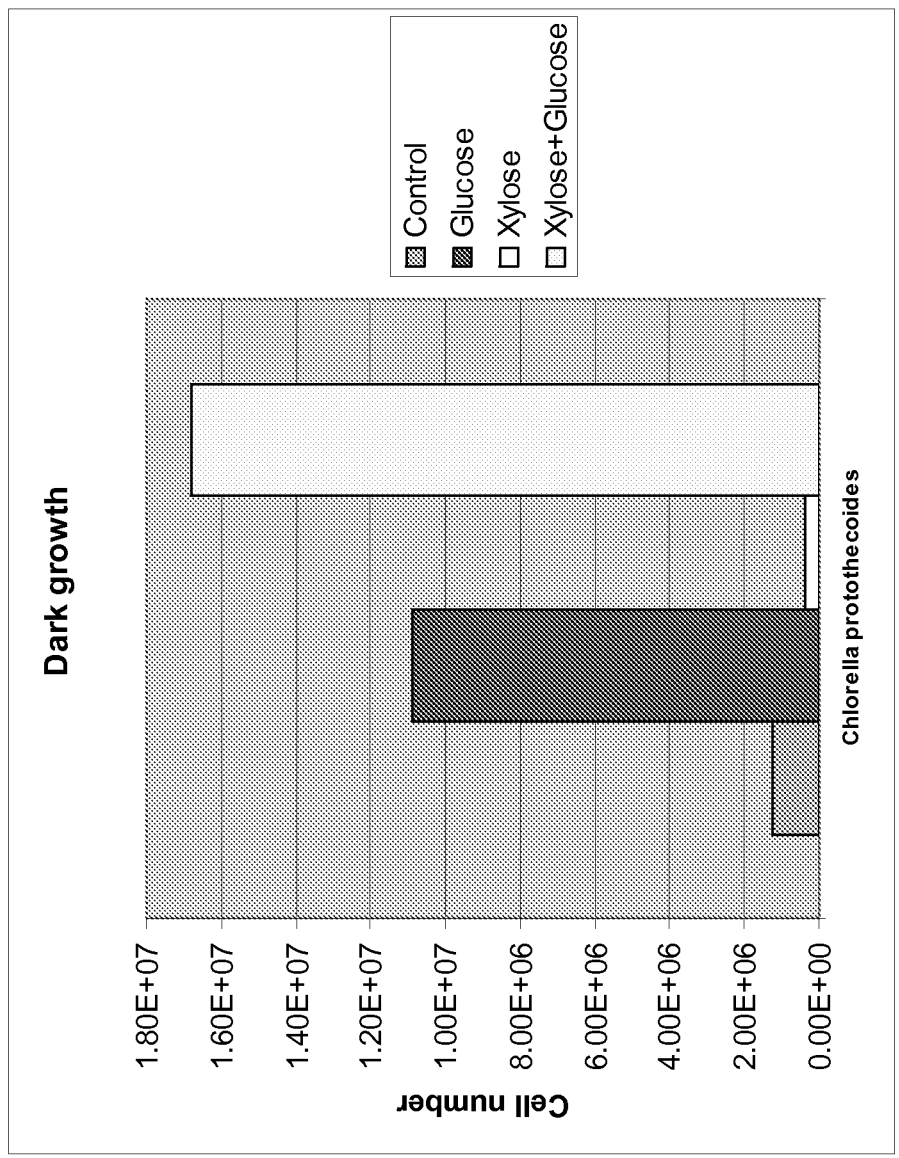
FIG. 15 shows a synergistic effect of a combination of xylose and glucose on growth of *Chlorella* compared to xylose or glucose alone.

Surprisingly, some species of *Chlorella* have been shown herein to exhibit higher levels of productivity when cultured on a combination of glucose and xylose than when cultured on either glucose or xylose alone. This synergistic effect provides a significant advantage in that it allows cultivation of *Chlorella* on combinations of xylose and glucose, such as cellulosic material, and is shown in FIG. 15.

In still another alternative heterotrophic growth method in accordance with the present invention, which itself may optionally be used in combination with the methods described above, sucrose, produced by example from sugar cane or sugar beet, is used as a feedstock. As described in greater detail in the section entitled "Microbe Engineering" below, lipid production can be facilitated or made more efficient through the engineering of microbes such as *Chlorella*, to utilize sucrose as a carbon source. For example, expression of a sucrose transporter and a sucrose invertase allows *Chlorella* to transport sucrose into the cell from the culture media and hydrolyze sucrose to yield glucose and fructose. Optionally, a fructokinase can be expressed as well in instances where endogenous hexokinase activity is insufficient for maximum phosphorylation of fructose. Examples of suitable sucrose transporters are Genbank accession numbers CAD91334, CAB92307, and CAA53390. Examples of suitable sucrose invertases are Genbank accession numbers CAB95010, NP_012104 and CAA06839. Examples of suitable fructokinases are Genbank accession numbers P26984, P26420 and CAA43322. Vectors for transformation of microalgae, including *Chlorella*, encoding one or more of such genes can be designed as described herein.

Secretion of a sucrose invertase can obviate the need for expression of a transporter that can transport sucrose into the cell. This is because a secreted invertase catalyzes the conversion of a molecule of sucrose into a molecule of glucose and a molecule of fructose, both of which can be transported and utilized by microbes disclosed herein. For example, expression of a sucrose invertase (such as SEQ ID NO:14) with a secretion signal (such as that of SEQ ID NO:15 (from yeast), SEQ ID NO:16 (from higher plants), SEQ ID NO:17 (eukaryotic consensus secretion signal), and SEQ ID NO:18 (combination of signal sequence from higher plants and eukaryotic consensus) generates invertase activity outside the cell. See Hawkins et al., Current Microbiology Vol. 38 (1999), pp. 335-341 for examples of secretion signals active in *Chlorella*. Expression of such a protein, as enabled by the genetic engineering methodology disclosed herein, allows cells already capable of utilizing extracellular glucose as an energy source to utilize sucrose as an extracellular energy source. In cells such as *Chlorella protothecoides, Chlorella minutissima*, and *Chlorella emersonii* which as demonstrated herein can use both extracellular fructose and extracellular glucose as an energy source, secretion of an invertase can provide the sole catalytic activity necessary for use of sucrose as an efficient, inexpensive energy source.

Figure 25:
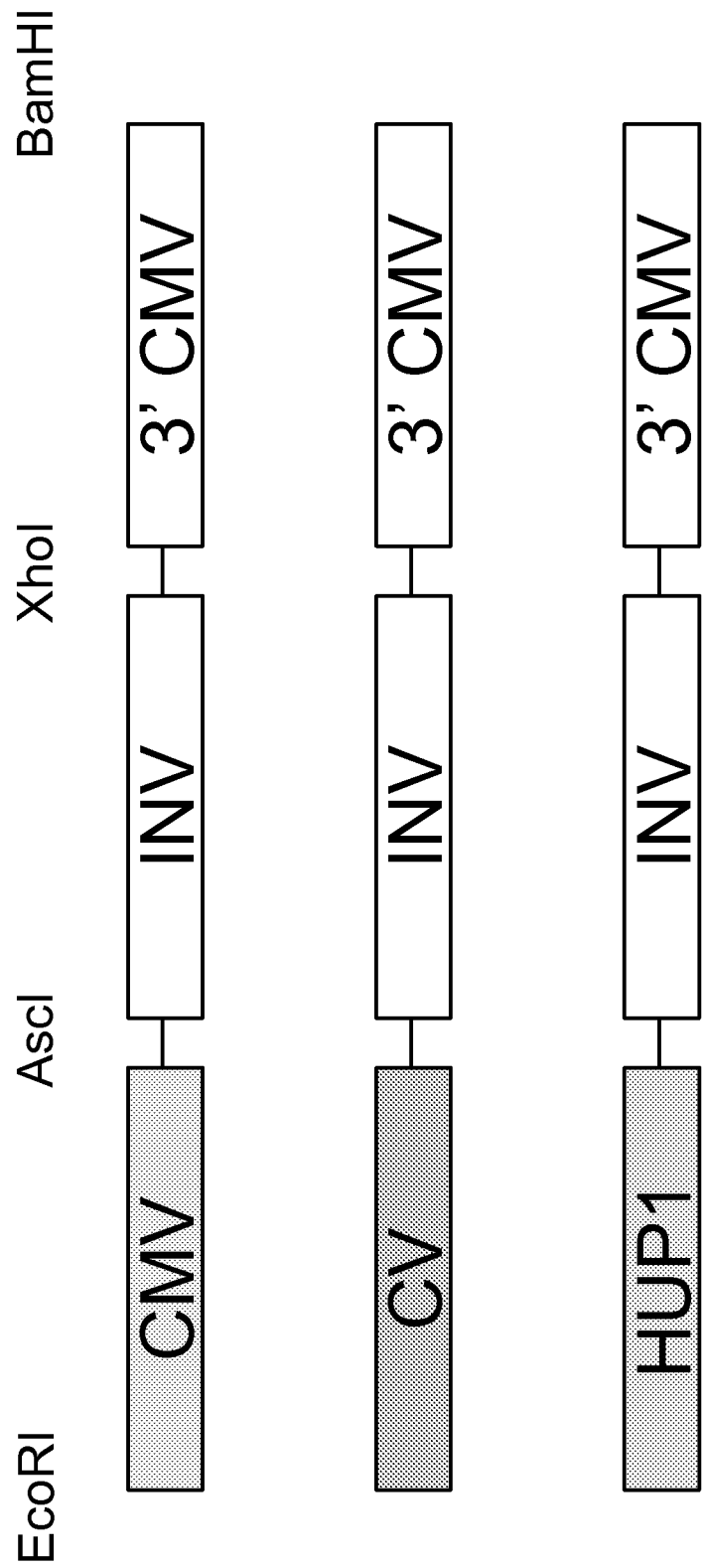
FIG. 25 shows an illustration of various plasmid constructs of yeast invertase (SUC2) with three different promoters (designated CMV, CV and HUP1) as well as restriction sites useful for subcloning.
Figure 26:
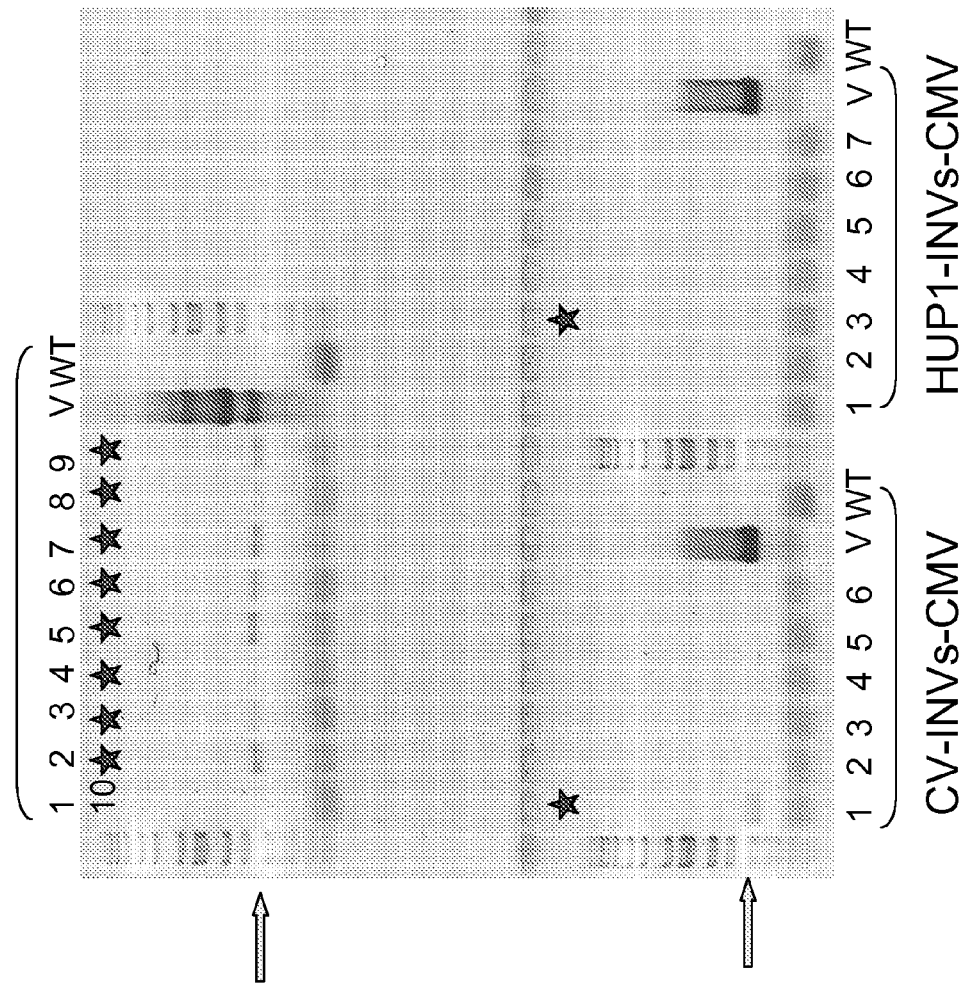
FIG. 26 shows genotyping of *Chlorella protothecoides* transformants selected on sucrose in the dark containing an exogenous sucrose invertase gene.

For example, as shown in FIG. 26, *Chlorella protothecoides* can be engineered with a sucrose invertase gene under the regulatory control of one of three promoters (Cauliflower mosaic virus 35S promoter (CMV), *Chlorella* virus promoter (CV), or *Chlorella* HUP1 promoter (HUP1)). The sucrose invertase gene used in this example comprises a modification to the S. cerevisiae SUC2 gene to optimize for *C. protothecoides* codon usage. The cDNA and amino acid sequences of the optimized gene correspond to SEQ ID NO:8 and SEQ ID NO:19, respectively. An illustration of the plasmid constructs used in the transformation is shown in FIG. 25. Expression of a secretable sucrose invertase, such as that described herein, permits the use of molasses, sugar cane juice, and other sucrose-containing feedstocks for cell fermentation.

Similarly, FIGS. 27 and 28 show the results of transformation of *Chlorella protothecoides*, and *Chlorella minutissima* and *Chlorella emersonii*, respectively, with the sucrose invertase gene from *S. cerevisiae* under the control of the CMV promoter.

Figure 23:
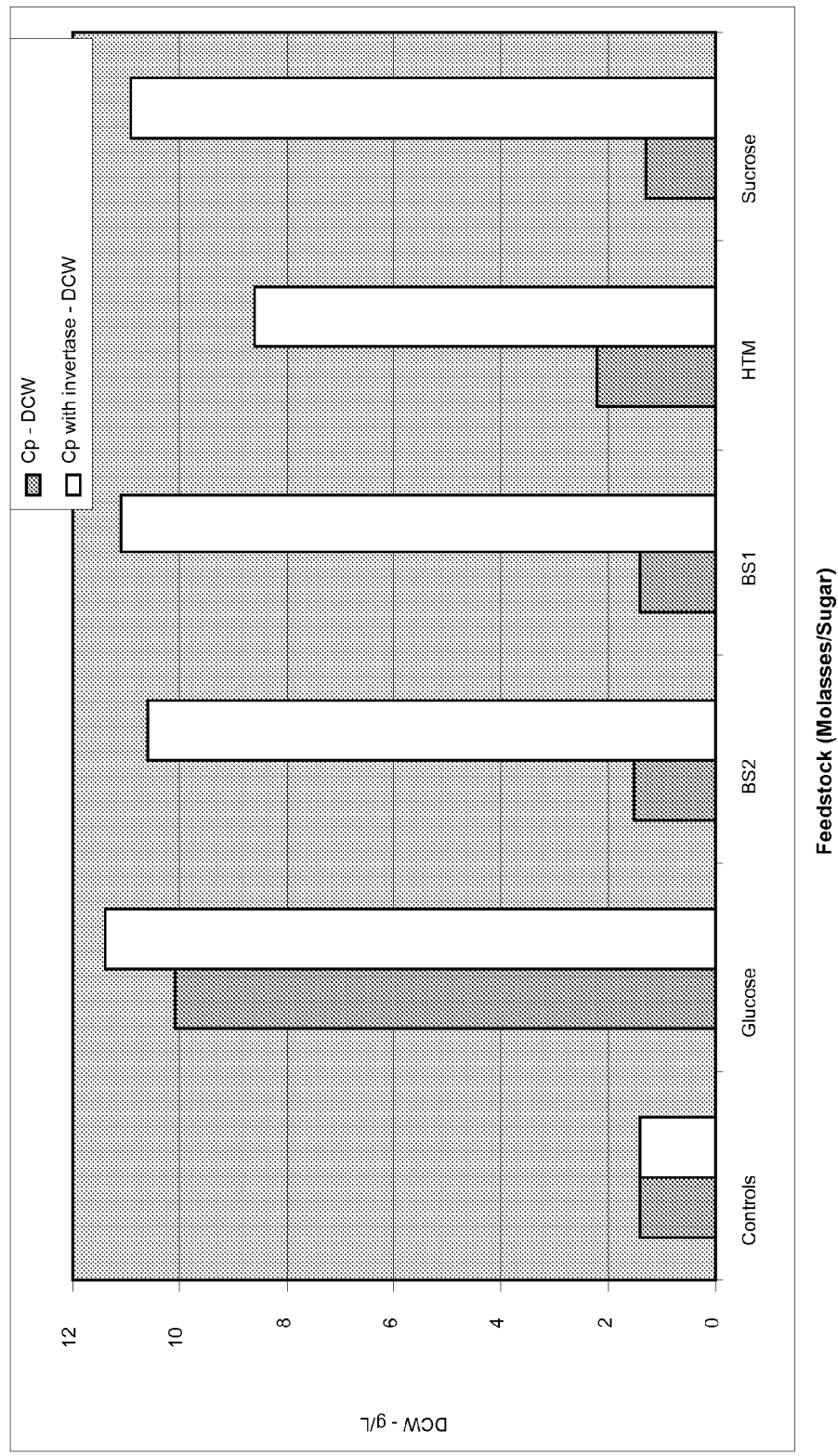
FIG. 23 shows dry cell weight per liter of *Chlorella protothecoides* when cultured in the presence of glucose, sucrose, or one of several molasses samples (designated BS1, BS2 and HTM) in the presence or absence of a sucrose invertase.
Figure 24:
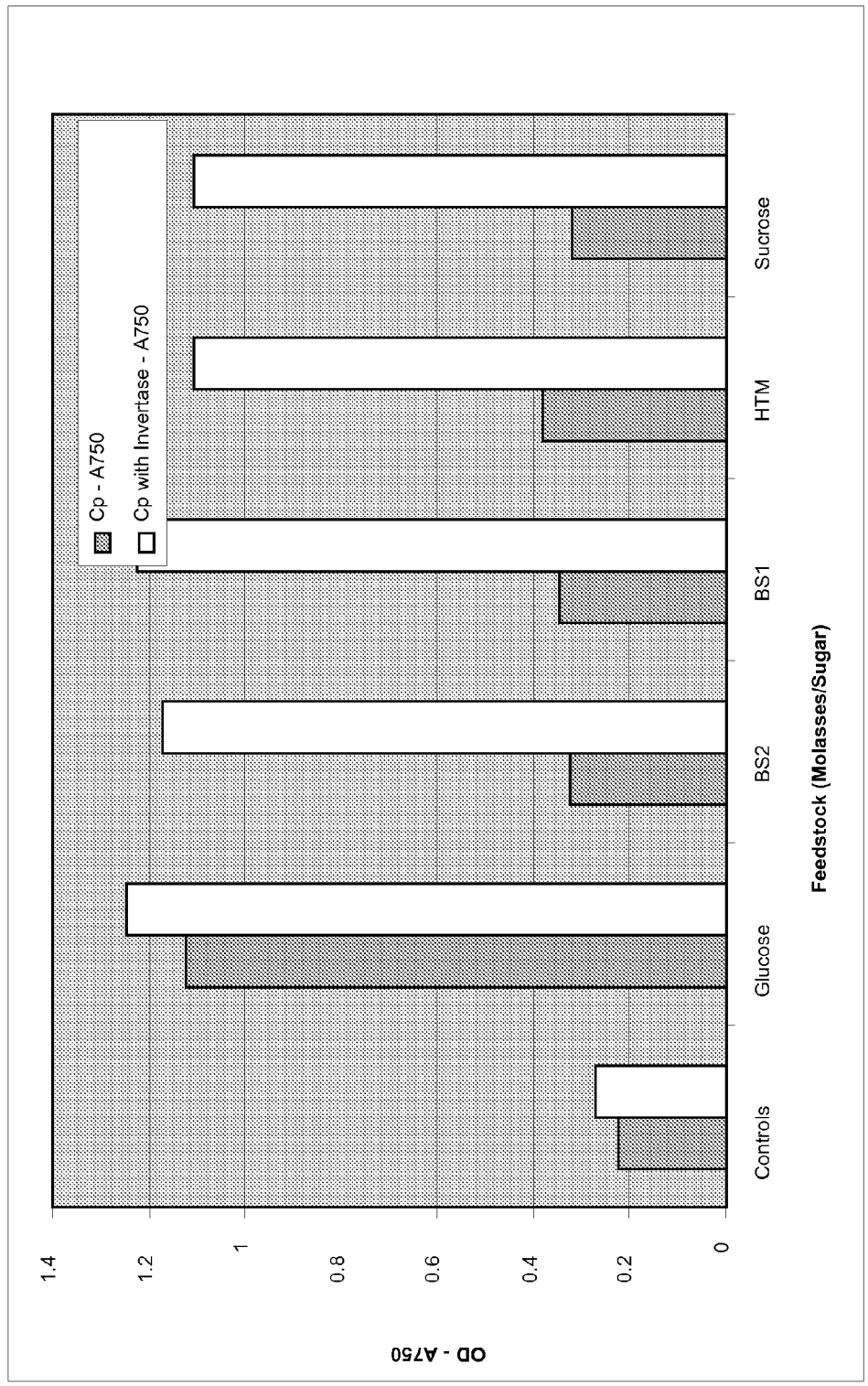
FIG. 24 shows growth of *Chlorella protothecoides* when cultured in the presence of glucose, sucrose, or one of several molasses samples (designated BS1, BS2 and HTM) in the presence or absence of a sucrose invertase as measured by relative cell density.

The growth potential of microorganisms expressing an exogenous secretable sucrose invertase is illustrated by the addition of an invertase to the culture medium of *Chlorella protothecoides*, as described in further detail in the Examples. FIGS. 23 and 24 illustrate the surprising result that *Chlorella* cells grow as well on waste molasses from sugar cane processing as they do on pure reagent-grade glucose; the use of this low-value waste product of sugar cane processing can provide significant cost savings in the production of hydrocarbons and other oils. Molasses contains lignin and other cellulosic waste products that poison many microorganisms and retard their growth, however it was discovered that *Chlorella* cells thrive in the presence of such poisons. FIGS. 23-24 show the growth of cells on three unique sources of molasses (designated BS1, BS2 and HTM), as compared to growth on glucose or sucrose in the presence or absence of an extracellular sucrose invertase.

Alternatively, a sucrose invertase can also be expressed intracellularly in cells that express a sucrose transporter, as well as in cells that express any carbohydrate transporter that allows sucrose to enter the cell.

A foreign gene was transformed into and expressed in *Chlorella protothecoides*, as described in Example 12. Expression of sucrose utilization genes can be accomplished using the same or similar methodology and vector design.

Bioreactors can be employed for use in heterotrophic growth methods. As will be appreciated, provisions made to make light available to the cells in photosynthetic growth methods are unnecessary when using a fixed-carbon source in the heterotrophic growth methods described herein.

The specific examples of process conditions and heterotrophic growth methods described herein can be combined in any suitable manner to improve efficiencies of microbial growth and lipid production. In addition, the invention includes the selection and/or genetic engineering of microbes, such as microalgae, to produce microbes that are even more suitable for use in the above-described methods. For example, the microbes having a greater ability to utilize any of the above-described feedstocks for increased proliferation and/or lipid (e.g., fatty acid) production are within the scope of the invention.

C. Mixotrophic Growth

Mixotrophic growth is the use of both light and fixed carbon source(s) as energy sources for cells to grow and produce hydrocarbons. Mixotrophic growth can be conducted in a photobioreactor. Microalgae can be grown and maintained in closed photobioreactors made of different types of transparent or semitransparent material. Such material can include Plexiglas® enclosures, glass enclosures, bags made from substances such as polyethylene, transparent or semitransparent pipes, and other materials. Microalgae can be grown and Maintained in open photobioreactors such as raceway ponds, settling ponds, and other non-enclosed containers.

D. Growth Media

Microorganisms useful in accordance with the methods of the present invention are found in various locations and environments throughout the world. As a consequence of their isolation from other species and their resulting evolutionary divergence, the particular growth medium for optimal growth and generation of lipid and/or hydrocarbon constituents can be difficult to predict. In some cases, certain strains of microorganisms may be unable to grow on a particular growth medium because of the presence of some inhibitory component or the absence of some essential nutritional requirement required by the particular strain of microorganism.

Solid and liquid growth media are generally available from a wide variety of sources, and instructions for the preparation of particular media that is suitable for a wide variety of strains of microorganisms can be found, for example, online at http://www.utex.org/, a site maintained by the University of Texas at Austin for its culture collection of algae (UTEX). For example, various fresh water and salt water media include those shown in Table 4, below.

TABLE 4

Exemplary Algal Media.

| Fresh Water Media | Salt Water Media |
|---|---|
| ½ CHEV Diatom Medium | 1% F/2 |
| ⅓ CHEV Diatom Medium | ½ Enriched Seawater Medium |
| ⅕ CHEV Diatom Medium | ½ Erdschreiber Medium |
| 1:1 DYIII/PEA + Gr+ | ½ Soil + Seawater Medium |
| ⅔ CHEV Diatom Medium | ⅓ Soil + Seawater Medium |
| 2X CHEV Diatom Medium | ¼ ERD |
| Ag Diatom Medium | ¼ Soil + Seawater Medium |
| Allen Medium | ⅕ Soil + Seawater Medium |
| BG11-1 Medium | ⅔ Enriched Sewater Medium |
| Bold 1NV Medium | 20% Allen + 80% ERD |
| Bold 3N Medium | 2X Erdschreiber's Medium |
| *Botryococcus* Medium | 2X Soil + Seawater Medium |
| Bristol Medium | 5% F/2 Medium |
| CHEV Diatom Medium | ⅚ Soil + Seawater Agar Medium |
| Chu's Medium | Artificial Seawater Medium |
| CR1 Diatom Medium | BG11-1 + .36% NaCl Medium |
| CR1+ Diatom Medium | BG11-1 + 1% NaCl Medium |
| CR1-S Diatom Medium | Bold 1NV:Erdshreiber (1:1) |
| *Cyanidium* Medium | Bold 1NV:Erdshreiber (4:1) |
| *Cyanophycean* Medium | Bristol-NaCl Medium |
| Desmid Medium | Dasycladales Seawater Medium |
| DYIII Medium | Enriched Seawater Medium |
| *Euglena* Medium | Erdschreiber's Medium |
| HEPES Medium | ES/10 Enriched Seawater Medium |
| J Medium | ES/2 Enriched Seawater Medium |
| Malt Medium | ES/4 Enriched Seawater Medium |
| MES Medium | F/2 Medium |
| Modified Bold 3N Medium | F/2 + NH4 |
| Modified COMBO Medium | LDM Medium |
| N/20 Medium | Modified 2 X CHEV |
| *Ochromonas* Medium | Modified 2 X CHEV + Soil |
| P49 Medium | Modified Artificial Seawater Medium |
| *Polytomella* Medium | Modified CHEV |
| Proteose Medium | Porphridium Medium |
| Snow Algae Media | Soil + Seawater Medium |
| Soil Extract Medium | SS Diatom Medium |
| Soilwater: BAR Medium | |
| Soilwater: GR– Medium | |
| Soilwater: GR–/NH4 Medium | |
| Soilwater: GR+ Medium | |
| Soilwater: GR+/NH4 Medium | |
| Soilwater: PEA Medium | |
| Soilwater: Peat Medium | |
| Soilwater: VT Medium | |
| *Spirulina* Medium | |
| Tap Medium | |
| *Trebouxia* Medium | |
| Volvocacean Medium | |
| Volvocacean-3N Medium | |
| *Volvox* Medium | |
| *Volvox*-Dextrose Medium | |
| Waris Medium | |
| Waris + Soil Extract Medium | |

In a particular example, a medium suitable for culturing *Chlorella protothecoides* (UTEX 31) comprises Proteose Medium. This medium is suitable for axenic cultures, and a 1 L volume of the medium (pH~6.8) can be prepared by addition of 1 g of proteose peptone to 1 liter of Bristol Medium. Bristol medium comprises 2.94 mM $NaNO_3$, 0.17 mM $CaCl_2.2H_2O$, 0.3 mM $MgSO_4.7H_2O$, 0.43 mM, 1.29 mM $KH_2PO_4$, and 1.43 mM NaCl in an aqueous solution. For 1.5% agar medium, 15 g of agar can be added to 1 L of the solution. The solution is covered and autoclaved, and then stored at a refrigerated temperature prior to use.

Other suitable media for use with the methods of the invention can be readily identified by consulting the URL identified above, or by consulting other organizations that maintain cultures of microorganisms, such as SAG, CCAP, or CCALA. SAG refers to the Culture Collection of Algae at the University of Göttingen (Göttingen, Germany), CCAP refers to the culture collection of algae and protozoa managed by the Scottish Association for Marine Science (Scotland, United Kingdom), and CCALA refers to the culture collection of algal laboratory at the Institute of Botany (Třrboň, Czech Republic).

E. Increasing Yield of Lipids

Process conditions can be adjusted to increase the yield of lipids suitable for a particular use and/or to reduce production cost. For example, in certain embodiments, a microbe (e.g., a microalgae) is cultured in the presence of a limiting concentration of one or more nutrients, such as, for example, carbon and/or nitrogen, phosphorous, or sulfur, while providing an excess of fixed carbon energy such as glucose. Nitrogen limitation tends to increase microbial lipid yield over microbial lipid yield in a culture in which nitrogen is provided in excess. In particular embodiments, the increase in lipid yield is at least about: 10%, 20%, 30%, 40%, 50%, 75%, 100%, 200%, 300%, 400%, or 500%. The microbe can be cultured in the presence of a limiting amount of a nutrient for a portion of the total culture period or for the entire period. In particular embodiments, the nutrient concentration is cycled between a limiting concentration and a non-limiting concentration at least twice during the total culture period.

To increase lipid yield, acetic acid can be employed in the feedstock for a lipid-producing microbe (e.g., a microalgae). Acetic acid feeds directly into the point of metabolism that initiates fatty acid synthesis (i.e., acetyl-CoA); thus providing acetic acid in the culture can increase fatty acid production. Generally, the microbe is cultured in the presence of a sufficient amount of acetic acid to increase microbial lipid yield, and/or microbial fatty acid yield, specifically, over microbial lipid (e.g., fatty acid) yield in the absence of acetic acid.

In another embodiment, lipid yield is increased by culturing a lipid-producing microbe (e.g., microalgae) in the presence of one or more cofactor(s) for a lipid pathway enzyme (e.g., a fatty acid synthetic enzyme). Generally, the concentration of the cofactor(s) is sufficient to increase microbial lipid (e.g., fatty acid) yield over microbial lipid yield in the absence of the cofactor(s). In a particular embodiment, the cofactor(s) are provided to the culture by including in the culture a microbe (e.g., microalgae) containing an exogenous gene encoding the cofactor(s). Alternatively, cofactor(s) may be provided to a culture by including a microbe (e.g., microalgae) containing an exogenous gene that encodes a protein that participates in the synthesis of the cofactor. In certain embodiments, suitable cofactors include any vitamin required by a lipid pathway enzyme, such as, for example: biotin, pantothenate. Genes encoding cofactors suitable for use in the invention or that participate in the synthesis of such cofactors are well known and can be introduced into microbes (e.g., microalgae), using contructs and techniques such as those described above.

V. Lipid Pathway Engineering

In some embodiments of the present invention, microorganisms of the present invention are modified to alter the properties and/or proportions of lipids produced and/or to increase carbon flux into lipids. The pathway can further, or alternatively, be modified to alter the properties and/or proportions of various hydrocarbon molecules produced through enzymatic processing of lipids.

A. Alteration of Properties or Proportions of Lipids or Hydrocarbons Produced In the case of microalgae, some wild-type cells already have good growth characteristics but do not produce the desired types or quantities of lipids. Examples include *Pyrobotrys, Phormidium, Agmenellum, Carteria, Lepocinclis, Pyrobotrys, Nitzschia, Lepocinclis, Anabaena, Euglena, Spirogyra, Chlorococcum, Tetraedron, Oscillatoria, Phagus*, and *Chlorogonium*, which have the desirable growth characteristic of growing in municipal sewage or wastewater. Such cells, as well as species of *Chlorella* and other microbes, can be engineered to have improved lipid production characteristics. Desired characteristics include optimizing lipid yield per unit volume and/or per unit time, carbon chain length (e.g., for biodiesel production or for industrial applications requiring hydrocarbon feedstock), reducing the number of double or triple bonds, optionally to zero, removing or eliminating rings and cyclic structures, and increasing the hydrogen:carbon ratio of a particular species of lipid or of a population of distinct lipid. In addition, microalgae that produce appropriate hydrocarbons can also be engineered to have even more desirable hydrocarbon outputs. Examples of such microalgae include species of the genus *Chlorella*.

1. Regulation of Enzymes that Control Branch Points in Fatty Acid Synthesis In particular embodiments, one or more key enzymes that control branch points in metabolism to fatty acid synthesis can be up-regulated or down-regulated to improve lipid production. Up-regulation can be achieved, for example, by transforming cells with expression constructs in which a gene encoding the enzyme of interest is expressed, e.g., using a strong promoter and/or enhancer elements that increase transcription. Such constructs can include a selectable marker such that the transformants can be subjected to selection, which can result in amplification of the construct and an increase in the expression level of the encoded enzyme. Examples of enzymes suitable for up-regulation according to the methods of the invention include pyruvate dehydrogenase, which plays a role in converting pyruvate to acetyl-CoA (examples, some from microalgae, include Genbank accession numbers NP_415392; AAA53047; Q1XDM1; and CAF05587). Up-regulation of pyruvate dehydrogenase can increase production of acetyl-CoA, and thereby increase fatty acid synthesis. Acetyl-CoA carboxylase catalyzes the initial step in fatty acid synthesis. Accordingly, this enzyme can be up-regulated to increase production of fatty acids (examples, some from microalgae, include Genbank accession numbers BAA94752; AAA75528; AAA81471; YP_537052; YP_536879; NP_045833; and BAA57908). Fatty acid production can also be increased by up-regulation of acyl carrier protein (ACP), which carries the growing acyl chains during fatty acid synthesis (examples, some from microalgae, include Genbank accession numbers A0T0F8; P51280; NP_849041;YP_874433). Glycerol-3-phosphate acyltransferase catalyzes the rate-limiting step of fatty acid synthesis. Up-regulation of this enzyme can increase fatty acid production (examples, some from microalgae, include Genbank accession numbers AAA74319; AAA33122; AAA37647; P44857; and ABO94442). The preceding proteins are candidates for expression in microalge, including species of the genus *Chlorella*.

Down-regulation of an enzyme of interest can achieved using, e.g., antisense, catalytic RNA/DNA, RNA interference (RNA$_i$), "knock-out," "knock-down," or other mutagenesis techniques. Enzyme expression/function can also be inhibited using intrabodies. Examples of enzymes suitable for down-regulation according to the methods of the invention include citrate synthase, which consumes acetyl-CoA as part of the tricarboxylic acid (TCA) cycle. Down-regulation of citrate synthase can force more acetyl-CoA into the fatty acid synthetic pathway.

2. Modulation of Global Regulators of Fatty Acid Synthetic Genes

Global regulators modulate the expression of the genes of the fatty acid biosynthetic pathways. Accordingly, one or more global regulators of fatty acid synthesis can be up- or down-regulated, as appropriate, to inhibit or enhance, respectively, the expression of a plurality of fatty acid synthetic genes and, ultimately, to increase lipid production. Examples include sterol regulatory element binding proteins (SREBPs), such as SREBP-1a and SREBP-1c (for examples see Genbank accession numbers NP_035610 and Q9WTN3). Global regulators can be up- or down-regulated, for example, as described above with respect to regulation of control point enzymes.

3. Regulation of Hydrocarbon Modification Enzymes

The methods of the invention also include transforming cells with one or more genes encoding hydrocarbon modification enzymes such as, for example, a fatty acyl-ACP thioesterase (see examples in Table 5 with accession numbers), a fatty acyl-CoA/aldehyde reductase (see examples in Table 6 with accession numbers), a fatty acyl-CoA reductase (see examples in Table 7 with accession numbers), a fatty aldehyde decarbonylase (see examples in Table 8 with accession numbers), a fatty aldehyde reductase, or a squalene synthase gene (see GenBank Accession number AF205791). In some embodiments, genes encoding a fatty acyl-ACP thioesterase and a naturally co-expressed acyl carrier protein may be transformed into a cell, optionally with one or more genes encoding other hydrocarbon modification enzymes. In other embodiments, the ACP and the fatty acyl-ACP thioesterase may have an affinity for one another that imparts an advantage when the two are used together in the microbes and methods of the present invention, irrespective of whether they are or are not naturally co-expressed in a particular tissue or organism. Thus, the present invention contemplates both naturally co-expressed pairs of these enzymes as well as those that share an affinity for interacting with one another to facilitate cleavage of a length-specific carbon chain from the ACP.

In still other embodiments, an exogenous gene encoding a desaturase can be transformed into the cell in conjunction with one or more genes encoding other hydrocarbon modification enzymes in order to provide modifications with respect to hydrocarbon saturation. Stearoyl-ACP desaturase (see, e.g., GenBank Accession numbers AAF15308; ABM45911; and AAY86086), for example, catalyzes the conversion of stearoyl-ACP to oleoyl-ACP. Up-regulation of this gene can increase the proportion of monounsaturated fatty acids produced by a cell; whereas down-regulation can reduce the proportion of monounsaturates. Similarly, the expression of one or more glycerolipid desaturases can be controlled to alter the ratio of unsaturated to saturated fatty acids such as ω-6 fatty acid desaturase, ω-3 fatty acid desaturase, or ω-6-oleate desaturase. In some embodiments, the desaturase can be selected with reference to a desired carbon chain length, such that the desaturase is capable of making location specific modifications within a specified carbon-length substrate, or substrates having a carbon-length within a specified range.

In particular embodiments, microbes of the present invention are genetically engineered to express one or more exogenous genes selected from a fatty acyl-ACP thioesterase, a fatty acyl-CoA/aldehyde reductase, a fatty acyl-CoA reductase, a fatty aldehyde reductase, a fatty aldehyde decarbonylase, or a naturally co-expressed acyl carrier protein. Suitable expression methods are described above with respect to the expression of a lipase gene, including, among other methods, inducible expression and compartmentalized expression.

Without intending to be bound by any particular theory or cellular mechanism, a fatty acyl-ACP thioesterase cleaves a fatty acid from an acyl carrier protein (ACP) during lipid synthesis. Through further enzymatic processing, the cleaved fatty acid is then combined with a coenzyme to yield an acyl-CoA molecule. This acyl-CoA is the substrate for the enzymatic activity of a fatty acyl-CoA reductase to yield an aldehyde, as well as for a fatty acyl-CoA/aldehyde reductase to yield an alcohol. The aldehyde produced by the action of the fatty acyl-CoA reductase identified above is the substrate for further enzymatic activity by either a fatty aldehyde reductase to yield an alcohol, or a fatty aldehyde decarbonylase to yield an alkane or alkene.

The enzymes described directly above have a specificity for acting on a substrate which includes a specific number of carbon atoms. For example, a fatty acyl-ACP thioesterase may have a specificity for cleaving a fatty acid having 12 carbon atoms from the ACP. In some embodiments, the ACP and the length-specific thioesterase may have an affinity for one another that makes them particularly useful as a combination (e.g., the exogenous ACP and thioesterase genes may be naturally co-expressed in a particular tissue or organism from which they are derived). Therefore, in various embodiments, the microbe can contain an exogenous gene that encodes a protein with specificity for catalyzing an enzymatic activity (e.g., cleavage of a fatty acid from an ACP, reduction of an acyl-CoA to an aldehyde or an alcohol, or conversion of an aldehyde to an alkane) with regard to the number of carbon atoms contained in the substrate. The enzymatic specificity can, in various embodiments, be for a substrate having from 8 to 34 carbon atoms, preferably from 8 to 18 carbon atoms, and more preferably from 10 to 14 carbon atoms. The most preferred specificity is for a substrate having 12 carbon atoms. In other embodiments the specificity can be for 20 to 30 carbon atoms.

Fatty acyl-ACP thioesterases suitable for use with the microbes and methods of the invention include, without limitation, those listed in Table 5.

TABLE 5

Fatty acyl-ACP thioesterases and GenBank accession numbers.

Umbellularia californica fatty acyl-ACP thioesterase (GenBank #AAC49001)
Cinnamomum camphora fatty acyl-ACP thioesterase (GenBank #Q39473)
Umbellularia californica fatty acyl-ACP thioesterase (GenBank #Q41635)
Myristica fragrans fatty acyl-ACP thioesterase (GenBank #AAB71729)
Myristica fragrans fatty acyl-ACP thioesterase (GenBank #AAB71730)
Elaeis guineensis fatty acyl-ACP thioesterase (GenBank #ABD83939)

TABLE 5-continued

Fatty acyl-ACP thioesterases and GenBank accession numbers.

Elaeis guineensis fatty acyl-ACP thioesterase (GenBank #AAD42220)
Populus tomentosa fatty acyl-ACP thioesterase (GenBank #ABC47311)
Arabidopsis thaliana fatty acyl-ACP thioesterase (GenBank #NP_172327)
Arabidopsis thaliana fatty acyl-ACP thioesterase (GenBank #CAA85387)
Arabidopsis thaliana fatty acyl-ACP thioesterase (GenBank #CAA85388)
Gossypium hirsutum fatty acyl-ACP thioesterase (GenBank #Q9SQI3)
Cuphea lanceolata fatty acyl-ACP thioesterase (GenBank #CAA54060)
Cuphea hookeriana fatty acyl-ACP thioesterase (GenBank #AAC72882)
Cuphea calophylla subsp. mesostemon fatty acyl-ACP thioesterase (GenBank #ABB71581)
Cuphea lanceolata fatty acyl-ACP thioesterase (GenBank #CAC19933)
Elaeis guineensis fatty acyl-ACP thioesterase (GenBank #AAL15645)
Cuphea hookeriana fatty acyl-ACP thioesterase (GenBank #Q39513)
Gossypium hirsutum fatty acyl-ACP thioesterase (GenBank #AAD01982)
Vitis vinifera fatty acyl-ACP thioesterase (GenBank #CAN81819)
Garcinia mangostana fatty acyl-ACP thioesterase (GenBank #AAB51525)
Brassica juncea fatty acyl-ACP thioesterase (GenBank #ABI18986)
Madhuca longifolia fatty acyl-ACP thioesterase (GenBank #AAX51637)
Brassica napus fatty acyl-ACP thioesterase (GenBank #ABH11710)
Oryza sativa (indica cultivar-group) fatty acyl-ACP thioesterase (GenBank #EAY86877)
Oryza sativa (japonica cultivar-group) fatty acyl-ACP thioesterase (GenBank #NP_001068400)
Oryza sativa (indica cultivar-group) fatty acyl-ACP thioesterase (GenBank #EAY99617)
Cuphea hookeriana fatty acyl-ACP thioesterase (GenBank #AAC49269)

Fatty acyl-CoA/aldehyde reductases suitable for use with the microbes and methods of the invention include, without limitation, those listed in Table 6.

TABLE 6

Fatty acyl-CoA/aldehyde reductases listed by GenBank accession numbers.

AAC45217, YP_047869, BAB85476, YP_001086217, YP_580344, YP_001280274, YP_264583, YP_436109, YP_959769, ZP_01736962, ZP_01900335, ZP_01892096, ZP_01103974, ZP_01915077, YP_924106, YP_130411, ZP_01222731, YP_550815, YP_983712, YP_001019688, YP_524762, YP_856798, ZP_01115500, YP_001141848, NP_336047, NP_216059, YP_882409, YP_706156, YP_001136150, YP_952365, ZP_01221833, YP_130076, NP_567936, AAR88762, ABK28586, NP_197634, CAD30694, NP_001063962, BAD46254, NP_001030809, EAZ10132, EAZ43639, EAZ07989, NP_001062488, CAB88537, NP_001052541, CAH66597, CAE02214, CAH66590, CAB88538, EAZ39844, AAZ06658, CAA68190, CAA52019, and BAC84377

Fatty acyl-CoA reductases suitable for use with the microbes and methods of the invention include, without limitation, those listed in Table 7.

TABLE 7

Fatty acyl-CoA reductases listed by GenBank accession numbers.

NP_187805, ABO14927, NP_001049083, CAN83375, NP_191229, EAZ42242, EAZ06453, CAD30696, BAD31814, NP_190040, AAD38039, CAD30692, CAN81280, NP_197642, NP_190041, AAL15288, and NP_190042

Fatty aldehyde decarbonylases suitable for use with the microbes and methods of the invention include, without limitation, those listed in Table 8.

TABLE 8

Fatty aldehyde decarbonylases listed by GenBank accession numbers.

NP_850932, ABN07985, CAN60676, AAC23640, CAA65199, AAC24373, CAE03390, ABD28319, NP_181306, EAZ31322, CAN63491, EAY94825, EAY86731, CAL55686, XP_001420263, EAZ23849, NP_200588, NP_001063227, CAN83072, AAR90847, and AAR97643

Combinations of naturally co-expressed fatty acyl-ACP thioesterases and acyl carrier proteins are suitable for use with the microbes and methods of the invention.

Additional examples of hydrocarbon modification enzymes include amino acid sequences contained in, referenced in, or encoded by nucleic acid sequences contained or referenced in, any of the following U.S. Pat. Nos. 6,610,527; 6,451,576; 6,429,014; 6,342,380; 6,265,639; 6,194,185; 6,114,160; 6,083,731; 6,043,072; 5,994,114; 5,891,697; 5,871,988; 6,265,639, and further described in GenBank Accession numbers: AAO18435; ZP_00513891; Q38710; AAK60613; AAK60610; AAK60611; NP_113747; CAB75874; AAK60612; AAF20201; BAA11024; AF205791; and CAA03710.

Other suitable enzymes for use with the microbes and the methods of the invention include those that have at least 70% amino acid identity with one of the proteins listed in Tables 5-8, and that exhibit the corresponding desired enzymatic activity (e.g., cleavage of a fatty acid from an acyl carrier protein, reduction of an acyl-CoA to an aldehyde or an alcohol, or conversion of an aldehyde to an alkane). In additional embodiments, the enzymatic activity is present in a sequence that has at least about 75%, at least about 80%, at least about 85%, at least about 90%, at least about 95%, or at least about 99% identity with one of the above described sequences, all of which are hereby incorporated by reference as if fully set forth.

The hydrocarbon modification enzymes described above are useful in the production of various hydrocarbons from a microbe (e.g., a microalgae, an oleaginous yeast, or a fungus) or population of microbes, whereby a fatty acyl-ACP thioesterase cleaves a fatty acid from an acyl carrier protein (ACP) during lipid synthesis. Through further enzymatic processing, the cleaved fatty acid is then combined with a coenzyme to yield an acyl-CoA molecule. This acyl-CoA is the substrate for the enzymatic activity of a fatty acyl-CoA reductase to yield an aldehyde, as well as for a fatty acyl-CoA/aldehyde reductase to yield an alcohol. The aldehyde produced by the action of the fatty acyl-CoA reductase identified above is the substrate for further enzymatic activity by either a fatty aldehyde reductase to yield an alcohol, or a fatty aldehyde decarbonylase to yield an alkane or alkene.

The hydrocarbon modification enzymes have a specificity for acting on a substrate which includes a specific number of carbon atoms. For example, a fatty acyl-ACP thioesterase may have a specificity for cleaving a fatty acid having 12 carbon atoms from the ACP. Therefore, in various embodiments, the microbe can contain an exogenous gene that encodes a protein with specificity for catalyzing an enzymatic activity (e.g., cleavage of a fatty acid from an ACP, reduction of an acyl-CoA to an aldehyde or an alcohol, or conversion of an aldehyde to an alkane) with regard to the number of carbon atoms contained in the substrate. The enzymatic specificity can, in various embodiments, be for a substrate having from 8 to 34 carbon atoms, preferably from 8 to 18 carbon atoms, and more preferably from 10 to 14 carbon atoms. The most preferred specificity is for a substrate having 12 carbon atoms. In other embodiments the specificity can be for 20 to 30 carbon atoms.

In some embodiments, fatty acids, or the corresponding primary alcohols, aldehydes, alkanes or alkenes, generated by the methods described herein, contain at least about 8, at least about 10, at least about 12, at least about 14, at least about 16, at least about 18, at least about 20, at least about 22, at least about 24, at least about 26, at least about 28, at least about 30, at least about 32, or at least about 34 carbon atoms or more. Preferred fatty acids for the production of biodiesel, renewable diesel, or jet fuel, or the corresponding primary alcohols, aldehydes, alkanes and alkenes, for industrial applications contain at least about 8 carbon atoms or more. In certain embodiments, the above fatty acids, as well as the other corresponding hydrocarbon molecules, are saturated (with no carbon-carbon double or triple bonds); mono unsaturated (single double bond); poly unsaturated (two or more double bonds); are linear (not cyclic); and/or have little or no branching in their structures.

By selecting the desired combination of exogenous genes to be expressed, one can tailor the product generated by the microbe, which may then be extracted from the aqueous biomass. For example, the microbe can contain: (i) an exogenous gene encoding a fatty acyl-ACP thioesterase; and, optionally, (ii) a naturally co-expressed acyl carrier protein or an acyl carrier protein otherwise having affinity for the fatty acyl-ACP thioesterase (or conversely); and, optionally, (iii) an exogenous gene encoding a fatty acyl-CoA/aldehyde reductase or a fatty acyl-CoA reductase; and, optionally, (iv) an exogenous gene encoding a fatty aldehyde reductase or a fatty aldehyde decarbonylase. The microbe, when cultured as described below, synthesizes a fatty acid linked to an ACP and the fatty acyl-ACP thioesterase catalyzes the cleavage of the fatty acid from the ACP to yield, through further enzymatic processing, a fatty acyl-CoA molecule. When present, the fatty acyl-CoA/aldehyde reductase catalyzes the reduction of the acyl-CoA to an alcohol. Similarly, the fatty acyl-CoA reductase, when present, catalyzes the reduction of the acyl-CoA to an aldehyde. In those embodiments in which an exogenous gene encoding a fatty acyl-CoA reductase is present and expressed to yield an aldehyde product, a fatty aldehyde reductase, encoded by the third exogenous gene, catalyzes the reduction of the aldehyde to an alcohol. Similarly, a fatty aldehyde decarbonylase catalyzes the conversion of the aldehyde to an alkane or an alkene, when present.

Genes encoding such enzymes can be obtained from cells already known to exhibit significant lipid production such as *Chlorella protothecoides*. Genes already known to have a role in lipid production, e.g., a gene encoding an enzyme that saturates double bonds, can be transformed individually into recipient cells. However, to practice the invention it is not necessary to make a priori assumptions as to which genes are required. A library of DNA containing different genes, such as cDNAs from a good lipid-production organism, can be transformed into recipient cells. The cDNA is preferably in operable linkage with a promoter active in microalgae. Different recipient microalgae cells transformed by a library receive different genes from the library. Transformants having improved lipid production are identified though screening methods known in the art, such as, for example, HPLC, gas chromatography, and mass spectrometry methods of hydrocarbon analysis (for examples of such analysis, see Biomass and Bioenergy Vol. 6. No. 4. pp. 269-274 (1994); Experientia 38; 47-49 (1982); and Phytochemistry 65 (2004) 3159-3165). These transformants are then subjected to further transformation with the original library and/or optionally interbred to generate a further round of organisms having improved lipid production. General procedures for evolving whole organisms to acquire a desired property are described in, e.g., U.S. Pat. No. 6,716,631. Such methods entail, e.g., introducing a library of DNA fragments into a plurality of cells, whereby at least one of the fragments undergoes recombination with a segment in the genome or an episome of the cells to produce modified cells. The modified cells are then screened for modified cells that have evolved toward acquisition of the desired function. Vectors and methods for transformation are analogous to those discussed in connection with expression of lipase genes.

Furthermore, subtractive libraries can be used to identify genes whose transcription is induced under different conditions, especially conditions employed in culturing microorganisms for biodiesel production, or for the production of hydrocarbons useful as a feedstock for industrial applications. Subtractive libraries contain nucleotide sequences reflecting the differences between two different samples. Such libraries are prepared by procedures that include the steps of denaturing and hybridizing populations of polynucleotides (e.g., mRNA, cDNA, amplified sequences) from each sample. Sequences common to both samples hybridize and are removed, leaving the sequences that differ between the samples. In this manner, sequences that are induced under particular conditions can be identified. This technique can be employed, for example, to identify genes useful for increasing lipid (e.g., fatty acid) production and, in particular, lipid production under any desired culture conditions. The subtractive hybridization technique can also be employed to identify promoters, e.g., inducible promoters, useful in expression constructs according to the invention.

Thus, for example, subtractive libraries can be prepared from microorganism cultures grown autotrophically (in the light without a fixed carbon source) or heterotrophically (in the dark in the presence of a fixed carbon source). In particular, heterotrophic genes may be induced during dark growth in the presence of a fixed carbon source and may therefore be present in a library generated by subtracting sequences from autotrophic cells from sequences from dark heterotrophic cells. Subtractive libraries can also be prepared from cultures to which a particular carbon substrate, such as glucose, has been added to identify genes that play a role in metabolizing the substrate. Subtractive libraries prepared from cultures grown in the presence of excess versus limited nitrogen can be used to identify genes that control cell division as opposed to hydrocarbon accumulation production. The preparation of a subtractive library from a culture to which lipids (e.g., fatty acids) have been added can help identify genes whose overexpression increases fatty acid production. More specifically, the addition of fatty acids to a culture of cells that can use the added fatty acids will lead to the down-regulation of fatty acid synthetic genes to down-regulate fatty acid production. The overexpression of one or more such genes will have the opposite effect.

B. Increased Carbon Flux into Lipid Pathway

Some microalgae produce significant quantities of non-lipid metabolites, such as, for example, polysaccharides. Because polysaccharide biosynthesis can use a significant proportion of the total metabolic energy available to cells, mutagenesis of lipid-producing cells followed by screening for reduced or eliminated polysaccharide production generates novel strains that are capable of producing higher yields of lipids.

The phenol: sulfuric acid assay detects carbohydrates (see Hellebust, Handbook of Phycological Methods, Cambridge University Press, 1978; and Cuesta G., et al., J Microbiol Methods. 2003 January; 52(1):69-73). The 1,6 dimethylmethylene blue assay detects anionic polysaccharides. (see for example Braz J Med Biol Res. 1999 May; 32(5):545-50; Clin Chem. 1986 November; 32(11):2073-6).

Polysaccharides can also be analyzed through methods such as HPLC, size exclusion chromatography, and anion exchange chromatography (see for example Prosky L, Asp N, Schweizer T F, DeVries J W & Furda I (1988) Determination of insoluble, soluble and total dietary fiber in food and food products: Interlaboratory study. Journal of the Association of Official Analytical Chemists 71, 1017±1023; Int J Biol Macromol. 2003 November; 33(1-3):9-18). Polysaccharides can also be detected using gel electrophoresis (see for example Anal Biochem. 2003 Oct. 15; 321(2):174-82; Anal Biochem. 2002 Jan. 1; 300(1):53-68).

VI. Methods of Recovering Lipids and Hydrocarbons

Hydrocarbons (e.g., lipids, fatty acids, aldehydes, alcohols, and alkanes) produced by cells of the invention can be harvested, or otherwise collected, by any convenient means. For example, hydrocarbons secreted from cells can be centrifuged to separate the hydrocarbons in a hydrophobic layer from contaminants in an aqueous layer and optionally from any solid materials as a precipitate in after centrifugation. Material containing cell or cell fractions can be treated with proteases to degrade contaminating proteins before or after centrifugation. In some instances the contaminating proteins are associated, possibly covalently, to hydrocarbons or hydrocarbon precursors which form hydrocarbons upon removal of the protein. In other instances the hydrocarbon molecules are in a preparation that also contains proteins. Proteases can be added to hydrocarbon preparations containing proteins to degrade proteins (for example, the protease from *Streptomyces griseus* can be used (SigmaAldrich catalog number P5147). After digestion, the hydrocarbons are preferably purified from residual proteins, peptide fragments, and amino acids. This purification can be accomplished, for example, by methods listed above such as centrifugation and filtration.

Extracellular hydrocarbons can also be extracted in vivo from living microalgae cells which are then returned to a bioreactor by exposure of the cells, in an otherwise sterile environment, to a non-toxic extraction solvent, followed by separation of the living cells and the hydrophobic fraction of extraction solvent and hydrocarbons, wherein the separated living cells are then returned to a culture container such as a stainless steel fermentor or photobioreactor (see Biotechnol Bioeng. 2004 Dec. 5; 88(5):593-600 and Biotechnol Bioeng. 2004 Mar. 5; 85(5):475-81).

Hydrocarbons can also be isolated by whole cell extraction. The cells are first disrupted, as described in the section entitled "Lysing Cells", and then intracellular and cell membrane/cell wall-associated hydrocarbons as well as extracellular hydrocarbons can be collected from the whole cell mass, such as by use of centrifugation as described above.

Various methods are available for separating hydrocarbons and lipids from cellular lysates produced by the above methods. For example, hydrocarbons can be extracted with a hydrophobic solvent such as hexane (see Frenz et al. 1989, Enzyme Microb. Technol., 11:717). Hydrocarbons can also be extracted using liquefaction (see for example Sawayama et al. 1999, Biomass and Bioenergy 17:33-39 and Inoue et al. 1993, Biomass Bioenergy 6(4):269-274); oil liquefaction (see for example Minowa et al. 1995, Fuel 74(12):1735-1738); and supercritical $CO_2$ extraction (see for example Mendes et al. 2003, Inorganica Chimica Acta 356:328-334).

Miao and Wu describe a protocol of the recovery of microalgal lipid from a culture of *Chlorella protothecoides* in which the cells were harvested by centrifugation, washed with distilled water and dried by freeze drying. The resulting cell powder was pulverized in a mortor and then extracted with n-hexane. Miao and Wu, Biosource Technology (2006) 97:841-846.

A. Lysine Cells

Intracellular lipids and hydrocarbons produced in microorganisms are, in some embodiments, extracted after lysing the cells of the microorganism. Once extracted, the lipids and/or hydrocarbons can be further refined to produce oils, fuels, or oleochemicals.

After completion of culturing, the microorganisms can be separated from the fermentation broth. Optionally, the separation is effected by centrifugation to generate a concentrated paste. Centrifugation does not remove significant amounts of intracellular water from the microorganisms and is not a drying step. The biomass can then be washed with a washing solution (e.g., DI water) to get rid of the fermentation broth and debris. Optionally, the washed microbial biomass may also be dried (oven dried, lyophilized, etc.) prior to cell disruption. Alternatively, cells can be lysed without separation from some or all of the fermentation broth when the fermentation is complete. For example, the cells can be at a ratio of less than 1:1 v:v cells to extracellular liquid when the cells are lysed.

Microorganisms containing a lipid and/or hydrocarbon can be lysed to produce a lysate. As detailed herein, the step of lysing a microorganism (also referred to as cell lysis) can be achieved by any convenient means, including heat-induced lysis, adding a base, adding an acid, using enzymes such as proteases and polysaccharide degradation enzymes such as amylases, using ultrasound, mechanical lysis, using osmotic shock, infection with a lytic virus, and/or expression of one or more lytic genes. Lysis is performed to release intracellular molecules which have been produced by the microorganism. Each of these methods for lysing a microorganism can be used as a single method or in combination simultaneously or sequentially.

The extent of cell disruption can be observed by microscopic analysis. Using one or more of the methods described herein, typically more than 70% cell breakage is observed. Preferably, cell breakage is more than 80%, more preferably more than 90% and most preferred about 100%.

In particular embodiments, the microorganism is lysed after growth, for example to increase the exposure of cellular lipid and/or hydrocarbon for extraction or further processing. The timing of lipase expression (e.g., via an inducible promoter) or cell lysis can be adjusted to optimize the yield of lipids and/or hydrocarbons. Below are described a number of lysis techniques. These techniques can be used individually or in combination.

1. Heat-Induced Lysis

In a preferred embodiment of the present invention, the step of lysing a microorganism comprises heating of a cellular suspension containing the microorganism. In this embodiment, the fermentation broth containing the microorganisms (or a suspension of microorganisms isolated from the fermentation broth) is heated until the microorganisms, i.e., the cell walls and membranes of microorganisms degrade or breakdown. Typically, temperatures applied are at least 50° C. Higher temperatures, such as, at least 30° C. at least 60° C., at least 70° C., at least 80° C., at least 90° C., at least 100° C., at least 110° C., at least 120° C., at least 130° C. or higher are used for more efficient cell lysis.

Lysing cells by heat treatment can be performed by boiling the microorganism. Alternatively, heat treatment (without boiling) can be performed in an autoclave. The heat treated lysate may be cooled for further treatment.

Cell disruption can also be performed by steam treatment, i.e., through addition of pressurized steam. Steam treatment of microalgae for cell disruption is described, for example, in U.S. Pat. No. 6,750,048.

2. Lysis Using a Base

In another preferred embodiment of the present invention, the step of lysing a microorganism comprises adding a base to a cellular suspension containing the microorganism.

The base should be strong enough to hydrolyze at least a portion of the proteinaceous compounds of the microorganisms used. Bases which are useful for solubilizing proteins are known in the art of chemistry. Exemplary bases which are useful in the methods of the present invention include, but are not limited to, hydroxides, carbonates and bicarbonates of lithium, sodium, potassium, calcium, and mixtures thereof. A preferred base is KOH. Base treatment of microalgae for cell disruption is described, for example, in U.S. Pat. No. 6,750,048.

3. Acidic Lysis

In another preferred embodiment of the present invention, the step of lysing a microorganism comprises adding an acid to a cellular suspension containing the microorganism. Acid lysis can be effected using an acid at a concentration of 10-500 mN or preferably 40-160 nM. Acid lysis is preferably performed at above room temperature (e.g., at 40-160°, and preferably a temperature of 50-130°. For moderate temperatures (e.g., room temperature to 100° C. and particularly room temperature to 65°, acid treatment can usefully be combined with sonication or other cell disruption methods.

4. Lysing Cells Using Enzymes

In another preferred embodiment of the present invention, the step of lysing a microorganism comprises lysing the microorganism by using an enzyme. Preferred enzymes for lysing a microorganism are proteases and polysaccharide-degrading enzymes such as hemicellulase (e.g., hemicellulase from *Aspergillus niger*; Sigma Aldrich, St. Louis, Mo.; #H2125), pectinase (e.g., pectinase from *Rhizopus* sp.; Sigma Aldrich, St. Louis, Mo.; #P2401), Mannaway 4.0 L (Novozymes), cellulase (e.g., cellulose from *Trichoderma viride*; Sigma Aldrich, St. Louis, Mo.; #C9422), and driselase (e.g., driselase from *Basidiomycetes* sp.; Sigma Aldrich, St. Louis, Mo.; #D9515.

a) Cellulases

In a preferred embodiment of the present invention, a cellulase for lysing a microorganism is a polysaccharide-degrading enzyme, optionally from *Chlorella* or a *Chlorella* virus.

b) Proteases

Proteases such as *Streptomyces griseus* protease, chymotrypsin, proteinase K, proteases listed in Degradation of Polylactide by Commercial Proteases, Oda Y et al., Journal of Polymers and the Environment, Volume 8, Number 1, January 2000, pp. 29-32(4), and other proteases can be used to lyse microorganisms. Other proteases that can be used include Alcalase 2.4 FG (Novozymes) and Flavourzyme 100 L (Novozymes).

c) Combinations

Any combination of a protease and a polysaccharide-degrading enzyme can also be used, including any combination of the preceding proteases and polysaccharide-degrading enzymes.

5. Lysing Cells Using Ultrasound

In another preferred embodiment of the present invention, the step of lysing a microorganism is performed by using ultrasound, i.e., sonication. Thus, cells can also by lysed with high frequency sound. The sound can be produced electronically and transported through a metallic tip to an appropriately concentrated cellular suspension. This sonication (or ultrasonication) disrupts cellular integrity based on the creation of cavities in cell suspension.

6. Mechanical Lysis

In another preferred embodiment of the present invention, the step of lysing a microorganism is performed by mechanical lysis. Cells can be lysed mechanically and optionally homogenized to facilitate hydrocarbon (e.g., lipid) collection. For example, a pressure disrupter can be used to pump a cell containing slurry through a restricted orifice valve. High pressure (up to 1500 bar) is applied, followed by an instant expansion through an exiting nozzle. Cell disruption is accomplished by three different mechanisms: impingement on the valve, high liquid shear in the orifice, and sudden pressure drop upon discharge, causing an explosion of the cell. The method releases intracellular molecules.

Alternatively, a ball mill can be used. In a ball mill, cells are agitated in suspension with small abrasive particles, such as beads. Cells break because of shear forces, grinding between beads, and collisions with beads. The beads disrupt the cells to release cellular contents. Cells can also be disrupted by shear forces, such as with the use of blending (such as with a high speed or Waring blender as examples), the french press, or even centrifugation in case of weak cell walls, to disrupt cells.

7. Lysing Cells by Osmotic Shock (Cytolysis)

In another preferred embodiment of the present invention, the step of lysing a microorganism is performed by applying an osmotic shock.

8. Infection with a Lytic Virus

In a preferred embodiment of the present invention, the step of lysing a microorganism comprises infection of the microorganism with a lytic virus. A wide variety of viruses are known to lyse microorganisms suitable for use in the present invention, and the selection and use of a particular lytic virus for a particular microorganism is within the level of skill in the art.

For example, *paramecium bursaria chlorella* virus (PBCV-1) is the prototype of a group (family Phycodnaviridae, genus *Chlorovirus*) of large, icosahedral, plaque-forming, double-stranded DNA viruses that replicate in, and lyse, certain unicellular, eukaryotic *chlorella*-like green algae. Accordingly, any susceptible microalgae can be lysed by infecting the culture with a suitable *chlorella* virus. Methods of infecting species of *Chlorella* with a *chlorella* virus are known. See for example *Adv. Virus Res.* 2006; 66:293-336; *Virology,* 1999 Apr. 25; 257(1):15-23; *Virology,* 2004 Jan. 5; 318(1):214-23; *Nucleic Acids Symp. Ser.* 2000; (44):161-2; *J. Virol.* 2006 March; 80(5):2437-44; and *Annu. Rev. Microbiol.* 1999; 53:447-94.

9. Autolysis (Expression of a Lytic Gene)

In another preferred embodiment of the present invention, the step of lysing a microorganism comprises autolysis. In this embodiment, a microorganism according to the invention is genetically engineered to produce a lytic protein that will lyse the microorganism. This lytic gene can be expressed using an inducible promoter so that the cells can first be grown to a desirable density in a fermentor, followed by induction of the promoter to express the lytic gene to lyse the cells. In one embodiment, the lytic gene encodes a polysaccharide-degrading enzyme.

In certain other embodiments, the lytic gene is a gene from a lytic virus. Thus, for example, a lytic gene from a *Chlorella* virus can be expressed in an algal cell of the genus *Chlorella*, such as *C. protothecoides*.

Suitable expression methods are described herein with respect to the expression of a lipase gene. Expression of lytic genes is preferably done using an inducible promoter, such as a promoter active in microalgae that is induced by a stimulus such as the presence of a small molecule, light, heat, and other stimuli. Lytic genes from *chlorella* viruses are known. For example, see *Virology* 260, 308-315 (1999); *FEMS Microbiology Letters* 180 (1999) 45-53; *Virology* 263, 376-387 (1999); and *Virology* 230, 361-368 (1997).

B. Extraction of Lipids and Hydrocarbons

Lipids and hydrocarbons generated by the microorganisms of the present invention can be recovered by extraction with an organic solvent. In some cases, the preferred organic solvent is hexane. Typically, the organic solvent is added directly to the lysate without prior separation of the lysate components. In one embodiment, the lysate generated by one or more of the methods described above is contacted with an organic solvent for a period of time sufficient to allow the lipid and/or hydrocarbon components to form a solution with the organic solvent. In some cases, the solution can then be further refined to recover specific desired lipid or hydrocarbon components. Hexane extraction methods are well known in the art.

VII. Methods of Processing Lipids and Hydrocarbons

A. Enzymatic Modification

Hydrocarbons (e.g., lipids, fatty acids, aldehydes, alcohols, and alkanes) produced by cells as described herein can be modified by the use of one or more enzymes, including a lipase, as described above. When the hydrocarbons are in the extracellular environment of the cells, the one or more enzymes can be added to that environment under conditions in which the enzyme modifies the hydrocarbon or completes its synthesis from a hydrocarbon precursor. Alternatively, the hydrocarbons can be partially, or completely, isolated from the cellular material before addition of one or more catalysts such as enzymes. Such catalysts are exogenously added, and their activity occurs outside the cell or in vitro.

B. Thermal and Other Catalytic Modification

Hydrocarbons produced by cells in vivo, or enzymatically modified in vitro, as described herein can be optionally further processed by conventional means. The processing can include "cracking" to reduce the size, and thus increase the hydrogen:carbon ratio, of hydrocarbon molecules. Catalytic and thermal cracking methods are routinely used in hydrocarbon and triglyceride oil processing. Catalytic methods involve the use of a catalyst, such as a solid acid catalyst. The catalyst can be silica-alumina or a zeolite, which result in the heterolytic, or asymmetric, breakage of a carbon-carbon bond to result in a carbocation and a hydride anion. These reactive intermediates then undergo either rearrangement or hydride transfer with another hydrocarbon. The reactions can thus regenerate the intermediates to result in a self-propagating chain mechanism. Hydrocarbons can also be processed to reduce, optionally to zero, the number of carbon-carbon double, or triple, bonds therein. Hydrocarbons can also be processed to remove or eliminate a ring or cyclic structure therein. Hydrocarbons can also be processed to increase the hydrogen:carbon ratio. This can include the addition of hydrogen ("hydrogenation") and/or the "cracking" of hydrocarbons into smaller hydrocarbons.

Thermal methods involve the use of elevated temperature and pressure to reduce hydrocarbon size. An elevated temperature of about 800° C. and pressure of about 700 kPa can be used. These conditions generate "light," a term that is sometimes used to refer to hydrogen-rich hydrocarbon molecules (as distinguished from photon flux), while also generating, by condensation, heavier hydrocarbon molecules which are relatively depleted of hydrogen. The methodology provides homolytic, or symmetrical, breakage and produces alkenes, which may be optionally enzymatically saturated as described above.

Catalytic and thermal methods are standard in plants for hydrocarbon processing and oil refining. Thus hydrocarbons produced by cells as described herein can be collected and processed or refined via conventional means. See Hillen et al. (Biotechnology and Bioengineering, Vol. XXIV:193-205 (1982)) for a report on hydrocracking of microalgae-produced hydrocarbons. In alternative embodiments, the fraction is treated with another catalyst, such as an organic compound, heat, and/or an inorganic compound. For processing of lipids into biodiesel, a transesterification process is used as described in Section IV herein.

Hydrocarbons produced via methods of the present invention are useful in a variety of industrial applications. For example, the production of linear alkylbenzene sulfonate (LAS), an anionic surfactant used in nearly all types of detergents and cleaning preparations, utilizes hydrocarbons generally comprising a chain of 10-14 carbon atoms. See, for example, U.S. Pat. Nos. 6,946,430; 5,506,201; 6,692,730; 6,268,517; 6,020,509; 6,140,302; 5,080,848; and 5,567,359. Surfactants, such as LAS, can be used in the manufacture of personal care compositions and detergents, such as those described in U.S. Pat. Nos. 5,942,479; 6,086,903; 5,833,999; 6,468,955; and 6,407,044.

VIII. Methods of Producing Fuels Suitable for Use in Diesel Vehicles and Jet Engines Increasing interest is directed to the use of hydrocarbon components of biological origin in fuels, such as biodiesel, renewable diesel, and jet fuel, since renewable biological starting materials that may replace starting materials derived from fossil fuels are available, and the use thereof is desirable. There is an urgent need for methods for producing hydrocarbon components from biological materials. The present invention fulfills this need by providing methods for production of biodiesel, renewable diesel, and jet fuel using the lipids generated by the methods described herein as a biological material to produce biodiesel, renewable diesel, and jet fuel.

Traditional diesel fuels are petroleum distillates rich in paraffinic hydrocarbons. They have boiling ranges as broad as 370° to 780° F., which are suitable for combustion in a compression ignition engine, such as a diesel engine vehicle. The American Society of Testing and Materials (ASTM) establishes the grade of diesel according to the boiling range, along with allowable ranges of other fuel properties, such as cetane number, cloud point, flash point, viscosity, aniline point, sulfur content, water content, ash content, copper strip corrosion, and carbon residue. Technically, any hydrocarbon distillate material derived from biomass or otherwise that meets the appropriate ASTM specification can be defined as diesel fuel (ASTM D975), jet fuel (ASTM D1655), or as biodiesel (ASTM D6751).

After extraction, lipid and/or hydrocarbon components recovered from the microbial biomass described herein can be subjected to chemical treatment to manufacture a fuel for use in diesel vehicles and jet engines.

A. Biodiesel

Biodiesel is a liquid which varies in color—between golden and dark brown—depending on the production feedstock. It is practically immiscible with water, has a high boiling point and low vapor pressure. Biodiesel refers to a diesel-equivalent processed fuel for use in diesel-engine vehicles. Biodiesel is biodegradable and non-toxic. An additional benefit of biodiesel over conventional diesel fuel is lower engine wear.

Typically, biodiesel comprises C14-C18 alkyl esters. Various processes convert biomass or a lipid produced and isolated as described herein to diesel fuels. A preferred method to produce biodiesel is by transesterification of a lipid as described herein. A preferred alkyl ester for use as biodiesel is a methyl ester or ethyl ester.

Biodiesel produced by a method described herein can be used alone or blended with conventional diesel fuel at any concentration in most modern diesel-engine vehicles. When blended with conventional diesel fuel (petroleum diesel), biodiesel may be present from about 0.1% to about 99.9%. Much of the world uses a system known as the "B" factor to state the amount of biodiesel in any fuel mix. For example, fuel containing 20% biodiesel is labeled B20. Pure biodiesel is referred to as B100.

Biodiesel can also be used as a heating fuel in domestic and commercial boilers. Existing oil boilers may contain rubber parts and may require conversion to run on biodiesel. The conversion process is usually relatively simple, involving the exchange of rubber parts for synthetic parts due to biodiesel being a strong solvent. Due to its strong solvent power, burning biodiesel will increase the efficiency of boilers.

Biodiesel can be used as an additive in formulations of diesel to increase the lubricity of pure Ultra-Low Sulfur Diesel (ULSD) fuel, which is advantageous because it has virtually no sulfur content.

Biodiesel is a better solvent than petrodiesel and can be used to break down deposits of residues in the fuel lines of vehicles that have previously been run on petrodiesel.

1. Production of Biodiesel

Biodiesel can be produced by transesterification of triglycerides contained in oil-rich biomass. Thus, in another aspect of the present invention a method for producing biodiesel is provided. In a preferred embodiment, the method for producing biodiesel comprises the steps of (a) cultivating a lipid-containing microorganism using methods disclosed herein (b) lysing a lipid-containing microorganism to produce a lysate, (c) isolating lipid from the lysed microorganism, and (d) transesterifying the lipid composition, whereby biodiesel is produced.

Methods for growth of a microorganism, lysing a microorganism to produce a lysate, treating the lysate in a medium comprising an organic solvent to form a heterogeneous mixture and separating the treated lysate into a lipid composition have been described above and can also be used in the method of producing biodiesel.

Lipid compositions can be subjected to transesterification to yield long-chain fatty acid esters useful as biodiesel. Preferred transesterification reactions are outlined below and include base catalyzed transesterification and transesterification using recombinant lipases.

In a base-catalyzed transesterification process, the triacylglycerides are reacted with an alcohol, such as methanol or ethanol, in the presence of an alkaline catalyst, typically potassium hydroxide. This reaction forms methyl or ethyl esters and glycerin (glycerol) as a byproduct.

a). General Chemical Process

Animal and plant oils are typically made of triglycerides which are esters of free fatty acids with the trihydric alcohol, glycerol. In transesterification, the glycerol in a triacylglyceride (TAG) is replaced with a short-chain alcohol such as methanol or ethanol. A typical reaction scheme is as follows:

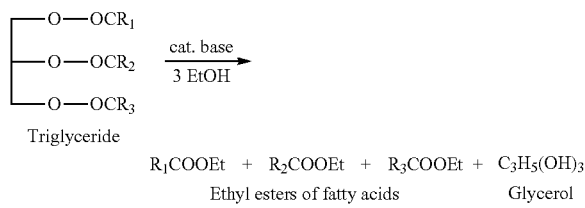

In this scheme, the alcohol is deprotonated with a base to make it a stronger nucleophile. Commonly, ethanol or methanol is used in vast excess (up to 50-fold). Normally, this reaction will proceed either exceedingly slowly or not at all. Heat, as well as an acid or base can be used to help the reaction proceed more quickly. The acid or base are not consumed by the transesterification reaction, thus they are not reactants but catalysts. Almost all biodiesel has been produced using the base-catalyzed technique as it requires only low temperatures and pressures and produces over 98% conversion yield (provided the starting oil is low in moisture and free fatty acids).

b). Using Recombinant Lipases

Transesterification has also been carried out experimentally using an enzyme, such as a lipase instead of a base. Lipase-catalyzed transesterification can be carried out, for example, at a temperature between the room temperature and 80° C., and a mole ratio of the TAG to the lower alcohol of greater than 1:1, preferably about 3:1.

Lipases suitable for use in transesterification include, but are not limited to, those listed in Table 9. Other examples of lipases useful for transesterification are found in, e.g. U.S. Pat. Nos. 4,798,793; 4,940,845 5,156,963; 5,342,768; 5,776,741 and WO89/01032.

TABLE 9

Lipases suitable for use in transesterification.

*Aspergillus niger* lipase ABG73614, *Candida antarctica* lipase B (novozym-435) CAA83122, *Candida cylindracea* lipase AAR24090, *Candida lipolytica* lipase (Lipase L; Amano Pharmaceutical Co., Ltd.), *Candida rugosa* lipase (e.g., Lipase-OF; Meito Sangyo Co., Ltd.), *Mucor miehei* lipase (Lipozyme IM 20), *Pseudomonas fluorescens* lipase AAA25882, *Rhizopus japonicas* lipase (Lilipase A-10FG) Q7M4U7_1, *Rhizomucor miehei* lipase B34959, *Rhizopus oryzae* lipase (Lipase F) AAF32408, *Serratia marcescens* lipase (SM Enzyme) ABI13521, *Thermomyces lanuginosa* lipase CAB58509, Lipase P (Nagase ChemteX Corporation), and QLM Lipase (Meito Sangyo Co., Ltd., Nagoya, Japan)

One challenge to using a lipase for the production of fatty acid esters suitable for biodiesel is that the price of lipase is much higher than the price of sodium hydroxide (NaOH) used by the strong base process. This challenge has been addressed by using an immobilized lipase, which can be recycled. However, the activity of the immobilized lipase must be maintained after being recycled for a minimum number of cycles to allow a lipase-based process to compete with the strong base process in terms of the production cost. Immobilized lipases are subject to poisoning by the lower alcohols typically used in transesterification. U.S. Pat. No. 6,398,707 (issued Jun. 4, 2002 to Wu et al.) describes methods for enhancing the activity of immobilized lipases and regenerating immobilized lipases having reduced activity.

In particular embodiments, a recombinant lipase is expressed in the same microorganisms that produce the lipid on which the lipase acts. Suitable recombinant lipases include those listed above in Table 9 and/or having GenBank Accession numbers listed above in Table 9, or a polypeptide that has at least 70% amino acid identity with one of the lipases listed above in Table 9 and that exhibits lipase activity. In additional embodiments, the enzymatic activity is present in a sequence that has at least about 75%, at least about 80%, at least about 85%, at least about 90%, at least about 95%, or at least about 99% identity with one of the above described sequences, all of which are hereby incorporated by reference as if fully set forth. DNA encoding the lipase and selectable marker is preferably codon-optimized cDNA. Methods of recoding genes for expression in microalgae are described in U.S. Pat. No. 7,135,290.

2. Standards

The common international standard for biodiesel is EN 14214. ASTM D6751 is the most common biodiesel standard referenced in the United States and Canada. Germany uses DIN EN 14214 and the UK requires compliance with BS EN 14214.

Basic industrial tests to determine whether the products conform to these standards typically include gas chromatography, HPLC, and others. Biodiesel meeting the quality standards is very non-toxic, with a toxicity rating ($LD_{50}$) of greater than 50 mL/kg.

B. Renewable Diesel

Renewable diesel comprises alkanes, such as C16:0 and C18:0 and thus, are distinguishable from biodiesel. High quality renewable diesel conforms to the ASTM D975 standard.

The lipids produced by the methods of the present invention can serve as feedstock to produce renewable diesel. Thus, in another aspect of the present invention, a method for producing renewable diesel is provided. Renewable diesel can be produced by at least three processes: hydrothermal processing (hydrotreating); hydroprocessing; and indirect liquefaction. These processes yield non-ester distillates. During these processes, triacylglycerides produced and isolated as described herein, are converted to alkanes.

In a preferred embodiment, the method for producing renewable diesel comprises (a) cultivating a lipid-containing microorganism using methods disclosed herein (b) lysing the microorganism to produce a lysate, (c) isolating lipid from the lysed microorganism, and (d) deoxygenating and hydrotreating the lipid to produce an alkane, whereby renewable diesel is produced. Lipids suitable for manufacturing renewable diesel can be obtained via extraction from microbial biomass using an organic solvent such as hexane, or via other methods, such as those described in U.S. Pat. No. 5,928,696.

In some methods, the microbial lipid is first cracked in conjunction with hydrotreating to reduce carbon chain length and saturate double bonds, respectively. The material is then isomerized, also in conjunction with hydrotreating. The naptha fraction can then be removed through distillation, followed by additional distillation to vaporize and distill components desired in the diesel fuel to meet a D975 standard while leaving components that are heavier than desired for meeting a D 975 standard. Hydrotreating, hydrocracking, deoxygenation and isomerization methods of chemically modifying oils, including triglyceride oils, are well known in the art. See for example European patent applications EP1741768 (A1); EP1741767 (A1); EP1682466 (A1); EP1640437 (A1); EP1681337 (A1); EP1795576 (A1); and U.S. Pat. Nos. 7,238,277; 6,630,066; 6,596,155; 6,977,322; 7,041,866; 6,217,746; 5,885,440; 6,881,873.

1. Hydrotreating

In a preferred embodiment of the method for producing renewable diesel, treating the lipid to produce an alkane is performed by hydrotreating of the lipid composition. In hydrothermal processing, typically, biomass is reacted in water at an elevated temperature and pressure to form oils and residual solids. Conversion temperatures are typically 300° to 660° F., with pressure sufficient to keep the water primarily as a liquid, 100 to 170 standard atmosphere (atm). Reaction times are on the order of 15 to 30 minutes. After the reaction is completed, the organics are separated from the water. Thereby a distillate suitable for diesel is produced.

2. Hydroprocessing

A renewable diesel, referred to as "green diesel," can be produced from fatty acids by traditional hydroprocessing technology. The triglyceride-containing oils can be hydroprocessed either as co-feed with petroleum or as a dedicated feed. The product is a diesel fuel that conforms with the ASTM D975 specification. Thus, in another preferred embodiment of the method for producing renewable diesel, treating the lipid composition to produce an alkane is performed by hydroprocessing of the lipid composition.

In some methods of making renewable diesel, the first step of treating a triglyceride is hydroprocessing to saturate double bonds, followed by deoxygenation at elevated temperature in the presence of hydrogen and a catalyst. In some methods, hydrogenation and deoxygenation occur in the same reaction. In other methods deoxygenation occurs before hydrogenation. Isomerization is then optionally performed, also in the presence of hydrogen and a catalyst. Naphtha components are preferably removed through distillation. For examples, see U.S. Pat. No. 5,475,160 (hydrogenation of triglycerides); U.S. Pat. No. 5,091,116 (deoxygenation, hydrogenation and gas removal); U.S. Pat. No. 6,391,815 (hydrogenation); and U.S. Pat. No. 5,888,947 (isomerization).

Petroleum refiners use hydroprocessing to remove impurities by treating feeds with hydrogen. Hydroprocessing conversion temperatures are typically 300° to 700° F. Pressures are typically 40 to 100 atm. The reaction times are typically on the order of 10 to 60 minutes.

Solid catalysts are employed to increase certain reaction rates, improve selectivity for certain products, and optimize hydrogen consumption.

Hydrotreating and hydroprocessing ultimately lead to a reduction in the molecular weight of the feed. In the case of triglyceride-containing oils, the triglyceride molecule is reduced to four hydrocarbon molecules under hydroprocessing conditions: a propane molecule and three heavier hydrocarbon molecules, typically in the C8 to C18 range.

3. Indirect Liquefaction

A traditional ultra-low sulfur diesel can be produced from any form of biomass by a two-step process. First, the biomass is converted to a syngas, a gaseous mixture rich in hydrogen and carbon monoxide. Then, the syngas is catalytically converted to liquids. Typically, the production of liquids is accomplished using Fischer-Tropsch (FT) synthesis. This technology applies to coal, natural gas, and heavy oils. Thus, in yet another preferred embodiment of the method for producing renewable diesel, treating the lipid composition to produce an alkane is performed by indirect liquefaction of the lipid composition.

C. Jet Fuel

The annual U.S. usage of jet fuel in 2006 was about 21 billion gallons (about 80 billion liters). Aeroplane fuel is clear to straw colored. The most common fuel is an unleaded/paraffin oil-based fuel classified as Aeroplane A-1, which is produced to an internationally standardized set of specifications. Aeroplane fuel is a mixture of a large number of different hydrocarbons, possibly as many as a thousand or more. The range of their sizes (molecular weights or carbon numbers) is restricted by the requirements for the product, for example, freezing point or smoke point. Kerosone-type Aeroplane fuel (including Jet A and Jet A-1) has a carbon number distribution between about 8 and 16 carbon numbers. Wide-cut or naphta-type Aeroplane fuel (including Jet B) typically has a carbon number distribution between about 5 and 15 carbons.

Both Aeroplanes (Jet A and jet B) may contain a number of additives. Useful additives include, but are not limited to, antioxidants, antistatic agents, corrosion inhibitors, and fuel system icing inhibitor (FSII) agents. Antioxidants prevent gumming and usually, are based on alkylated phenols, for example, AO-30, AO-31, or AO-37. Antistatic agents dissipate static electricity and prevent sparking. Stadis 450 with dinonylnaphthylsulfonic acid (DINNSA) as the active ingredient, is an example. Corrosion inhibitors, e.g., DCI-4A is used for civilian and military fuels and DCI-6A is used for military fuels. FSII agents, include, e.g., Di-EGME.

A solution is blending algae fuels with existing jet fuel. The present invention provides such a solution. The lipids produced by the methods of the present invention can serve as feedstock to produce jet fuel. Thus, in another aspect of the present invention, a method for producing jet fuel is provided. Herewith two methods for producing jet fuel from the lipids produced by the methods of the present invention are provided: fluid catalytic cracking (FCC); and hydrodeoxygenation (HDO).

1. Fluid Catalytic Cracking

Fluid Catalytic Cracking (FCC) is one method which is used to produce olefins, especially propylene from heavy crude fractions. There are reports in the literature that vegetable oils such as canola oil could be processed using FCC to give a hydrocarbon stream useful as a gasoline fuel.

The lipids produced by the method of the present invention can be converted to olefins. The process involves flowing the lipids produced through an FCC zone and collecting a product stream comprised of olefins, which is useful as a jet fuel. The lipids produced are contacted with a cracking catalyst at cracking conditions to provide a product stream comprising olefins and hydrocarbons useful as jet fuel.

In a preferred embodiment, the method for producing jet fuel comprises (a) cultivating a lipid-containing microorganism using methods disclosed herein, (b) lysing the lipid-containing microorganism to produce a lysate, (c) isolating lipid from the lysate, and (d) treating the lipid composition, whereby jet fuel is produced.

In a preferred embodiment of the method for producing a jet fuel, the lipid composition can be flowed through a fluid catalytic cracking zone, which, in one embodiment, may comprise contacting the lipid composition with a cracking catalyst at cracking conditions to provide a product stream comprising $C_2$-$C_5$ olefins.

In certain embodiments of this method it may be desirable to remove any contaminants that may be present in the lipid composition. Thus, prior to flowing the lipid composition through a fluid catalytic cracking zone, the lipid composition is pretreated. Pretreatment may involve contacting the lipid composition with an ion-exchange resin. The ion exchange resin is an acidic ion exchange resin, such as Amberlyst™-15 and can be used as a bed in a reactor through which the lipid composition is flowed, either upflow or downflow. Other pretreatments may include mild acid washes by contacting the lipid composition with an acid, such as sulfuric, acetic, nitric, or hydrochloric acid. Contacting is done with a dilute acid solution usually at ambient temperature and atmospheric pressure.

The lipid composition, optionally pretreated, is flowed to an FCC zone where the hydrocarbonaceous components are cracked to olefins. Catalytic cracking is accomplished by contacting the lipid composition in a reaction zone with a catalyst composed of finely divided particulate material. The reaction is catalytic cracking, as opposed to hydrocracking, and is carried out in the absence of added hydrogen or the consumption of hydrogen. As the cracking reaction proceeds, substantial amounts of coke are deposited on the catalyst. The catalyst is regenerated at high temperatures by burning coke from the catalyst in a regeneration zone. Coke-containing catalyst, referred to herein as "coked catalyst", is continually transported from the reaction zone to the regeneration zone to be regenerated and replaced by essentially coke-free regenerated catalyst from the regeneration zone. Fluidization of the catalyst particles by various gaseous streams allows the transport of catalyst between the reaction zone and regeneration zone. Methods for cracking hydrocarbons, such as those of the lipid composition described herein, in a fluidized stream of catalyst, transporting catalyst between reaction and regeneration zones, and combusting coke in the regenerator are well known by those skilled in the art of FCC processes. Exemplary FCC applications and catalysts useful for cracking the lipid composition to produce $C_2$-$C_5$ olefins are described in U.S. Pat. Nos. 6,538,169, 7,288,685, which are incorporated in their entirety by reference.

In one embodiment, cracking the lipid composition of the present invention, takes place in the riser section or, alternatively, the lift section, of the FCC zone. The lipid composition is introduced into the riser by a nozzle resulting in the rapid vaporization of the lipid composition. Before contacting the catalyst, the lipid composition will ordinarily have a temperature of about 149° C. to about 316° C. (300° F. to 600° F.). The catalyst is flowed from a blending vessel to the riser where it contacts the lipid composition for a time of abort 2 seconds or less.

The blended catalyst and reacted lipid composition vapors are then discharged from the top of the riser through an outlet and separated into a cracked product vapor stream including olefins and a collection of catalyst particles covered with substantial quantities of coke and generally referred to as "coked catalyst." In an effort to minimize the contact time of the lipid composition and the catalyst which may promote further conversion of desired products to undesirable other products, any arrangement of separators such as a swirl arm arrangement can be used to remove coked catalyst from the product stream quickly. The separator, e.g. swirl arm separator, is located in an upper portion of a chamber with a stripping zone situated in the lower portion of the chamber. Catalyst separated by the swirl arm arrangement drops down into the stripping zone. The cracked product vapor stream comprising cracked hydrocarbons including light olefins and some catalyst exit the chamber via a conduit which is in communication with cyclones. The cyclones remove remaining catalyst particles from the product vapor stream to reduce particle concentrations to very low levels. The product vapor stream then exits the top of the separating vessel. Catalyst separated by the cyclones is returned to the separating vessel and then to the stripping zone. The stripping zone removes adsorbed hydrocarbons from the surface of the catalyst by counter-current contact with steam.

Low hydrocarbon partial pressure operates to favor the production of light olefins. Accordingly, the riser pressure is set at about 172 to 241 kPa (25 to 35 psia) with a hydrocarbon partial pressure of about 35 to 172 kPa (5 to 25 psia), with a preferred hydrocarbon partial pressure of about 69 to 138 kPa (10 to 20 psia). This relatively low partial pressure for hydrocarbon is achieved by using steam as a diluent to the extent that the diluent is 10 to 55 wt-% of lipid composition and preferably about 15 wt-% of lipid composition. Other diluents such as dry gas can be used to reach equivalent hydrocarbon partial pressures.

The temperature of the cracked stream at the riser outlet will be about 510° C. to 621° C. (950° F. to 1150° F.). However, riser outlet temperatures above 566° C. (1050° F.) make more dry gas and more olefins. Whereas, riser outlet temperatures below 566° C. (1050° F.) make less ethylene and propylene. Accordingly, it is preferred to run the FCC process at a preferred temperature of about 566° C. to about 630° C., preferred pressure of about 138 kPa to about 240 kPa (20 to 35 psia). Another condition for the process is the catalyst to lipid composition ratio which can vary from about 5 to about 20 and preferably from about 10 to about 15.

In one embodiment of the method for producing a jet fuel, the lipid composition is introduced into the lift section of an FCC reactor. The temperature in the lift section will be very hot and range from about 700° C. (1292° F.) to about 760° C. (1400° F.) with a catalyst to lipid composition ratio of about 100 to about 150. It is anticipated that introducing the lipid composition into the lift section will produce considerable amounts of propylene and ethylene.

Gas and liquid hydrocarbon products produced can be analyzed by gas chromatography, HPLC, etc.

2. Hydrodeoxygenation

In another embodiment of the method for producing a jet fuel using the lipid composition or the lipids produced as described herein, the structure of the lipid composition or the lipids is broken by a process referred to as hydrodeoxygenation (HDO).

HDO means removal of oxygen by means of hydrogen, that is, oxygen is removed while breaking the structure of the material. Olefinic double bonds are hydrogenated and any sulphur and nitrogen compounds are removed. Sulphur removal is called hydrodesulphurization (HDS). Pretreatment and purity of the raw materials (lipid composition or the lipids) contribute to the service life of the catalyst.

Generally in the HDO/HDS step, hydrogen is mixed with the feed stock (lipid composition or the lipids) and then the mixture is passed through a catalyst bed as a co-current flow, either as a single phase or a two phase feed stock. After the HDO/MDS step, the product fraction is separated and passed to a separate isomerization reactor. An isomerization reactor for biological starting material is described in the literature (FI 100 248) as a co-current reactor.

The process for producing a fuel by hydrogenating a hydrocarbon feed, e.g., the lipid composition or the lipids herein, can also be performed by passing the lipid composition or the lipids as a co-current flow with hydrogen gas through a first hydrogenation zone, and thereafter the hydrocarbon effluent is further hydrogenated in a second hydrogenation zone by passing hydrogen gas to the second hydrogenation zone as a counter-current flow relative to the hydrocarbon effluent. Exemplary HDO applications and catalysts useful for cracking the lipid composition to produce $C_2$-$C_5$ olefins are described in U.S. Pat. No. 7,232,935, which is incorporated in its entirety by reference.

Typically, in the hydrodeoxygenation step, the structure of the biological component, such as the lipid composition or lipids herein, is decomposed, oxygen, nitrogen, phosphorus and sulphur compounds, and light hydrocarbons as gas are removed, and the olefinic bonds are hydrogenated. In the second step of the process, i.e. in the so-called isomerization step, isomerization is carried out for branching the hydrocarbon chain and improving the performance of the paraffin at low temperatures.

In the first step i.e. HDO step of the cracking process, hydrogen gas and the lipid composition or lipids herein which are to be hydrogenated are passed to a HDO catalyst bed system either as co-current or counter-current flows, said catalyst bed system comprising one or more catalyst bed(s), preferably 1-3 catalyst beds. The HDO step is typically operated in a co-current manner. In case of a HDO catalyst bed system comprising two or more catalyst beds, one or more of the beds may be operated using the counter-current flow principle.

In the HDO step, the pressure varies between 20 and 150 bar, preferably between 50 and 100 bar, and the temperature varies between 200 and 500° C., preferably in the range of 300-400° C.

In the HDO step, known hydrogenation catalysts containing metals from Group VII and/or VIB of the Periodic System may be used. Preferably, the hydrogenation catalysts are supported Pd, Pt, Ni, NiMo or a CoMo catalysts, the support being alumina and/or silica. Typically, NiMo/$Al_2O_3$ and CoMo/$Al_2O_3$ catalysts are used.

Prior to the HDO step, the lipid composition or lipids herein may optionally be treated by prehydrogenation under milder conditions thus avoiding side reactions of the double bonds. Such prehydrogenation is carried out in the presence of a prehydrogenation catalyst at temperatures of 50 400° C. and at hydrogen pressures of 1 200 bar, preferably at a temperature between 150 and 250° C. and at a hydrogen pressure between 10 and 100 bar. The catalyst may contain metals from Group VIII and/or VIB of the Periodic System. Preferably, the prehydrogenation catalyst is a supported Pd, Pt, Ni, NiMo or a CoMo catalyst, the support being alumina and/or silica.

A gaseous stream from the HDO step containing hydrogen is cooled and then carbon monoxide, carbon dioxide, nitrogen, phosphorus and sulphur compounds, gaseous light hydrocarbons and other impurities are removed therefrom. After compressing, the purified hydrogen or recycled hydrogen is returned back to the first catalyst bed and/or between the catalyst beds to make up for the withdrawn gas stream. Water is removed from the condensed liquid. The liquid is passed to the first catalyst bed or between the catalyst beds.

After the HDO step, the product is subjected to an isomerization step. It is substantial for the process that the impurities are removed as completely as possible before the hydrocarbons are contacted with the isomerization catalyst. The isomerization step comprises an optional stripping step, wherein the reaction product from the HDO step may be purified by stripping with water vapour or a suitable gas such as light hydrocarbon, nitrogen or hydrogen. The optional stripping step is carried out in counter-current manner in a unit upstream of the isomerization catalyst, wherein the gas and liquid are contacted with each other, or before the actual isomerization reactor in a separate stripping unit utilizing counter-current principle.

After the stripping step the hydrogen gas and the hydrogenated lipid composition or lipids herein, and optionally an n-paraffin mixture, are passed to a reactive isomerization unit comprising one or several catalyst bed(s). The catalyst beds of the isomerization step may operate either in co-current or counter-current manner.

It is important for the process that the counter-current flow principle is applied in the isomerization step. In the isomerization step this is done by carrying out either the optional stripping step or the isomerization reaction step or both in counter-current manner.

The isomerization step and the HDO step may be carried out in the same pressure vessel or in separate pressure vessels. Optional prehydrogenation may be carried out in a separate pressure vessel or in the same pressure vessel as the HDO and isomerization steps.

In the isomerization step, the pressure varies in the range of 20 150 bar, preferably in the range of 20 100 bar, the temperature being between 200 and 500° C., preferably between 300 and 400° C.

In the isomerization step, isomerization catalysts known in the art may be used. Suitable isomerization catalysts contain molecular sieve and/or a metal from Group VII and/or a carrier. Preferably, the isomerization catalyst contains SAPO-11 or SAPO41 or ZSM-22 or ZSM-23 or ferrierite and Pt, Pd or Ni and $Al_2O_3$ or $SiO_2$. Typical isomerization catalysts are, for example, Pt/SAPO-11/$Al_2O_3$, Pt/ZSM-22/$Al_2O_3$, Pt/ZSM-23/$Al_2O_3$ and Pt/SAPO-11/$SiO_2$.

As the product, a high quality hydrocarbon component of biological origin, useful as a diesel fuel or a component thereof, is obtained, the density, cetane number and performance at low temperate of said hydrocarbon component being excellent.

IX. Microbe Engineering

As noted above, in certain embodiments of the present invention it is desirable to genetically modify a microorganism to enhance lipid production, modify the properties or proportions of components generated by the microorganism, or to improve or provide de novo growth characteristics on a variety of feedstock materials. *Chlorella*, particularly *Chlorella protothecoides, Chlorella minutissima, Chlorella sorokiniana, Chlorella ellipsoidea, Chlorella* sp., and *Chlorella emersonii* are preferred microorganisms for use in the genetic engineering methods described herein, although other *Chlorella* species as well as other varieties of microorganisms can be used.

Promoters, cDNAs, and 3'UTRs, as well as other elements of the vectors, can be generated through cloning techniques using fragments isolated from native sources (see for example Molecular Cloning: A Laboratory Manual, Sambrook et al. (3d edition, 2001, Cold Spring Harbor Press; and U.S. Pat. No. 4,683,202). Alternatively, elements can be generated synthetically using known methods (see for example Gene. 1995 Oct. 16; 164(1):49-53).

A. Codon-Optimization for Expression

DNA encoding a polypeptide to be expressed in a microorganism, e.g., a lipase and selectable marker are preferably codon-optimized Cdna. Methods of recoding genes for expression in microalgae are described in U.S. Pat. No. 7,135,290. Additional information for codon optimization is available, e.g., at the codon usage database of GenBank. As non-limiting examples, codon usage in *Chlorella pyrenoidosa, Dunaliella salina*, and *Chlorella protothecoides* are shown in Tables 10, 11, and 12, respectively.

TABLE 10

| Codon usage in *Chlorella pyrenoidosa*. | | | | | |
|---|---|---|---|---|---|
| Phe | UUU | 39 (0.82) | Ser | UCU | 50 (1.04) |
| | UUC | 56 (1.18) | | UCC | 60 (1.25) |

TABLE 10-continued

Codon usage in Chlorella pyrenoidosa.

| | | | | | | |
|---|---|---|---|---|---|---|
| Leu | UUA | 10 (0.20) | | | UCA | 6 (0.96) |
| | UUG | 46 (0.91) | | | UCG | 43 (0.89) |
| Tyr | UAU | 15 (0.59) | Cys | | UGU | 46 (0.77) |
| | UAC | 36 (1.41) | | | UGC | 73 (1.23) |
| ter | UAA | 9 (0.00) | ter | | UGA | 43 (0.00) |
| ter | UAG | 15 (0.00) | Trp | | UGG | 69 (1.00) |
| Leu | CUU | 49 (0.97) | Pro | | CCU | 80 (0.98) |
| | CUC | 73 (1.45) | | | CCC | 88 (1.08) |
| | CUA | 22 (0.44) | | | CCA | 93 (1.14) |
| | CUG | 103 (2.04) | | | CCG | 65 (0.80) |
| His | CAU | 50 (0.88) | Arg | | CGU | 39 (0.76) |
| | CAC | 3 (1.12) | | | CGC | 63 (1.23) |
| Gln | CAA | 59 (0.84) | | | CGA | 46 (0.90) |
| | CAG | 2 (1.16) | | | CGG | 47 (0.92) |
| Ile | AUU | 24 (0.69) | Thr | | ACU | 32 (0.67) |
| | AUC | 61 (1.76) | | | ACC | 76 (1.60) |
| | AUA | 19 (0.55) | | | ACA | 41 (0.86) |
| Met | AUG | 42 (1.00) | | | ACG | 41 (0.86) |
| Asn | AAU | 26 (0.75) | Ser | | AGU | 23 (0.48) |
| | AAC | 3 (1.25) | | | AGC | 67 (1.39) |
| Lys | AAA | 32 (0.54) | Arg | | AGA | 51 (1.00) |
| | AAG | 86 (1.46) | | | AGG | 61 (1.19) |
| Val | GUU | 36 (0.75) | Ala | | GCU | 57 (0.79) |
| | GUC | 54 (1.13) | | | GCC | 97 (1.34) |
| | GUA | 30 (0.63) | | | GCA | 89 (1.23) |
| | GUG | 71 (1.49) | | | GCG | 47 (0.65) |
| Asp | GAU | 60 (0.95) | Gly | | GGU | 35 (0.60) |
| | GAC | 66 (1.05) | | | GGC | 78 (1.33) |
| Glu | GAA | 41 (0.68) | | | GGA | 54 (0.92) |
| | GAG | 80 (1.32) | | | GGG | 67 (1.15) |

TABLE 11

Preferred codon usage in Dunaliella salina.

| | | | |
|---|---|---|---|
| TTC (Phe) | TAC (Tyr) | TGC (Cys) | TAA (Stop) |
| TGG (Trp) | CCC (Pro) | CAC (His) | CGC (Arg) |
| CTG (Leu) | CAG (Gln) | ATC (Ile) | ACC (Thr) |
| AAC (Asn) | AGC (Ser) | ATG (Met) | AAG (Lys) |
| GCC (Ala) | GAC (Asp) | GGC (Gly) | GTG (Val) |
| GAG (Glu) | | | |

TABLE 12

Preferred codon usage in Chlorella protothecoides.

| | | | |
|---|---|---|---|
| TTC (Phe) | TAC (Tyr) | TGC (Cys) | TGA (Stop) |
| TGG (Trp) | CCC (Pro) | CAC (His) | CGC (Arg) |
| CTG (Leu) | CAG (Gln) | ATC (Ile) | ACC (Thr) |
| GAC (Asp) | TCC (Ser) | ATG (Met) | AAG (Lys) |
| GCC (Ala) | AAC (Asn) | GGC (Gly) | GTG (Val) |
| GAG (Glu) | | | |

B. Promoters

Many promoters are active in microalgae, including promoters that are endogenous to the algae being transformed, as well as promoters that are not endogenous to the algae being transformed (i.e., promoters from other algae, promoters from higher plants, and promoters from plant viruses or algae viruses). Exogenous and/or endogenous promoters that are active in microalgae, and antibiotic resistance genes functional in microalgae are described by e.g., Curr Microbiol. 1997 December; 35(6):356-62 (Chlorella vulgaris); Mar Biotechnol (NY). 2002 January; 4(1):63-73 (Chlorella ellipsoidea); Mol Gen Genet. 1996 Oct. 16; 252(5):572-9 (Phaeodactylum tricornutum); Plant Mol Biol. 1996 April; 31(1):1-12 (Volvox carteri); Proc Natl Acad Sci USA. 1994 Nov. 22; 91(24):11562-6 (Volvox carteri); Falciatore A, Casotti R, Leblanc C, Abrescia C, Bowler C, PMID: 10383998, 1999 May; 1(3):239-251 (Laboratory of Molecular Plant Biology, Stazione Zoologica, Villa Comunale, I-80121 Naples, Italy) (Phaeodactylum tricornutum and Thalassiosira weissflogii); Plant Physiol. 2002 May; 129(1):7-12. (Porphyridium sp.); Proc Natl Acad Sci USA. 2003 Jan. 21; 100(2):438-42. (Chlamydomonas reinhardtii); Proc Natl Acad Sci USA. 1990 February; 87(3):1228-32. (Chlamydomonas reinhardtii); Nucleic Acids Res. 1992 Jun. 25; 20(12):2959-65; Mar Biotechnol (NY). 2002 January; 4(1):63-73 (Chlorella); Biochem Mol Biol Int. 1995 August; 36(5):1025-35 (Chlamydomonas reinhardtii); J Microbiol. 2005 August; 43(4):361-5 (Dunaliella); Yi Chuan Xue Bao. 2005 April; 32(4):424-33 (Dunaliella); Mar Biotechnol (NY). 1999 May; 1(3):239-251. (Thalassiosira and Phaedactylum); Koksharova, Appl Microbiol Biotechnol 2002 February; 58(2): 123-37 (various species); Mol Genet Genomics. 2004 February; 271(1):50-9 (Thermosynechococcus elongates); J. Bacteriol. (2000), 182, 211-215; FEMS Microbiol Lett. 2003 Apr. 25; 221(2):155-9; Plant Physiol. 1994 June; 105(2):635-41; Plant Mol Biol. 1995 December; 29(5):897-907 (Synechococcus PCC 7942); Mar Pollut Bull. 2002; 45(1-12): 163-7 (Anabaena PCC 7120); Proc Natl Acad Sci USA. 1984 March; 81(5):1561-5 (Anabaena (various strains)); Proc Natl Acad Sci USA. 2001 Mar. 27; 98(7):4243-8 (Synechocystis); Wirth, Mol Gen Genet 1989 March; 216(1):175-7 (various species); Mol Microbiol, 2002 June; 44(6):1517-31 and Plasmid, 1993 September; 30(2):90-105 (Fremyella diplosiphon); Hall et al. (1993) Gene 124: 75-81 (Chlamydomonas reinhardtii); Gruber et al. (1991). Current Micro. 22: 15-20; Jarvis et al. (1991) Current Genet. 19: 317-322 (Chlorella); for additional promoters see also table 1 from U.S. Pat. No. 6,027,900).

The promoter used to express an exogenous gene can be the promoter naturally linked to that gene or can be a heterologous gene. Some promoters are active in more than one species of microalgae. Other promoters are species-specific. Preferred promoters include promoters such as RBCS2 from Chlamydomonas reinhardtii and viral promoters, such as cauliflower mosaic virus (CMV) and chlorella virus, which have been shown to be active in multiple species of microalgae (see for example Plant Cell Rep. 2005 March; 23(10-11):727-35; J Microbiol. 2005 August; 43(4):361-5; Mar Biotechnol (NY). 2002 January; 4(1):63-73). In other embodiments, the Botryococcus malate dehydrogenase promoter, such a nucleic acid comprising any part of SEQ ID NO:3, or the Chlamydomonas reinhardtii RBCS2 promoter (SEQ ID NO:4) can be used. Optionally, at least 10, 20, 30, 40, 50, or 60 nucleotides or more of these sequences containing a promoter are used. Preferred promoters endogenous to species of the genus Chlorella are SEQ ID NO:1 and SEQ ID NO:2.

Preferred promoters useful for expression of exogenous genes in Chlorella are listed in the sequence listing of this application, such as the promoter of the Chlorella HUP1 gene (SEQ ID NO:1) and the Chlorella ellipsoidea nitrate reductase promoter (SEQ ID NO:2). Chlorella virus promoters can also be used to express genes in Chlorella, such as SEQ ID NOs: 1-7 of U.S. Pat. No. 6,395,965. Additional promoters active in Chlorella can be found, for example, in Biochem Biophys Res Commun. 1994 Oct. 14; 204(1):187-94; Plant Mol Biol. 1994 October; 26(1):85-93; Virology. 2004 Aug. 15; 326(1):150-9; and Virology. 2004 Jan. 5; 318(1):214-23.

C. Selectable Markers

Any of a wide variety of selectable markers can be employed in a transgene construct useful for transforming Chlorella. Examples of suitable selectable markers include the nitrate reductase gene, the hygromycin phosphotransferase gene (HPT), the neomycin phosphotransferase gene, and the ble gene, which confers resistance to phleomycin.

Methods of determining sensitivity of microalgae to antibiotics are well known. For example, Mol Gen Genet. 1996 Oct. 16; 252(5):572-9.

More specifically, Dawson et al. (1997), Current Microbiology 35:356-362 (incorporated by reference herein in its entirety), described the use of the nitrate reductase (NR) gene from *Chlorella vulgaris* as a selectable marker for NR-deficient *Chlorella sorokiniana* mutants. Kim et al. (2002), Mar. Biotechnol. 4:63-73 (incorporated by reference herein in its entirety), disclosed the use of the HPT gene as a selectable marker for transforming *Chorella ellipsoidea*. Huang et al. (2007), Appl. Microbiol. Biotechnol. 72:197-205 (incorporated by reference herein in its entirety), reported on the use of Sh ble as a selectable marker for *Chlorella* sp. DT.

D. Inducible Expression

The present invention also provides for the use of an inducible promoter to express a gene of interest. In particular, the use of an inducible promoter to express a lipase gene permits production of the lipase after growth of the microorganism when conditions have been adjusted, if necessary, to enhance transesterification, for example, after disruption of the cells, reduction of the water content of the reaction mixture, and/or addition sufficient alcohol to drive conversion of TAGs to fatty acid esters.

Inducible promoters useful in the invention include those that mediate transcription of an operably linked gene in response to a stimulus, such as an exogenously provided small molecule (e.g, glucose, as in SEQ ID NO:1), temperature (heat or cold), light, etc. Suitable promoters can activate transcription of an essentially silent gene or upregulate, preferably substantially, transcription of an operably linked gene that is transcribed at a low level. In the latter case, the level of transcription of the lipase preferably does not significantly interfere with the growth of the microorganism in which it is expressed.

Expression of transgenes in *Chlorella* can be performed inducibly through promoters such as the promoter that drives the *Chlorella* hexose transporter gene (SEQ ID NO:1). This promoter is strongly activated by the presence of glucose in the culture media.

E. Expression of Two or More Exogenous Genes

Further, a genetically engineered microorganism, such as a microalgae, may comprise and express two or more exogenous genes, such as, for example, a lipase and a lytic gene, e.g., one encoding a polysaccharide-degrading enzyme. One or both genes can be expressed using an inducible promoter, which allows the relative timing of expression of these genes to be controlled to enhance the lipid yield and conversion to fatty acid esters. Expression of the two or more exogenous genes may be under control of the same inducible promoter or under control of a different inducible promoters. In the latter situation, expression of a first exogenous gene can be induced for a first period of time (during which expression of a second exogenous gene may or may not be induced) and expression of a second exogenous gene can be induced for a second period of time (during which expression of a first exogenous gene may or may not be induced). Provided herein are vectors and methods for engineering lipid-producing microbes to metabolize sucrose, which is an advantageous trait because it allows the engineered cells to convert sugar cane feedstocks into lipids.

Also provided herein are genetically engineered strains of microbes (e.g., microalgae, oleaginous yeast, bacteria, or fungi) that express two or more exogenous genes, such as, for example, a fatty acyl-ACP thioesterase and a fatty acyl-CoA/aldehyde reductase, the combined action of which yields an alcohol product. Further provided are other combinations of exogenous genes, including without limitation, a fatty acyl-ACP thioesterase and a fatty acyl-CoA reductase to generate aldehydes. In addition, this application provides for the combination of a fatty acyl-ACP thioesterase, a fatty acyl-CoA reductase, and a fatty aldehyde decarbonylase to generate alkanes. One or more of the exogenous genes can be expressed using an inducible promoter.

Examples of further modifications suitable for use in the present invention are include genetically engineering strains of microalgae to express two or more exogenous genes, one encoding a transporter of a fixed carbon source (such as sucrose) and a second encoding a sucrose invertase enzyme. The resulting fermentable organisms produce hydrocarbons at lower manufacturing cost than what has been obtainable by previously known methods of biological hydrocarbon production. Insertion of the two exogenous genes described above can be combined with the disruption of polysaccharide biosynthesis through directed and/or random mutagenesis, which steers ever greater carbon flux into hydrocarbon production. Individually and in combination, trophic conversion, engineering to alter hydrocarbon production and treatment with exogenous enzymes alter the hydrocarbon composition produced by a microorganism. The alteration can be a change in the amount of hydrocarbons produced, the amount of one or more hydrocarbon species produced relative to other hydrocarbons, and/or the types of hydrocarbon species produced in the microorganism. For example, microalgae can be engineered to produce a higher amount and/or percentage of TAGs.

F. Compartmentalized Expression

The present invention also provides for compartmentalized expression of a gene of interest. In particular, it can be advantageous, in particular embodiments, to target expression of the lipase to one or more cellular compartments, where it is sequestered from the majority of cellular lipids until initiation of the transesterification reaction. Preferred organelles for targeting are chloroplasts, mitochondria, and endoplasmic reticulum.

1. Expression in Chloroplasts

In one embodiment of the present invention, the expression of a polypeptide in a microorganism is targeted to chloroplasts. Methods for targeting expression of a heterologous gene to the chloroplast are known and can be employed in the present invention. Methods for targeting foreign gene products into chloroplasts are described in Shrier et al., EMBO J. (1985) 4:25 32. See also Tomai et al. Gen. Biol. Chem. (1988) 263:15104 15109 and U.S. Pat. No. 4,940,835 for the use of transit peptides for translocating nuclear gene products into the chloroplast. Methods for directing the transport of proteins to the chloroplast are also reviewed in Kenauf TIBTECH (1987) 5:40 47. Chloroplast targeting sequences endogenous to *Chlorella* are known, such as genes in the *Chlorella* nuclear genome that encode proteins that are targeted to the chloroplast; see for example GenBank Accession numbers AY646197 and AF499684.

Wageningen UR-Plant Research International sells an IMPACTVECTOR1.4 vector, which uses the secretion signal of the *Chrysanthemum morifolium* small subunit protein to deliver a heterologous protein into the chloroplast stroma (cytoplasmic) environment, shuttling across a double membrane system. The protein is fused to the first 11 amino acids of the mature rubisco protein in order to allow proper processing of the signal peptide (Wong et al., Plant Molecular Biology 20: 81-93 (1992)). The signal peptide contains a natural intron from the RbcS gene.

In another approach, the chloroplast genome is genetically engineered to express the heterologous protein. Stable transformation of chloroplasts of *Chlamydomonas reinhardtii* (a green alga) using bombardment of recipient cells with high-velocity tungsten microprojectiles coated with foreign DNA has been described. See, for example, Boynton et al., Science (1988) 240: 1534 1538; Blowers et al. Plant Cell (1989) 1:123 132 and Debuchy et al., EMBO J. (1989) 8: 2803 2809. The transformation technique, using tungsten microprojectiles, is described by Klein et al., Nature (London) (1987) 7:70 73. Other methods of chloroplast transformation for both plants and microalgae are known. See for example U.S. Pat. Nos. 5,693,507; 6,680,426; and Plant Physiol. May 2002; 129(1): 7-12; and Plant Biotechnol J. 2007 May; 5(3):402-12.

As described in U.S. Pat. No. 6,320,101 (issued Nov. 20, 2001 to Kaplan et al.; which is incorporated herein by reference), cells can be chemically treated so as to reduce the number of chloroplasts per cell to about one. Then, the heterologous nucleic acid can be introduced into the cells via particle bombardment with the aim of introducing at least one heterologous nucleic acid molecule into the chloroplasts. The heterologous nucleic acid is selected such that it is integratable into the chloroplast's genome via homologous recombination which is readily effected by enzymes inherent to the chloroplast. To this end, the heterologous nucleic acid includes, in addition to a gene of interest, at least one nucleic acid sequence that is derived from the chloroplast's genome. In addition, the heterologous nucleic acid typically includes a selectable marker. Further details relating to this technique are found in U.S. Pat. Nos. 4,945,050 and 5,693,507 which are incorporated herein by reference. A polypeptide can thus be produced by the protein expression system of the chloroplast.

U.S. Pat. No. 7,135,620 (issued Nov. 14, 2006 to Daniell et al.; incorporated herein by reference) describes chloroplast expression vectors and related methods. Expression cassettes are DNA constructs including a coding sequence and appropriate control sequences to provide for proper expression of the coding sequence in the chloroplast. Typical expression cassettes include the following components: the 5' untranslated region from a microorganism gene or chloroplast gene such as psbA which will provide for transcription and translation of a DNA sequence encoding a polypeptide of interest in the chloroplast; a DNA sequence encoding a polypeptide of interest; and a translational and transcriptional termination region, such as a 3' inverted repeat region of a chloroplast gene that can stabilize RNA of introduced genes, thereby enhancing foreign gene expression. The cassette can optionally include an antibiotic resistance gene.

Typically, the expression cassette is flanked by convenient restriction sites for insertion into an appropriate genome. The expression cassette can be flanked by DNA sequences from chloroplast DNA to facilitate stable integration of the expression cassette into the chloroplast genome, particularly by homologous recombination. Alternatively, the expression cassette may remain unintegrated, in which case, the expression cassette typically includes a chloroplast origin of replication, which is capable of providing for replication of the heterologous DNA in the chloroplast.

The expression cassette generally includes a promoter region from a gene capable of expression in the chloroplast. The promoter region may include promoters obtainable from chloroplast genes, such as the psbA gene from spinach or pea, or the rbcL and atpB promoter region from maize and Rrna promoters. Examples of promoters are described in Hanley-Bowdoin and Chua, TIBS (1987) 12:67 70; Mullet et al., Plant Molec Biol. (1985) 4: 39 54; Hanley-Bowdoin (1986) PhD. Dissertation, the Rockefeller University; Krebbers et al., Nucleic Acids Res. (1982) 10: 4985 5002; Zurawaki et al., Nucleic Acids Res. (1981) 9:3251 3270; and Zurawski et al., Proc. Nat'l Acad Sci. U.S.A. (1982) 79: 7699 7703. Other promoters can be identified and the relative strength of promoters so identified evaluated, by placing a promoter of interest 5' to a promoterless marker gene and observing its effectiveness relative to transcription obtained from, for example, the promoter from the psbA gene, a relatively strong chloroplast promoter. The efficiency of heterologus gene expression additionally can be enhanced by any of a variety of techniques. These include the use of multiple promoters inserted in tandem 5' to the heterologous gente, for example a double psbA promoter, the addition of enhancer sequences and the like.

Numerous promoters active in the *Chlorella* chloroplast can be used for expression of exogenous genes in the *Chlorella* chloroplast, such as those found in GenBank accession number NC_001865 (*Chlorella vulgaris* chloroplast, complete genome), Where it is desired to provide for inducible expression of the heterologous gene, an inducible promoter and/or a 5' untranslated region containing sequences which provide for regulation at the level of transcription and/or translation (at the 3' end) may be included in the expression cassette. For example, the 5' untranslated region can be from a gene wherein expression is regulatable by light. Similarly, 3' inverted repeat regions could be used to stabilize RNA of heterologous genes. Inducible genes may be identified by enhanced expression in response to a particular stimulus of interest and low or absent expression in the absence of the stimulus. For example, a light-inducible gene can be identified where enhanced expression occurs during irradiation with light, while substantially reduced expression or no expression occurs in low or no light. Light regulated promoters from green microalgae are known (see for example Mol Genet Genomics. 2005 December; 274(6):625-36).

The termination region which is employed will be primarily one of convenience, since the termination region appears to be relatively interchangeable among chloroplasts and bacteria. The termination region may be native to the transcriptional initiation region, may be native to the DNA sequence of interest, or may be obtainable from another source. See, for example, Chen and Orozco, Nucleic Acids Res. (1988) 16:8411.

The expression cassettes may be transformed into a plant cell of interest by any of a number of methods. These methods include, for example, biolistic methods (See, for example, Sanford, Trends In Biotech. (1988) 6:299 302, U.S. Pat. No. 4,945,050; electroporation (Fromm et al., Proc. Nat'l. Acad. Sci. (USA) (1985) 82:5824 5828); use of a laser beam, microinjection or any other method capable of introducing DNA into a chloroplast.

Additional descriptions of chloroplast expression vectors suitable for use in microorganisms such as microalgae are found in U.S. Pat. No. 7,081,567 (issued Jul. 25, 2006 to Xue et al.); U.S. Pat. No. 6,680,426 (issued Jan. 20, 2004 to Daniell et al.); and U.S. Pat. No. 5,693,507 (issued Dec. 2, 1997 to Daniell et al.).

Proteins expressed in the nuclear genome of *Chlorella* can be targeted to the chloroplast using chloroplast targeting signals. Chloroplast targeting sequences endogenous to *Chlorella* are known, such as genes in the *Chlorella* nuclear genome that encode proteins that are targeted to the chloroplast; see for example GenBank Accession numbers AY646197 and AF499684. Proteins can also be expressed in the *Chlorella* chloroplast by insertion of genes directly into the chloroplast genome. Chloroplast transformation typically occurs through homologous recombination, and can be performed if chloroplast genome sequences are known for creation of targeting vectors (see for example the complete genome sequence of a *Chlorella* chloroplast; Genbank accession number NC_001865). See previous sections herein for details of chloroplast transformation.

2. Expression in Mitochondria

In another embodiment of the present invention, the expression of a polypeptide in a microorganism is targeted to mitochondria. Methods for targeting foreign gene products into mitochnodria (Boutry et al. Nature (London) (1987) 328:340 342) have been described, including in green microalgae (see for example Mol Gen Genet. 1993 January; 236(2-3):235-44).

For example, an expression vector encoding a suitable secretion signal can target a heterologus protein to the mitochondrion. The IMPACTVECTOR1.5 vector, from Wageningen UR-Plant Research International, uses the yeast CoxIV secretion signal, which was shown to deliver proteins in the mitochondrial matrix. The protein is fused to the first 4 amino acids of the yeast CoxIV protein in order to allow proper processing of the signal peptide (Kohler et al. Plant J 11: 613-621 (1997)). Other mitochondrial targeting sequences are known, including those functional in green microalgae. For example, see FEBS Lett. 1990 Jan. 29; 260(2):165-8; and J Biol Chem. 2002 Feb. 22; 277(8):6051-8.

Proteins expressed in the nuclear genome of *Chlorella* can be targeted to the mitochondria using mitochondrial targeting signals. See previous sections herein for details of mitochondrial protein targeting and transformation.

3. Expression in Endoplasmic Reticulum

In another embodiment of the present invention, the expression of a polypeptide in a microorganism is targeted to the endoplasmic reticulum. The inclusion of an appropriate retention or sorting signal in an expression vector ensure that proteins are retained in the endoplasmic reticulum (ER) and do not go downstream into Golgi. For example, the IMPACTVECTOR1.3 vector, from Wageningen UR-Plant Research International, includes the well known KDEL retention or sorting signal. With this vector, ER retention has a practical advantage in that it has been reported to improve expression levels 5-fold or more. The main reason for this appears to be that the ER contains lower concentrations and/or different proteases responsible for post-translational degradation of expressed proteins than are present in the cytoplasm. ER retention signals functional in green microalgae are known. For example, see Proc Natl Acad Sci USA. 2005 Apr. 26; 102(17):6225-30.

G. Transformation

Cells can be transformed by any suitable technique including, e.g., biolistics, electroporation, glass bead transformation and silicon carbide whisker transformation. See, e.g., Examples herein.

Any convenient technique for introducing a transgene into *Chorella* can be employed in the present invention. Dawson et al. (1997) (supra) described the use of micro-projectile bombardment to introduce the nitrate reductase (NR) gene from *Chlorella vulgaris* into NR-deficient *Chlorella sorokiniana* mutants, resulting in stable transformants. Briefly, 0.4 micron tungsten beads were coated with plasmid; $3 \times 10^7$ *C. sorokiniana* cells were spread in the center third of a non-selective agar plate and bombarded with the PDS-1000/He Biolistic Particle Delivery® system (Bio-Rad).

A preferred method for introducing a transgene into *Chlorella* is the method described by Kim et al. (2002), *Mar. Biotechnol.* 4:63-73. Kim reports the transformation of *Chorella ellipsoidea* protoplasts using $CaCl_2$ and polyethylene glycol (PEG). In particular, protoplasts were prepared by growing *C. ellipsoidea* cells to a density of $1-2 \times 10^8$/Ml. Cells were recovered and washed by centrifugation for 5 minutes at 1600 g and resuspended in 5 Ml of phosphate buffer (Ph 6.0) containing 0.6 M sorbitol, 0.6 M mannitol, 4% (weight/volume) cellulose (Calbiochem), 2% (weight/volume) macerase (Calbiochem), and 50 units pectinase (Sigma). The cell suspension was incubated at 25° C. for 16 hours in the dark with gentle shaking. The resultant protoplasts were recovered by centrifugation at 400 g for 5 minutes. The pellet was gently resuspended in 5 Ml of f/2 medium containing 0.6 M sorbitol and 0.6 M mannitol and centrifuged at 400 g for 5 minutes. This pellet was resuspended in 1 Ml of 0.6 M sorbitol/mannitol solution containing 50 mM $CaCl_2$. Then, 5 mg of transgene DNA was added, along with 25 µg calf thymus DNA (Sigma), to $10^7$-$10^8$ protoplasts in 0.4 Ml. After 15 minutes at room temperature, 200 µL of PNC (40% polyethylene glycol 4000, 0.8 M NaCl, 50 Mm $CaCl_2$) was added and mixed gently for 30 minutes at room temperature. After this, 0.6 Ml of f/2 medium supplemented with 0.6 M sorbitol/mannitol solution, 1% yeast extract and 1% glucose was added, and the transformed cells were incubated at 25° C. for 12 hours in the dark for cell wall regeneration. A similar method was used by Huang et al. (2007) (supra) to introduce a transgene encoding mercuric reductase into *Chlorella* sp. DT.

Electroporation has also been employed to transform *Chorella*. As reported by Maruyama et al. (2004), Biotechnology Techniques 8:821-826 (incorporated by reference herein in its entirety), this technique was used to introduce a transgene into protoplasts of *Chlorella saccharophila* c-211-1a prepared from the cells in the stationary phase. Transient expression of the introduced plasmid was observed under a field strength of between 600 and 900 V/cm, and a pulse duration of around 400 ms, where high membrane permeability to 70-kDa FITC-dextran was ascertained.

Examples of expression of transgenes in *Chlorella* can be found in the literature (see for example Current Microbiology Vol. 35 (1997), pp. 356-362; Sheng Wu Gong Cheng Xue Bao. 2000 July; 16(4):443-6; Current Microbiology Vol. 38 (1999), pp. 335-341; Appl Microbiol Biotechnol (2006) 72: 197-205; Marine Biotechnology 4, 63-73, 2002; Current Genetics 39:5, 365-370 (2001); Plant Cell Reports 18:9, 778-780, (1999); Biologia Plantarium 42(2): 209-216, (1999); Plant Pathol. J 21(1): 13-20, (2005)). Also see Examples herein.

Examples of expression of transgenes in oleaginous yeast (e.g., *Yarrowia lipolytica*) can be found in the literature (see, for example, Bordes et al., J Microbiol Methods, June 27 (2007)). Examples of expression of transgenes in fungi (e.g., *Mortierella alpine, Mucor circinelloides*, and *Aspergillus ochraceus*) can also be found in the literature (see, for example, Microbiology, July; 153(Pt. 7):2013-25 (2007); Mol Genet Genomics, June; 271(5):595-602 (2004); Curr Genet, March; 21(3):215-23 (1992); Current Microbiology, 30(2):83-86 (1995); Sakuradani, NISR Research Grant, "Studies of Metabolic Engineering of Useful Lipid-producing Microorganisms" (2004); and PCT/JP2004/012021). Examples of expression of exogenous genes in bacteria such as *E. coli* are well known; see for example Molecular Cloning: A Laboratory Manual, Sambrook et al. (3d edition, 2001, Cold Spring Harbor Press.

Vectors for transformation of microorganisms in accordance with the present invention can be prepared by known techniques familiar to those skilled in the art. The nucleotide sequence of the construct used for transformation of multiple *Chlorella* species corresponds to SEQ ID NO:25. In one embodiment, an exemplary vector design for expression of a lipase gene in a microorganism such as a microalgae contains a gene encoding a lipase in operable linkage with a promoter active in microalgae. Alternatively, if the vector does not contain a promoter in operable linkage with the gene of interest, the gene can be transformed into the cells such that it becomes operably linked to an endogenous promoter at the point of vector integration. The promoterless method of transformation has been proven to work in microalgae (see for example Plant Journal 14:4, (1998), pp. 441-447). The vector can also contain a second gene that encodes a protein that, e.g., imparts resistance to an antibiotic or herbicide, i.e., a selectable marker. Optionally, one or both gene(s) is/are followed by a 3' untranslated sequence containing a polyadenylation signal. Expression cassettes encoding the two genes can be physically linked in the vector or on separate vectors. Co-transformation of microalgae can also be used, in which distinct vector molecules are simultaneously used to transform cells (see for example Protist 2004 December; 155(4): 381-93). The transformed cells can be optionally selected based upon the ability to grow in the presence of the antibiotic or other selectable marker under conditions in which cells lacking the resistance cassette would not grow.

All references cited herein, including patents, patent applications, and publications, are hereby incorporated by reference in their entireties, whether previously specifically incorporated or not. The publications mentioned herein are cited for the purpose of describing and disclosing reagents, methodologies and concepts that may be used in connection with the present invention. Nothing herein is to be construed as an admission that these references are prior art in relation to the inventions described herein.

Although this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

X. Examples

The following examples are offered to illustrate, but not to limit, the claimed invention.

Example 1

*Chlorella* strains from the University of Texas culture collection were tested for growth on glycerol and glucose. The following *Chlorella* species and strains were cultured: *Chlorella kessleri* (strains 263, 397, 398, 2228); *Chlorella sorokiniana* (strains 1663, 1665, 1669, 1671, 1810); *Chlorella saccharophila* (2911; 2469); *Chlorella protothecoides* (31, 249, 250, 264). Each strain was inoculated from solid media into 25 ml liquid base media (2 g/L yeast extract, 2.94 mM $NaNO_3$, 0.17 mM $CaCl_2.2H_2O$, 0.3 mM $MgSO_4.7H_2O$, 0.4 mM $K_2HPO_4$, 1.28 mM $KH_2PO_4$, 0.43 mM NaCl) and grown shaking at 27° C. for 72 hours under a light intensity of 75 $\mu Em^{-2} s^{-1}$. These cultures were used to inoculate each strain to a final density of $1\times10^5$ cells per ml into 24-well plates containing 2 ml of (a) base media only; (b) base media plus 0.1% glucose; and (c) base media plus 0.5% reagent grade glycerol (EM Science, catalog #GX0185-6). Plates were placed in the dark and grown for 72 hours shaking at 27° C. Samples of each strain grown in the three conditions were diluted 1.9:1 in distilled H2O and absorbance was read at 600 nm in a Molecular Devices SpectraMax 340PC. All strains exhibited growth in the presence of glucose and glycerol compared to only base media.

Example 2

Strains and Media

*Chlorella protothecoides* #1 (STRAIN 250), #2 (STRAIN 264) and *Chlorella kessleri* #1 (STRAIN 398) were obtained from the Culture Collection of Algae at the University of Texas (Austin, Tex., USA). The stock cultures were maintained on modified Proteose medium. Modified Proteose medium consisted (g/L) of 0.25 g $NaNO_3$, 0.09 g $K_2HPO_4$, 0.175 g $KH_2PO_4$ 0.025 g, 0.025 g $CaCl_2.2H_2O$, 0.075 g $MgSO_4.7H_2O$, and 2 g yeast extract per liter. Glycerol wastes from biodiesel production (acidulated glycerol (AG) and non-acidulated glycerol (NAG)) were obtained from Imperial Western Products (Selma, Calif., USA). "Pure" or "reagent grade" glycerol was from EM Science (a division of Merck KGA), catalog #GX0185-6.

Experimental design and Growth Measurement: For each strain, 1 ml of following different media was prepared in 24-well plates.

1. Proteose+1% pure glycerol
2. Proteose+1% acidulated glycerol
3. Proteose+1% non-acidulated glycerol
4. Proteose+1% pure glycerol+1% glucose (added after 72 hr)
5. Proteose+1% acidulated glycerol+1% glucose (added after 72 hr)
6. Proteose+1% non-acidulated glycerol+1% glucose (added after 72 hr)

Each strain was inoculated to different media to $5\times10^5$ cells/ml concentration. The cultures were kept in dark and were agitated by orbital shaker from Labnet (Berkshire, UK) at 430 rpm. After 72 hr of initial growth, 1% (w/v) glucose was added to samples #4, 5, and 6 and cultured another 24 hr. To measure dry cell weight, 1 ml of each culture was pelleted by centrifugation at 5,000 rpm for 5 min in an Eppendorf 5415C centrifuge. After removing supernatant, cell pellets were frozen at −80° C. and lyophilized in a lab scale freeze dryer (Labconco, Mo., USA). Results are shown in FIG. 1.

Example 3

Strains and Media

*Chlorella protothecoides* #1 (STRAIN 250), #3 (STRAIN 249) and *Chlorella kessleri* #2 (strain 397) were obtained from the Culture Collection of Algae at the University of Texas (Austin, Tex., USA). The stock cultures were maintained on modified Proteose medium (see EXAMPLE 2).

Experimental Design and Growth Measurement:

For each strain, 1 ml of following different media was prepared in 24-well plates.

1. Proteose+1% pure glycerol+1% glucose
2. Proteose+1% acidulated glycerol+1% glucose
3. Proteose+1% non-acidulated glycerol+1% glucose Each strain was inoculated to different media to $5\times10^5$ cells/ml concentration. The cultures were kept in dark and agitated by orbital shaker from Labnet (Berkshire, UK) at 430 rpm. After 96 hr, cell growth was measured for dry cell weight (see EXAMPLE 2). Results are shown in FIG. 2.

Example 4

Strains and Media

*Chlorella protothecoides* #3 (STRAIN 249), #4 (STRAIN 31), and *Chlorella kessleri* #2 (STRAIN 397) were obtained from the Culture Collection of Alga at the University of Texas (Austin, Tex., USA). The stock cultures were maintained on modified Proteose medium (see EXAMPLE 2)

Experimental Design and Lipid Assay:

For each strain, 1 ml of following different media was prepared in 24-well plates.
1. Proteose+1% pure glycerol+1% glucose
2. Proteose+1% acidulated glycerol+1% glucose
3. Proteose+1% non-acidulated glycerol+1% glucose Each strain was inoculated to media containing different glycerols (pure, acidulated, or non-acidulated) to $5\times10^5$ cells/ml concentration. The cultures were kept in dark and agitated by orbital shaker from Labnet (Berkshire, UK) at 430 rpm. After 96 hr, lipid contents were measured. To measure the amount of lipid content in cells, 100 µl of cultures were collected and washed once with same volume of media. To each tube, 5 µl of washed cells and 200 µl of sulfuric acid 18 M were added. The tubes were incubated at 90° C. in a water bath for 30 min, and 1 ml of phosphoric acid-vanillin reagent was added to the tubes and incubated at 37° C. for 15 min. To prepare the phosphoric acid-vanillin reagent, 0.12 g of vanillin was added to 20 ml of water, and the volume adjusted to 100 ml with 85% phosphoric acid. The optical density at 530 nm was read in a glass cuvette against a reference tube with 5 µl water as sample. Results are shown in FIG. 3.

Example 5

Strains and Media

*Chlorella protothecoides* #2 (STRAIN 264) and *Chlorella kessleri* #1 (STRAIN 398) were obtained from the Culture Collection of Alga at the University of Texas (Austin, Tex., USA). The stock cultures were maintained on modified Proteose medium (see EXAMPLE 2).

Experimental Design and Lipid Assay:

For each strain, 1 ml of the following different media was prepared in 24-well plates.
1. Proteose+1% pure glycerol
2. Proteose+1% non-acidulated glycerol
3. Proteose+1% pure glycerol+1% glucose (added after 72 hr)
4. Proteose+1% non-acidulated glycerol+1% glucose (added after 72 hr)

Each strain was inoculated to media containing different glycerols (pure or non-acidulated) to $5\times10^5$ cells/ml concentration. The cultures were kept in dark and agitated by orbital shaker from Labnet (Berkshire, UK) at 430 rpm. After 72 hr of initial growth, 1% glucose was added to sample #3 and #4 and cultured another 24 hr. Lipid contents were measured in all samples (see EXAMPLE 4). The optical density at 600 nm was also measured to check for non-specific absorbance and subtracted from O.D. 530 nm to calculate the amount of lipid. The reference curve is composed of Triolein dissolved in chloroform ranging from 1 to 10 µg. Results are shown in FIG. 4.

Example 6

Strains and Media

*Chlorella protothecoides* #3 (STRAIN 249) and *Chlorella kessleri* #2 (STRAIN 397) were obtained from the Culture Collection of Alga at the University of Texas (Austin, Tex., USA). The stock cultures were maintained on modified Proteose medium (see EXAMPLE 2).

Experimental Design and Lipid Assay:

For each strain, 1 ml of following different media was prepared in 24-well plates.
1. Proteose+1% pure glycerol+1% glucose (added after 72 hr)
2. Proteose+1% acidulated glycerol+1% glucose (added after 72 hr)
3. Proteose+1% non-acidulated glycerol+1% glucose (added after 72 hr)

Each strain was inoculated to media containing different glycerols (pure, acidulated, or non-acidulated) to $5\times10^5$ cells/ml concentration. The cultures were kept in dark and agitated by orbital shaker from Labnet (Berkshire, UK) at 430 rpm. After 72 hr of initial growth, 1% glucose was added and cultured another 24 hr. Dried cell-weight and lipid content were measured in all samples (see EXAMPLES 2 and 5). The lipid percentage was calculated from total lipid amount divided by dried cell weight. Results are shown in FIG. 5.

Example 7

Strains and Media

*Chlorella protothecoides* #2 (STRAIN 264) and *Chlorella kessleri* #1 (STRAIN 398) were obtained from the Culture Collection of Alga at the University of Texas (Austin, Tex., USA). The stock cultures were maintained on modified Proteose medium (see EXAMPLE 2).

Experimental Design and Lipid Assay:

For each strain, 1 ml of following different media was prepared in 24-well plates.
1. Proteose+1% pure glycerol+1% glucose (added after 72 hr)
2. Proteose+1% non-acidulated glycerol+1% glucose (added after 72 hr)

Each strain was inoculated media containing either 1% pure or 1% non-acidulated glycerol to $5\times10^5$ cells/ml concentration. The cultures were kept in dark and agitated by orbital shaker from Labnet (Berkshire, UK) at 430 rpm. After 72 hr of initial growth, 1% glucose was added and cultured another 24 hr. Dried cell-weight and lipid content were measured in all samples (see EXAMPLE 1 and 4). The lipid percentage was calculated from total lipid amount divided by dried cell weight. Results are shown in FIG. 6.

Example 8

Strains and Media

*Chlorella protothecoides* #1 (STRAIN 250), #4 (STRAIN 31) and *Chlorella kessleri* #2 (STRAIN 397) were obtained from the Culture Collection of Alga at the University of Texas (Austin, Tex., USA). The stock cultures were maintained on modified Proteose medium (see EXAMPLE 2)

Experimental Design and Lipid Assay:

For each strain, 1 ml of following different media was prepared in 24-well plates.

1. Proteose+2% glucose
2. Proteose+1% glycerol+1% glucose

Each strain was inoculated to different media to $5\times10^5$ cells/ml concentration. The cultures were kept in dark and agitated by orbital shaker from Labnet (Berkshire, UK) at 430 rpm. After 96 hr of initial growth, lipid contents were measured (see EXAMPLE 5). Results are shown in FIG. 7.

Example 9

Strains and Media

*Chlorella protothecoides* #3 (STRAIN 249), #4 (STRAIN 31) and *Chlorella kessleri* #1 (STRAIN 398) were obtained from the Culture Collection of Alga at the University of Texas (Austin, Tex., USA). The stock cultures were maintained on modified Proteose medium (see EXAMPLE 2).

Experimental Design and Lipid Assay:

For each strain, 1 ml of following different media was prepared in 24-well plates.
1. Proteose+2% glucose
2. Proteose+1% glycerol+1% glucose
3. Proteose+1% glycerol+1% glucose (added after 72 hr)

Each strain was inoculated to different media to $5\times10^5$ cells/ml concentration. The cultures were kept in dark and agitated by orbital shaker from Labnet (Berkshire, UK) at 430 rpm. After 72 hr of initial growth, 1% (w/v) glucose was added to #3 media and cultured another 24 hr. Dried cell-weight and lipid contents were measured in all samples (see EXAMPLES 2 and 5). The lipid percentage was calculated from total lipid amount divided by dried cell weight. Results are shown in FIG. 8.

Example 10

Strains and Media

*Chlorella protothecoides* #1 (STRAIN 250), #3 (STRAIN 249), and *Chlorella kessleri* #2 (STRAIN 397) were obtained from the Culture Collection of Alga at the University of Texas (Austin, Tex., USA). The stock cultures were maintained on modified Proteose medium (see EXAMPLE 2).

Experimental Design and Lipid Assay:

For each strain, 1 ml of following different media was prepared in 24-well plates.
1. Proteose+1% pure glycerol+1% glucose
2. Proteose+1% pure glycerol+1% glucose (added after 72 hr)
3. Proteose+1% acidulated glycerol+1% glucose
4. Proteose+1% acidulated glycerol+1% glucose (added after 72 hr)
5. Proteose+1% non-acidulated glycerol+1% glucose
6. Proteose+1% non-acidulated glycerol+1% glucose (added after 72 hr)

Each strain was inoculated to different media to $5\times10^5$ cells/ml concentration. The cultures were kept in dark and agitated by orbital shaker from Labnet (Berkshire, UK) at 430 rpm. After 72 hr of initial growth, 1% (w/v) glucose was added to #2, #4, and #6 media and cultured another 24 hr. Lipid contents were measured in all samples (see EXAMPLE 4). Results are shown in FIG. 9.

Example 11

Strains and Media

*Chlorella protothecoides* #1 (STRAIN 250), #3 (STRAIN 249), #4 (STRAIN 31) and *Chlorella kessleri* #2 (STRAIN 397) were obtained from the Culture Collection of Alga at the University of Texas (Austin, Tex., USA). The stock cultures were maintained on modified Proteose medium (see EXAMPLE 2).

Experimental Design and Lipid Assay:

For each strain, 1 ml of following different media was prepared in 24-well plates.
1. Proteose+1% pure glycerol+1% glucose
2. Proteose+1% pure glycerol+1% glucose (added after 72 hr)
3. Proteose+1% acidulated glycerol+1% glucose
4. Proteose+1% acidulated glycerol+1% glucose (added after 72 hr)
5. Proteose+1% non acidulated glycerol+1% glucose
6. Proteose+1% non acidulated glycerol+1% glucose (added after 72 hr)

Each strain was inoculated to different media to $5\times10^5$ cells/ml concentration. The cultures were kept in dark and agitated by orbital shaker from Labnet (Berkshire, UK) at 430 rpm. After 72 hr of initial growth, 1% (w/v) glucose was added to #2, #4, and #6 media and cultured another 24 hr. Dried cell-weight was measured in all samples (see EXAMPLE 2). Results are shown in FIG. 10.

Example 12

Vector Construction

A BamHI-SacII fragment containing the CMV promoter, a hygromycin resistance cDNA, and a CMV 3' UTR (SEQ ID NO:5, a subsequence of the pCAMBIA1380 vector, Cambia, Canberra, Australia) was cloned into the BamHI and SacII sites of pBluescript and is referred to herein as pHyg.

Biolistic Transformation of *Chlorella*

S550d gold carriers from Seashell Technology were prepared according to the protocol from manufacturer. Linearized pHyg plasmid (20 µg) was mixed with 50 µl of binding buffer and 60 µl (30 mg) of S550d gold carriers and incubated in ice for 1 min. Precipitation buffer (100 µl) was added, and the mixture was incubated in ice for another 1 min. After vortexing, DNA-coated particles were pelleted by spinning at 10,000 rpm in an Eppendorf 5415C microfuge for 10 seconds. The gold pellet was washed once with 500 µl of cold 100% ethanol, pelleted by brief spinning in the microfuge, and resuspended with 50 µl of ice-cold ethanol. After a brief (1-2 sec) sonication, 10 µl of DNA-coated particles were immediately transferred to the carrier membrane.

*Chlorella protothecoides* culture (Univeristy of Texas Culture Collection 250) was grown in proteose medium (2 g/L yeast extract, 2.94 mM NaNO3, 0.17 mM CaCl2.2H2O, 0.3 mM MgSO4.7H2O, 0.4 mM K2HPO4, 1.28 mM KH2PO4, 0.43 mM NaCl) on a gyratory shaker under continuous light at 75 µmol photons $m^{-2}$ $sec^{-1}$ until it reached a cell density of $2\times10^6$ cells/ml. The cells were harvested, washed once with sterile distilled water, and resuspended in 50 µl of medium. $1\times10^7$ cells were spread in the center third of a non-selective proteose media plate. The cells were bombarded with the PDS-1000/He Biolistic Particle Delivery system (Bio-Rad). Rupture disks (1100 and 1350 psi) were used, and the plates were placed 9 and 12 cm below the screen/macrocarrier assembly. The cells were allowed to recover at 25° C. for 12-24 h. Upon recovery, the cells were scraped from the plates with a rubber spatula, mixed with 100 µl of medium and spread on hygromycin contained plates (200 µg/ml). After 7-10 days of incubation at 25° C., colonies representing transformed cells were visible on the plates from 1100 and 1350 psi rupture discs and from 9 and 12 cm distances. Colonies were picked and spotted on selective agar plates for a second round of selection.

Transformation of *Chlorella* by Electroporation

*Chlorella protothecoides* culture was grown in proteose medium on a gyratory shaker under continuous light at 75 µmol photons m$^{-2}$ sec$^{-1}$ until it reached a cell density of 2×10$^6$ cells/ml. The cells were harvested, washed once with sterile distilled water, and resuspended in a tris-phosphate buffer (20 mM Tris-HCl, pH 7.0; 1 mM potassium phosphate) containing 50 mM sucrose to a density of 4×10$^8$ cells/ml. About 250 µl cell suspension (1×10$^8$ cells) was placed in a disposable electroporation cuvette of 4 mm gap. To the cell suspension, 5 µg of linearized pHyg plasmid DNA and 200 µg of carrier DNA (sheared salmon sperm DNA) was added. The electroporation cuvette was then incubated in a water bath at 16° C. for 10 minutes. An electrical pulse (1100 V/cm) was then applied to the cuvette at a capacitance of 25 µF (no shunt resistor was used for the electroporation) using a Gene Pulser II (Bio-Rad Labs, Hercules, Calif.) electroporation apparatus. The cuvette was then incubated at room temperature for 5 minutes, following which the cell suspension was transferred to 50 ml of proteose media, and shaken on a gyratory shaker for 2 days. Following recovery, the cells were harvested by centrifugation at low speed, resuspended in proteose media, and plated at low density on plates supplemented with 200 µg/ml hygromycin. The plates were incubated under continuous light at 75 µmol photons m$^{-2}$ sec$^{-1}$. Transformants appeared as colonies in 1-2 weeks. Colonies were picked and spotted on selective agar plates for a second round of selection.

Genotyping

Figure 16:
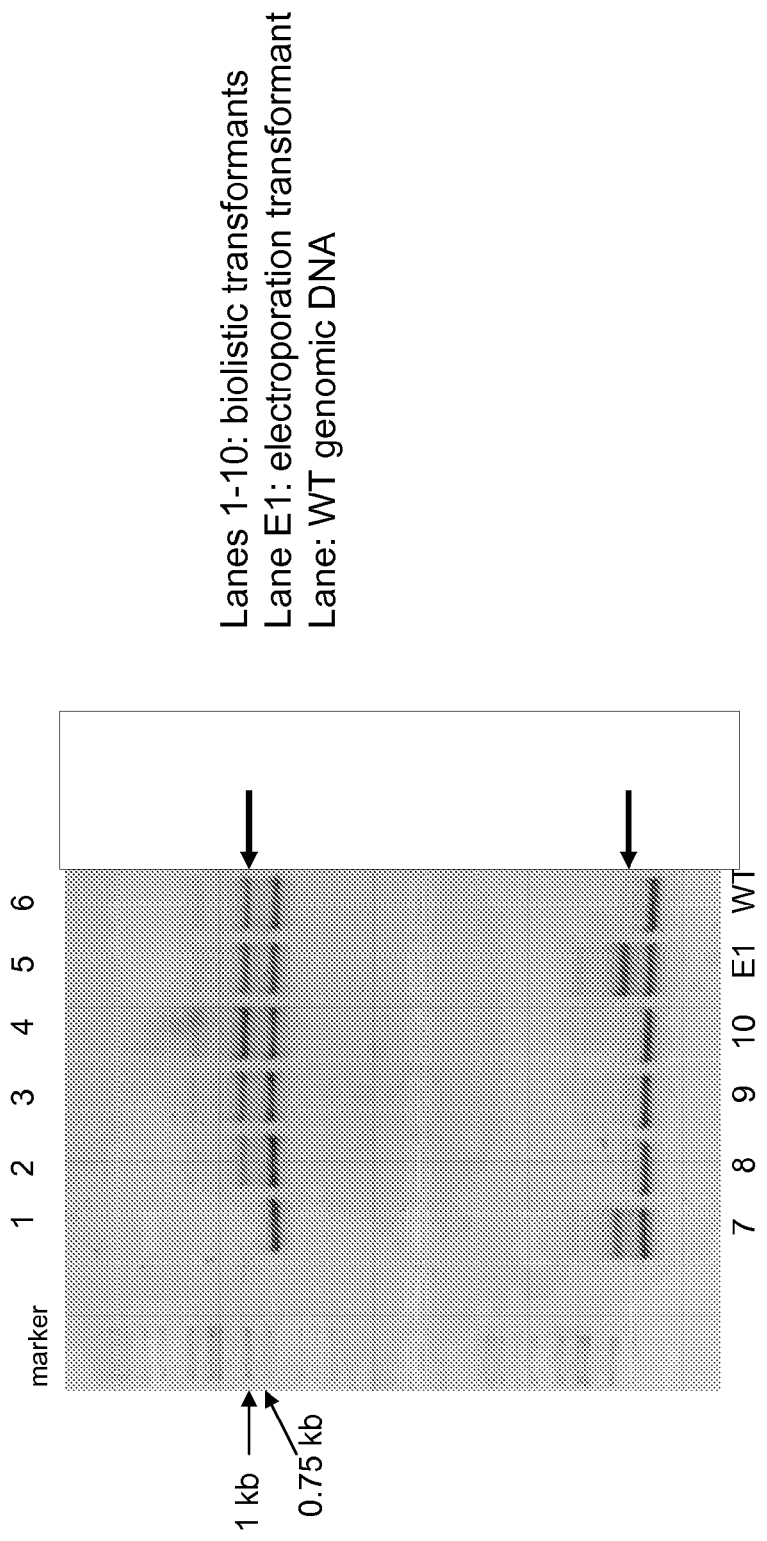
FIG. 16 shows genotyping of *Chlorella protothecoides* transformants containing an exogenous gene.
Figure 19:
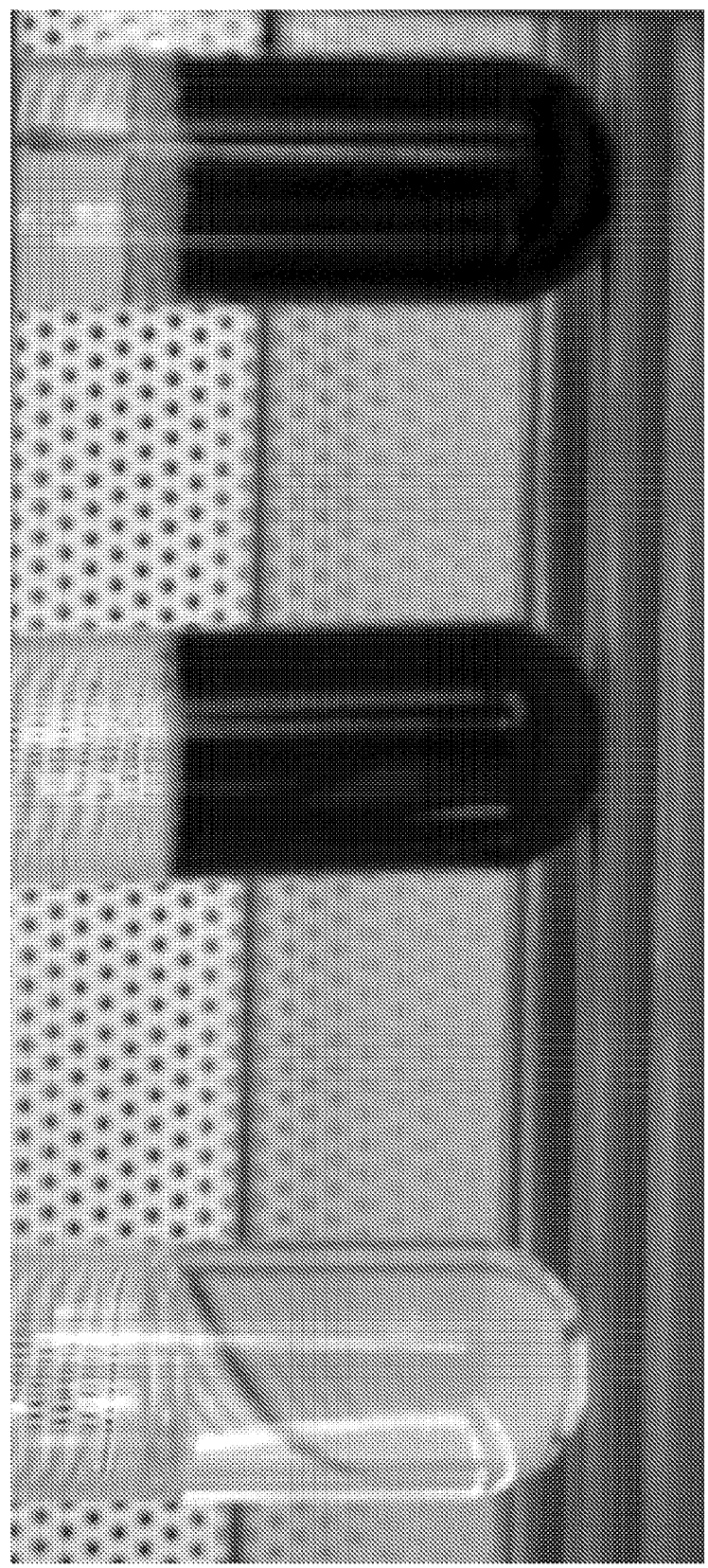
FIG. 19 shows (a) reagent grade glycerol; (b) non-acidulated biodiesel byproduct glycerol; and (c) acidulated biodiesel byproduct glycerol, all of which were used in experiments described in the Examples.

A subset of colonies that survived a second round of selection were cultured in small volume and harvested. Pellets of approximately 5-10 uL volume were resuspended in 50 uL of 10 mM NaEDTA by vortexing and then incubated at 100° C. for 10. The tubes were then vortexed briefly and sonicated for 10 seconds, then centrifuged at 12,000×g for 1 minute. 2 uL of supernatant as template was used in a 50 uL PCR reaction. Primers used for genotyping were SEQ ID NO:6 and SEQ ID NO:7. PCR conditions were as follows: 95° C. 5 min×1 cycle; 95° C. 30 sec-58° C. 30 sec-72° C. 1 min 30 sec×35 cycles; 72° C. 10 min×1 cycle. The expected 992 bp fragment was found in 6 of 10 colonies from the biolistic method and from a single electroporation colony. A lower sized, nonspecific band was present in all lanes. Results are shown in FIG. 16. To confirm the identity of the amplified 992 bp fragment, two biolistic bands and the electroporation band were excised from the gel and individually sequenced. The sequence of all three bands corresponded to the expected 992 bp fragment. (DNA ladder: Bionexus® All Purpose Hi-Lo® DNA ladder catalog #BN2050).

Example 13

Strains and Media (a) *Spirulina platensis* (UTEX 2340) and (b) *Navicula pelliculosa* (UTEX 667) were obtained from the Culture Collection of Algae at the University of Texas (Austin, Tex., USA). The stock culture of *Spirulina* was maintained in *Spirulina* medium and *Navicula* was maintained in soil extract medium (SEM). *Spirulina* medium consisted of 162 mM NaHCO$_3$, 38 mM Na$_2$CO$_3$, 1.9 mM K$_2$HPO$_4$, 29 mM NaNO$_3$, 5.75 mM K$_2$SO$_4$, 17.1 mM NaCl, 0.8 mM MgSO$_4$.7H$_2$O, 0.25 mM CaCl$_2$.2H$_2$O, 2 mM Na$_2$EDTA, 0.36 mM FeCl$_3$.6H$_2$O, 0.21 mM MnCl$_2$.4H$_2$O, 0.037 mM ZnCl$_2$, 0.0085 mM CoCl$_2$.6H$_2$O, 0.017 mM NaMoO$_4$.2H$_2$O, 0.78 µM CuSO$_4$.5H$_2$O, 0.15 µM ZnSO$_4$.7H$_2$O, 10 µM H$_3$BO$_3$, and 0.001 mM Vitamin B$_{12}$. Soil extract medium consisted of 2.94 mM NaNO$_3$, 0.17 mM CaCl$_2$.2H$_2$O, 0.3 mM MgSO$_4$.7H$_2$O, 0.43 mM K$_2$HPO$_4$, 1.29 mM KH$_2$PO$_4$, 0.43 mM NaCl, and soil extract. Glycerol wastes from biodiesel production (acidulated glycerol (AG) and non-acidulated glycerol (NAG)) were obtained from Imperial Western Products (Selma, Calif., USA).

Experimental Design and Growth Measurement:

For each strain, 1 ml of following different media was prepared in 24-well plates.

(a)
7. Spirulina medium+2% glucose
8. Spirulina medium+2% reagent grade glycerol
9. Spirulina medium+2% non-acidulated glycerol
10. Spirulina medium+1% non-acidulated glycerol+1% glucose (b)
1. SEM+2% glucose
2. SEM+2% reagent grade glycerol
3. SEM+1% reagent grade glycerol+1% glucose
4. SEM+2% acidulated glycerol
5. SEM+1% acidulated glycerol+1% glucose
6. SEM+2% non-acidulated glycerol
7. SEM+1% non-acidulated glycerol+1% glucose Each strain was inoculated to different media to 5×10$^5$ cells/ml concentration. The cultures were kept in dark and agitated by orbital shaker from Labnet (Berkshire, UK) at 430 rpm. After 96 hr, lipid contents were measured. To measure the amount of lipid content in cells, 100 µl of cultures were collected and washed once with same volume of media. To each tube, 5 µl of washed cells and 200 µl of sulfuric acid 18 M were added. The tubes were incubated at 90° C. water bath for 30 min, and 1 ml of phosphoric acid-vanillin reagent were added to the tubes and incubated at 37° C. for 15 mM. To prepare the phosphoric acid-vanillin reagent, 0.12 g of vanillin was added to 20 ml of water, and the volume adjusted to 100 ml with 85% phosphoric acid. The optical density at 530 nm was read in a glass cuvette against a reference tube with 5 µl water as sample. The reference curve is composed of Triolein dissolved in chloroform ranging from 1 to 10 µg.

To measure dried cell-weight, 0.5 ml of each culture was pelleted by centrifugation at 5000 rpm for 5 min. After removing supernatant, cell pellets were frozen at −80° C. and dried overnight in a Freeze Dry system (Labconco, Mo., USA). The lipid percentage was calculated from total lipid amount divided by dried cell weight. Results are shown in FIG. 11.

Example 14

Strains and Media

*Scenedesmus armatus* (UTEX 2552) was obtained from the Culture Collection of Algae at the University of Texas (Austin, Tex., USA). The stock cultures were maintained on modified Proteose medium. Modified Proteose medium consisted (g/L) of 0.25 g NaNO$_3$, 0.09 g K$_2$HPO$_4$, 0.175 g KH$_2$PO$_4$ 0.025 g, 0.025 g CaCl$_2$.2H$_2$O, 0.075 g MgSO$_4$.7H$_2$O, and 2 g yeast extract per liter.

Experimental Design and Growth and Lipid Measurement:

For each growth condition, 1 ml of following different media was prepared in 24-well plates.

(a), (b)
1. Proteose+2% glucose
2. Proteose+2% glycerol
3. Proteose+2% acidulated glycerol 4. Proteose+2% non-acidulated glycerol 5. Proteose+1% non-acidulated glycerol+1% glucose

*Scenedesmus armatus* (UTEX 2552) was inoculated to different media to $5\times10^5$ cells/ml concentration. The cultures were kept in dark and agitated by orbital shaker from Labnet (Berkshire, UK) at 430 rpm. After 96 hr, cell growth was measured by dried cell-weight, and lipid content was measured by phosphor-vanillin assay. (see EXAMPLE 13). The lipid percentage was calculated from total lipid amount divided by dried cell weight. Results are shown in FIG. 12.

Example 15

Strains and Media

*Navicula pelliculosa* (UTEX 667) was obtained from the Culture Collection of Algae at the University of Texas (Austin, Tex., USA). The stock cultures were maintained on soil extract medium (see EXAMPLE 13)

Experimental Design and Growth Measurement:

For each growth condition, 1 ml of following different media was prepared in 24-well plates.

1. SEM+2% glucose
2. SEM+2% glycerol
3. SEM+2% acidulated glycerol
4. SEM+1% acidulated glycerol+1% glucose
5. SEM+2% non-acidulated glycerol
6. SEM+1% non-acidulated glycerol+1% glucose

*Navicula pelliculosa* (UTEX 667) was inoculated to media containing glucose or different glycerols (pure, acidulated, or non-acidulated) to $5\times10^5$ cells/ml concentration. The cultures were kept in dark and agitated by orbital shaker from Labnet (Berkshire, UK) at 430 rpm. After 96 hr, cell growth was measured by dried cell-weight (see EXAMPLE 13). Results are shown in FIG. 13.

Example 16

Strains and Media

*Scenedesmus armatus* (UTEX 2552) and *Navicula pelliculosa* (UTEX 667) were obtained from the Culture Collection of Algae at the University of Texas (Austin, Tex., USA). The stock cultures were maintained on modified Proteose medium for *Scenedesmus armatus* and soil extract medium for *Navicula pelliculosa* (see EXAMPLE 1).

Experimental Design and Growth Measurement:

For each strain, 1 ml of following different media was prepared in 24-well plates.

*Scenedesmus armatus*

5. Proteose+1% acidulated glycerol+1% glucose
6. Proteose+1% acidulated glycerol+1% glucose (added after 72 hr)

*Navicula pelliculosa*

1. SEM+1% acidulated glycerol+1% glucose
2. SEM+1% acidulated glycerol+1% glucose (added after 72 hr)

Each strain was inoculated to media to $5\times10^5$ cells/ml concentration. The cultures were kept in dark and agitated by orbital shaker from Labnet (Berkshire, UK) at 430 rpm. After 72 hr of initial growth, 1% glucose was added to sample #2 and cultured another 24 hr. Cell growth was measured by dried cell-weight (see EXAMPLE 13). Results are shown in FIG. 14.

Example 17

Strains and Media

*Chlorella protothecoides* (UTEX 31) was obtained from the Culture Collection of Algae at the University of Texas (Austin, Tex., USA). The stock cultures were maintained on modified Proteose medium (see EXAMPLE 1)

Experimental Design:

For each condition, 1 ml of following different media was prepared in 24-well plates.

4. Proteose
5. Proteose+0.5% glucose
6. Proteose+0.5% xylose
7. Proteose+0.25% glucose+0.25% xylose

*Chlorella protothecoides* #4 (UTEX 31) was inoculated to media containing different sugars (glucose, or xylose) to $3\times10^5$ cells/ml concentration. The cultures were kept in dark and agitated by orbital shaker from Labnet (Berkshire, UK) at 430 rpm. After 72 hr of growth, cell growth was measured by counting cell numbers of each culture. Results are shown in FIG. 15.

Example 18

*Chlorella protothecoides* strains #1, #3, and #4 were obtained from the Culture Collection of Algae at the University of Texas (Austin, Tex., USA). The stock cultures were maintained on modified Proteose medium (see EXAMPLE 1). For each condition, 1 ml of following different media was prepared in 24-well plates.

1. Proteose
2. Proteose+1% glucose
3. Proteose+1% fructose

Figure 20:
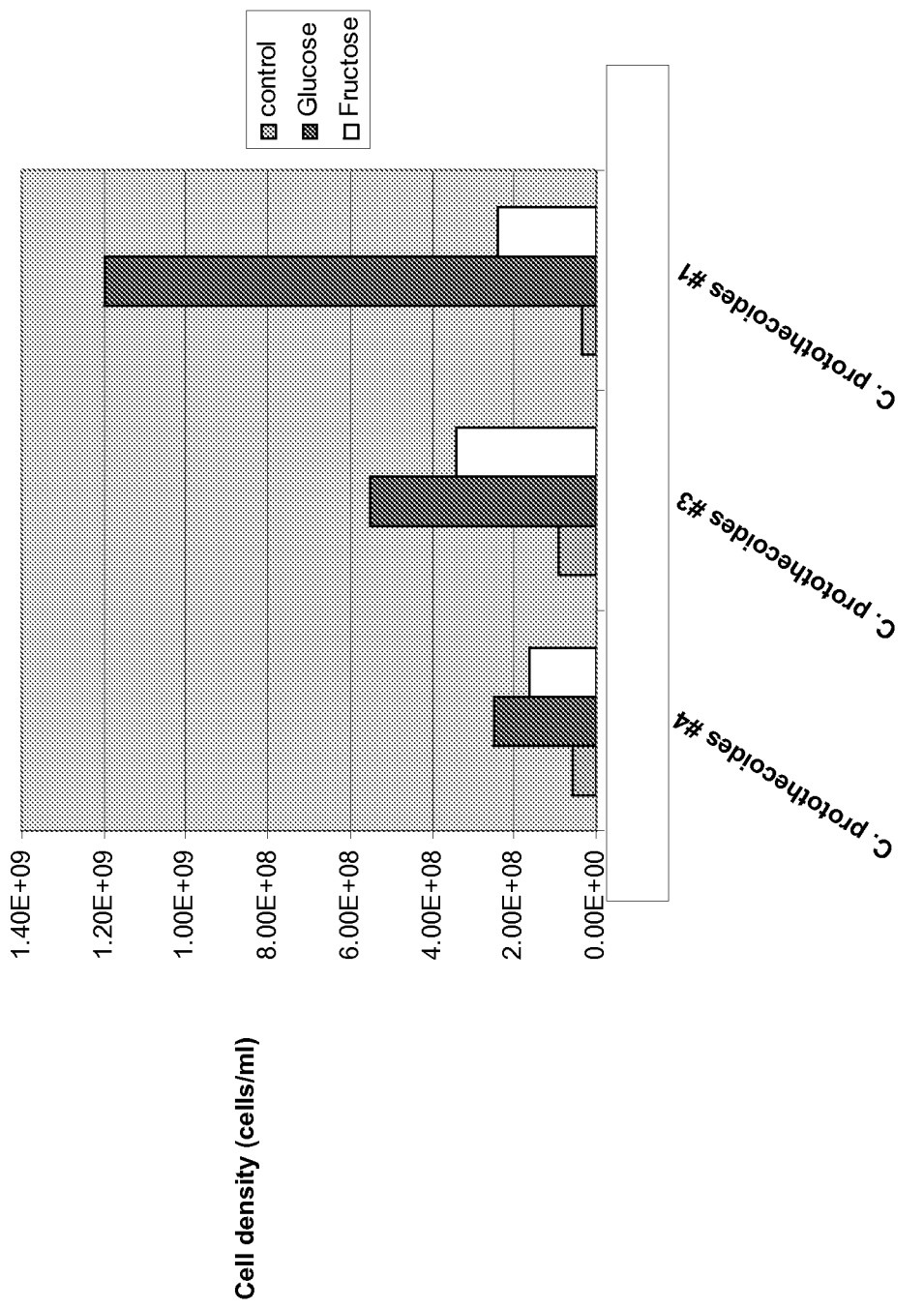
FIG. 20 shows growth of *Chlorella protothecoides* on glucose and fructose.

Each strain was inoculated to media containing different sugars (glucose, or fructose) to $1\times10^6$ cells/ml concentration. The cultures were kept in dark and agitated by orbital shaker from Labnet (Berkshire, UK) at 430 rpm. After 96 hr of growth, cell density was measured by counting cell numbers of each culture. Results are shown in FIG. 20.

Example 19

*Chlorella* on Sucrose

Materials and Methods: *Chlorella protothecoides* (UTEX 249) was inoculated into three 50 ml flasks of Proteose media with 1% sucrose (2.94 mM NaNO$_3$, 0.428 mM K$_2$HPO$_4$, 1.28 mM KH$_2$PO$_4$, 0.427 mM NaCl, 0.17 mM CaCl$_2$-2H$_2$O, 0.3 mM MgSO$_4$-7H$_2$O, proteose peptone 1 g/L) to a final cell density of $4\times10^5$ cells per ml. Invertase (Sigma #14504) was added to two of the cultures at 0.01 U/ml and 0.05 U/ml. All three cultures were grown in the dark for ~60 hrs shaking at 150 rpm.

Results: Final cell counts were performed on all three cultures after ~60 hrs of shaking in the dark. The control flask reached $4.4\times10^5$ cells per ml while the 0.01 U/ml and 0.05 U/ml flasks reached cell densities of $1\times10^8$ and $3\times10^8$ respectively. Each flask was checked for contamination at the end of the experiment by microscopic analysis and all were clean.

Example 20

Chlorella Strains Growing on Sucrose

Cultures of *Chlorella kessleri* ((a) UTEX 397 and (b) UTEX 398) and *Chlorella fusca* ((a) UTEX 251 and (b) UTEX 1801) were inoculated from autotrophic liquid cultures into 10 ml of Proteose+1% sucrose media in 50 ml flasks at $1 \times 10^6$ cells/ml. Control cultures were also inoculated at the same density with only Proteose media. Cultures were grown at 28° C. in the dark shaking at 250 rpm for 7 days, at which point cell density was measured by hemocytometer. As shown in FIGS. 21-22, all four strains grew on sucrose compared to the initial cell density and the proteose-only control.

Example 21

Chlorella protothecoides Growth on Molasses with a Sucrose Invertase

Preparation of *Chlorella* cells for Inoculation: A 10 ml liquid culture of *Chlorella* was started taking the inoculum from a solid Proteose plate. The cultures were grown in light for approximately 2 days at 26° C. Growth was measured using an optical densitomer (OD) at 750 nm and by determining dry cell weights.

Preparation of Molasses and Sugar Stock Solutions: A 5% stock solution was prepared with glucose, sucrose and three different molasses samples (labeled BS1, BS2 and HTM) obtained from the commercial processing of sugarcane into sugar, as shown in the following Table 13. The pH of all stocks was verified to be in the range of 6-6.6, and the stocks were then autoclaved.

TABLE 13

Molasses and sugar solutions.

| Molasses | % Sugar | 5% sugar dil. in 100 mls grams or mls |
|---|---|---|
| HTM | 78.72 | 6.4 |
| BS1 (FL) | 44.25 | 11.3 |
| BS2 (AU) | 51.55 | 9.7 |
| Sucrose | 100 | 5 |
| Glucose | 100 | 5 |

Preparation of Invertase Solution: A 40 units/ml stock solution of invertase was prepared by reconstituting 1 mg of a 400 unit/mg Invertase (Sigma) in 10 milliliters of distilled water.

Experimental Conditions and Setup: 10 ml cultures were prepared, each consisting of 1% final molasses/sugar concentration, 0.05 units/ml Invertase, and $1.0 \times 10^6$ cells per ml of *Chlorella protothecoides* in a base Proteose media. The cultures were numbered as follows: (1) media only control; (2) 1% HTM; (3) 1% BS1; (4) 1% BS2; (5) 1% glucose; and (6) 1% sucrose. A similar control set was also prepared without the addition of Invertase. The cultures were grown in darkness for five days shaking at 250 rpm at 28° C.

Results: Growth of the *Chlorella protothecoides* cells was evaluated following the five days of incubation on the respective feedstock in darkness. As shown in FIGS. 23-24, the cells can be grown on molasses in the presence of a sucrose invertase with yields comparable to that of growth on pure reagent-grade glucose.

Example 22

Genetic Engineering of Chlorella protothecoides to Express an Exogenous Sucrose Invertase Strains and Media: *Chlorella protothecoides* (UTEX 250) was obtained from the Culture Collection of Alga at the University of Texas (Austin, Tex., USA). The stock cultures were maintained on modified Proteose medium. Modified Proteose medium consists of 0.25 g $NaNO_3$, 0.09 g $K_2HPO_4$, 0.175 g $KH_2PO_4$ 0.025 g, 0.025 g $CaCl_2.2H_2O$, 0.075 g $MgSO_4.7H_2O$, and 2 g yeast extract per liter (g/L).

Plasmid Construction: To express the secreted form of invertase in *Chlorella protothecoides*, a *Saccharomyces cerevisiae* SUC2 gene was placed under the control of three different promoters: Cauliflower mosaic virus 35S promoter (CMV), *Chlorella* virus promoter (NC-1A), and *Chlorella* HUP1 promoter. A yeast SUC2 gene was synthesized to accommodate codon usage optimized for *C. protothecoides* and includes a signal sequence required for directing extracellular secretion of invertase. Each construct was built in pBluescript KS+, and EcoRI/AscI, AscI/XhoI, and XhoI/BamHI sites were introduced to each promoter, invertase gene, and CMV 3'UTR, respectively, by PCR amplification using specific primers. Purified PCR products were cloned sequentially. An illustration of the final constructs is shown in FIG. 25.

Transformation of *Chlorella protothecoides*: A *Chlorella protothecoides* culture was grown in modified Proteose medium on a gyratory shaker under continuous light at 75 µmol photons $m^{-2}$ $sec^{-1}$ till it reached a cell density of of $6 \times 10^6$ cells/ml.

For biolistic transformation, S550d gold carriers from Seashell Technology were prepared according to the protocol from the manufacturer. Briefly, a linearized construct (20 µg) by BsaI was mixed with 50 µl of binding buffer and 60 µl (3 mg) of S550d gold carriers and incubated in ice for 1 min. Precipitation buffer (100 µl) was added, and the mixture was incubated in ice for another 1 min. After mild vortexing, DNA-coated particles were pelleted by spinning at 10,000 rpm in an Eppendorf microfuge for 10 seconds. The gold pellet was washed once with 500 µl of cold 100% ethanol, pelleted by brief spinning in the microfuge, and resuspended with 50 µl of ice-cold ethanol. After a brief (1-2 sec) sonication, 10 µl of DNA-coated particles were immediately transferred to the carrier membrane. The cells were harvested, washed once with sterile distilled water, resuspended in 50 µl of medium ($1 \times 10^7$ cells), and were spread in the center third of a non-selective Proteous plate. The cells were bombarded with the PDS-1000/He Biolistic Particle Delivery system (Bio-Rad). Rupture disks (1100 and 1350 psi) were used, and the plates were placed 9-12 cm below the screen/macrocarrier assembly. The cells were allowed to recover at 25° C. for 12-24 hours. Upon recovery, the cells were scraped from the plates with a rubber spatula, mixed with 100 µl of medium and spread on modified Proteose plates with 1% sucrose. After 7-10 days of incubation at 25° C. in the dark, colonies representing transformed cells were visible on the plates.

For transformation with electroporation, cells were harvested, washed once with sterile distilled water, and resuspended in a Tris-phosphate buffer (20 mM Tris-HCl, pH 7.0; 1 mM potassium phosphate) containing 50 mM sucrose to a density of $4\times10^8$ cells/ml. About 250 µl cell suspension ($1\times10^8$ cells) was placed in a disposable electroporation cuvette of 4 mm gap. To the cell suspension, 5 µg of linearized plasmid DNA and 200 µg of carrier DNA (sheared salmon sperm DNA) were added. The electroporation cuvette was then incubated in an ice water bath at 16° C. for 10 min. An electrical pulse (1100 V/cm) was then applied to the cuvette at a capacitance of 25 µF (no shunt resistor was used for the electroporation) using a Gene Pulser II (Bio-Rad Labs, Hercules, Calif.) electroporation apparatus. The cuvette was then incubated at room temperature for 5 minutes, following which the cell suspension was transferred to 50 ml of modified Proteose media, and shaken on a gyratory shaker for 2 days. Following recovery, the cells were harvested at low speed (4000 rpm), resuspended in modified Proteose media, and plated out at low density on modified Proteose plates with 1% sucrose. After 7-10 days of incubation at 25° C. in the dark, colonies representing transformed cells were visible on the plates.

Screening Transformants and Genotyping: The colonies were picked from dark grown-modified Proteose plates with 1% sucrose, and approximately the same amount of cells were transferred to 24 well-plates containing 1 ml of modified Proteose liquid media with 1% sucrose. The cultures were kept in dark and agitated by orbital shaker from Labnet (Berkshire, UK) at 430 rpm for 5 days.

To verify the presence of the invertase gene introduced in *Chlorella* transformants, DNA of each transformant was isolated and amplified with a set of gene-specific primers (CMV construct: forward primer (CAACCACGTCTTCAAAG-CAA) (SEQ ID NO:6)/reverse primer (TCCGGTGTGTTG-TAAGTCCA) (SEQ ID NO:9), CV constructs: forward primer (TTGTCGGAATGTCATATCAA) (SEQ ID NO:10)/reverse primer (TCCGGTGTGTTGTAAGTCCA) (SEQ ID NO:11), and HUP1 construct: forward primer (AACGC-CTTTGTACAACTGCA) (SEQ ID NO:12)/reverse primer (TCCGGTGTGTTGTAAGTCCA) (SEQ ID NO:13)). For quick DNA isolation, a volume of cells (approximately 5-10 uL in size) were resuspended in 50 uL of 10 mM Na-EDTA. The cell suspension was incubated at 100° C. for 10 min and sonicated for 10 sec. After centrifugation at 12000 g for 1 min, 3 uL of supernatant was used for the PCR reaction. PCR amplification was performed in the DNA thermal cycler (Perkin-Elmer GeneAmp 9600). The reaction mixture (50 uL) contained 3 uL extracted DNA, 100 pmol each of the respective primers described above, 200 uM dNTP, 0.5 units of Taq DNA polymerase (NEB), and Taq DNA polymerase buffer according to the manufacturer's instructions. Denaturation of DNA was carried out at 95° C. for 5 min for the first cycle, and then for 30 sec. Primer annealing and extension reactions were carried out at 58° C. for 30 sec and 72° C. for 1 min respectively. The PCR products were then visualized on 1% agarose gels stained with ethidium bromide. FIG. 26 shows the PCR genotype results of *C. protothecoides* transformants using the gene-specific primers identified above. Arrows show the expected size of the PCR product, and stars represent DNA samples from each transformant showing the PCR product matched to the expected size (V: Vector only, WT: wild-type).

Growth in Liquid Culture: After five days growth in darkness, the genotype-positive transformants showed growth on minimal liquid Proteose media+1% sucrose in darkness, while wild-type cells showed no growth in the same media in darkness.

Example 23

Transformation of Algal Strains with a Secreted Invertase Derived from *S. cerevisiae*

Secreted Invertase: A gene encoding a secreted sucrose invertase (Gen Bank Accession no. NP_012104 from *Saccharomyces cerevisiae*) was synthesized de-novo as a 1599 bp Asc I-Xho fragment that was subsequently sub-cloned into a pUC19 derivative possessing the Cauliflower Mosaic Virus 35s promoter and 3' UTR as EcoR I/Asc I and Xho/Sac I cassettes, respectively.

Growth of Algal Cells: Media used in these experiments was liquid base media (see Example 1) and solid base media (+1.5% agarose) containing fixed carbon in the form of sucrose or glucose (as designated) at 1% final concentration. The strains used in this experiment did not grow in the dark on base media in the absence of an additional fixed carbon source. Species were struck out on plates, and grown in the dark at 28° C. Single colonies were picked and used to inoculate 500 mL of liquid base media containing 1% glucose and allowed to grow in the dark until mid-log phase, measuring cell counts each day. Each of the following strains had been previously tested for growth on sucrose in the dark as a sole carbon source and exhibited no growth, and were thus chosen for transformation with a secreted invertase: (1) *Chlorella protothecoides* (UTEX 31); (2) *Chlorella minutissima* (UTEX 2341); and (3) *Chlorella emersonii* (CCAP 211/15).

Transformation of Algal Cells via Particle Bombardment: Sufficient culture was centrifuged to give approximately 1-5× $10^8$ total cells. The resulting pellet was washed with base media with no added fixed carbon source. Cells were centrifuged again and the pellet was resuspended in a volume of base media sufficient to give $5\times10^7$ to $2\times10^8$ cells/ml. 250-1000 µl of cells were then plated on solid base media supplemented with 1% sucrose and allowed to dry onto the plate in a sterile hood. Plasmid DNA was precipitated onto gold particles according to the manufacturer's recommendations (Seashell Technology, La Jolla, Calif.). Transformations were carried out using a BioRad PDS He-1000 particle delivery system using 1350 psi rupture disks with the macrocarrier assembly set at 9 cm from the rupture disk holder. Following transformations, plates were incubated in the dark at 28° C. All strains generated multiple transformant colonies. Control plates transformed with no invertase insert, but otherwise prepared in an identical fashion, contained no colonies.

Analysis of *Chlorella protothecoides* transformants: Genomic DNA was extracted from *Chlorella protothecoides* wild type cells and transformant colonies as follows: Cells were resuspended in 100 ul extraction buffer (87.5 mM Tris Cl, pH 8.0, 50 mM NaCl, 5 mM EDTA, pH 8.0, 0.25% SDS) and incubated at 60° C., with occasional mixing via inversion, for 30 minutes. For PCR, samples were diluted 1:100 in 20 mM Tris Cl, pH 8.0.

Genotyping was done on genomic DNA extracted from WT, the transformants and plasmid DNA. The samples were genotyped for the marker gene. Primers 2383 (5' CTGAC-CCGACCTATGGGAGCGCTCTTGGC 3') (SEQ ID NO:20) and 2279 (5' CTTGACTTCCCTCACCTGGAATTTGTCG 3') (SEQ ID NO:21) were used in this genotyping PCR. The PCR profile used was as follows: 94° C. denaturation for 5 min; 35 cycles of 94° C.-30 sec, 60° C.-30 sec, 72° C.-3 min; 72° C.-5 min. A band of identical size was amplified from the positive controls (plasmid) and two transformants of *Chlorella protothecoides* (UTEX 31), as shown in FIG. 27.

Analysis of *Chlorella minutissima* and *Chlorella emersonii* transformants: Genomic DNA was extracted from *Chlorella* WT and the tranformants as follows: Cells were resuspended in 100 ul extraction buffer (87.5 mM Tris Cl, pH 8.0, 50 mM NaCl, 5 mM EDTA, pH 8.0, 0.25% SDS) and incubated at 60° C., with occasional mixing via inversion, for 30 minutes. For PCR, samples were diluted 1:100 in 20 mM Tris Cl, pH 8.0. Genotyping was done on genomic DNA extracted from WT, the transformants and plasmid DNA. The samples were genotyped for the marker gene. Primers 2336 (5' GTG-GCCATATGGACTTACAA 3') (SEQ ID NO:22) and 2279 (5' CTTGACTTCCCTCACCTGGAATTTGTCG 3') (SEQ ID NO:21) were designated primer set 2 (1215 bp expected product), while primers 2465 (5' CAAGGGCTGGATGAAT-GACCCCAATGGACTGTGGTACGACG 3') (SEQ ID NO:23) and 2470 (5' CACCCGTCGTCATGTTCACG-GAGCCCAGTGCG 3') (SEQ ID NO:24) were designated primer set 4 (1442 bp expected product). The PCR profile used was as follows: 94° C. denaturation for 2 min; 29 cycles of 94° C.-30 sec, 60° C.-30 sec, 72° C.-1 min, 30 sec; 72° C.-5 min. A plasmid control containing the secreted invertase was used as a PCR control. FIG. 28 shows the transformation of the *Chlorella minutissima* (UTEX 2341) and *Chlorella emersonii* (CCAP 211/15) species of microalgae with the gene encoding a secreted invertase.

The sequence of the invertase construct corresponds to SEQ ID NO:25.

Example 24

Growth of Algal Strains Compared to *S. cerevisiae* on a Cellulosic Feedstock Prepared with Celluclast Strains and Culture Conditions: Algal strains used in this study are listed in Table 14 below, and were grown in Proteose media with exogenously provided cellulosic material and in some cases additional fixed carbon in the form of glucose. Twenty four algal strains were used in this study, including five different genera encompassing eleven different species of *Chlorella*, two of *Parachlorella* and *Prototheca*, and one each of *Bracteococcus* and *Pseudochlorella*. *Saccharomyces cerevisiae* (strain PJ-69-4A) was grown in YPD media (per liter, 10 g Bacto-yeast extract, 20 g Bacto peptone and 20 g glucose). Both algae and yeast were grown at 28° C. in the dark. Growth of these strains on Proteose media in the dark in the absence of cellulosic material or other additional fixed carbon either did not occur or was extremely minimal.

Liberation of Glucose from Cellulosic Material via Enzymatic Depolymerization Treatment: Wet, exploded corn stover material was prepared by the National Renewable Energy Laboratory (Golden, Colo.) by cooking corn stover in a 1.4% sulfuric acid solution and dewatering the resultant slurry. Using a Mettler Toledo Moisture analyzer, the dry solids in the wet corn stover were determined to be 24%. A 100 g wet sample was resuspended in deionized water to a final volume of 420 ml and the pH was adjusted to 4.8 using 10 N NaOH. Celluclast™ (Novozymes) (a cellulase) was added to a final concentration of 4% and the resultant slurry incubated with shaking at 50° C. for 72 hours. The pH of this material was then adjusted to 7.5 with NaOH (negligible volume change), filter sterilized through a 0.22 um filter and stored at –20° C. A sample was reserved for determination of glucose concentration using a hexokinase based kit from Sigma, as described below.

Determination of Glucose Concentration Liberated by Celluclast Treatment of Wet Corn Stover: Glucose concentrations were determined using Sigma Glucose Assay Reagent #G3293. Samples, treated as outlined above, were diluted 400 fold and 40 μl was added to the reaction. The corn stover cellulosic preparation was determined to contain approximately 23 g/L glucose.

TABLE 14

Algal strains grown on cellulosic feedstock.

| Genus/Species | Source/Designation |
|---|---|
| *Bracteococcus minor* | UTEX 66 |
| *Chlorella ellipsoidea* | SAG 2141 |
| *Chlorella kessleri* | UTEX 1808 |
| *Chlorella kessleri* | UTEX 397 |
| *Chlorella emersonii* | CCAP 211/15 |
| *Chlorella luteoviridis* | SAG 2133 |
| *Chlorella luteoviridis* | SAG 2198 |
| *Chlorella luteoviridis* | SAG 2214 |
| *Chlorella luteoviridis* | UTEX 22 |
| *Bracteococcus medionucleatus* | UTEX 1244 |
| *Chlorella minutissima* | CCALA 20024 |
| *Chlorella minutissima* | UTEX 2341 |
| *Chlorella ovalis* | CCAP 211/21A |
| *Chlorella protothecoides* | CCAP 211/8d |
| *Chlorella protothecoides* | UTEX 250 |
| *Chlorella saccharophila* | UTEX 2911 |
| *Chlorella sorokiniana* | UTEX 1230 |
| *Chlorella* sp. | SAG 241.80 |
| *Chlorella vulgaris* | CCAP 211/11C |
| *Parachlorella kessleri* | SAG 12.80 |
| *Parachlorella kessleri* | SAG 27.87 |
| *Prototheca moriformis* | UTEX 1441 |
| *Prototheca moriformis* | UTEX 1434 |
| *Pseudochlorella aquatica* | SAG 2149 |

In Table 14, and as used herein, UTEX refers to the culture collection of algae at the University of Texas (Austin, Tex., USA), SAG refers to the Culture Collection of Algae at the University of Göttingen (Göttingen, Germany), CCAP refers to the culture collection of algae and protozoa managed by the Scottish Association for Marine Science (Scotland, United Kingdom) and CCALA refers to the culture collection of algal laboratory at the Institute of Botany (Třeboň, Czech Republic).

Determination of Growth on Cellulosic Material: After enzymatic treatment and saccharification of cellulose to glucose, xylose, and other monosaccharide sugars, the material prepared above was evaluated as a feedstock for the growth of 24 algal strains or *S. cerevisiae* in Proteose media or YPD media respectively. Proteose media was made up to a final glucose concentration of 23 g/L (the final concentration of glucose generated via cellulolytic treatment of corn stover), as was YPD for growth of *S. cerevisiae*, by adding varying amounts of pure glucose and/or depolymerized cellulosic material. Varying concentrations of cellulosic material were included, providing 0, 12.5, 25, 50 and 100% of the 23 g/L glucose in each media, the components of which are shown in Table 15 below. One ml of the appropriate media was added to wells of a 24 well plate. *S. cerevisiae* grown heterotrophically at 28° C. in YPD served as inoculum (20 ul) for the yeast wells. Twenty microliters of inoculum for the 24 algal strains was furnished by alga cells grown mixotrophically in Proteose media containing 20 g/L glucose.

TABLE 15

Cellulosic feedstock preparations.

| Vol. of YPD 23.1 g/L Glucose (ml) | Vol. of Proteose Media 23.1 g/L Glucose (ml) | Vol. of 100% Cellulosics Made up to Proteose Media (ml) | Vol. of 100% Cellulosics Made up to YPD (ml) | Final Volume (ml) | Percent Cellulosics |
|---|---|---|---|---|---|
| 0 | 1 | 0 | 0 | 1 | 0 |
| 0 | 0.875 | 0.125 | 0 | 1 | 12.5 |
| 0 | 0.75 | 0.25 | 0 | 1 | 25 |
| 0 | 0.5 | 0.5 | 0 | 1 | 50 |
| 0 | 0 | 1 | 0 | 1 | 100 |
| 1 | 0 | 0 | 0 | 1 | 0 |
| 0.875 | 0 | 0 | 0.125 | 1 | 12.5 |
| 0.75 | 0 | 0 | 0.25 | 1 | 25 |
| 0.5 | 0 | 0 | 0.5 | 1 | 50 |
| 0 | 0 | 0 | 1 | 1 | 100 |

Table 15 shows the volumes of depolymerized corn stover modified to contain Proteose or YPD media components that were added to Proteose or YPD media respectively to yield medias containing the indicated percentage of cellulosics. Medias were prepared in order to obtain a final glucose concentration of 23 g/L in all cases. Volume of media prior to the addition of either 20 μl of mid-log phase grown yeast or alga cells was 1 ml. Cells were incubated two days in the dark on the varying concentrations of cellulosic feedstocks at 28° C. with shaking (300 rpm). Growth was assessed by measurement of absorbance at 750 nm in a UV spectrophotometer. Surprisingly, all strains grew on the cellulosic material prepared with Celluclast, including media conditions in which 100% of fermentable sugar was cellulosic-derived.

Example 25

Growth of 24 Algal Strains and *S. cerevisiae* on Various Cellulosic Feedstocks Prepared with Accellerase 1000™ and Celluclast™

Strains and Culture Conditions: Algal strains used in this Example are listed in Table 14 (above) and were grown in Proteose media plus additional fixed carbon in the form of depolymerized cellulosic material and/or pure glucose. *Saccharomyces cerevisiae* (strain pJ69-4a) was grown in YPD media plus additional fixed carbon in the form of depolymerized cellulosic material and/or pure glucose. Both algae and yeast were grown at 28° C. in the dark.

Liberation of Glucose from Cellulosic Material via Enzymatic Depolymerization Treatment: Wet, exploded corn stover material was prepared by the National Renewable Energy Laboratory (Golden, Colo.) by cooking corn stover in a 1.4% sulfuric acid solution and dewatering the resultant slurry. Switchgrass was also prepared by The National Renewable Energy Laboratory (Golden, Colo.) utilizing the same method as for corn stover. Sugar beet pulp, generated via pectinase treatment, was supplied by Atlantic Biomass, Inc. of Frederick, Md. Using a Mettler Toledo Moisture analyzer, the dry solids were 24% in the wet corn stover, 26% in switch grass and 3.5% in sugar beet pulp. A 100 g wet sample of corn stover or switchgrass was resuspended in deionized water to a final volume of 420 ml and the pH adjusted to 4.8 using 10 N NaOH. For beet pulp, 8.8 grams dry solids were brought to 350 ml with deionized water and pH adjusted to 4.8 with 10N NaOH. For all feed stocks, Accellerase 1000™ (Genencor) (a cellulase enzyme complex) was used at a ratio of 0.25 ml enzyme per gram dry biomass. Samples were incubated with agitation (110 rpm) at 50° C. for 72 hours. The pH of this material was then adjusted to 7.5 with NaOH (negligible volume change), filter sterilized through a 0.22 um filter and used in growth experiments outlined below. A sample was reserved for determination of glucose concentration using a hexokinase-based kit from Sigma, as described below. The same set of cellulosic feedstocks were also prepared using Celluclast™ (Novozymes) (a cellulase) as described in the previous example.

Determination of Glucose Concentrations in Various Cellulosic Feedstocks Treated with Accellerase 1000: Glucose concentrations were determined using Sigma Glucose Assay Reagent #G3293. Samples, treated as outlined above, were diluted 400 fold and 40 ul was added to the reaction. The cellulosic preparations from corn stover, switch grass and beet pulp were determined to contain approximately 23.6, 17.1 and 13.7 g/L glucose, respectively.

Determination of Growth on Cellulosic Material: After enzymatic depolymerization of cellulosic sources to glucose, xylose, and other monosaccharides, the materials prepared above were evaluated as feedstocks for the growth of the 24 algal strains listed in the Table 14 and *S. cerevisiae* in Proteose or YPD medias respectively. The medias were designed to contain a consistent concentration of glucose while varying the amount of cellulosic material derived from corn stover, switchgrass or beet pulp. A first set of Proteose and YPD media contained 23.6 g/L pure glucose, while a second set of media contained depolymerized corn stover, switchgrass and beet pulp, each of which contained 23.6 g/L glucose. The switchgrass and beet pulp medias were supplemented with 6.5 and 9.9 g/L pure glucose to normalize glucose in all cellulosic medias at 23.6 g/L. One ml of the appropriate media was added to wells of a 24 well plate. *S. cerevisiae* grown heterotrophically at 28° C. in YPD served as inoculum (20 ul) for the yeast wells. Twenty microliters of inoculum for the 24 algal strains was furnished by alga cells grown mixotrophically in Proteose media containing 20 g/L glucose. all cells were incubated two days in the dark on the varying concentrations of cellulosic feedstocks at 28° C. with shaking (300 rpm). Growth was assessed by measurement of absorbance at 750 nm in a UV spectrophotometer. Surprisingly, all algae strains grew on the corn stover, switchgrass and beet pulp material prepared with Accellerase 1000™ or Celluclast™, including media conditions in which 100% of fermentable sugar was cellulosic-derived. Under no combination of cellulosic feedstock and depolymerization enzyme did *S. cerevisiae* outperform growth on an equivalent amount of pure glucose, indicating that inhibitors to yeast growth in the cellulosic material made a major impact on the productivity of the fermentation. Combinations of algae strains, depolymerization enzymes and feedstocks with 100% cellulosic-derived monosaccharides that outperformed 100% pure glucose are shown in Table 16.

TABLE 16

Combinations of algae, enzymes, and feedstocks.

| Feedstock and Depolymerization Enzyme | Genus/Species | Source/ Designation |
|---|---|---|
| corn stover/celluclast ™ | Bracteococcus minor | UTEX 66 |
| beet pulp/accellerase ™ | Chlorella ellipsoidea | SAG 2141 |
| switchgrass/accellerase ™ | Chlorella kessleri | UTEX 252 |
| beet pulp/accellerase ™ | Chlorella kessleri | UTEX 397 |
| switchgrass/accellerase ™ | Chlorella luteoviridis | SAG 2133 |
| beet pulp/accellerase ™ | Chlorella luteoviridis | SAG 2133 |
| switchgrass/accellerase ™ | Chlorella luteoviridis | UTEX 22 |
| beet pulp/accellerase ™ | Chlorella luteoviridis | UTEX 22 |
| corn stover/accellerase ™ | Chlorella luteoviridis | UTEX 22 |
| beet pulp/accellerase ™ | Chlorella protothecoides | UTEX 250 |
| beet pulp/accellerase ™ | Chlorella sp. | SAG 241.80 |
| beet pulp/accellerase ™ | Parachlorella kessleri | SAG 12.80 |
| switchgrass/accellerase ™ | Prototheca moriformis | UTEX 1441 |
| beet pulp/accellerase ™ | Prototheca moriformis | UTEX 1441 |
| corn stover/accellerase ™ | Prototheca moriformis | UTEX 1441 |
| corn stover/celluclast ™ | Prototheca moriformis | UTEX 1441 |
| corn stover/accellerase ™ | Prototheca moriformis | UTEX 1434 |
| beet pulp/accellerase ™ | Pseudochlorella aquatica | SAG 2149 |

Example 26

Carbon Utilization Screens

Strains and Culture Conditions: Seed cultures of the various strains of microalgae identified below were started as 1 ml liquid cultures in 24 well plates and were grown autotrophically for 48 hours in light, agitating at ~350 rpm. Plates were setup with 1.5% agarose-based solid Proteose media containing 1% of glucose, glycerol, xylose, sucrose, fructose, arabinose, mannose, galactose, or acetate as the sole fixed carbon source. For each strain, 5 µl of culture from the autotrophic 24 well plate was spotted onto the solid media. Plates were incubated for 7 days in the dark at 28° C. and examined for growth compared to a control plate containing no additional fixed carbon. Growth was observed for each of the species tested with each respective feedstock, as shown in Table 17 below. Growth of these strains on Proteose media in the dark in the absence of additional fixed carbon either did not occur or was extremely minimal.

TABLE 17

Algal species grown on various fixed-carbon feedstocks.

| Fixed Carbon Source | Genus/Species | Source/ Designation |
|---|---|---|
| Glucose | Chlorella protothecoides | UTEX 250 |
| Glucose | Chlorella kessleri | UTEX 397 |
| Glucose | Chlorella sorokiniana | UTEX 2805 |
| Glucose | Parachlorella kessleri | SAG 12.80 |
| Glucose | Pseudochlorella aquatica | SAG 2149 |
| Glucose | Chlorella reisiglii | CCAP 11/8 |
| Glucose | Bracteococcus medionucleatus | UTEX 1244 |
| Glucose | Prototheca stagnora | UTEX 1442 |
| Glucose | Prototheca moriformis | UTEX 1434 |
| Glucose | Prototheca moriformis | UTEX 1435 |
| Glucose | Scenedesmus rubescens | CCAP 232/1 |
| Glycerol | Parachlorella kessleri | SAG 12.80 |
| Glycerol | Chlorella protothecoides | CCAP 211/8d |
| Glycerol | Bracteococcus medionucleatus | UTEX 1244 |
| Glycerol | Prototheca moriformis | UTEX 288 |

TABLE 17-continued

Algal species grown on various fixed-carbon feedstocks.

| Fixed Carbon Source | Genus/Species | Source/ Designation |
|---|---|---|
| Glycerol | Prototheca moriformis | UTEX 1435 |
| Glycerol | Chlorella minutissima | UTEX 2341 |
| Glycerol | Chlorella sp. | CCAP 211/61 |
| Glycerol | Chlorella sorokiniana | UTEX 1663 |
| Xylose | Chlorella luteoviridis | SAG 2133 |
| Xylose | Chlorella ellipsoidea | SAG 2141 |
| Xylose | Pseudochlorella aquatica | SAG 2149 |
| Xylose | Chlorella sp. | CCAP 211/75 |
| Xylose | Prototheca moriformis | UTEX 1441 |
| Xylose | Prototheca moriformis | UTEX 1435 |
| Sucrose | Chlorella saccharophila | UTEX 2469 |
| Sucrose | Chlorella luteoviridis | UTEX 22 |
| Sucrose | Chlorella sp. | UTEX EE102 |
| Sucrose | Chlorella luteoviridis | SAG 2198 |
| Sucrose | Bracteococcus medionucleatus | UTEX 1244 |
| Sucrose | Chlorella minutissima | CCALA 20024 |
| Fructose | Chlorella kessleri | UTEX 398 |
| Fructose | Chlorella trebouxiodes | SAG 3.95 |
| Fructose | Parachlorella kessleri | SAG 27.87 |
| Fructose | Chlorella luteoviridis | SAG 2214 |
| Fructose | Chlorella protothecoides | UTEX 31 |
| Fructose | Chlorella protothecoides | UTEX 250 |
| Fructose | Chlorella reisiglii | CCAP 11/8 |
| Fructose | Chlorella protothecoides | CCAP 211/8d |
| Fructose | Prototheca moriformis | UTEX 1435 |
| Fructose | Scenedesmus rubescens | CCAP 232/1 |
| Arabinose | Chlorella sp. | CCAP 211/75 |
| Mannose | Chlorella kessleri | UTEX 263 |
| Mannose | Chlorella saccharophila | UTEX 2911 |
| Mannose | Parachlorella kessleri | SAG 12.80 |
| Mannose | Chlorella sp. | SAG 241.80 |
| Mannose | Chlorella angustoellipsoidea | SAG 265 |
| Mannose | Chlorella ellipsoidea | SAG 2141 |
| Mannose | Chlorella protothecoides | UTEX 250 |
| Mannose | Chlorella emersonii | CCAP 211/15 |
| Mannose | Bracteococcus minor | UTEX 66 |
| Mannose | Prototheca stagnora | UTEX 1442 |
| Mannose | Prototheca moriformis | UTEX 1439 |
| Mannose | Chlorella cf. minutissima | CCALA 20024 |
| Mannose | Scenedesmus rubescens | CCAP 232/1 |
| Galactose | Bracteococcus minor | UTEX 66 |
| Galactose | Parachlorella kessleri | SAG 14.82 |
| Galactose | Parachlorella beijerinckii | SAG 2046 |
| Galactose | Chlorella protothecoides | UTEX 25 |
| Galactose | Chlorella sorokiniana | UTEX 1602 |
| Galactose | Parachlorella kessleri | SAG 12.80 |
| Galactose | Pseudochlorella aquatica | SAG 2149 |
| Galactose | Chlorella luteoviridis | SAG 2214 |
| Galactose | Chlorella ellipsoidea | CCAP 211/42 |
| Galactose | Chlorella ellipsoidea | CCAP 211/50 |
| Galactose | Chlorella protothecoides | UTEX 250 |
| Galactose | Chlorella protothecoides | UTEX 264 |
| Galactose | Bracteococcus medionucleatus | UTEX 1244 |
| Galactose | Prototheca moriformis | UTEX 1439 |
| Galactose | Prototheca moriformis | UTEX 1441 |
| Galactose | Chlorella kessleri | CCALA 252 |
| Acetate | Chlorella sorokiniana | UTEX 1230 |
| Acetate | Chlorella sorokiniana | UTEX 1810 |
| Acetate | Chlorella luteoviridis | UTEX 22 |
| Acetate | Parachlorella kessleri | SAG 12.80 |
| Acetate | Parachlorella kessleri | SAG 27.87 |
| Acetate | Chlorella sp. | SAG 241.80 |
| Acetate | Chlorella luteoviridis | SAG 2214 |
| Acetate | Chlorella protothecoides | UTEX 31 |
| Acetate | Chlorella protothecoides | UTEX 411 |
| Acetate | Chlorella ellipsoidea | CCAP 211/42 |
| Acetate | Chlorella ovalis | CCAP 211/21A |
| Acetate | Chlorella protothecoides | CCAP 211/8d |
| Acetate | Prototheca stagnora | UTEX 1442 |
| Acetate | Chlorella protothecoides | UTEX 250 |
| Acetate | Chlorella sorokiniana | CCALA 260 |
| Acetate | Chlorella vulgaris | CCAP 211/79 |
| Acetate | Parachlorella kessleri | SAG 14.82 |

Example 27

Production of Renewable Diesel

Cell Production: An F-Tank batch of *Chlorella protothecoides* (UTEX 250) (about 1,200 gallons) was used to generate biomass for extraction processes. The batch (#ZA07126) was allowed to run for 100 hours, while controlling the glucose levels at 16 g/L, after which time the corn syrup feed was terminated. Residual glucose levels dropped to <0 g/L two hours later. This resulted in a final age of 102 hours. The final broth volume was 1,120 gallons. Both in-process contamination checks and a thorough analysis of a final broth sample failed to show any signs of contamination. The fermentation broth was centrifuged and drum dried. Drum dried cells were resuspended in hexane and homogenized at approximately 1000 bar. Hexane extraction was then performed using standard methods, and the resulting algal triglyceride oil was determined to be free of residual hexane.

Production of Renewable Diesel: The algal triglyceride oil had a lipid profile of approximately 3% C18:0, 71% C18:1, 15% C18:2, 1% C18:3, 8% C16:0, and 2% other components. The oil was first subjected to hydrocracking, resulting in an approximate 20% yield loss to water and gases. Hydroisomerization was then performed, with an approximate 10% loss in yield to gases. A first distillation was then performed to remove the naptha fraction, leaving the desired product. Approximately 20% of the material was lost to naptha in this first distillation. A second distillation was then performed at a temperature sufficient to remove fractions necessary to meet the ASTM D975 specification but leave a bottom fraction that did not meet the 90% point for a D975 distillation. Approximately 30% of the material was left in the bottom fraction in the second distillation. The resulting material was then tested for all ASTM D975 specifications.

Figure 29:
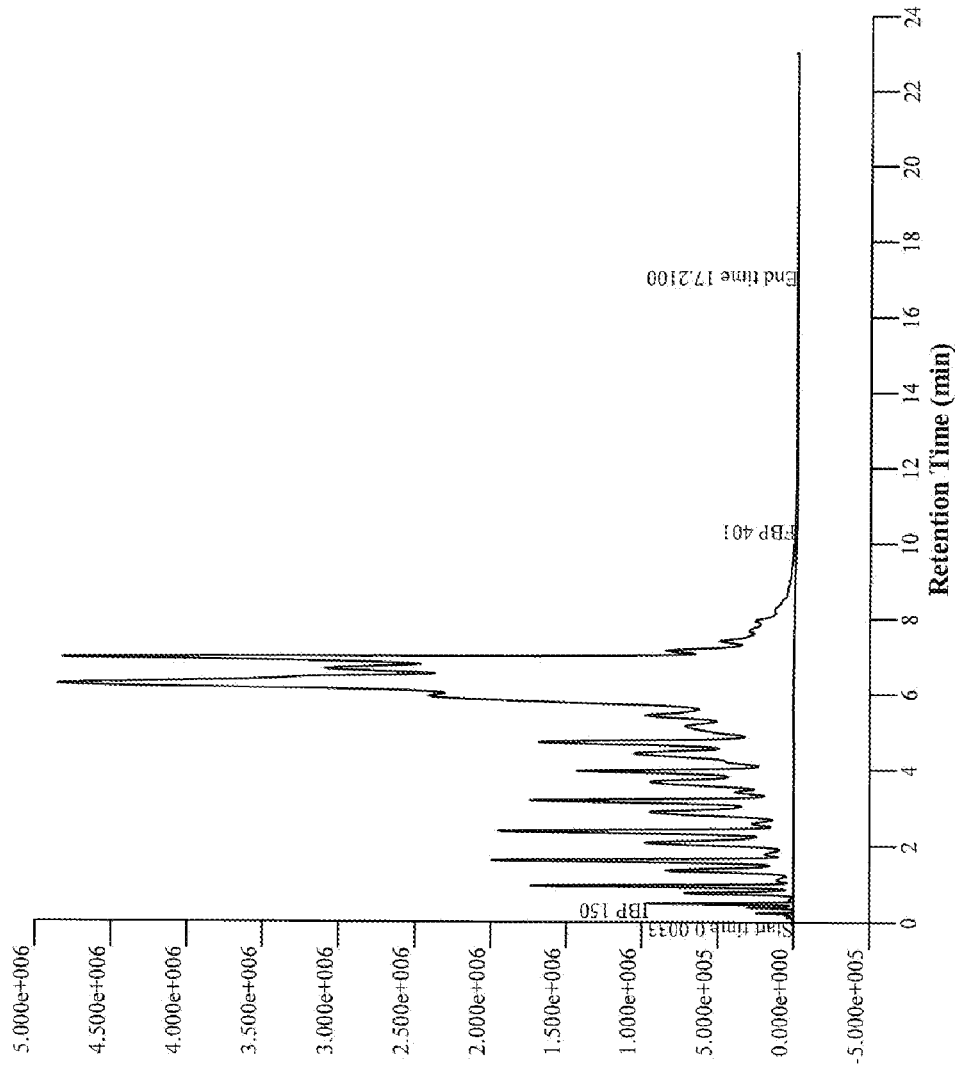
FIG. 29 illustrates a gas chromatograph generated by analysis of a renewable diesel product produced in accordance with the methods of the present invention, and described in Example 27.
Figure 30:
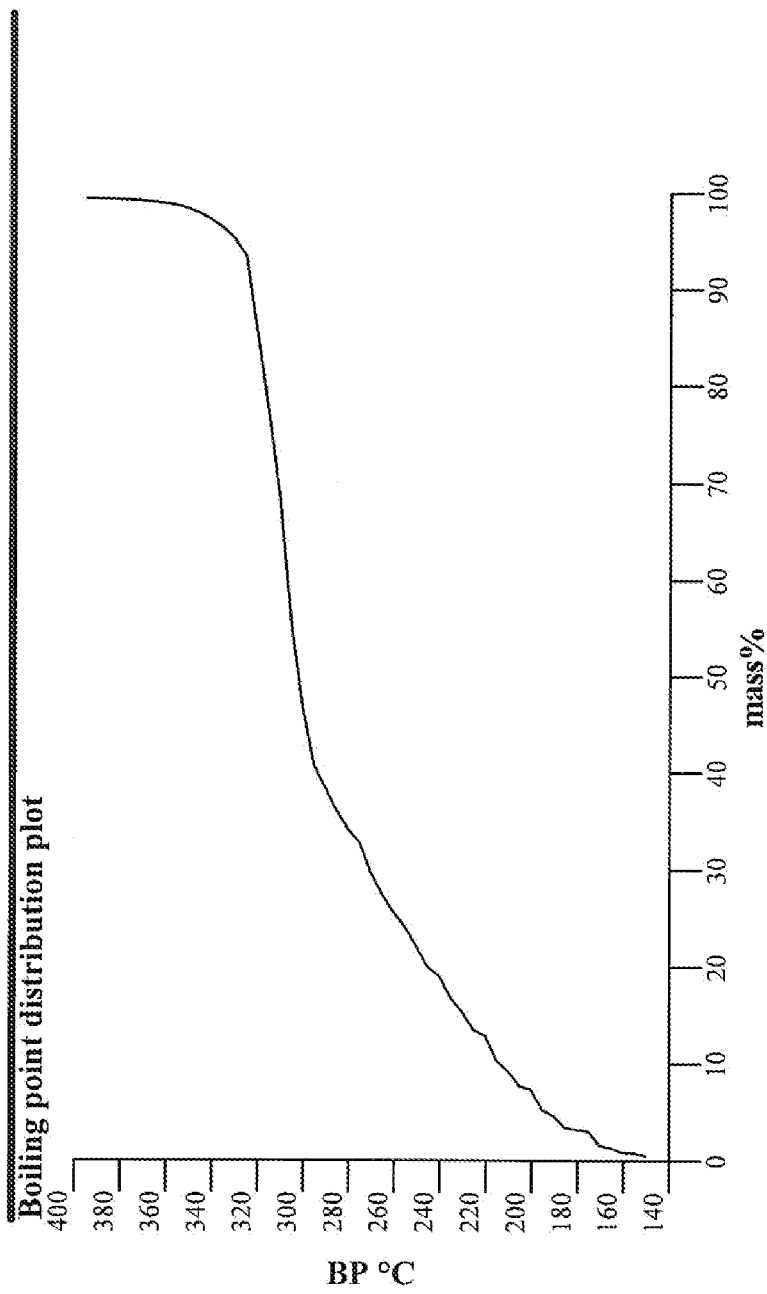
FIG. 30 illustrates a boiling point distribution plot for a renewable diesel product produced in accordance with the methods of the presence invention, and described in Example 27.

FIGS. 29 and 30 illustrate a gas chromatograph and a boiling point distribution plot, respectively, of the final renewable diesel product produced by the method of the invention. Table 18 shows the boiling point distribution of the resulting renewable diesel product, and Table 19 shows the results of an analysis of the final product for compliance with the ASTM D975 specifications.

TABLE 18

Boiling point distribution of renewable diesel product.

| Recovered mass % | BP ° C. |
|---|---|
| IBP | 150.4 |
| 1.0 | 163.6 |
| 2.0 | 173.4 |
| 3.0 | 175.2 |
| 4.0 | 188.0 |
| 5.0 | 194.8 |
| 6.0 | 196.6 |
| 7.0 | 197.8 |
| 8.0 | 207.4 |
| 9.0 | 210.0 |
| 10.0 | 214.4 |
| 11.0 | 216.6 |
| 12.0 | 217.6 |
| 13.0 | 221.4 |
| 14.0 | 227.6 |
| 15.0 | 229.8 |
| 16.0 | 233.2 |
| 17.0 | 235.8 |
| 18.0 | 236.8 |
| 19.0 | 240.2 |
| 20.0 | 245.6 |
| 21.0 | 248.0 |
| 22.0 | 250.2 |
| 23.0 | 253.6 |
| 24.0 | 255.2 |
| 25.0 | 256.8 |
| 26.0 | 261.8 |
| 27.0 | 264.6 |
| 28.0 | 266.2 |
| 29.0 | 268.2 |
| 30.0 | 271.0 |
| 31.0 | 272.4 |
| 32.0 | 273.4 |
| 33.0 | 276.2 |
| 34.0 | 280.0 |
| 35.0 | 282.4 |
| 36.0 | 285.2 |
| 37.0 | 287.8 |
| 38.0 | 289.6 |
| 39.0 | 291.8 |
| 40.0 | 294.2 |
| 41.0 | 295.8 |
| 42.0 | 296.8 |
| 43.0 | 297.6 |
| 44.0 | 298.4 |
| 45.0 | 299.2 |
| 46.0 | 299.8 |
| 47.0 | 300.6 |
| 48.0 | 301.2 |
| 49.0 | 302.0 |
| 50.0 | 302.6 |
| 51.0 | 303.2 |
| 52.0 | 303.8 |
| 53.0 | 304.4 |
| 54.0 | 304.8 |
| 55.0 | 305.2 |
| 56.0 | 305.6 |
| 57.0 | 306.0 |
| 58.0 | 306.4 |
| 59.0 | 306.6 |
| 60.0 | 307.0 |
| 61.0 | 307.4 |
| 62.0 | 307.6 |
| 63.0 | 308.0 |
| 64.0 | 308.4 |
| 65.0 | 308.8 |
| 66.0 | 309.2 |
| 67.0 | 309.6 |
| 68.0 | 310.2 |
| 69.0 | 310.6 |
| 70.0 | 311.2 |
| 71.0 | 311.6 |
| 72.0 | 312.2 |
| 73.0 | 313.0 |
| 74.0 | 313.6 |
| 75.0 | 314.2 |
| 76.0 | 314.8 |
| 77.0 | 315.4 |
| 78.0 | 315.8 |
| 79.0 | 316.4 |
| 80.0 | 317.0 |
| 81.0 | 317.6 |
| 82.0 | 318.4 |
| 83.0 | 319.0 |
| 84.0 | 319.6 |
| 85.0 | 320.2 |
| 86.0 | 320.8 |
| 87.0 | 321.2 |
| 88.0 | 321.8 |
| 89.0 | 322.2 |
| 90.0 | 322.4 |
| 91.0 | 322.8 |
| 92.0 | 323.2 |
| 93.0 | 324.4 |
| 94.0 | 326.8 |

TABLE 18-continued

Boiling point distribution of renewable diesel product.

| Recovered mass % | BP °C. |
|---|---|
| 95.0 | 329.4 |
| 96.0 | 333.6 |
| 97.0 | 339.4 |
| 98.0 | 346.2 |
| 99.0 | 362.8 |
| FBP | 401.4 |

TABLE 19

Analytical report for renewable diesel product using D975 specifications.

| Method Number | Test Description | Results | Units |
|---|---|---|---|
| D93A | Flash Point (PMCC) | 70 | °C. |
| D2709 | Water and Sediment | 0 | Vol % |
| D86 | Distillation 90% (Recovered) | 301.0/573.9 | °C./°F. |
| D445 | Kinematic Viscosity @ 40.0° C. (104.0° F.) | 2.868 | mm2/sec |
| D482 | Ash | <0.001 | Wt % |
| D5453 | Sulfur | 2.4 | ppm |
| D130 | Copper Corrosion 3 hours @ 50° C. | 1b | |
| D613 | Cetane Number *** | >65 | |
| D976 | Calculated Cetane Index | 71.2 | |
| D2500 | Cloud Point | −3 | °C. |
| D524 | Ramsbottom 10% Carbon Residue | 0.02 | Wt % |
| D97 | Pour Point | −3 | °C. |
| D2274 | Total insolubles (Oxidation Stability) 40 Hour Test *** | 4.0 | mg/100 mL |
| D4052 | Density @ 15.0° C. (59.0° F.) | 793.8 | kg/m$^3$ |
| D4176-1 | Appearance by Visual Inspection (Lab) | Clear and Bright- Pass | Visual |
| D4176-1 | Appearance by Visual Inspection (Lab) | Free Water- Pass | Visual |
| D4176-1 | Appearance by Visual Inspection (Lab) | Particulates- Pass | Visual |
| D1500 | ASTM Color | L 0.5 | |
| D664 | Acid Number | <0.10 | mg KOH/g |
| D6079 | Lubricity (Wear Scar) | 405 | µm |

What is claimed is:

1. A triglyceride oil produced by cultivating heterotrophically in the dark a genetically engineered *Chlorella prototheocoides* cell comprising an exogenous gene encoding a sucrose invertase, wherein the exogenous gene is codon optimized for expression in the *Chlorella prototheocoides* cell; wherein the cell is cultured on a fixed carbon source selected from the group consisting of glycerol, depolymerized cellulosic material, sucrose, molasses, glucose, galactose, fructose, mannose, acetate, and any combination thereof.

2. The oil of claim 1, wherein the one or more exogenous genes of the genetically engineered *Chlorella prototheocoides* is codon optimized using codons comprising

| | | | |
|---|---|---|---|
| TTC (Phe) | TAC (Tyr) | TGC (Cys) | TGA (Stop) |
| TGG (Trp) | CCC (Pro) | CAC (His) | CGC (Arg) |
| CTG (Leu) | CAG (Gln) | ATC (Ile) | ACC (Thr) |
| GAC (Asp) | TCC (Ser) | ATG (Met) | AAG (Lys) |
| GCC (Ala) | AAC (Asn) | GGC (Gly) | GTG (Val) |
| GAG (Glu). | | | |

3. The oil of claim 1, wherein the fixed carbon source is glucose.

4. The oil of claim 1, wherein the fixed carbon source is sucrose.

* * * * *

SEQUENCE LISTING

```
<160> NUMBER OF SEQ ID NOS: 25

<210> SEQ ID NO 1
<211> LENGTH: 1187
<212> TYPE: DNA
<213> ORGANISM: Artificial
<220> FEATURE:
<223> OTHER INFORMATION: Synthetic HUP promoter from Chlorella
      (subsequence of GenBank accession number X55349)

<400> SEQUENCE: 1
gatcagacgg gcctgacctg cgagataatc aagtgctcgt aggcaaccaa ctcagcagct      60
gcttggtgtt gggtctgcag gatagtgttg cagggcccca aggacagcag gggaacttac    120
accttgtccc cgacccagtt ttatggagtg cattgcctca agagcctagc cggagcgcta    180
ggctacatac ttgccgcacc ggtatgaggg gatatagtac tcgcactgcg ctgtctagtg    240
agatgggcag tgctgcccat aaacaactgg ctgctcagcc atttgttggc ggaccattct    300 ggggggggcca gcaatgcctg actttcgggt agggtgaaaa ctgaacaaag actaccaaaa    360
cagaatttct tcctccttgg aggtaagcgc aggccggcc gcctgcgccc acatggcgct    420
ccgaacacct ccatagctgt aagggcgcaa acatggccgg actgttgtca gcactctttc    480
atggccatac aaggtcatgt cgagattagt gctgagtaag acactatcac cccatgttcg    540
attgaagccg tgacttcatg ccaacctgcc cctgggcgta gcagacgtat gccatcatga    600
ccactagccg acatgcgctg tcttttgcca ccaaaacaac tggtacaccg ctcgaagtcg    660
tgccgcacac ctccgggagt gagtccggcg actcctcccc ggcgggccgc ggccctacct    720
gggtagggtc gccatacgcc cacgaccaaa cgacgcagga ggggattggg gtagggaatc    780
ccaaccagcc taaccaagac ggcacctata ataataggtg gggggactaa cagccctata    840
tcgcaagctt tgggtgccta tcttgagaag cacgagttgg agtggctgtg tacggtcgac    900
cctaaggtgg gtgtgccgca gcctgaaaca aagcgtctag cagctgcttc tataatgtgt    960
cagccgttgt gtttcagtta tattgtatgc tattgtttgt tcgtgctagg gtggcgcagg   1020
```

```
cccacctact gtggcgggcc attggttggt gcttgaattg cctcaccatc taaggtctga    1080
acgctcactc aaacgccttt gtacaactgc agaactttcc ttggcgctgc aactacagtg    1140
tgcaaaccag cacatagcac tcccttacat cacccagcag tacaaca                 1187

<210> SEQ ID NO 2
<211> LENGTH: 1414
<212> TYPE: DNA
<213> ORGANISM: Artificial
<220> FEATURE:
<223> OTHER INFORMATION: Synthetic Chlorella ellipsoidea nitrate
      reductase promoter from AY307383

<400> SEQUENCE: 2
cgctgcgcac cagggccgcc agctcgctga tgtcgctcca aatgcggtcc cccgattttt     60
tgttcttcat cttctccacc ttggtggcct tcttggccag ggccttcagc tgcatgcgca    120
cagaccgttg agctcctgat cagcatcctc aggaggccct ttgacaagca agcccctgtg    180
caagcccatt cacggggtac cagtggtgct gaggtagatg ggtttgaaaa ggattgctcg    240
gtcgattgct gctcatggaa ttggcatgtg catgcatgtt cacaatatgc caccaggctt    300
tggagcaaga gagcatgaat gccttcaggc aggttgaaag ttcctggggg tgaagaggca    360
gggccgagga ttggaggagg aaagcatcaa gtcgtcgctc atgctcatgt tttcagtcag    420
agtttgccaa gctcacagga gcagagacaa gactggctgc tcaggtgttg catcgtgtgt    480
gtggtggggg gggggggtt aatacggtac gaaatgcact tggaattccc acctcatgcc    540
agcggaccca catgcttgaa ttcgaggcct gtggggtgag aaatgctcac tctgccctcg    600
ttgctgaggt acttcaggcc gctgagctca agtcgatgc cctgctcgtc tatcagggcc     660
tgcacctctg ggctgaccgg ctcagcctcc ttcgcgggca tggagtaggc gccggcagcg    720
ttcatgtccg ggcccagggc agcggtggtg ccataaatgt cggtgatggt ggggagggg     780 gccgtcgcca caccattgcc gttgctggct gacgcatgca catgtggcct ggctggcacc    840
ggcagcactg gtctccagcc agccagcaag tggctgttca ggaaagcggc catgttgttg    900
gtccctgcgc atgtaattcc ccagatcaaa ggagggaaca gcttggattt gatgtagtgc    960
ccaaccggac tgaatgtgcg atggcaggtc cctttgagtc tcccgaatta ctagcagggc   1020
actgtgacct aacgcagcat gccaaccgca aaaaatgat tgacagaaaa tgaagcggtg    1080
tgtcaatatt tgctgtattt attcgttta atcagcaacc aagttcgaaa cgcaactatc    1140
gtggtgatca agtgaacctc atcagactta cctcgttcgg caaggaaacg gaggcaccaa   1200
attccaattt gatattatcg cttgccaagc tagagctgat ctttgggaaa ccaactgcca    1260
gacagtggac tgtgatggag tgccccgagt ggtggagcct cttcgattcg gttagtcatt    1320
actaacgtga accctcagtg aagggaccat cagaccagaa agaccagatc tcctcctcga    1380
caccgagaga gtgttgcggc agtaggacga caag                                1414

<210> SEQ ID NO 3
<211> LENGTH: 1113
<212> TYPE: DNA
<213> ORGANISM: Artificial
<220> FEATURE:
<223> OTHER INFORMATION: Synthetic B. braunii malate dehydrogenase 5'UTR

<400> SEQUENCE: 3
aattggaaac cccgcgcaag accgggttgt ttggccgcct gaccggaaag ggggggcctg     60
tcccgaaggg ggtctatctc ttgggggatg tcgggcgcgg aaagtcgatg ttgatggacc    120
```

```
tcttcttcga ccatgtcggg gtcgaggcca agagccgcgt ccatttcgcc gagttcatga      180
tggaggtgaa tgaccgcatc gccaccgaac gcgccaagaa gcgggcgacc gatcgccccc      240
gtcgctgcag cccttgccga ggaagtccgg ctgctggcgt tcgacgagat gatggtgacg      300
aacagcccgg acgcgatgat cctgtcgcgg ctgttcaccg cgctgatcga ggcggggtg       360 acgatcgtca ccacctccaa ccggccgccc agggatctct ataagaacgg gctcaaccgc      420
gagcatttcc tgcccttcat cgcgctgatc gaggcgcggc tggacgtgct ggcgctgaac      480
ggcccgaccg actatcggcg cgaccggctg gggcggctgg acacgtggtt ggtgcccaat      540
ggccccaagg cgacgattac cttgtcggcg gcgttcttcc gcctgaccga ctatccggtc      600
gaggatgccg cgcatgtgcc ctctgaggac ctgaaggtgg gcgggcgcgt gctgaatgtc      660
cccaaggcgc tgaagggcgt cgcggtcttc tcgttcaagc ggttgtgcgg cgaagcgcgg      720
ggggcggcgg actatctggc ggtcgcgcgg ggcttccaca ccgtcatcct ggtcggaatc      780
cccaagctgg gggcggagaa ccgcaacgag gcggggcgct cgtccagct gatcgacgcg       840 ctctacgaac ataaggtcaa gctgctcgcc gcagccgatg ccagcccgcc gaactctatg      900
aaaccggcga cggccggttc gagtttgagc gcagatcagc cggttggaag agatgcgctc      960
cgaggattat ctggcccaag gccatggctc ggaggggcct tgatcaggcc ttaatgcact     1020
tcgcaaccat tatcgtttaa aatcttaaac tctgtggaat aacggttccc cgacgccgca    1080
atacacgtac gtccactacg gagtaggatt gga                                  1113

<210> SEQ ID NO 4
<211> LENGTH: 253
<212> TYPE: DNA
<213> ORGANISM: Artificial
<220> FEATURE:
<223> OTHER INFORMATION: Synthetic Chlamydomonas RBCS2 promoter

<400> SEQUENCE: 4
cgcttagaag atttcgataa ggcgccagaa ggagcgcagc caaaccagga tgatgtttga      60
tggggtattt gagcacttgc aacccttatc cggaagcccc ctggcccaca aaggctaggc     120
gccaatgcaa gcagttcgca tgcagcccct ggagcggtgc cctcctgata aaccggccag     180
ggggcctatg ttctttactt ttttacaaga gaagtcactc aacatcttaa acggtcttaa     240
gaagtctatc cgg                                                        253

<210> SEQ ID NO 5
<211> LENGTH: 2435
<212> TYPE: DNA
<213> ORGANISM: Artificial
<220> FEATURE:
<223> OTHER INFORMATION: Synthetic CMV-Hyg-CMV BamHI-SacII cassette from
      pCAMBIA

<400> SEQUENCE: 5
ggatccccgg gaattcggcg cgccgggccc aacatggtgg agcacgacac tctcgtctac      60
tccaagaata tcaaagatac agtctcagaa gaccaaaggg ctattgagac ttttcaacaa     120
agggtaatat cggaaacct cctcggattc cattgcccag ctatctgtca cttcatcaaa      180
aggacagtag aaaaggaagg tggcacctac aaatgccatc attgcgataa aggaaaggct     240
atcgttcaag atgcctctgc cgacagtggt cccaaagatg gacccccacc cacgaggagc     300
atcgtggaaa aagaagacgt tccaaccacg tcttcaaagc aagtggattg atgtgataac     360
atggtggagc acgacactct cgtctactcc aagaatatca agatacagt ctcagaagac      420
```

```
caaagggcta ttgagacttt tcaacaaagg gtaatatcgg gaaacctcct cggattccat    480
tgcccagcta tctgtcactt catcaaaagg acagtagaaa aggaaggtgg cacctacaaa    540
tgccatcatt gcgataaagg aaaggctatc gttcaagatg cctctgccga cagtggtccc    600
aaagatggac ccccacccac gaggagcatc gtggaaaaag aagacgttcc aaccacgtct    660
tcaaagcaag tggattgatg tgatatctcc actgacgtaa gggatgacgc acaatcccac    720
tatccttcgc aagaccttcc tctatataag gaagttcatt tcatttggag aggacacgct    780
gaaatcacca gtctctctct acaaatctat ctctctcgag ctttcgcaga tcccgggggg    840
caatgagata tgaaaaagcc tgaactcacc gcgacgtctg tcgagaagtt tctgatcgaa    900
aagttcgaca gcgtctccga cctgatgcag ctctcggagg gcgaagaatc tcgtgctttc    960
agcttcgatg taggagggcg tggatatgtc ctgcgggtaa atagctgcgc cgatggtttc   1020
tacaaagatc gttatgttta tcggcacttt gcatcggccg cgctcccgat tccggaagtg   1080
cttgacattg gggagtttag cgagagcctg acctattgca tctcccgccg tgcacagggt   1140
gtcacgttgc aagacctgcc tgaaaccgaa ctgcccgctg ttctacaacc ggtcgcggag   1200
gctatggatg cgatcgctgc ggccgatctt agccagacga gcgggttcgg cccattcgga   1260
ccgcaaggaa tcggtcaata cactacatgg cgtgatttca tatgcgcgat tgctgatccc   1320
catgtgtatc actggcaaac tgtgatggac gacaccgtca gtgcgtccgt cgcgcaggct   1380
ctcgatgagc tgatgctttg gccgaggac tgccccgaag tccggcacct cgtgcacgcg   1440
gatttcggct ccaacaatgt cctgacggac aatggccgca taacagcggt cattgactgg   1500
agcgaggcga tgttcgggga ttcccaatac gaggtcgcca acatcttctt ctggaggccg   1560
tggttggctt gtatggagca gcagacgcgc tacttcgagc ggaggcatcc ggagcttgca   1620
ggatcgccac gactccgggc gtatatgctc cgcattggtc ttgaccaact ctatcagagc   1680
ttggttgacg gcaatttcga tgatgcagct tgggcgcagg gtcgatgcga cgcaatcgtc   1740
cgatccggag ccgggactgt cgggcgtaca caaatcgccc gcagaagcgc ggccgtctgg   1800
accgatggct gtgtagaagt actcgccgat agtggaaacc gacgcccag cactcgtccg    1860 agggcaaaga aatagagtag atgccgaccg gatctgtcga tcgacaagct cgagtttctc   1920
cataataatg tgtgagtagt tcccagataa gggaattagg gttcctatag ggtttcgctc   1980
atgtgttgag catataagaa acccttagta tgtatttgta tttgtaaaat acttctatca   2040 ataaatttc taattcctaa aaccaaaatc cagtactaaa atccagatcc cccgaattaa   2100
ttcggcgtta attcagtaca ttaaaaacgt ccgcaatgtg ttattaagtt gtctaagcgt   2160
caatttgttt acaccacaat atatcctgcc accagccagc caacagctcc ccgaccggca   2220
gctcggcaca aaatcaccac tcgatacagg cagcccatca gtccgggacg gcgtcagcgg   2280
gagagccgtt gtaaggcggc agactttgct catgttaccg atgctattcg gaagaacggc   2340
aactaagctg ccgggtttga aacacggatg atctcgcgga gggtagcatg ttgattgtaa   2400
cgatgacaga gcgttgctgc ctgtgatcac cgcgg                              2435
```

<210> SEQ ID NO 6  
<211> LENGTH: 20  
<212> TYPE: DNA  
<213> ORGANISM: Artificial  
<220> FEATURE:  
<223> OTHER INFORMATION: Synthetic Chlorella virus promoter - CMV construct forward primer

<400> SEQUENCE: 6

```
caaccacgtc ttcaaagcaa                                               20

<210> SEQ ID NO 7
<211> LENGTH: 20
<212> TYPE: DNA
<213> ORGANISM: Artificial
<220> FEATURE:
<223> OTHER INFORMATION: Synthetic Chlorella virus promoter

<400> SEQUENCE: 7
agcaatcgcg catatgaaat                                               20

<210> SEQ ID NO 8
<211> LENGTH: 1599
<212> TYPE: DNA
<213> ORGANISM: Artificial
<220> FEATURE:
<223> OTHER INFORMATION: Synthetic sucrose invertase gene

<400> SEQUENCE: 8
atgcttcttc aggcctttct ttttcttctt gctggttttg ctgccaagat cagcgcctct    60
atgacgaacg aaacctcgga tagaccactt gtgcacttta caccaaacaa gggctggatg   120
aatgacccca tggactgtgt gtacgacgaa aaagatgcca agtggcatct gtactttcaa   180
tacaacccga acgatactgt ctggggacg ccattgtttt ggggccacgc cacgtccgac   240
gacctgacca attgggagga ccaaccaata gctatcgctc gaagaggaa cgactccgga   300 gcattctcgg gttccatggt ggttgactac aacaatactt ccggcttttt caacgatacc   360
attgacccga gacaacgctg cgtggccata tggacttaca acacaccgga gtccgaggag   420
cagtacatct cgtatagcct ggacggtgga tacacttttta cagagtatca gaagaaccct   480
gtgcttgctg caaattcgac tcagttccga gatccgaagg tctttggta cgagccctcg   540 cagaagtgga tcatgacagc ggcaaagtca caggactaca agatcgaaat ttactcgtct   600
gacgacctta atcctggaa gctcgaatcc gcgttcgcaa acgagggctt tctcggctac   660
caatacgaat gcccaggcct gatagaggtc ccaacagagc aagatcccag caagtcctac   720
tgggtgatgt ttatttccat taatccagga gcaccggcag gaggttcttt taatcagtac   780
ttcgtcggaa gctttaacgg aactcatttc gaggcatttg ataaccaatc aagagtagtt   840
gattttggaa aggactacta tgccctgcag actttcttca atactgaccc gacctatggg   900
agcgctcttg gcattgcgtg ggcttctaac tgggagtatt ccgcattcgt tcctacaaac   960
ccttggaggt cctccatgtc gctcgtgagg aaattctctc tcaacactga gtaccaggcc  1020
aacccggaaa ccgaactcat aaacctgaaa gccgaaccga tcctgaacat tagcaacgct  1080 ggccctgga gccggtttgc aaccaacacc acgttgacga agccaacag ctacaacgtc  1140 gatctttcga atagcaccgg tacacttgaa tttgaactgg tgtatgccgt caataccacc  1200
caaacgatct cgaagtcggt gttcgcggac ctctccctct ggtttaaagg cctggaagac  1260
cccgaggagt acctcagaat gggttttcgag gttttctgcgt cctccttctt ccttgatcgc  1320
gggaacagca agtaaaatt tgttaaggag aacccatatt ttaccaacag gatgagcgtt  1380
aacaaccaac cattcaagag cgaaaacgac ctgtcgtact acaaagtgta tggtttgctt  1440
gatcaaaata tcctggaact ctacttcaac gatggtgatg tcgtgtccac caacacatac  1500
ttcatgacaa ccgggaacgc actgggctcc gtgaacatga cgacgggtgt ggataacctg  1560
ttctacatcg acaaattcca ggtgagggaa gtcaagtga                         1599
```

-continued

```
<210> SEQ ID NO 9
<211> LENGTH: 20
<212> TYPE: DNA
<213> ORGANISM: Artificial
<220> FEATURE:
<223> OTHER INFORMATION: Synthetic CMV construct reverse primer

<400> SEQUENCE: 9
tccggtgtgt tgtaagtcca                                                20

<210> SEQ ID NO 10
<211> LENGTH: 20
<212> TYPE: DNA
<213> ORGANISM: Artificial
<220> FEATURE:
<223> OTHER INFORMATION: Synthetic CV construct forward primer

<400> SEQUENCE: 10
ttgtcggaat gtcatatcaa                                                20

<210> SEQ ID NO 11
<211> LENGTH: 20
<212> TYPE: DNA
<213> ORGANISM: Artificial
<220> FEATURE:
<223> OTHER INFORMATION: Synthetic CV construct reverse primer

<400> SEQUENCE: 11
tccggtgtgt tgtaagtcca                                                20

<210> SEQ ID NO 12
<211> LENGTH: 20
<212> TYPE: DNA
<213> ORGANISM: Artificial
<220> FEATURE:
<223> OTHER INFORMATION: Synthetic HUP1 construct forward primer

<400> SEQUENCE: 12
aacgcctttg tacaactgca                                                20

<210> SEQ ID NO 13
<211> LENGTH: 20
<212> TYPE: DNA
<213> ORGANISM: Artificial
<220> FEATURE:
<223> OTHER INFORMATION: Synthetic HUP1 construct reverse primer

<400> SEQUENCE: 13
tccggtgtgt tgtaagtcca                                                20

<210> SEQ ID NO 14
<211> LENGTH: 512
<212> TYPE: PRT
<213> ORGANISM: Artificial
<220> FEATURE:
<223> OTHER INFORMATION: Synthetic sucrose invertase

<400> SEQUENCE: 14
```

Met Thr Asn Glu Thr Ser Asp Arg Pro Leu Val His Phe Thr Pro Asn
1               5                   10                  15

Lys Gly Trp Met Asn Asp Pro Asn Gly Leu Trp Tyr Asp Glu Lys Asp
            20                  25                  30

Ala Lys Trp His Leu Tyr Phe Gln Tyr Asn Pro Asn Asp Thr Val Trp
        35                  40                  45

```
Gly Thr Pro Leu Phe Trp Gly His Ala Thr Ser Asp Asp Leu Thr Asn
 50                  55                  60

Trp Glu Asp Gln Pro Ile Ala Ile Ala Pro Lys Arg Asn Asp Ser Gly
 65                  70                  75                  80

Ala Phe Ser Gly Ser Met Val Val Asp Tyr Asn Asn Thr Ser Gly Phe
                 85                  90                  95

Phe Asn Asp Thr Ile Asp Pro Arg Gln Arg Cys Val Ala Ile Trp Thr
            100                 105                 110

Tyr Asn Thr Pro Glu Ser Glu Gln Tyr Ile Ser Tyr Ser Leu Asp
        115                 120                 125

Gly Gly Tyr Thr Phe Thr Glu Tyr Gln Lys Asn Pro Val Leu Ala Ala
        130                 135                 140

Asn Ser Thr Gln Phe Arg Asp Pro Lys Val Phe Trp Tyr Glu Pro Ser
145                 150                 155                 160

Gln Lys Trp Ile Met Thr Ala Ala Lys Ser Gln Asp Tyr Lys Ile Glu
                165                 170                 175

Ile Tyr Ser Ser Asp Asp Leu Lys Ser Trp Lys Leu Glu Ser Ala Phe
            180                 185                 190

Ala Asn Glu Gly Phe Leu Gly Tyr Gln Tyr Glu Cys Pro Gly Leu Ile
        195                 200                 205

Glu Val Pro Thr Glu Gln Asp Pro Ser Lys Ser Tyr Trp Val Met Phe
210                 215                 220

Ile Ser Ile Asn Pro Gly Ala Pro Ala Gly Gly Ser Phe Asn Gln Tyr
225                 230                 235                 240

Phe Val Gly Ser Phe Asn Gly Thr His Phe Glu Ala Phe Asp Asn Gln
                245                 250                 255

Ser Arg Val Val Asp Phe Gly Lys Asp Tyr Tyr Ala Leu Gln Thr Phe
            260                 265                 270

Phe Asn Thr Asp Pro Thr Tyr Gly Ser Ala Leu Gly Ile Ala Trp Ala
        275                 280                 285

Ser Asn Trp Glu Tyr Ser Ala Phe Val Pro Thr Asn Pro Trp Arg Ser
290                 295                 300

Ser Met Ser Leu Val Arg Lys Phe Ser Leu Asn Thr Glu Tyr Gln Ala
305                 310                 315                 320

Asn Pro Glu Thr Glu Leu Ile Asn Leu Lys Ala Glu Pro Ile Leu Asn
                325                 330                 335

Ile Ser Asn Ala Gly Pro Trp Ser Arg Phe Ala Thr Asn Thr Thr Leu
            340                 345                 350

Thr Lys Ala Asn Ser Tyr Asn Val Asp Leu Ser Asn Ser Thr Gly Thr
        355                 360                 365

Leu Glu Phe Glu Leu Val Tyr Ala Val Asn Thr Thr Gln Thr Ile Ser
370                 375                 380

Lys Ser Val Phe Ala Asp Leu Ser Leu Trp Phe Lys Gly Leu Glu Asp
385                 390                 395                 400

Pro Glu Glu Tyr Leu Arg Met Gly Phe Glu Val Ser Ala Ser Ser Phe
                405                 410                 415

Phe Leu Asp Arg Gly Asn Ser Lys Val Lys Phe Val Lys Glu Asn Pro
            420                 425                 430

Tyr Phe Thr Asn Arg Met Ser Val Asn Asn Gln Pro Phe Lys Ser Glu
        435                 440                 445

Asn Asp Leu Ser Tyr Tyr Lys Val Tyr Gly Leu Leu Asp Gln Asn Ile
450                 455                 460

Leu Glu Leu Tyr Phe Asn Asp Gly Asp Val Val Ser Thr Asn Thr Tyr
```

```
                465                 470                 475                 480
Phe Met Thr Thr Gly Asn Ala Leu Gly Ser Val Asn Met Thr Thr Gly
                    485                 490                 495

Val Asp Asn Leu Phe Tyr Ile Asp Lys Phe Gln Val Arg Glu Val Lys
                500                 505                 510

<210> SEQ ID NO 15
<211> LENGTH: 20
<212> TYPE: PRT
<213> ORGANISM: Artificial
<220> FEATURE:
<223> OTHER INFORMATION: Synthetic secretion signal from yeast

<400> SEQUENCE: 15

Met Leu Leu Gln Ala Phe Leu Phe Leu Leu Ala Gly Phe Ala Ala Lys
1               5                   10                  15

Ile Ser Ala Ser
            20

<210> SEQ ID NO 16
<211> LENGTH: 18
<212> TYPE: PRT
<213> ORGANISM: Artificial
<220> FEATURE:
<223> OTHER INFORMATION: Synthetic secretion signal from higher plants

<400> SEQUENCE: 16

Met Ala Asn Lys Ser Leu Leu Leu Leu Leu Leu Gly Ser Leu Ala
1               5                   10                  15

Ser Gly

<210> SEQ ID NO 17
<211> LENGTH: 10
<212> TYPE: PRT
<213> ORGANISM: Artificial
<220> FEATURE:
<223> OTHER INFORMATION: Synthetic eukaryotic consensus secretion signal

<400> SEQUENCE: 17

Met Ala Arg Leu Pro Leu Ala Ala Leu Gly
1               5                   10

<210> SEQ ID NO 18
<211> LENGTH: 20
<212> TYPE: PRT
<213> ORGANISM: Artificial
<220> FEATURE:
<223> OTHER INFORMATION: Synthetic combination of signal sequence from
      higher plants and eukaryotic consensus

<400> SEQUENCE: 18

Met Ala Asn Lys Leu Leu Leu Leu Leu Leu Leu Leu Leu Pro Leu
1               5                   10                  15

Ala Ala Ser Gly
            20

<210> SEQ ID NO 19
<211> LENGTH: 532
<212> TYPE: PRT
<213> ORGANISM: Artificial
<220> FEATURE:
<223> OTHER INFORMATION: Synthetic sucrose invertase gene

<400> SEQUENCE: 19
```

```
Met Leu Leu Gln Ala Phe Leu Phe Leu Leu Ala Gly Phe Ala Ala Lys
1               5                   10                  15
Ile Ser Ala Ser Met Thr Asn Glu Thr Ser Asp Arg Pro Leu Val His
                20                  25                  30
Phe Thr Pro Asn Lys Gly Trp Met Asn Asp Pro Asn Gly Leu Trp Tyr
            35                  40                  45
Asp Glu Lys Asp Ala Lys Trp His Leu Tyr Phe Gln Tyr Asn Pro Asn
        50                  55                  60
Asp Thr Val Trp Gly Thr Pro Leu Phe Trp Gly His Ala Thr Ser Asp
65                  70                  75                  80
Asp Leu Thr Asn Trp Glu Asp Gln Pro Ile Ala Ile Ala Pro Lys Arg
                85                  90                  95
Asn Asp Ser Gly Ala Phe Ser Gly Ser Met Val Val Asp Tyr Asn Asn
            100                 105                 110
Thr Ser Gly Phe Phe Asn Asp Thr Ile Asp Pro Arg Gln Arg Cys Val
        115                 120                 125
Ala Ile Trp Thr Tyr Asn Thr Pro Glu Ser Glu Glu Gln Tyr Ile Ser
    130                 135                 140
Tyr Ser Leu Asp Gly Gly Tyr Thr Phe Thr Glu Tyr Gln Lys Asn Pro
145                 150                 155                 160
Val Leu Ala Ala Asn Ser Thr Gln Phe Arg Asp Pro Lys Val Phe Trp
                165                 170                 175
Tyr Glu Pro Ser Gln Lys Trp Ile Met Thr Ala Ala Lys Ser Gln Asp
            180                 185                 190
Tyr Lys Ile Glu Ile Tyr Ser Ser Asp Asp Leu Lys Ser Trp Lys Leu
        195                 200                 205
Glu Ser Ala Phe Ala Asn Glu Gly Phe Leu Gly Tyr Gln Tyr Glu Cys
    210                 215                 220
Pro Gly Leu Ile Glu Val Pro Thr Glu Gln Asp Pro Ser Lys Ser Tyr
225                 230                 235                 240
Trp Val Met Phe Ile Ser Ile Asn Pro Gly Ala Pro Ala Gly Gly Ser
                245                 250                 255
Phe Asn Gln Tyr Phe Val Gly Ser Phe Asn Gly Thr His Phe Glu Ala
            260                 265                 270
Phe Asp Asn Gln Ser Arg Val Val Asp Phe Gly Lys Asp Tyr Tyr Ala
        275                 280                 285
Leu Gln Thr Phe Phe Asn Thr Asp Pro Thr Tyr Gly Ser Ala Leu Gly
    290                 295                 300
Ile Ala Trp Ala Ser Asn Trp Glu Tyr Ser Ala Phe Val Pro Thr Asn
305                 310                 315                 320
Pro Trp Arg Ser Ser Met Ser Leu Val Arg Lys Phe Ser Leu Asn Thr
                325                 330                 335
Glu Tyr Gln Ala Asn Pro Glu Thr Glu Leu Ile Asn Leu Lys Ala Glu
            340                 345                 350
Pro Ile Leu Asn Ile Ser Asn Ala Gly Pro Trp Ser Arg Phe Ala Thr
        355                 360                 365
Asn Thr Thr Leu Thr Lys Ala Asn Ser Tyr Asn Val Asp Leu Ser Asn
    370                 375                 380
Ser Thr Gly Thr Leu Glu Phe Glu Leu Val Tyr Ala Val Asn Thr Thr
385                 390                 395                 400
Gln Thr Ile Ser Lys Ser Val Phe Ala Asp Leu Ser Leu Trp Phe Lys
                405                 410                 415
Gly Leu Glu Asp Pro Glu Glu Tyr Leu Arg Met Gly Phe Glu Val Ser
```

```
                    420             425             430
Ala Ser Ser Phe Phe Leu Asp Arg Gly Asn Ser Lys Val Lys Phe Val
        435                 440                 445

Lys Glu Asn Pro Tyr Phe Thr Asn Arg Met Ser Val Asn Asn Gln Pro
    450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
                485                 490                 495

Thr Asn Thr Tyr Phe Met Thr Thr Gly Asn Ala Leu Gly Ser Val Asn
                500                 505                 510

Met Thr Thr Gly Val Asp Asn Leu Phe Tyr Ile Asp Lys Phe Gln Val
        515                 520                 525

Arg Glu Val Lys
    530

<210> SEQ ID NO 20
<211> LENGTH: 29
<212> TYPE: DNA
<213> ORGANISM: Artificial
<220> FEATURE:
<223> OTHER INFORMATION: Synthetic primer 2383

<400> SEQUENCE: 20
ctgacccgac ctatgggagc gctcttggc                                         29

<210> SEQ ID NO 21
<211> LENGTH: 28
<212> TYPE: DNA
<213> ORGANISM: Artificial
<220> FEATURE:
<223> OTHER INFORMATION: Synthetic primer 2279

<400> SEQUENCE: 21
cttgacttcc ctcacctgga atttgtcg                                          28

<210> SEQ ID NO 22
<211> LENGTH: 20
<212> TYPE: DNA
<213> ORGANISM: Artificial
<220> FEATURE:
<223> OTHER INFORMATION: Synthetic primer 2336

<400> SEQUENCE: 22
gtggccatat ggacttacaa                                                   20

<210> SEQ ID NO 23
<211> LENGTH: 41
<212> TYPE: DNA
<213> ORGANISM: Artificial
<220> FEATURE:
<223> OTHER INFORMATION: Synthetic primer 2465

<400> SEQUENCE: 23
caagggctgg atgaatgacc ccaatggact gtggtacgac g                           41

<210> SEQ ID NO 24
<211> LENGTH: 32
<212> TYPE: DNA
<213> ORGANISM: Artificial
<220> FEATURE:
<223> OTHER INFORMATION: Synthetic primer 2470
```

<400> SEQUENCE: 24

```
cacccgtcgt catgttcacg gagcccagtg cg                                    32
```

<210> SEQ ID NO 25
<211> LENGTH: 2615
<212> TYPE: DNA
<213> ORGANISM: Artificial
<220> FEATURE:
<223> OTHER INFORMATION: Synthetic nucleotide sequence of the construct used for transformation of multiple Chlorella species

<400> SEQUENCE: 25

```
gaattcccca acatggtgga gcacgacact ctcgtctact ccaagaatat caaagataca       60
gtctcagaag accaaagggc tattgagact tttcaacaaa gggtaatatc gggaaacctc      120
ctcggattcc attgcccagc tatctgtcac ttcatcaaaa ggacagtaga aaaggaaggt      180
ggcacctaca aatgccatca ttgcgataaa ggaaaggcta tcgttcaaga tgcctctgcc      240
gacagtggtc ccaaagatgg acccccaccc acgaggagca tcgtgaaaaa agaagacgtt      300
ccaaccacgt cttcaaagca agtggattga tgtgaacatg gtggagcacg acactctcgt      360
ctactccaag aatatcaaag atacagtctc agaagaccaa aggctattg agacttttca      420
acaagggta atatcgggaa acctcctcgg attccattgc ccagctatct gtcacttcat      480
caaaaggaca gtagaaaagg aaggtggcac ctacaaatgc catcattgcg ataaaggaaa      540
ggctatcgtt caagatgcct ctgccgacag tggtcccaaa gatggacccc cacccacgag      600
gagcatcgtg aaaagaag acgttccaac cacgtcttca aagcaagtgg attgatgtga      660
tatctccact gacgtaaggg atgacgcaca atcccactat ccttcgcaag acccttcctc      720
tatataagga agttcatttc atttggagag acacgctga atcaccagt ctctctctac        780
aaatctatct ctggcgcgcc atatcaatgc ttcttcaggc ctttcttttt cttcttgctg      840
gttttgctgc caagatcagc gcctctatga cgaacgaaac ctcggataga ccacttgtgc      900
actttacacc aaacaagggc tggatgaatg accccaatgg actgtggtac gacgaaaaag      960
atgccaagtg gcatctgtac tttcaataca acccgaacga tactgtctgg gggacgccat     1020
tgttttgggg ccacgccacg tccgacgacc tgaccaattg ggaggaccaa ccaatagcta     1080
tcgctccgaa gaggaacgac tccggagcat tctcggggttc catggtggtt gactacaaca     1140
atacttccgg ctttttcaac gataccattg acccgagaca acgctgcgtg ccatatggaa     1200
cttacaacac accggagtcc gaggagcagt acatctcgta tagcctggac ggtggataca     1260
cttttacaga gtatcagaag aaccctgtgc ttgctgcaaa ttcgactcag ttccgagatc     1320
cgaaggtctt ttggtacgag ccctcgcaga gtggatcat gacagcggca aagtcacagg     1380
actacaagat cgaaatttac tcgtctgacg accttaaatc ctggaagctc gaatccgcgt     1440
tcgcaaacga gggctttctc ggctaccaat acgaatgccc aggcctgata gaggtcccaa     1500
cagagcaaga tcccagcaag tcctactggg tgatgtttat ttccattaat ccaggagcac     1560
cggcaggagg ttctttttaat cagtacttcg tcggaagctt taacggaact catttcgagg     1620
catttgataa ccaatcaaga gtagttgatt ttggaaagga ctactatgcc ctgcagactt     1680
tcttcaatac tgacccgacc tatggagcg ctcttggcat tgcgtgggct tctaactggg     1740
agtattccgc attcgttcct acaaaccctt ggaggtcctc catgtcgctc gtgaggaaat     1800
tctctctcaa cactgagtac caggccaacc cggaaaccga actcataaac ctgaaagccg     1860
aaccgatcct gaacattagc aacgctggcc cctggagccg gtttgcaacc aacaccacgt     1920
```

```
tgacgaaagc caacagctac aacgtcgatc tttcgaatag caccggtaca cttgaatttg    1980
aactggtgta tgccgtcaat accacccaaa cgatctcgaa gtcggtgttc gcggacctct    2040
ccctctggtt taaaggcctg gaagacgccg aggagtacct cagaatgggt ttcgaggttt    2100
ctgcgtcctc cttcttcctt gatcgcggga acagcaaagt aaaatttgtt aaggagaacc    2160
catattttac caacaggatg agcgttaaca accaaccatt caagagcgaa aacgacctgt    2220
cgtactacaa agtgtatggt ttgcttgatc aaaatatcct ggaactctac ttcaacgatg    2280
gtgatgtcgt gtccaccaac acatacttca tgacaaccgg gaacgcactg ggctccgtga    2340
acatgacgac gggtgtggat aacctgttct acatcgacaa attccaggtg agggaagtca    2400
agtgagatct gtcgatcgac aagctcgagt ttctccataa taatgtgtga gtagttccca    2460
gataagggaa ttagggttcc tatagggttt cgctcatgtg ttgagcatat aagaaaccct    2520
tagtatgtat ttgtatttgt aaaatacttc tatcaataaa atttctaatt cctaaaacca    2580
aaatccagta ctaaaatcca gatcccccga attaa                               2615
```